US011944566B2

(12) United States Patent
Jacobson et al.

(10) Patent No.: US 11,944,566 B2
(45) Date of Patent: Apr. 2, 2024

(54) SYSTEMS, METHODS, AND DEVICES FOR ALLEVIATING ERECTILE DYSFUNCTION

(71) Applicant: Giddy Holdings, Inc., Austin, TX (US)

(72) Inventors: Brett Jacobson, Austin, TX (US); Sebastian Miller, Philadelphia, PA (US)

(73) Assignee: Giddy Holdings, Inc., Austin, TX (US)

( * ) Notice: Subject to any disclaimer, the term of this patent is extended or adjusted under 35 U.S.C. 154(b) by 0 days.

(21) Appl. No.: 17/610,128

(22) PCT Filed: May 8, 2020

(86) PCT No.: PCT/US2020/032021
§ 371 (c)(1),
(2) Date: Nov. 9, 2021

(87) PCT Pub. No.: WO2020/231780
PCT Pub. Date: Nov. 19, 2020

(65) Prior Publication Data
US 2022/0218509 A1    Jul. 14, 2022

Related U.S. Application Data

(60) Provisional application No. 62/933,930, filed on Nov. 11, 2019, provisional application No. 62/846,572, filed on May 10, 2019.

(51) Int. Cl.
*A61F 5/41* (2006.01)
*A61H 19/00* (2006.01)

(52) U.S. Cl.
CPC ............... *A61F 5/41* (2013.01); *A61H 19/30* (2013.01); *A61H 19/34* (2013.01);
(Continued)

(58) Field of Classification Search
CPC ..... A61F 5/41; A61F 2005/414; A61H 19/30; A61H 19/34; A61H 2201/1695; A61H 2205/087
See application file for complete search history.

(56) References Cited

U.S. PATENT DOCUMENTS

| 1,225,341 A | 5/1917 | Lederer |
| 3,511,230 A | 5/1970 | Strong |

(Continued)

FOREIGN PATENT DOCUMENTS

| CA | 2838404 A1 | 7/2015 |
| EP | 3965707 A1 | 3/2022 |

(Continued)

OTHER PUBLICATIONS

PCT/US2020/032021 International Preliminary Report on Patentability dated Nov. 25, 2021.
(Continued)

*Primary Examiner* — Samuel G Gilbert
(74) *Attorney, Agent, or Firm* — Kowert, Hood, Munyon, Rankin & Goetzel, P.C.; Matthew C. Washburn

(57) ABSTRACT

Provided herein are devices, systems, and methods configured to alleviate erectile dysfunction by preventing outwards blood flow away from the penis while allowing inward blood flow into the penis to aid in erection initiation, maintenance, and stamina. The geometry, configuration, flexibility, and pliability of the device enable its use on flaccid or erect penises. The penile constriction device and band enables the system to apply an adjustable compressive force on a flaccid or an erect penis.

17 Claims, 64 Drawing Sheets

(52) U.S. Cl.
CPC .................. *A61F 2005/414* (2013.01); *A61H 2201/1695* (2013.01); *A61H 2205/087* (2013.01)

(56) References Cited

U.S. PATENT DOCUMENTS

| | | | |
|---|---|---|---|
| 3,759,253 A * | 9/1973 | Cray | A61F 5/41 600/41 |
| 3,794,020 A | 2/1974 | Bagby | |
| 4,203,432 A | 5/1980 | Koch | |
| D343,454 S | 1/1994 | Osbon | |
| 5,306,227 A | 4/1994 | Osbon et al. | |
| 5,327,910 A | 7/1994 | Flynn | |
| 5,336,157 A * | 8/1994 | Hale | A61F 5/41 606/151 |
| 6,319,194 B1 | 11/2001 | Wulf | |
| 6,659,938 B1 * | 12/2003 | Orlowski | A61F 5/41 600/38 |
| 6,907,883 B2 | 6/2005 | Lin | |
| D523,958 S | 6/2006 | Fang | |
| D552,748 S | 10/2007 | Gromosaik et al. | |
| D552,749 S | 10/2007 | Gromosaik et al. | |
| D552,750 S | 10/2007 | Gromosaik et al. | |
| D557,805 S | 12/2007 | Gromosaik et al. | |
| D557,806 S | 12/2007 | Gromosaik et al. | |
| D564,666 S | 3/2008 | Klearman | |
| D581,544 S | 11/2008 | Adams | |
| D643,129 S | 8/2011 | Talbot et al. | |
| D674,477 S | 1/2013 | Beresford-Wylie | |
| D674,910 S | 1/2013 | Adams et al. | |
| D676,141 S | 2/2013 | Wu | |
| D684,701 S | 6/2013 | Uygur | |
| D694,897 S | 12/2013 | Small | |
| D702,363 S | 4/2014 | Tai | |
| D704,346 S | 5/2014 | Tai | |
| D704,347 S | 5/2014 | Tai | |
| D706,436 S | 6/2014 | Hahr et al. | |
| D706,437 S | 6/2014 | Hahr et al. | |
| D706,438 S | 6/2014 | Hahr et al. | |
| D706,439 S | 6/2014 | Hahr et al. | |
| D706,443 S | 6/2014 | Hahr et al. | |
| D707,840 S | 6/2014 | Levine | |
| D707,841 S | 6/2014 | Levine | |
| D725,283 S | 3/2015 | Sedic | |
| D727,526 S | 4/2015 | Mercado Diaz | |
| D742,535 S | 11/2015 | Wu | |
| D752,298 S | 3/2016 | Stephens | |
| D771,270 S | 11/2016 | Tai et al. | |
| D771,831 S | 11/2016 | Barnard et al. | |
| D773,066 S | 11/2016 | Sedic | |
| 9,700,454 B2 | 7/2017 | Parlante | |
| D793,571 S | 8/2017 | Iurchenko | |
| D808,034 S | 1/2018 | Matsuura | |
| D824,037 S | 7/2018 | Yueh | |
| 10,064,750 B2 | 9/2018 | Howard | |
| D983,391 S | 4/2023 | Jacobson et al. | |
| 2003/0024536 A1 | 2/2003 | Bagby | |
| 2003/0083598 A1 | 5/2003 | Kobayashi et al. | |
| 2005/0277907 A1 | 12/2005 | Jackson | |
| 2005/0283044 A1 | 12/2005 | Chang | |
| 2007/0118199 A1 | 5/2007 | Yang | |
| 2009/0012355 A1 | 1/2009 | Lin | |
| 2009/0069629 A1 | 3/2009 | Uson Calvo | |
| 2009/0306468 A1 | 12/2009 | Tasker et al. | |
| 2009/0318755 A1 | 12/2009 | Adams et al. | |
| 2010/0179379 A1 | 7/2010 | Park | |
| 2012/0259254 A1 | 10/2012 | Chen | |
| 2015/0157531 A1 | 6/2015 | Sedic | |
| 2015/0290023 A1 | 10/2015 | Parlante | |
| 2015/0313749 A1 | 11/2015 | Hahr et al. | |
| 2016/0106569 A1 | 4/2016 | Hahr et al. | |
| 2017/0042757 A1 | 2/2017 | Wang | |
| 2018/0193221 A1 | 7/2018 | Li | |
| 2018/0193620 A1 | 7/2018 | Barasch | |
| 2020/0069511 A1 | 3/2020 | Lopez | |
| 2020/0093685 A1 | 3/2020 | Luke | |

FOREIGN PATENT DOCUMENTS

| | | |
|---|---|---|
| WO | WO-2020231780 A1 | 11/2020 |
| WO | WO-2022046911 A2 | 3/2022 |

OTHER PUBLICATIONS

Amazon, "Couple Vibrator," Nov. 20, 2019. https://www.amazon.com/Couple-Vibrator-Penis-Clitoral-Stimulation/dp/B07YSB7S7D.

PCT/US2020/032021 International Search Report and Written Opinion dated Aug. 12, 2020.

Veale et al., Am I normal? A systematic review and construction of nomograms for flaccid and erect penis length and circumference in up to 15,521 men. BJU International 115(6): 26 pages (2014).

European Patent Application No. 20805793.5 Extended European Search Report dated Nov. 25, 2022.

International Search Report and Written Opinion dated Feb. 16, 2022 for International Application No. PCT/US2021/047556.

\* cited by examiner

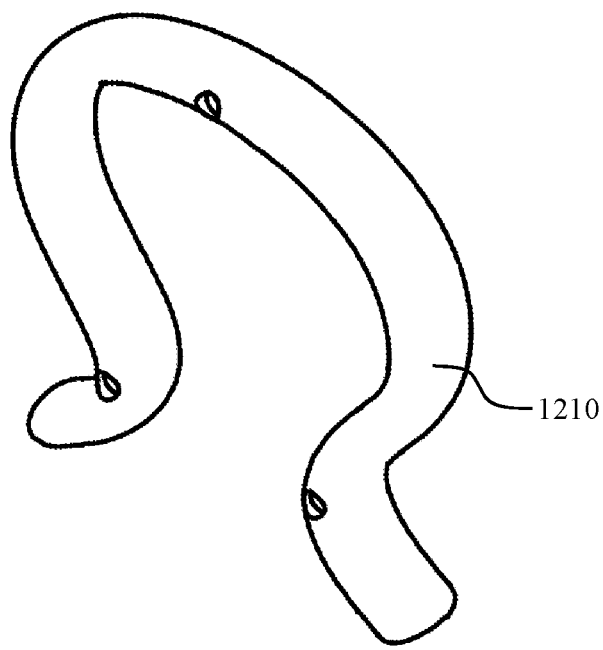
FIG 12J
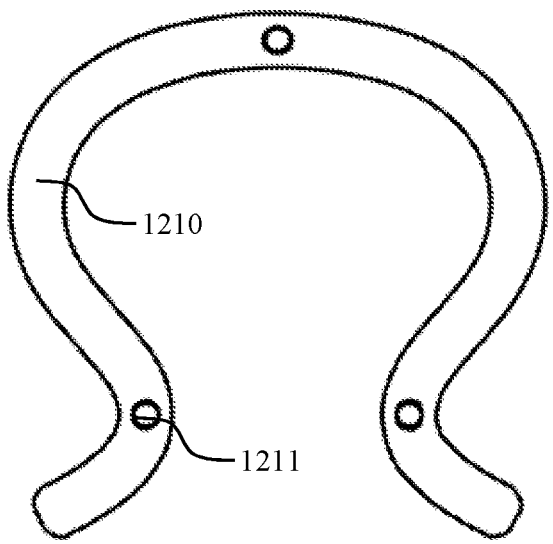 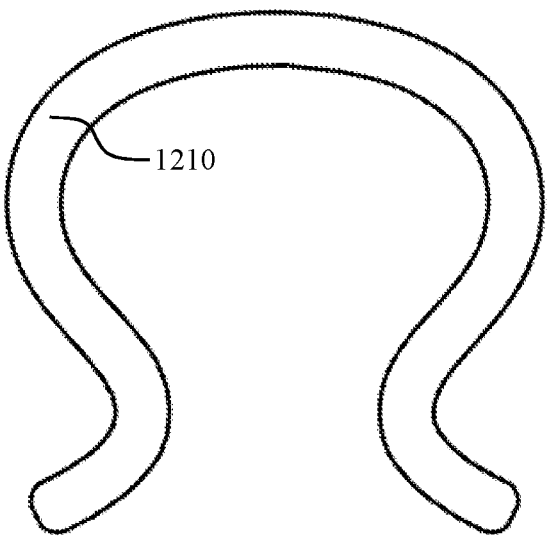
FIG 12K          FIG 12L

ED Guide Exercise getmegiddy.com/ed-guide

"Taste the Rainbow" Exercise
Week 1

Expert
Dr. Lauryn Lax — *Integrative and Functional Medicine*

This week's focus
Adding 1 new color to your plate (the rainbow), to introduce new and healthier foods into your diet. See below for examples of different food "colors".

The purpose of this exercise
To make realistic, attainable improvements to your diet and lifestyle, for the purpose of improving your ED symptoms over time. This week, we're primarily aiming for vegetables on your plate during lunch or dinner, and are focusing on just one new color instead of reinventing your diet overnight.

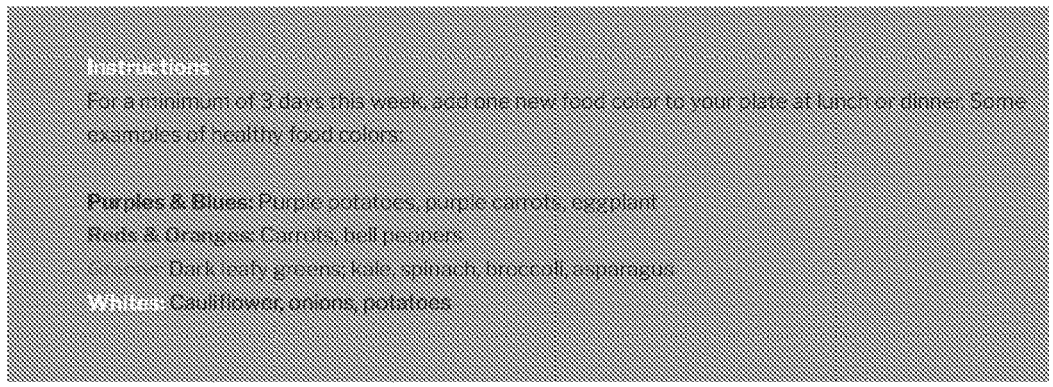

FIG. 25

ED Guide Exercise getmegiddy.com/ed-guide

Stress Relief & Better Sleep Exercise
Week 1

Expert
Dr. Bob Harding — *Integrative and Functional Medicine*

This week's focus
4-7-8 Breathing; a timed breathing exercise that can help decrease stress.

The purpose of this exercise
Most of us are breathing too shallow, and too fast. We know this by looking at our carbon dioxide levels. The purpose of the 4-7-8 breathing technique is to decrease the sympathetic tone, or "Fight or Flight" nervous system, decrease stress hormones, and increase the parasympathetic nervous system, or feelings of relaxation, which can help improve ED symptoms.

Definitions

| | |
|---|---|
| Sympathetic Tone | The primary function of the sympathetic system is to stimulate your fight-or-flight response which is a physiological reaction that happens in response to a perceived harmful event, attack or threat to survival. |
| Parasympathetic Nervous System | your circadian rhythm is a 24-hour internal clock that is running in the background of your brain and cycles between sleepiness and alertness at regular intervals. It's also known as your sleep/wake cycle. |

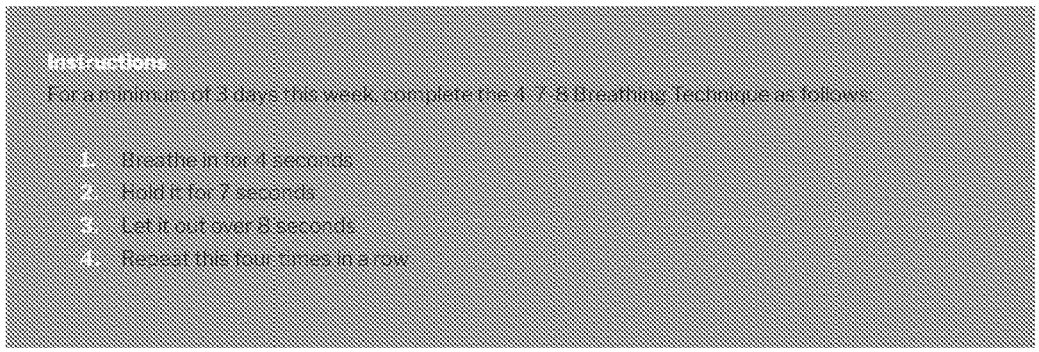

FIG. 26

ED Guide Exercise getmegiddy.com/ed-guide

4-Week Nutrition Exercise
Week 1

Expert
Dr. Lahana Vigliano — *Nutritionist*

This week's focus
Reduction. Choose an unhealthy food item you want to reduce this week. For many people, this could be sugar, or fried foods.

The purpose of this exercise
To improve your ED symptoms over time with an overall healthier diet and lifestyle, by focusing on realistic, attainable goals rather than major diet changes.

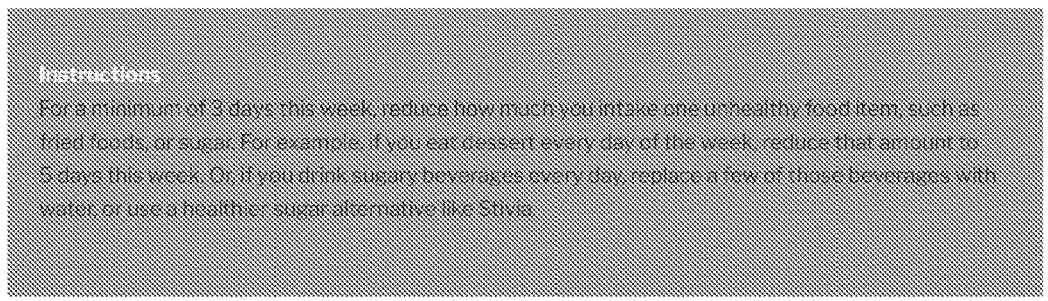

FIG. 27

Giddy
ED Guide Exercise getmegiddy.com/ed-guide

4-Week Kegel Progression Exercise
Week 1

Expert
Dr. Edwin Morales — *Urologist*

This week's focus
Strengthening your pelvic floor muscles by completing 10 kegel reps per day for 7 days.

The purpose of this exercise
To strengthen your pelvic floor muscles for improved pelvic health, ED symptoms, and orgasms. This exercise can be done anytime; sitting in traffic, during dinner, on the couch watching TV, etc.

Instructions
First, practice a kegel rep by activating the muscles in your pelvic area; do this by squeezing as though you're trying to pinch off a stool, or stop a urine stream, without bearing down or increasing the pressure inside your abdomen area.

Then practice a kegel rep by winking your left anus, then winking your right anus, then shifting your "brown eye", or contracting your anal verge muscle, called the levator ani. This is called an "anal wink". This left eye right eye method can help you avoid bearing down and increasing abdominal pressure.

Complete 10 kegel reps per day for 7 days, holding the rep for 1 second each time.

FIG. 28

ED Guide Exercise getmegiddy.com/ed-guide

"Food-and-Poo" Log Exercise
Week 1

Expert
Dr. Lauryn Lax — *Integrative and Functional Medicine*

This week's focus
Starting your "Food-and-Poo" Log to start building awareness about your food habits.

The purpose of this exercise
Keeping a log of what you eat and how you feel can help you identify what foods may be resulting in undesirable symptoms, like feeling bloated, lethargic, or foods that could be contributing to ED symptoms. Alternatively, a log can help you identify healthy, more desirable effects from different food habits, like increased energy levels, or increased libido (sex drive).

Once you can start to recognize the causes and effects of your food habits, you can optimize your diet not only to help with ED symptoms, but for your overall health and wellness.

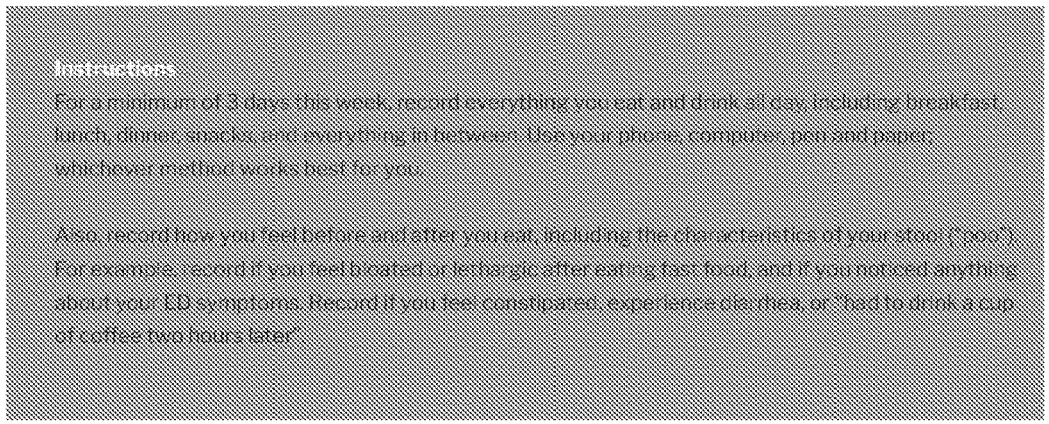

FIG. 29

ED Guide Exercise getmegiddy.com/ed-guide

De-Stressing Bedtime Exercise
Week 1

Expert
Dr. Lauryn Lax — *Integrative and Functional Medicine*

This week's focus
"Candling Down", or adjusting your routine before bedtime for improved sleep.

The purpose of this exercise
The focus this week is to bring down your circadian rhythms to healthy levels in the evening hours. So, the focus this week is "candling down", and improving your process of getting ready for bed. This will help to optimize your sleep, which is great for accomplishing the REM sleep that can destress anxiety levels, which can improve ED symptoms.

Definitions

| | |
|---|---|
| Candling down | a term used by Dr. Lauryn Lax to describe the process of preparing for healthier sleep by adjusting the lighting in your environment. Light exposure can cause our biological clock to advance or delay, which affects our sleep and wake cycle. |
| Circadian Rhythm | your circadian rhythm is a 24-hour internal clock that is running in the background of your brain and cycles between sleepiness and alertness at regular intervals. It's also known as your sleep/wake cycle. |
| REM Sleep | REM sleep is the portion of sleep when there are rapid eye movements (REMs). Dreams occur during REM sleep. We typically have 3 to 5 periods of REM sleep per night. They occur at intervals of 1-2 hours and are quite variable in length. An episode of REM sleep may last 5 minutes or over an hour. Source: MedicineNet |

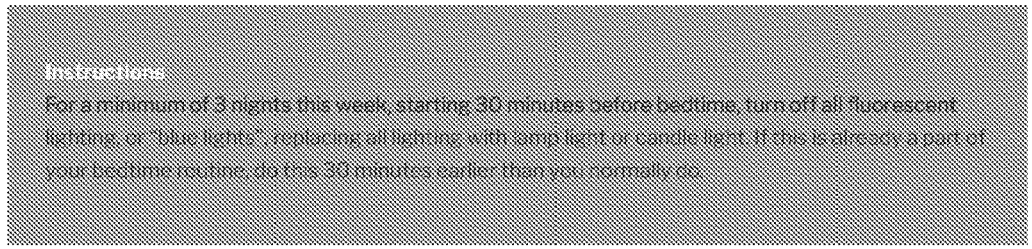

FIG. 30

Giddy™

Information • Instructions • Warnings

About your ED Device

Intended Use

This device is intended to be placed around the base of the penis for the duration of sexual intercourse, to restrict blood flow leaving the penis, to maintain sufficient penile rigidity for sexual intercourse. This product is intended for use by men ages 18+.

Manual Safety Release

Constriction from the device can be manually released by removing the tension band from the legs of the device, then widening the legs of the device, and removing the device from the penis with two hands.

Pliable Materials

Your device was designed to minimize the risk of injury to yourself and your partner when

FIG. 32 used as intended, by using soft, medical grade materials including polycarbonate coated in medical-grade proprietary thermoplastic elastomer (TPE). Your device was designed to be body-safe and is free of PVC, latex, and phthalates.

Shape & Surface Design

Your device features a smooth, oval-shaped design that conforms to the natural shape of the penis. There are special protrusions (dorsal apexes) on your device designed to provide pressure on the dorsal vein and arteries for assisting with achieving and maintaining erections. Your device also features small protrusions (enhancement ridges) designed to provide added stimulation for female partners.

FIG. 33

Instructions for Use

*Important: Read these instructions before using your device*

Please refer to Giddy's sizing questionnaire, the "Fit Quiz", to determine the appropriate sizing for your device. Please note that improper use of the Fit Quiz can result in the improper sizing of your device, which can increase the risk of damage, injury, or lessened effect of the device. Please contact support at yeehaw@getmegiddy.com for assistance.

1. Place the device at the base of the shaft of your penis, in front of the testicles, with the opening facing down. The device is reversible; your penis can be inserted into either side.

FIG. 34

2. Once your device is around the base of your penis, apply one of the variable-strength tension bands.

3. The device can be applied safely through any stage of an erection; from flaccid to erect.

FIG. 35

Instructions for Use
*See illustrations below*
1. 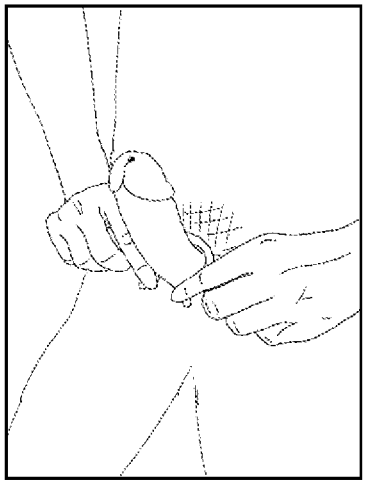
2. 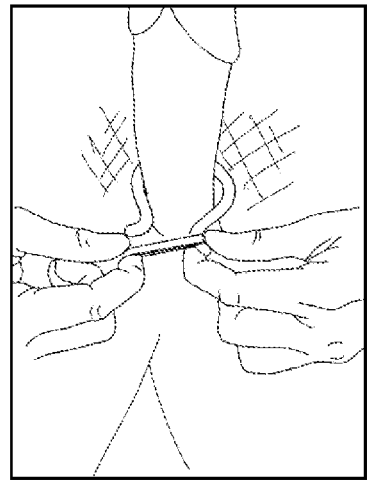
3. 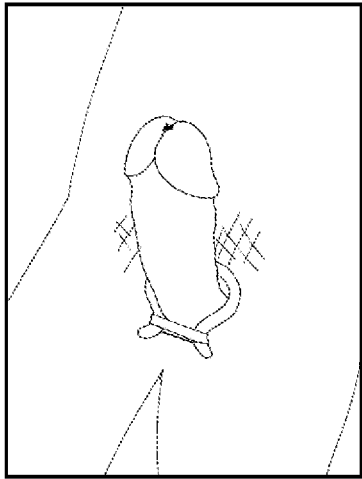
FIG. 36

System Overview
*Diagram of major components*

How to Clean Your ED Device

*Follow all instructions for cleaning, storing, and transporting your device between uses.* Rinse the device with warm water. Then lather it with a non-abrasive, anti-bacterial soap. Avoid using bleach, chlorine, or any chemicals that could irritate the skin. Always take into account any allergies you or your partner may have while using and cleaning your device. Once lathered with soap and thoroughly washed with a washcloth or clean hands, rinse your device again. Dry the device using a paper towel, a towel, or air-dry. Once dry, we recommend storing and transporting the device in your carrying case. It is recommended to replace your device every 6 months depending on your frequency of use.

FIG. 38

How to Clean Your ED Device
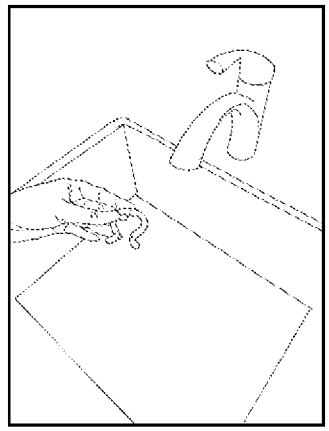
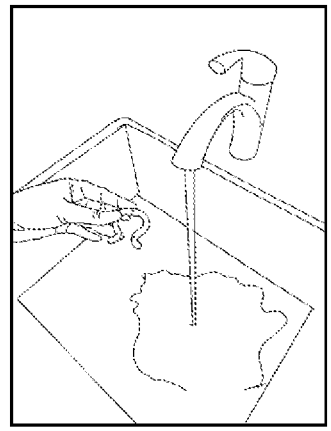
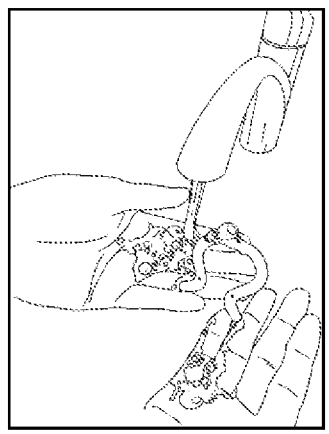
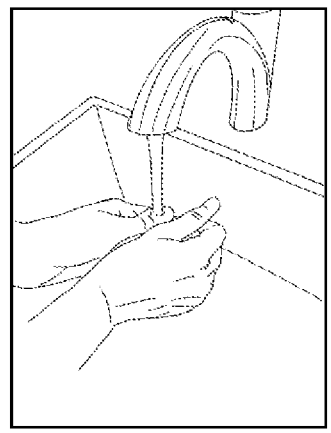
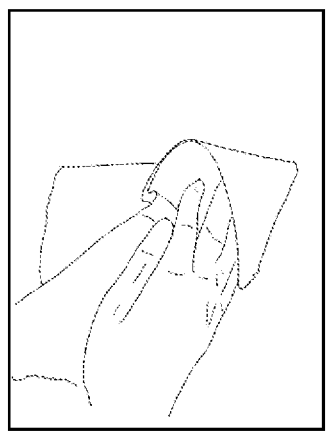
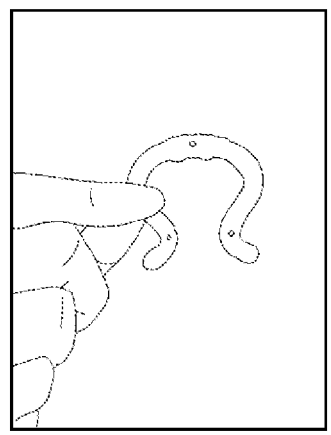
FIG. 39

Warnings

Consult a physician if any complications occur.

Discontinue use of the device if complications continue.

When using lubricants with the device, use water-based, oil-based, or silicone-based lubricants only.

FIG. 40

Delayed Diagnosis of Other Conditions

If you have symptoms of erectile dysfunction (the inability to achieve an erection that is sufficient for sexual intercourse), consult your physician prior to using this device to avoid a potentially harmful delay in diagnosing any of the most common causes of this condition, such as diabetes, multiple sclerosis, cirrhosis of the liver, chronic renal failure, or alcoholism.

Use with Impaired Pain Perception

Do not use this device if you have decreased sensation of pain in the area of the penis, to avoid accidental injury as a result of lack of sensation.

FIG. 41

Use with Decreased Hand Strength

Do not use the device if you have decreased hand strength because this may make removal of the device difficult.

FIG. 42

FDA Warnings & Precautions about Constriction Devices

Do not fall asleep while wearing the device, since prolonged use may cause permanent injury to the penis.

Allow at least 60 minutes between uses, as more frequent use may increase the risk of injury to the penis.

Do not use the device under the influence of alcohol or drugs, since such use may impair your judgment and increase the risk of injury to the penis.

Misuse of the device may cause bruising, painful injury, or permanent damage to the penis.

FIG. 43

Use of the device may aggravate already existing medical conditions such as Peyronie's disease (the formation of hardened tissue in the penis that causes pain, curvature, and distortion, usually during erection); priapism (persistent, usually painful erection of the penis as a consequence of disease and not related to sexual arousal); and urethral strictures (urethral stricture is an area of hardened tissue, which narrows the urethra sometimes making it difficult to urinate).

*Limit use of the device to no longer than 30 minutes per use.*

*Prolonged use of the device (i.e., without removal) may cause permanent injury to the penis.*

FIG. 44

Device use may bruise or rupture the blood vessels within the penis or scrotum, resulting in petechiae (a small purplish spot on a body surface, such as the skin or a mucous membrane, caused by a minute hemorrhage), hemorrhage (flow of blood from ruptured blood vessels), or the formation of a hematoma (localized swelling filled with blood resulting from a break in a blood vessel).

Use the least constrictive device size that maintains an erection, since excessive constriction could injure the penis. See previous section regarding the Fit Quiz.

Alternative treatment methods for erectile dysfunction include counseling, drug therapy, hormonal therapy, vascular surgery, and implanted prosthetic devices.

FIG. 45

Contact your physician for more information regarding these alternative treatments.

It is not recommended to use the same device with multiple partners if one partner is diagnosed with a Sexually Transmitted Infection or other contagious medical condition.

This device does not prevent pregnancy.

This device does not protect against sexually transmitted infections.

FIG. 46

SYSTEMS, METHODS, AND DEVICES FOR ALLEVIATING ERECTILE DYSFUNCTION

CROSS-REFERENCE

This application claims the benefit of U.S. Provisional Application No. 62/846,572, filed May 10, 2019, and U.S. Provisional Application No. 62/933,930, filed Nov. 11, 2019 which are hereby incorporated by reference in its entirety herein.

BACKGROUND OF THE INVENTION

Erectile dysfunction (ED), also known as impotence, is a type of sexual dysfunction characterized by the inability to develop or maintain an erection of the penis sufficient for sexual activity. Erectile dysfunction may have psychological consequences as it can be tied to relationship difficulties and self-image.

Some studies regarding erectile dysfunction have reported an average prevalence of 52%, which tends to increase with age. Some studies have further shown that approximately 40% and 70% of 40-year-old men and 70-year-old men are affected, respectively, whereby age is the variable most strongly associated with ED. ED has been further shown to increase with stress.

SUMMARY OF THE INVENTION

The present invention generally relates to medical devices, systems, and methods, and more particularly relates to devices, systems, and methods related to alleviating erectile dysfunction.

Erection is generally enabled in men through, in part, increased blood flow into the penis through arteries on the ventral side of the penis and decreased blood flow out from the penis through the veins on the dorsal side of the penis. Currently available ED devices attempt to alleviate ED in one of two ways—each with their own deficiencies.

The first type of ED device is rigid (e.g., made of metal, wood, glass, etc.). As the penis is shaped like an oval (wider than it is tall) and these devices are based on a circle, trying to fit an oval in a circle results in additional pressure being put on the sides in an effort to achieve minimal pressure on the top. This additional pressure on the side of the penis creates a distortion of the penis and an encumbrance of the arteries and corpora cavernosa. This works against the natural physiology of an erection. This pressure from rigid devices may be detrimental to the health of the tissue, arteries, and veins in the penis. Additionally, this pressure may hinder the ability of the user to employ Kegel exercises or other activities to their maximum effectiveness to increase inward blood flow and maintain the erection. Further, this uniform pressure may also limit natural inward blood flow into the penis, limiting the erection. Moreover, these rigid ED devices are less effective on a flaccid penis or an individual with severe ED, making these devices not ideal for initiating an erection. The second type of ED device is typically soft and malleable. However, these softer ED devices are ineffective in providing the appropriate constriction to either initiate or maintain a sufficient erection. These devices typically apply uniform pressure around the circumference of the penis to slow the outwards blood flow from the penis. However, the uniform pressure from these devices may be detrimental to the health of the tissue, arteries, and veins in the penis. Additionally, this uniform pressure may hinder the ability for the user to employ Kegel exercises or other activities to their maximum effectiveness to increase inward blood flow and maintain the erection. Further, this uniform pressure may also limit natural inward blood flow into the penis, limiting the erection.

In addition, currently available ED device configurations do not account for the particular shape (e.g., the devices are shaped like a perfect circle) or the specific anatomical regions and characteristics therein (e.g., location, size, and function of the superficial and deep dorsal veins, dorsal arteries, dorsal nerves, cavernous arteries, urethra, and corpus spongiosum) of the penis, which is not shaped like a circle. Nor do currently available ED devices provide adequate features on the exterior of the device to directly stimulate the partner's sexual experience, which may have negative psychological impact on the user and exacerbate any ED issues. Finally, none of the currently available ED devices offer instructions or guidance on selecting the properly sized device for the specific user.

Provided herein are ED methods, devices, and systems configured to more effectively prevent outwards blood flow from the penis to the body. Further provided herein are methods, devices, and systems that more effectively promote inward blood flow into the penis. Further provided herein are methods, devices, and systems that aid initiation and maintenance of an erection. Further provided herein are methods, devices, and systems that more directly and effectively stimulate the partner's sexual experience. Further provided herein are methods, devices, and systems that are configured to reduce physical ED symptoms and/or eliminate ED exacerbating performance stress.

A first aspect provided herein are penile constriction devices comprising an arched rod comprising: a first arm comprising a first coupling end and a first converging end having a first terminus; a second arm comprising a second coupling end and a second converging end having a second terminus disconnected from the first terminus, wherein the first converging end and the second converging end converge to form a constriction region; and a bridge connecting the first coupling end to the second coupling end, the bridge comprising a compression region rising inferiorly from an inferior side of the bridge.

Optionally, in this or any other embodiment, the device has a constriction gap width, wherein the constriction gap width is measured as a minimum distance between the first converging end and the second converging end within the constriction region. Optionally, in this or any other embodiment, the device has a constriction gap width of about 0 inches to about 1.25 inches. Optionally, in this or any other embodiment, the device has a constriction gap width of at least about 0 inches. Optionally, in this or any other embodiment, the device has a constriction gap width of at most about 1.25 inches. Optionally, in this or any other embodiment, the device has a constriction gap width of about 0 inches to about 0.125 inches, about 0 inches to about 0.375 inches, about 0 inches to about 0.5 inches, about 0 inches to about 0.625 inches, about 0 inches to about 0.75 inches, about 0 inches to about 0.875 inches, about 0 inches to about 1 inch, about 0 inches to about 1.125 inches, about 0 inches to about 1.25 inches, about 0.125 inches to about 0.375 inches, about 0.125 inches to about 0.5 inches, about 0.125 inches to about 0.625 inches, about 0.125 inches to about 0.75 inches, about 0.125 inches to about 0.875 inches, about 0.125 inches to about 1 inch, about 0.125 inches to about 1.125 inches, about 0.125 inches to about 1.25 inches, about 0.375 inches to about 0.5 inches, about 0.375 inches to about 0.625 inches, about 0.375 inches to about 0.75 inches, about 0.375 inches to about 0.875 inches, about 0.375 inches to about 1 inch, about 0.375 inches to about 1.125 inches, about 0.375 inches to about 1.25 inches, about 0.5 inches to about 0.625 inches, about 0.5 inches to about 0.75 inches, about 0.5 inches to about 0.875 inches, about 0.5 inches to about 1 inch, about 0.5 inches to about 1.125 inches, about 0.5 inches to about 1.25 inches, about 0.625 inches to about 0.75 inches, about 0.625 inches to about 0.875 inches, about 0.625 inches to about 1 inch, about 0.625 inches to about 1.125 inches, about 0.625 inches to about 1.25 inches, about 0.75 inches to about 0.875 inches, about 0.75 inches to about 1 inch, about 0.75 inches to about 1.125 inches, about 0.75 inches to about 1.25 inches, about 0.875 inches to about 1 inch, about 0.875 inches to about 1.125 inches, about 0.875 inches to about 1.25 inches, about 1 inch to about 1.125 inches, about 1 inch to about 1.25 inches, or about 1.125 inches to about 1.25 inches. Optionally, in this or any other embodiment, the device has a constriction gap width of about 0 inches, about 0.125 inches, about 0.375 inches, about 0.5 inches, about 0.625 inches, about 0.75 inches, about 0.875 inches, about 1 inch, about 1.125 inches, or about 1.25 inches. Optionally, in this or any other embodiment, the device has a constriction gap width of at least about 0 inches, about 0.125 inches, about 0.375 inches, about 0.5 inches, about 0.625 inches, about 0.75 inches, about 0.875 inches, about 1 inch, about 1.125 inches, or about 1.25 inches. Optionally, in this or any other embodiment, the device has a constriction gap width of at most about 0.125 inches, about 0.375 inches, about 0.5 inches, about 0.625 inches, about 0.75 inches, about 0.875 inches, about 1 inch, about 1.125 inches, or about 1.25 inches.

Optionally, in this or any other embodiment, the device has a constriction height, wherein the constriction height is measured as a normal distance between a constriction point and the inferior side of the bridge, and wherein the constriction point is defined as the midpoint of the constriction gap width. Optionally, in this or any other embodiment, the device has a constriction height of about 0.5 inches to about 2.5 inches. Optionally, in this or any other embodiment, the device has a constriction height of at least about 0.5 inches. Optionally, in this or any other embodiment, the device has a constriction height of at most about 2.5 inches. Optionally, in this or any other embodiment, the device has a constriction height of about 0.5 inches to about 0.75 inches, about 0.5 inches to about 1 inch, about 0.5 inches to about 1.25 inches, about 0.5 inches to about 1.5 inches, about 0.5 inches to about 1.75 inches, about 0.5 inches to about 2 inches, about 0.5 inches to about 2.25 inches, about 0.5 inches to about 2.5 inches, about 0.75 inches to about 1 inch, about 0.75 inches to about 1.25 inches, about 0.75 inches to about 1.5 inches, about 0.75 inches to about 1.75 inches, about 0.75 inches to about 2 inches, about 0.75 inches to about 2.25 inches, about 0.75 inches to about 2.5 inches, about 1 inch to about 1.25 inches, about 1 inch to about 1.5 inches, about 1 inch to about 1.75 inches, about 1 inch to about 2 inches, about 1 inch to about 2.25 inches, about 1 inch to about 2.5 inches, about 1.25 inches to about 1.5 inches, about 1.25 inches to about 1.75 inches, about 1.25 inches to about 2 inches, about 1.25 inches to about 2.25 inches, about 1.25 inches to about 2.5 inches, about 1.5 inches to about 1.75 inches, about 1.5 inches to about 2 inches, about 1.5 inches to about 2.25 inches, about 1.5 inches to about 2.5 inches, about 1.75 inches to about 2 inches, about 1.75 inches to about 2.25 inches, about 1.75 inches to about 2.5 inches, about 2 inches to about 2.25 inches, about 2 inches to about 2.5 inches, or about 2.25 inches to about 2.5 inches. Optionally, in this or any other embodiment, the device has a constriction height of about 0.5 inches, about 0.75 inches, about 1 inch, about 1.25 inches, about 1.5 inches, about 1.75 inches, about 2 inches, about 2.25 inches, or about 2.5 inches. Optionally, in this or any other embodiment, the device has a constriction height of at least about 0.5 inches, about 0.75 inches, about 1 inch, about 1.25 inches, about 1.5 inches, about 1.75 inches, about 2 inches, about 2.25 inches, or about 2.5 inches. Optionally, in this or any other embodiment, the device has a constriction height of at most about 0.5 inches, about 0.75 inches, about 1 inch, about 1.25 inches, about 1.5 inches, about 1.75 inches, about 2 inches, about 2.25 inches, or about 2.5 inches.

Optionally, in this or any other embodiment, the device has a maximum inner width, wherein the maximum inner width is measured as a maximum normal distance between a mesial vertex of the surface of the first arm and a mesial vertex of the surface of the second arm, and wherein the maximum inner width is superior to the constriction gap. Optionally, in this or any other embodiment, the device has a maximum inner width of about 0.5 inches to about 3 inches. Optionally, in this or any other embodiment, the device has a maximum inner width of at least about 0.5 inches. Optionally, in this or any other embodiment, the device has a maximum inner width of at most about 3 inches. Optionally, in this or any other embodiment, the device has a maximum inner width of about 0.5 inches to about 0.75 inches, about 0.5 inches to about 1 inch, about 0.5 inches to about 1.25 inches, about 0.5 inches to about 1.5 inches, about 0.5 inches to about 1.75 inches, about 0.5 inches to about 2 inches, about 0.5 inches to about 2.25 inches, about 0.5 inches to about 2.5 inches, about 0.5 inches to about 2.75 inches, about 0.5 inches to about 3 inches, about 0.75 inches to about 1 inch, about 0.75 inches to about 1.25 inches, about 0.75 inches to about 1.5 inches, about 0.75 inches to about 1.75 inches, about 0.75 inches to about 2 inches, about 0.75 inches to about 2.25 inches, about 0.75 inches to about 2.5 inches, about 0.75 inches to about 2.75 inches, about 0.75 inches to about 3 inches, about 1 inch to about 1.25 inches, about 1 inch to about 1.5 inches, about 1 inch to about 1.75 inches, about 1 inch to about 2 inches, about 1 inch to about 2.25 inches, about 1 inch to about 2.5 inches, about 1 inch to about 2.75 inches, about 1 inch to about 3 inches, about 1.25 inches to about 1.5 inches, about 1.25 inches to about 1.75 inches, about 1.25 inches to about 2 inches, about 1.25 inches to about 2.25 inches, about 1.25 inches to about 2.5 inches, about 1.25 inches to about 2.75 inches, about 1.25 inches to about 3 inches, about 1.5 inches to about 1.75 inches, about 1.5 inches to about 2 inches, about 1.5 inches to about 2.25 inches, about 1.5 inches to about 2.5 inches, about 1.5 inches to about 2.75 inches, about 1.5 inches to about 3 inches, about 1.75 inches to about 2 inches, about 1.75 inches to about 2.25 inches, about 1.75 inches to about 2.5 inches, about 1.75 inches to about 2.75 inches, about 1.75 inches to about 3 inches, about 2 inches to about 2.25 inches, about 2 inches to about 2.5 inches, about 2 inches to about 2.75 inches, about 2 inches to about 3 inches, about 2.25 inches to about 2.5 inches, about 2.25 inches to about 2.75 inches, about 2.25 inches to about 3 inches, about 2.5 inches to about 2.75 inches, about 2.5 inches to about 3 inches, or about 2.75 inches to about 3 inches. Optionally, in this or any other embodiment, the device has a maximum inner width of about 0.5 inches, about 0.75 inches, about 1 inch, about 1.25 inches, about 1.5 inches, about 1.75 inches, about 2 inches, about 2.25 inches, about 2.5 inches, about 2.75 inches, or about 3 inches. Optionally, in this or any other embodiment, the device has a maximum inner width of at least about 0.5 inches, about 0.75 inches, about 1 inch, about 1.25 inches, about 1.5 inches, about 1.75 inches, about 2 inches, about 2.25 inches, about 2.5 inches, about 2.75 inches, or about 3 inches. Optionally, in this or any other embodiment, the device has a maximum inner width of at most about 0.5 inches, about 0.75 inches, about 1 inch, about 1.25 inches, about 1.5 inches, about 1.75 inches, about 2 inches, about 2.25 inches, about 2.5 inches, about 2.75 inches, or about 3 inches.

Optionally, in this or any other embodiment, the device has an inferior height, wherein the inferior height is measured as a normal distance between a center point, and the inferior side of the bridge, wherein the center point comprises the midpoint of the maximum inner width. Optionally, in this or any other embodiment, the device has an inferior height of about 0.25 inches to about 1 inch. Optionally, in this or any other embodiment, the device has an inferior height of at least about 0.25 inches. Optionally, in this or any other embodiment, the device has an inferior height of at most about 1 inch. Optionally, in this or any other embodiment, the device has an inferior height of about 0.25 inches to about 0.3 inches, about 0.25 inches to about 0.35 inches, about 0.25 inches to about 0.4 inches, about 0.25 inches to about 0.45 inches, about 0.25 inches to about 0.5 inches, about 0.25 inches to about 0.6 inches, about 0.25 inches to about 0.7 inches, about 0.25 inches to about 0.8 inches, about 0.25 inches to about 0.9 inches, about 0.25 inches to about 1 inch, about 0.3 inches to about 0.35 inches, about 0.3 inches to about 0.4 inches, about 0.3 inches to about 0.45 inches, about 0.3 inches to about 0.5 inches, about 0.3 inches to about 0.6 inches, about 0.3 inches to about 0.7 inches, about 0.3 inches to about 0.8 inches, about 0.3 inches to about 0.9 inches, about 0.3 inches to about 1 inch, about 0.35 inches to about 0.4 inches, about 0.35 inches to about 0.45 inches, about 0.35 inches to about 0.5 inches, about 0.35 inches to about 0.6 inches, about 0.35 inches to about 0.7 inches, about 0.35 inches to about 0.8 inches, about 0.35 inches to about 0.9 inches, about 0.35 inches to about 1 inch, about 0.4 inches to about 0.45 inches, about 0.4 inches to about 0.5 inches, about 0.4 inches to about 0.6 inches, about 0.4 inches to about 0.7 inches, about 0.4 inches to about 0.8 inches, about 0.4 inches to about 0.9 inches, about 0.4 inches to about 1 inch, about 0.45 inches to about 0.5 inches, about 0.45 inches to about 0.6 inches, about 0.45 inches to about 0.7 inches, about 0.45 inches to about 0.8 inches, about 0.45 inches to about 0.9 inches, about 0.45 inches to about 1 inch, about 0.5 inches to about 0.6 inches, about 0.5 inches to about 0.7 inches, about 0.5 inches to about 0.8 inches, about 0.5 inches to about 0.9 inches, about 0.5 inches to about 1 inch, about 0.6 inches to about 0.7 inches, about 0.6 inches to about 0.8 inches, about 0.6 inches to about 0.9 inches, about 0.6 inches to about 1 inch, about 0.7 inches to about 0.8 inches, about 0.7 inches to about 0.9 inches, about 0.7 inches to about 1 inch, about 0.8 inches to about 0.9 inches, about 0.8 inches to about 1 inch, or about 0.9 inches to about 1 inch. Optionally, in this or any other embodiment, the device has an inferior height of about 0.25 inches, about 0.3 inches, about 0.35 inches, about 0.4 inches, about 0.45 inches, about 0.5 inches, about 0.6 inches, about 0.7 inches, about 0.8 inches, about 0.9 inches, or about 1 inch. Optionally, in this or any other embodiment, the device has an inferior height of at least about 0.25 inches, about 0.3 inches, about 0.35 inches, about 0.4 inches, about 0.45 inches, about 0.5 inches, about 0.6 inches, about 0.7 inches, about 0.8 inches, about 0.9 inches, or about 1 inch. Optionally, in this or any other embodiment, the device has an inferior height of at most about 0.25 inches, about 0.3 inches, about 0.35 inches, about 0.4 inches, about 0.45 inches, about 0.5 inches, about 0.6 inches, about 0.7 inches, about 0.8 inches, about 0.9 inches, or about 1 inch.

Optionally, in this or any other embodiment, a ratio between the constriction gap width and the maximum inner width is about 0.3:1 to about 0.9:1. Optionally, in this or any other embodiment, a ratio between the constriction gap width and the maximum inner width is at least about 0.2:1. Optionally, in this or any other embodiment, a ratio between the constriction gap width and the maximum inner width is at most about 0.9:1. Optionally, in this or any other embodiment, a ratio between the constriction gap width and the maximum inner width is about 0.2:1 to about 0.25:1, about 0.2:1 to about 0.3:1, about 0.2:1 to about 0.35:1, about 0.2:1 to about 0.4:1, about 0.2:1 to about 0.5:1, about 0.2:1 to about 0.6:1, about 0.2:1 to about 0.7:1, about 0.2:1 to about 0.8:1, about 0.2:1 to about 0.9:1, about 0.25:1 to about 0.3:1, about 0.25:1 to about 0.35:1, about 0.25:1 to about 0.4:1, about 0.25:1 to about 0.5:1, about 0.25:1 to about 0.6:1, about 0.25:1 to about 0.7:1, about 0.25:1 to about 0.8:1, about 0.25:1 to about 0.9:1, about 0.3:1 to about 0.35:1, about 0.3:1 to about 0.4:1, about 0.3:1 to about 0.5:1, about 0.3:1 to about 0.6:1, about 0.3:1 to about 0.7:1, about 0.3:1 to about 0.8:1, about 0.3:1 to about 0.9:1, about 0.35:1 to about 0.4:1, about 0.35:1 to about 0.5:1, about 0.35:1 to about 0.6:1, about 0.35:1 to about 0.7:1, about 0.35:1 to about 0.8:1, about 0.35:1 to about 0.9:1, about 0.4:1 to about 0.5:1, about 0.4:1 to about 0.6:1, about 0.4:1 to about 0.7:1, about 0.4:1 to about 0.8:1, about 0.4:1 to about 0.9:1, about 0.5:1 to about 0.6:1, about 0.5:1 to about 0.7:1, about 0.5:1 to about 0.8:1, about 0.5:1 to about 0.9:1, about 0.6:1 to about 0.7:1, about 0.6:1 to about 0.8:1, about 0.6:1 to about 0.9:1, about 0.7:1 to about 0.8:1, about 0.7:1 to about 0.9:1, or about 0.8:1 to about 0.9:1. Optionally, in this or any other embodiment, a ratio between the constriction gap width and the maximum inner width is about 0.2:1, about 0.25:1, about 0.3:1, about 0.35:1, about 0.4:1, about 0.5:1, about 0.6:1, about 0.7:1, about 0.8:1, or about 0.9:1. Optionally, in this or any other embodiment, a ratio between the constriction gap width and the maximum inner width is at least about 0.2:1, about 0.25:1, about 0.3:1, about 0.35:1, about 0.4:1, about 0.5:1, about 0.6:1, about 0.7:1, about 0.8:1, or about 0.9:1. Optionally, in this or any other embodiment, a ratio between the constriction gap width and the maximum inner width is at most about 0.2:1, about 0.25:1, about 0.3:1, about 0.35:1, about 0.4:1, about 0.5:1, about 0.6:1, about 0.7:1, about 0.8:1, or about 0.9:1.

Optionally, in this or any other embodiment, a ratio between the constriction height and the maximum inner width is about 0.7:1 to about 0.99:1. Optionally, in this or any other embodiment, a ratio between the constriction height and the maximum inner width is at least about 0.7:1. Optionally, in this or any other embodiment, a ratio between the constriction height and the maximum inner width is at most about 0.99:1. Optionally, in this or any other embodiment, a ratio between the constriction height and the maximum inner width is about 0.7:1 to about 0.725:1, about 0.7:1 to about 0.75:1, about 0.7:1 to about 0.775:1, about 0.7:1 to about 0.8:1, about 0.7:1 to about 0.825:1, about 0.7:1 to about 0.85:1, about 0.7:1 to about 0.875:1, about 0.7:1 to about 0.9:1, about 0.7:1 to about 0.925:1, about 0.7:1 to about 0.95:1, about 0.7:1 to about 0.99:1, about 0.725:1 to about 0.75:1, about 0.725:1 to about 0.775:1, about 0.725:1 to about 0.8:1, about 0.725:1 to about 0.825:1, about 0.725:1 to about 0.85:1, about 0.725:1 to about 0.875:1, about 0.725:1 to about 0.9:1, about 0.725:1 to about 0.925:1, about 0.725:1 to about 0.95:1, about 0.725:1 to about 0.99:1, about 0.75:1 to about 0.775:1, about 0.75:1 to about 0.8:1, about 0.75:1 to about 0.825:1, about 0.75:1 to about 0.85:1, about 0.75:1 to about 0.875:1, about 0.75:1 to about 0.9:1, about 0.75:1 to about 0.925:1, about 0.75:1 to about 0.95:1, about 0.75:1 to about 0.99:1, about 0.775:1 to about 0.8:1, about 0.775:1 to about 0.825:1, about 0.775:1 to about 0.85:1, about 0.775:1 to about 0.875:1, about 0.775:1 to about 0.9:1, about 0.775:1 to about 0.925:1, about 0.775:1 to about 0.95:1, about 0.775:1 to about 0.99:1, about 0.8:1 to about 0.825:1, about 0.8:1 to about 0.85:1, about 0.8:1 to about 0.875:1, about 0.8:1 to about 0.9:1, about 0.8:1 to about 0.925:1, about 0.8:1 to about 0.95:1, about 0.8:1 to about 0.99:1, about 0.825:1 to about 0.85:1, about 0.825:1 to about 0.875:1, about 0.825:1 to about 0.9:1, about 0.825:1 to about 0.925:1, about 0.825:1 to about 0.95:1, about 0.825:1 to about 0.99:1, about 0.85:1 to about 0.875:1, about 0.85:1 to about 0.9:1, about 0.85:1 to about 0.925:1, about 0.85:1 to about 0.95:1, about 0.85:1 to about 0.99:1, about 0.875:1 to about 0.9:1, about 0.875:1 to about 0.925:1, about 0.875:1 to about 0.95:1, about 0.875:1 to about 0.99:1, about 0.9:1 to about 0.925:1, about 0.9:1 to about 0.95:1, about 0.9:1 to about 0.99:1, about 0.925:1 to about 0.95:1, about 0.925:1 to about 0.99:1, or about 0.95:1 to about 0.99:1. Optionally, in this or any other embodiment, a ratio between the constriction height and the maximum inner width is about 0.7:1, about 0.725:1, about 0.75:1, about 0.775:1, about 0.8:1, about 0.825:1, about 0.85:1, about 0.875:1, about 0.9:1, about 0.925:1, about 0.95:1, or about 0.99:1. Optionally, in this or any other embodiment, a ratio between the constriction height and the maximum inner width is at least about 0.7:1, about 0.725:1, about 0.75:1, about 0.775:1, about 0.8:1, about 0.825:1, about 0.85:1, about 0.875:1, about 0.9:1, about 0.925:1, about 0.95:1, or about 0.99:1. Optionally, in this or any other embodiment, a ratio between the constriction height and the maximum inner width is at most about 0.7:1, about 0.725:1, about 0.75:1, about 0.775:1, about 0.8:1, about 0.825:1, about 0.85:1, about 0.875:1, about 0.9:1, about 0.925:1, about 0.95:1, or about 0.99:1.

Optionally, in this or any other embodiment, a ratio between the inferior height and the maximum inner width is about 0.15:1 to about 0.6:1. Optionally, in this or any other embodiment, a ratio between the inferior height and the maximum inner width is at least about 0.15:1. Optionally, in this or any other embodiment, a ratio between the inferior height and the maximum inner width is at most about 0.6:1. Optionally, in this or any other embodiment, a ratio between the inferior height and the maximum inner width is about 0.15:1 to about 0.2:1, about 0.15:1 to about 0.25:1, about 0.15:1 to about 0.3:1, about 0.15:1 to about 0.35:1, about 0.15:1 to about 0.4:1, about 0.15:1 to about 0.45:1, about 0.15:1 to about 0.5:1, about 0.15:1 to about 0.55:1, about 0.15:1 to about 0.6:1, about 0.2:1 to about 0.25:1, about 0.2:1 to about 0.3:1, about 0.2:1 to about 0.35:1, about 0.2:1 to about 0.4:1, about 0.2:1 to about 0.45:1, about 0.2:1 to about 0.5:1, about 0.2:1 to about 0.55:1, about 0.2:1 to about 0.6:1, about 0.25:1 to about 0.3:1, about 0.25:1 to about 0.35:1, about 0.25:1 to about 0.4:1, about 0.25:1 to about 0.45:1, about 0.25:1 to about 0.5:1, about 0.25:1 to about 0.55:1, about 0.25:1 to about 0.6:1, about 0.3:1 to about 0.35:1, about 0.3:1 to about 0.4:1, about 0.3:1 to about 0.45:1, about 0.3:1 to about 0.5:1, about 0.3:1 to about 0.55:1, about 0.3:1 to about 0.6:1, about 0.35:1 to about 0.4:1, about 0.35:1 to about 0.45:1, about 0.35:1 to about 0.5:1, about 0.35:1 to about 0.55:1, about 0.35:1 to about 0.6:1, about 0.4:1 to about 0.45:1, about 0.4:1 to about 0.5:1, about 0.4:1 to about 0.55:1, about 0.4:1 to about 0.6:1, about 0.45:1 to about 0.5:1, about 0.45:1 to about 0.55:1, about 0.45:1 to about 0.6:1, about 0.5:1 to about 0.55:1, about 0.5:1 to about 0.6:1, or about 0.55:1 to about 0.6:1. Optionally, in this or any other embodiment, a ratio between the inferior height and the maximum inner width is about 0.15:1, about 0.2:1, about 0.25:1, about 0.3:1, about 0.35:1, about 0.4:1, about 0.45:1, about 0.5:1, about 0.55:1, or about 0.6:1. Optionally, in this or any other embodiment, a ratio between the inferior height and the maximum inner width is at least about 0.15:1, about 0.2:1, about 0.25:1, about 0.3:1, about 0.35:1, about 0.4:1, about 0.45:1, about 0.5:1, about 0.55:1, or about 0.6:1. Optionally, in this or any other embodiment, a ratio between the inferior height and the maximum inner width is at most about 0.15:1, about 0.2:1, about 0.25:1, about 0.3:1, about 0.35:1, about 0.4:1, about 0.45:1, about 0.5:1, about 0.55:1, or about 0.6:1.

Optionally, in this or any other embodiment, the arched rod has a thickness, wherein the thickness is measured as a maximum normal cross-sectional width of at least a portion of at least one of the first arm, the second arm, and the bridge. Optionally, in this or any other embodiment, the device has a thickness of about 0.125 inches to about 0.8 inches. Optionally, in this or any other embodiment, the device has a thickness of at least about 0.125 inches. Optionally, in this or any other embodiment, the device has a thickness of at most about 0.8 inches. Optionally, in this or any other embodiment, the device has a thickness of about 0.125 inches to about 0.15 inches, about 0.125 inches to about 0.2 inches, about 0.125 inches to about 0.25 inches, about 0.125 inches to about 0.3 inches, about 0.125 inches to about 0.35 inches, about 0.125 inches to about 0.4 inches, about 0.125 inches to about 0.45 inches, about 0.125 inches to about 0.5 inches, about 0.125 inches to about 0.6 inches, about 0.125 inches to about 0.7 inches, about 0.125 inches to about 0.8 inches, about 0.15 inches to about 0.2 inches, about 0.15 inches to about 0.25 inches, about 0.15 inches to about 0.3 inches, about 0.15 inches to about 0.35 inches, about 0.15 inches to about 0.4 inches, about 0.15 inches to about 0.45 inches, about 0.15 inches to about 0.5 inches, about 0.15 inches to about 0.6 inches, about 0.15 inches to about 0.7 inches, about 0.15 inches to about 0.8 inches, about 0.2 inches to about 0.25 inches, about 0.2 inches to about 0.3 inches, about 0.2 inches to about 0.35 inches, about 0.2 inches to about 0.4 inches, about 0.2 inches to about 0.45 inches, about 0.2 inches to about 0.5 inches, about 0.2 inches to about 0.6 inches, about 0.2 inches to about 0.7 inches, about 0.2 inches to about 0.8 inches, about 0.25 inches to about 0.3 inches, about 0.25 inches to about 0.35 inches, about 0.25 inches to about 0.4 inches, about 0.25 inches to about 0.45 inches, about 0.25 inches to about 0.5 inches, about 0.25 inches to about 0.6 inches, about 0.25 inches to about 0.7 inches, about 0.25 inches to about 0.8 inches, about 0.3 inches to about 0.35 inches, about 0.3 inches to about 0.4 inches, about 0.3 inches to about 0.45 inches, about 0.3 inches to about 0.5 inches, about 0.3 inches to about 0.6 inches, about 0.3 inches to about 0.7 inches, about 0.3 inches to about 0.8 inches, about 0.35 inches to about 0.4 inches, about 0.35 inches to about 0.45 inches, about 0.35 inches to about 0.5 inches, about 0.35 inches to about 0.6 inches, about 0.35 inches to about 0.7 inches, about 0.35 inches to about 0.8 inches, about 0.4 inches to about 0.45 inches, about 0.4 inches to about 0.5 inches, about 0.4 inches to about 0.6 inches, about 0.4 inches to about 0.7 inches, about 0.4 inches to about 0.8 inches, about 0.45 inches to about 0.5 inches, about 0.45 inches to about 0.6 inches, about 0.45 inches to about 0.7 inches, about 0.45 inches to about 0.8 inches, about 0.5 inches to about 0.6 inches, about 0.5 inches to about 0.7 inches, about 0.5 inches to about 0.8 inches, about 0.6 inches to about 0.7 inches, about 0.6 inches to about 0.8 inches, or about 0.7 inches to about 0.8 inches. Optionally, in this or any other embodiment, the device has a thickness of about 0.125 inches, about 0.15 inches, about 0.2 inches, about 0.25 inches, about 0.3 inches, about 0.35 inches, about 0.4 inches, about 0.45 inches, about 0.5 inches, about 0.6 inches, about 0.7 inches, or about 0.8 inches. Optionally, in this or any other embodiment, the device has a thickness of at least about 0.125 inches, about 0.15 inches, about 0.2 inches, about 0.25 inches, about 0.3 inches, about 0.35 inches, about 0.4 inches, about 0.45 inches, about 0.5 inches, about 0.6 inches, about 0.7 inches, or about 0.8 inches. Optionally, in this or any other embodiment, the device has a thickness of at most about 0.125 inches, about 0.15 inches, about 0.2 inches, about 0.25 inches, about 0.3 inches, about 0.35 inches, about 0.4 inches, about 0.45 inches, about 0.5 inches, about 0.6 inches, about 0.7 inches, or about 0.8 inches.

Optionally, in this or any other embodiment, has a first termination distance and a second termination distance, wherein the first termination distance may be measured as the maximum normal distance between the constriction gap width and the first terminus, and wherein the second termination distance may be measured as the maximum normal distance between the constriction gap width and the second terminus. Optionally, in this or any other embodiment, at least one of the first termination distance and the second termination distance is about 0.02 inches to about 0.08 inches. Optionally, in this or any other embodiment, at least one of the first termination distance and the second termination distance is at least about 0.02 inches. Optionally, in this or any other embodiment, at least one of the first termination distance and the second termination distance is at most about 0.08 inches. Optionally, in this or any other embodiment, at least one of the first termination distance and the second termination distance is about 0.02 inches to about 0.025 inches, about 0.02 inches to about 0.03 inches, about 0.02 inches to about 0.035 inches, about 0.02 inches to about 0.04 inches, about 0.02 inches to about 0.045 inches, about 0.02 inches to about 0.05 inches, about 0.02 inches to about 0.055 inches, about 0.02 inches to about 0.06 inches, about 0.02 inches to about 0.07 inches, about 0.02 inches to about 0.08 inches, about 0.025 inches to about 0.03 inches, about 0.025 inches to about 0.035 inches, about 0.025 inches to about 0.04 inches, about 0.025 inches to about 0.045 inches, about 0.025 inches to about 0.05 inches, about 0.025 inches to about 0.055 inches, about 0.025 inches to about 0.06 inches, about 0.025 inches to about 0.07 inches, about 0.025 inches to about 0.08 inches, about 0.03 inches to about 0.035 inches, about 0.03 inches to about 0.04 inches, about 0.03 inches to about 0.045 inches, about 0.03 inches to about 0.05 inches, about 0.03 inches to about 0.055 inches, about 0.03 inches to about 0.06 inches, about 0.03 inches to about 0.07 inches, about 0.03 inches to about 0.08 inches, about 0.035 inches to about 0.04 inches, about 0.035 inches to about 0.045 inches, about 0.035 inches to about 0.05 inches, about 0.035 inches to about 0.055 inches, about 0.035 inches to about 0.06 inches, about 0.035 inches to about 0.07 inches, about 0.035 inches to about 0.08 inches, about 0.04 inches to about 0.045 inches, about 0.04 inches to about 0.05 inches, about 0.04 inches to about 0.055 inches, about 0.04 inches to about 0.06 inches, about 0.04 inches to about 0.07 inches, about 0.04 inches to about 0.08 inches, about 0.045 inches to about 0.05 inches, about 0.045 inches to about 0.055 inches, about 0.045 inches to about 0.06 inches, about 0.045 inches to about 0.07 inches, about 0.045 inches to about 0.08 inches, about 0.05 inches to about 0.055 inches, about 0.05 inches to about 0.06 inches, about 0.05 inches to about 0.07 inches, about 0.05 inches to about 0.08 inches, about 0.055 inches to about 0.06 inches, about 0.055 inches to about 0.07 inches, about 0.055 inches to about 0.08 inches, about 0.06 inches to about 0.07 inches, about 0.06 inches to about 0.08 inches, or about 0.07 inches to about 0.08 inches. Optionally, in this or any other embodiment, at least one of the first termination distance and the second termination distance is about 0.02 inches, about 0.025 inches, about 0.03 inches, about 0.035 inches, about 0.04 inches, about 0.045 inches, about 0.05 inches, about 0.055 inches, about 0.06 inches, about 0.07 inches, or about 0.08 inches. Optionally, in this or any other embodiment, at least one of the first termination distance and the second termination distance is at least about 0.02 inches, about 0.025 inches, about 0.03 inches, about 0.035 inches, about 0.04 inches, about 0.045 inches, about 0.05 inches, about 0.055 inches, about 0.06 inches, about 0.07 inches, or about 0.08 inches. Optionally, in this or any other embodiment, at least one of the first termination distance and the second termination distance is at most about 0.02 inches, about 0.025 inches, about 0.03 inches, about 0.035 inches, about 0.04 inches, about 0.045 inches, about 0.05 inches, about 0.055 inches, about 0.06 inches, about 0.07 inches, or about 0.08 inches.

Optionally, in this or any other embodiment, the first terminus diverges from the constriction region to form a first elbow. Optionally, in this or any other embodiment, the second terminus diverges from the constriction region to form a second elbow. Optionally, in this or any other embodiment, the first elbow and the second elbow are configured to removably affix to a band. Optionally, in this or any other embodiment, the first arm and the second arm are configured to removably affix to a band.

Optionally, in this or any other embodiment, the compression region comprises: a first dorsal vein protrusion comprising: a first dorsal apex; and a first dorsal height measured as a first minimum normal distance between the first dorsal apex and a first lateral edge of the first dorsal vein protrusion where the first dorsal vein protrusion rises from the inferior side of the bridge. Optionally, in this or any other embodiment, the compression region comprises a second dorsal vein protrusion comprising: a second dorsal apex; and a second dorsal height measured as a second minimum normal distance between the second dorsal apex and a second lateral edge of the second dorsal vein protrusion where the second dorsal vein protrusion rises from the inferior side of the bridge. Optionally, in this or any other embodiment, the compression region comprises: a dorsal vein valley between the first dorsal vein apex and the second dorsal vein apex.

Optionally, in this or any other embodiment, the first dorsal vein protrusion, the dorsal vein valley, and the second dorsal vein protrusion are arranged sequentially within the compression region in a direction along the bridge from the first arm to the second arm.

Optionally, in this or any other embodiment, the device comprises a dorsal vein valley distance between the first dorsal apex and the second dorsal apex. Optionally, in this or any other embodiment, the dorsal vein valley distance is about 0.15 inches to about 0.75 inches. Optionally, in this or any other embodiment, the dorsal vein valley distance is at least about 0.15 inches. Optionally, in this or any other embodiment, the dorsal vein valley distance is at most about 0.75 inches. Optionally, in this or any other embodiment, the dorsal vein valley distance is about 0.15 inches to about 0.2 inches, about 0.15 inches to about 0.25 inches, about 0.15 inches to about 0.3 inches, about 0.15 inches to about 0.35 inches, about 0.15 inches to about 0.4 inches, about 0.15 inches to about 0.45 inches, about 0.15 inches to about 0.5 inches, about 0.15 inches to about 0.55 inches, about 0.15 inches to about 0.6 inches, about 0.15 inches to about 0.65 inches, about 0.15 inches to about 0.75 inches, about 0.2 inches to about 0.25 inches, about 0.2 inches to about 0.3 inches, about 0.2 inches to about 0.35 inches, about 0.2 inches to about 0.4 inches, about 0.2 inches to about 0.45 inches, about 0.2 inches to about 0.5 inches, about 0.2 inches to about 0.55 inches, about 0.2 inches to about 0.6 inches, about 0.2 inches to about 0.65 inches, about 0.2 inches to about 0.75 inches, about 0.25 inches to about 0.3 inches, about 0.25 inches to about 0.35 inches, about 0.25 inches to about 0.4 inches, about 0.25 inches to about 0.45 inches, about 0.25 inches to about 0.5 inches, about 0.25 inches to about 0.55 inches, about 0.25 inches to about 0.6 inches, about 0.25 inches to about 0.65 inches, about 0.25 inches to about 0.75 inches, about 0.3 inches to about 0.35 inches, about 0.3 inches to about 0.4 inches, about 0.3 inches to about 0.45 inches, about 0.3 inches to about 0.5 inches, about 0.3 inches to about 0.55 inches, about 0.3 inches to about 0.6 inches, about 0.3 inches to about 0.65 inches, about 0.3 inches to about 0.75 inches, about 0.35 inches to about 0.4 inches, about 0.35 inches to about 0.45 inches, about 0.35 inches to about 0.5 inches, about 0.35 inches to about 0.55 inches, about 0.35 inches to about 0.6 inches, about 0.35 inches to about 0.65 inches, about 0.35 inches to about 0.75 inches, about 0.4 inches to about 0.45 inches, about 0.4 inches to about 0.5 inches, about 0.4 inches to about 0.55 inches, about 0.4 inches to about 0.6 inches, about 0.4 inches to about 0.65 inches, about 0.4 inches to about 0.75 inches, about 0.45 inches to about 0.5 inches, about 0.45 inches to about 0.55 inches, about 0.45 inches to about 0.6 inches, about 0.45 inches to about 0.65 inches, about 0.45 inches to about 0.75 inches, about 0.5 inches to about 0.55 inches, about 0.5 inches to about 0.6 inches, about 0.5 inches to about 0.65 inches, about 0.5 inches to about 0.75 inches, about 0.55 inches to about 0.6 inches, about 0.55 inches to about 0.65 inches, about 0.55 inches to about 0.75 inches, about 0.6 inches to about 0.65 inches, about 0.6 inches to about 0.75 inches, or about 0.65 inches to about 0.75 inches. Optionally, in this or any other embodiment, the dorsal vein valley distance is about 0.15 inches, about 0.2 inches, about 0.25 inches, about 0.3 inches, about 0.35 inches, about 0.4 inches, about 0.45 inches, about 0.5 inches, about 0.55 inches, about 0.6 inches, about 0.65 inches, or about 0.75 inches. Optionally, in this or any other embodiment, the dorsal vein valley distance is at least about 0.15 inches, about 0.2 inches, about 0.25 inches, about 0.3 inches, about 0.35 inches, about 0.4 inches, about 0.45 inches, about 0.5 inches, about 0.55 inches, about 0.6 inches, about 0.65 inches, or about 0.75 inches. Optionally, in this or any other embodiment, the dorsal vein valley distance is at most about 0.15 inches, about 0.2 inches, about 0.25 inches, about 0.3 inches, about 0.35 inches, about 0.4 inches, about 0.45 inches, about 0.5 inches, about 0.55 inches, about 0.6 inches, about 0.65 inches, or about 0.75 inches.

Optionally, in this or any other embodiment, the device comprises a compression region width between the first lateral edge and the second lateral edge. Optionally, in this or any other embodiment, the compression region width is about 0.2 inches to about 0.8 inches. Optionally, in this or any other embodiment, the compression region width is at least about 0.2 inches. Optionally, in this or any other embodiment, the compression region width is at most about 0.8 inches. Optionally, in this or any other embodiment, the compression region width is about 0.2 inches to about 0.25 inches, about 0.2 inches to about 0.3 inches, about 0.2 inches to about 0.35 inches, about 0.2 inches to about 0.4 inches, about 0.2 inches to about 0.45 inches, about 0.2 inches to about 0.5 inches, about 0.2 inches to about 0.55 inches, about 0.2 inches to about 0.6 inches, about 0.2 inches to about 0.7 inches, about 0.2 inches to about 0.8 inches, about 0.25 inches to about 0.3 inches, about 0.25 inches to about 0.35 inches, about 0.25 inches to about 0.4 inches, about 0.25 inches to about 0.45 inches, about 0.25 inches to about 0.5 inches, about 0.25 inches to about 0.55 inches, about 0.25 inches to about 0.6 inches, about 0.25 inches to about 0.7 inches, about 0.25 inches to about 0.8 inches, about 0.3 inches to about 0.35 inches, about 0.3 inches to about 0.4 inches, about 0.3 inches to about 0.45 inches, about 0.3 inches to about 0.5 inches, about 0.3 inches to about 0.55 inches, about 0.3 inches to about 0.6 inches, about 0.3 inches to about 0.7 inches, about 0.3 inches to about 0.8 inches, about 0.35 inches to about 0.4 inches, about 0.35 inches to about 0.45 inches, about 0.35 inches to about 0.5 inches, about 0.35 inches to about 0.55 inches, about 0.35 inches to about 0.6 inches, about 0.35 inches to about 0.7 inches, about 0.35 inches to about 0.8 inches, about 0.4 inches to about 0.5 inches, about 0.4 inches to about 0.55 inches, about 0.4 inches to about 0.6 inches, about 0.4 inches to about 0.7 inches, about 0.4 inches to about 0.8 inches, about 0.45 inches to about 0.5 inches, about 0.45 inches to about 0.55 inches, about 0.45 inches to about 0.6 inches, about 0.45 inches to about 0.7 inches, about 0.45 inches to about 0.8 inches, about 0.5 inches to about 0.55 inches, about 0.5 inches to about 0.6 inches, about 0.5 inches to about 0.7 inches, about 0.5 inches to about 0.8 inches, about 0.55 inches to about 0.6 inches, about 0.55 inches to about 0.7 inches, about 0.55 inches to about 0.8 inches, about 0.6 inches to about 0.7 inches, about 0.6 inches to about 0.8 inches, or about 0.7 inches to about 0.8 inches. Optionally, in this or any other embodiment, the compression region width is about 0.2 inches, about 0.25 inches, about 0.3 inches, about 0.35 inches, about 0.4 inches, about 0.45 inches, about 0.5 inches, about 0.55 inches, about 0.6 inches, about 0.7 inches, or about 0.8 inches. Optionally, in this or any other embodiment, the compression region width is at least about 0.2 inches, about 0.25 inches, about 0.3 inches, about 0.35 inches, about 0.4 inches, about 0.45 inches, about 0.5 inches, about 0.55 inches, about 0.6 inches, about 0.7 inches, or about 0.8 inches. Optionally, in this or any other embodiment, the compression region width is at most about 0.2 inches, about 0.25 inches, about 0.3 inches, about 0.35 inches, about 0.4 inches, about 0.45 inches, about 0.5 inches, about 0.55 inches, about 0.6 inches, about 0.7 inches, or about 0.8 inches.

Optionally, in this or any other embodiment, the compression region within the dorsal vein valley at a center of the dorsal vein valley is superior to or has a same height relative to the first lateral edge as the first minimum normal distance or relative to the second lateral edge as the second minimum normal distance, or both. Optionally, in this or any other embodiment, the compression region is superior to or has a same height relative to the first lateral edge as the first minimum normal distance or relative to the second lateral edge as the second minimum normal distance, or both. Optionally, in this or any other embodiment, the compression region at the center of the dorsal vein valley is inferior to the first lateral edge, the second lateral edge, or both. Optionally, in this or any other embodiment, the compression region is inferior to the first lateral edge, the second lateral edge, or both.

Optionally, in this or any other embodiment, the device further comprises a plurality of friction protrusions on a superior side of the bridge. Optionally, in this or any other embodiment, the plurality of friction protrusions comprises about 2 protrusions to about 60 protrusions. Optionally, in this or any other embodiment, the plurality of friction protrusions comprises at least about 2 protrusions. Optionally, in this or any other embodiment, the plurality of friction protrusions comprises at most about 60 protrusions. Optionally, in this or any other embodiment, the plurality of friction protrusions comprises about 2 protrusions to about 4 protrusions, about 2 protrusions to about 6 protrusions, about 2 protrusions to about 8 protrusions, about 2 protrusions to about 10 protrusions, about 2 protrusions to about 15 protrusions, about 2 protrusions to about 20 protrusions, about 2 protrusions to about 25 protrusions, about 2 protrusions to about 30 protrusions, about 2 protrusions to about 40 protrusions, about 2 protrusions to about 50 protrusions, about 2 protrusions to about 60 protrusions, about 4 protrusions to about 6 protrusions, about 4 protrusions to about 8 protrusions, about 4 protrusions to about 10 protrusions, about 4 protrusions to about 15 protrusions, about 4 protrusions to about 20 protrusions, about 4 protrusions to about 25 protrusions, about 4 protrusions to about 30 protrusions, about 4 protrusions to about 40 protrusions, about 4 protrusions to about 50 protrusions, about 4 protrusions to about 60 protrusions, about 6 protrusions to about 8 protrusions, about 6 protrusions to about 10 protrusions, about 6 protrusions to about 15 protrusions, about 6 protrusions to about 20 protrusions, about 6 protrusions to about 25 protrusions, about 6 protrusions to about 30 protrusions, about 6 protrusions to about 40 protrusions, about 6 protrusions to about 50 protrusions, about 6 protrusions to about 60 protrusions, about 8 protrusions to about 10 protrusions, about 8 protrusions to about 15 protrusions, about 8 protrusions to about 20 protrusions, about 8 protrusions to about 25 protrusions, about 8 protrusions to about 30 protrusions, about 8 protrusions to about 40 protrusions, about 8 protrusions to about 50 protrusions, about 8 protrusions to about 60 protrusions, about 10 protrusions to about 15 protrusions, about 10 protrusions to about 20 protrusions, about 10 protrusions to about 25 protrusions, about 10 protrusions to about 30 protrusions, about 10 protrusions to about 40 protrusions, about 10 protrusions to about 50 protrusions, about 10 protrusions to about 60 protrusions, about 15 protrusions to about 20 protrusions, about 15 protrusions to about 25 protrusions, about 15 protrusions to about 30 protrusions, about 15 protrusions to about 40 protrusions, about 15 protrusions to about 50 protrusions, about 15 protrusions to about 60 protrusions, about 20 protrusions to about 25 protrusions, about 20 protrusions to about 30 protrusions, about 20 protrusions to about 40 protrusions, about 20 protrusions to about 50 protrusions, about 20 protrusions to about 60 protrusions, about 25 protrusions to about 30 protrusions, about 25 protrusions to about 40 protrusions, about 25 protrusions to about 50 protrusions, about 25 protrusions to about 60 protrusions, about 30 protrusions to about 40 protrusions, about 30 protrusions to about 50 protrusions, about 30 protrusions to about 60 protrusions, about 40 protrusions to about 50 protrusions, about 40 protrusions to about 60 protrusions, or about 50 protrusions to about 60 protrusions. Optionally, in this or any other embodiment, the plurality of friction protrusions comprises about 2 protrusions, about 4 protrusions, about 6 protrusions, about 8 protrusions, about 10 protrusions, about 15 protrusions, about 20 protrusions, about 25 protrusions, about 30 protrusions, about 40 protrusions, about 50 protrusions, or about 60 protrusions. Optionally, in this or any other embodiment, the plurality of friction protrusions comprises at most about 2 protrusions, about 4 protrusions, about 6 protrusions, about 8 protrusions, about 10 protrusions, about 15 protrusions, about 20 protrusions, about 25 protrusions, about 30 protrusions, about 40 protrusions, about 50 protrusions, or about 60 protrusions. Optionally, in this or any other embodiment, the plurality of friction protrusions comprises at least about 2 protrusions, about 4 protrusions, about 6 protrusions, about 8 protrusions, about 10 protrusions, about 15 protrusions, about 20 protrusions, about 25 protrusions, about 30 protrusions, about 40 protrusions, about 50 protrusions, or about 60 protrusions.

Optionally, in this or any other embodiment, the friction protrusions have a height of about 0.01 inches to about 0.06 inches. Optionally, in this or any other embodiment, the friction protrusions have a height of about 0.01 inches to about 0.02 inches, about 0.01 inches to about 0.03 inches, about 0.01 inches to about 0.04 inches, about 0.01 inches to about 0.05 inches, about 0.01 inches to about 0.06 inches, about 0.02 inches to about 0.03 inches, about 0.02 inches to about 0.04 inches, about 0.02 inches to about 0.05 inches, about 0.02 inches to about 0.06 inches, about 0.03 inches to about 0.04 inches, about 0.03 inches to about 0.05 inches, about 0.03 inches to about 0.06 inches, about 0.04 inches to about 0.05 inches, about 0.04 inches to about 0.06 inches, or about 0.05 inches to about 0.06 inches. Optionally, in this or any other embodiment, the friction protrusions have a height of about 0.01 inches, about 0.02 inches, about 0.03 inches, about 0.04 inches, about 0.05 inches, or about 0.06 inches. Optionally, in this or any other embodiment, the friction protrusions have a height of at least about 0.01 inches, about 0.02 inches, about 0.03 inches, about 0.04 inches, or about 0.05 inches. Optionally, in this or any other embodiment, the friction protrusions have a height of at most about 0.02 inches, about 0.03 inches, about 0.04 inches, about 0.05 inches, or about 0.06 inches.

Optionally, in this or any other embodiment, the friction protrusions have a width of about 0.01 inches to about 0.06 inches. Optionally, in this or any other embodiment, the friction protrusions have a width of about 0.01 inches to about 0.02 inches, about 0.01 inches to about 0.03 inches, about 0.01 inches to about 0.04 inches, about 0.01 inches to about 0.05 inches, about 0.01 inches to about 0.06 inches, about 0.02 inches to about 0.03 inches, about 0.02 inches to about 0.04 inches, about 0.02 inches to about 0.05 inches, about 0.02 inches to about 0.06 inches, about 0.03 inches to about 0.04 inches, about 0.03 inches to about 0.05 inches, about 0.03 inches to about 0.06 inches, about 0.04 inches to about 0.05 inches, about 0.04 inches to about 0.06 inches, or about 0.05 inches to about 0.06 inches. Optionally, in this or any other embodiment, the friction protrusions have a width of about 0.01 inches, about 0.02 inches, about 0.03 inches, about 0.04 inches, about 0.05 inches, or about 0.06 inches. Optionally, in this or any other embodiment, the friction protrusions have a width of at least about 0.01 inches, about 0.02 inches, about 0.03 inches, about 0.04 inches, or about 0.05 inches. Optionally, in this or any other embodiment, the friction protrusions have a width of at most about 0.02 inches, about 0.03 inches, about 0.04 inches, about 0.05 inches, or about 0.06 inches.

Optionally, in this or any other embodiment, the arched rod comprises a cover substantially surrounding a frame, wherein a frame modulus of elasticity of the frame is higher than a cover modulus of elasticity of the cover.

Another aspect provided herein is a penile constriction system comprising a band and a penile constriction device comprising an arched rod comprising: a first arm comprising a first coupling end and a first converging end having a first terminus; a second arm comprising a second coupling end and a second converging end having a second terminus disconnected from the first terminus, wherein the first converging end and the second converging end converge to form a constriction region; and a bridge connecting the first coupling end to the second coupling end, the bridge comprising a compression region rising inferiorly from an inferior side of the bridge.

Optionally, in this or any other embodiment, the device of the penile constriction system has a constriction gap width, wherein the constriction gap width is measured as a minimum distance between the first converging end and the second converging end within the constriction region. Optionally, in this or any other embodiment, the device of the penile constriction system has a constriction gap width of about 0 inches to about 1.25 inches. Optionally, in this or any other embodiment, the device of the penile constriction system has a constriction gap width of at least about 0 inches. Optionally, in this or any other embodiment, the device of the penile constriction system has a constriction gap width of at most about 1.25 inches. Optionally, in this or any other embodiment, the device of the penile constriction system has a constriction gap width of about 0 inches to about 0.125 inches, about 0 inches to about 0.375 inches, about 0 inches to about 0.5 inches, about 0 inches to about 0.625 inches, about 0 inches to about 0.75 inches, about 0 inches to about 0.875 inches, about 0 inches to about 1 inch, about 0 inches to about 1.125 inches, about 0 inches to about 1.25 inches, about 0.125 inches to about 0.375 inches, about 0.125 inches to about 0.5 inches, about 0.125 inches to about 0.625 inches, about 0.125 inches to about 0.75 inches, about 0.125 inches to about 0.875 inches, about 0.125 inches to about 1 inch, about 0.125 inches to about 1.125 inches, about 0.125 inches to about 1.25 inches, about 0.375 inches to about 0.5 inches, about 0.375 inches to about 0.625 inches, about 0.375 inches to about 0.75 inches, about 0.375 inches to about 0.875 inches, about 0.375 inches to about 1 inch, about 0.375 inches to about 1.125 inches, about 0.375 inches to about 1.25 inches, about 0.5 inches to about 0.625 inches, about 0.5 inches to about 0.75 inches, about 0.5 inches to about 0.875 inches, about 0.5 inches to about 1 inch, about 0.5 inches to about 1.125 inches, about 0.5 inches to about 1.25 inches, about 0.625 inches to about 0.75 inches, about 0.625 inches to about 0.875 inches, about 0.625 inches to about 1 inch, about 0.625 inches to about 1.125 inches, about 0.625 inches to about 1.25 inches, about 0.75 inches to about 0.875 inches, about 0.75 inches to about 1 inch, about 0.75 inches to about 1.125 inches, about 0.75 inches to about 1.25 inches, about 0.875 inches to about 1 inch, about 0.875 inches to about 1.125 inches, about 0.875 inches to about 1.25 inches, about 1 inch to about 1.125 inches, about 1 inch to about 1.25 inches, or about 1.125 inches to about 1.25 inches. Optionally, in this or any other embodiment, the device of the penile constriction system has a constriction gap width of about 0 inches, about 0.125 inches, about 0.375 inches, about 0.5 inches, about 0.625 inches, about 0.75 inches, about 0.875 inches, about 1 inch, about 1.125 inches, or about 1.25 inches. Optionally, in this or any other embodiment, the device of the penile constriction system has a constriction gap width of at least about 0 inches, about 0.125 inches, about 0.375 inches, about 0.5 inches, about 0.625 inches, about 0.75 inches, about 0.875 inches, about 1 inch, about 1.125 inches, or about 1.25 inches. Optionally, in this or any other embodiment, the device of the penile constriction system has a constriction gap width of at most about 0.125 inches, about 0.375 inches, about 0.5 inches, about 0.625 inches, about 0.75 inches, about 0.875 inches, about 1 inch, about 1.125 inches, or about 1.25 inches.

Optionally, in this or any other embodiment, the device of the penile constriction system has a constriction height, wherein the constriction height is measured as a normal distance between a constriction point and the inferior side of the bridge, and wherein the constriction point is defined as the midpoint of the constriction gap width. Optionally, in this or any other embodiment, the device of the penile constriction system has a constriction height of about 0.5 inches to about 2.5 inches. Optionally, in this or any other embodiment, the device of the penile constriction system has a constriction height of at least about 0.5 inches. Optionally, in this or any other embodiment, the device of the penile constriction system has a constriction height of at most about 2.5 inches. Optionally, in this or any other embodiment, the device of the penile constriction system has a constriction height of about 0.5 inches to about 0.75 inches, about 0.5 inches to about 1 inch, about 0.5 inches to about 1.25 inches, about 0.5 inches to about 1.5 inches, about 0.5 inches to about 1.75 inches, about 0.5 inches to about 2 inches, about 0.5 inches to about 2.25 inches, about 0.5 inches to about 2.5 inches, about 0.75 inches to about 1 inch, about 0.75 inches to about 1.25 inches, about 0.75 inches to about 1.5 inches, about 0.75 inches to about 1.75 inches, about 0.75 inches to about 2 inches, about 0.75 inches to about 2.25 inches, about 0.75 inches to about 2.5 inches, about 1 inch to about 1.25 inches, about 1 inch to about 1.5 inches, about 1 inch to about 1.75 inches, about 1 inch to about 2 inches, about 1 inch to about 2.25 inches, about 1 inch to about 2.5 inches, about 1.25 inches to about 1.5 inches, about 1.25 inches to about 1.75 inches, about 1.25 inches to about 2 inches, about 1.25 inches to about 2.25 inches, about 1.25 inches to about 2.5 inches, about 1.5 inches to about 1.75 inches, about 1.5 inches to about 2 inches, about 1.5 inches to about 2.25 inches, about 1.5 inches to about 2.5 inches, about 1.75 inches to about 2 inches, about 1.75 inches to about 2.25 inches, about 1.75 inches to about 2.5 inches, about 2 inches to about 2.25 inches, about 2 inches to about 2.5 inches, or about 2.25 inches to about 2.5 inches. Optionally, in this or any other embodiment, the device of the penile constriction system has a constriction height of about 0.5 inches, about 0.75 inches, about 1 inch, about 1.25 inches, about 1.5 inches, about 1.75 inches, about 2 inches, about 2.25 inches, or about 2.5 inches. Optionally, in this or any other embodiment, the device of the penile constriction system has a constriction height of at least about 0.5 inches, about 0.75 inches, about 1 inch, about 1.25 inches, about 1.5 inches, about 1.75 inches, about 2 inches, about 2.25 inches, or about 2.5 inches. Optionally, in this or any other embodiment, the device of the penile constriction system has a constriction height of at most about 0.5 inches, about 0.75 inches, about 1 inch, about 1.25 inches, about 1.5 inches, about 1.75 inches, about 2 inches, about 2.25 inches, or about 2.5 inches.

Optionally, in this or any other embodiment, the device of the penile constriction system has a maximum inner width, wherein the maximum inner width is measured as a maximum normal distance between a mesial vertex of the surface of the first arm and a mesial vertex of the surface of the second arm, and wherein the maximum inner width is superior to the constriction gap. Optionally, in this or any other embodiment, the device of the penile constriction system has a maximum inner width of about 0.5 inches to about 3 inches. Optionally, in this or any other embodiment, the device of the penile constriction system has a maximum inner width of at least about 0.5 inches. Optionally, in this or any other embodiment, the device of the penile constriction system has a maximum inner width of at most about 3 inches. Optionally, in this or any other embodiment, the device of the penile constriction system has a maximum inner width of about 0.5 inches to about 0.75 inches, about 0.5 inches to about 1 inch, about 0.5 inches to about 1.25 inches, about 0.5 inches to about 1.5 inches, about 0.5 inches to about 1.75 inches, about 0.5 inches to about 2 inches, about 0.5 inches to about 2.25 inches, about 0.5 inches to about 2.5 inches, about 0.5 inches to about 2.75 inches, about 0.5 inches to about 3 inches, about 0.75 inches to about 1 inch, about 0.75 inches to about 1.25 inches, about 0.75 inches to about 1.5 inches, about 0.75 inches to about 1.75 inches, about 0.75 inches to about 2 inches, about 0.75 inches to about 2.25 inches, about 0.75 inches to about 2.5 inches, about 0.75 inches to about 2.75 inches, about 0.75 inches to about 3 inches, about 1 inch to about 1.25 inches, about 1 inch to about 1.5 inches, about 1 inch to about 1.75 inches, about 1 inch to about 2 inches, about 1 inch to about 2.25 inches, about 1 inch to about 2.5 inches, about 1 inch to about 2.75 inches, about 1 inch to about 3 inches, about 1.25 inches to about 1.5 inches, about 1.25 inches to about 1.75 inches, about 1.25 inches to about 2 inches, about 1.25 inches to about 2.25 inches, about 1.25 inches to about 2.5 inches, about 1.25 inches to about 2.75 inches, about 1.25 inches to about 3 inches, about 1.5 inches to about 1.75 inches, about 1.5 inches to about 2 inches, about 1.5 inches to about 2.25 inches, about 1.5 inches to about 2.5 inches, about 1.5 inches to about 2.75 inches, about 1.5 inches to about 3 inches, about 1.75 inches to about 2 inches, about 1.75 inches to about 2.25 inches, about 1.75 inches to about 2.5 inches, about 1.75 inches to about 2.75 inches, about 1.75 inches to about 3 inches, about 2 inches to about 2.25 inches, about 2 inches to about 2.5 inches, about 2 inches to about 2.75 inches, about 2 inches to about 3 inches, about 2.25 inches to about 2.5 inches, about 2.25 inches to about 2.75 inches, about 2.25 inches to about 3 inches, about 2.5 inches to about 2.75 inches, about 2.5 inches to about 3 inches, or about 2.75 inches to about 3 inches. Optionally, in this or any other embodiment, the device of the penile constriction system has a maximum inner width of about 0.5 inches, about 0.75 inches, about 1 inch, about 1.25 inches, about 1.5 inches, about 1.75 inches, about 2 inches, about 2.25 inches, about 2.5 inches, about 2.75 inches, or about 3 inches. Optionally, in this or any other embodiment, the device of the penile constriction system has a maximum inner width of at least about 0.5 inches, about 0.75 inches, about 1 inch, about 1.25 inches, about 1.5 inches, about 1.75 inches, about 2 inches, about 2.25 inches, about 2.5 inches, about 2.75 inches, or about 3 inches. Optionally, in this or any other embodiment, the device of the penile constriction system has a maximum inner width of at most about 0.5 inches, about 0.75 inches, about 1 inch, about 1.25 inches, about 1.5 inches, about 1.75 inches, about 2 inches, about 2.25 inches, about 2.5 inches, about 2.75 inches, or about 3 inches.

Optionally, in this or any other embodiment, the device of the penile constriction system has an inferior height, wherein the inferior height is measured as a normal distance between a center point, and the inferior side of the bridge, wherein the center point comprises the midpoint of the maximum inner width. Optionally, in this or any other embodiment, the device of the penile constriction system has an inferior height of about 0.25 inches to about 1 inch. Optionally, in this or any other embodiment, the device of the penile constriction system has an inferior height of at least about 0.25 inches. Optionally, in this or any other embodiment, the device of the penile constriction system has an inferior height of at most about 1 inch. Optionally, in this or any other embodiment, the device of the penile constriction system has an inferior height of about 0.25 inches to about 0.3 inches, about 0.25 inches to about 0.35 inches, about 0.25 inches to about 0.4 inches, about 0.25 inches to about 0.45 inches, about 0.25 inches to about 0.5 inches, about 0.25 inches to about 0.6 inches, about 0.25 inches to about 0.7 inches, about 0.25 inches to about 0.8 inches, about 0.25 inches to about 0.9 inches, about 0.25 inches to about 1 inch, about 0.3 inches to about 0.35 inches, about 0.3 inches to about 0.4 inches, about 0.3 inches to about 0.45 inches, about 0.3 inches to about 0.5 inches, about 0.3 inches to about 0.6 inches, about 0.3 inches to about 0.7 inches, about 0.3 inches to about 0.8 inches, about 0.3 inches to about 0.9 inches, about 0.3 inches to about 1 inch, about 0.35 inches to about 0.4 inches, about 0.35 inches to about 0.45 inches, about 0.35 inches to about 0.5 inches, about 0.35 inches to about 0.6 inches, about 0.35 inches to about 0.7 inches, about 0.35 inches to about 0.8 inches, about 0.35 inches to about 0.9 inches, about 0.35 inches to about 1 inch, about 0.4 inches to about 0.45 inches, about 0.4 inches to about 0.5 inches, about 0.4 inches to about 0.6 inches, about 0.4 inches to about 0.7 inches, about 0.4 inches to about 0.8 inches, about 0.4 inches to about 0.9 inches, about 0.4 inches to about 1 inch, about 0.45 inches to about 0.5 inches, about 0.45 inches to about 0.6 inches, about 0.45 inches to about 0.7 inches, about 0.45 inches to about 0.8 inches, about 0.45 inches to about 0.9 inches, about 0.45 inches to about 1 inch, about 0.5 inches to about 0.6 inches, about 0.5 inches to about 0.7 inches, about 0.5 inches to about 0.8 inches, about 0.5 inches to about 0.9 inches, about 0.5 inches to about 1 inch, about 0.6 inches to about 0.7 inches, about 0.6 inches to about 0.8 inches, about 0.6 inches to about 0.9 inches, about 0.6 inches to about 1 inch, about 0.7 inches to about 0.8 inches, about 0.7 inches to about 0.9 inches, about 0.7 inches to about 1 inch, about 0.8 inches to about 0.9 inches, about 0.8 inches to about 1 inch, or about 0.9 inches to about 1 inch. Optionally, in this or any other embodiment, the device of the penile constriction system has an inferior height of about 0.25 inches, about 0.3 inches, about 0.35 inches, about 0.4 inches, about 0.45 inches, about 0.5 inches, about 0.6 inches, about 0.7 inches, about 0.8 inches, about 0.9 inches, or about 1 inch. Optionally, in this or any other embodiment, the device of the penile constriction system has an inferior height of at least about 0.25 inches, about 0.3 inches, about 0.35 inches, about 0.4 inches, about 0.45 inches, about 0.5 inches, about 0.6 inches, about 0.7 inches, about 0.8 inches, about 0.9 inches, or about 1 inch. Optionally, in this or any other embodiment, the device of the penile constriction system has an inferior height of at most about 0.25 inches, about 0.3 inches, about 0.35 inches, about 0.4 inches, about 0.45 inches, about 0.5 inches, about 0.6 inches, about 0.7 inches, about 0.8 inches, about 0.9 inches, or about 1 inch.

Optionally, in this or any other embodiment, a ratio between the constriction gap width and the maximum inner width is about 0.3:1 to about 0.9:1. Optionally, in this or any other embodiment, a ratio between the constriction gap width and the maximum inner width is at least about 0.2:1. Optionally, in this or any other embodiment, a ratio between the constriction gap width and the maximum inner width is at most about 0.9:1. Optionally, in this or any other embodiment, a ratio between the constriction gap width and the maximum inner width is about 0.2:1 to about 0.25:1, about 0.2:1 to about 0.3:1, about 0.2:1 to about 0.35:1, about 0.2:1 to about 0.4:1, about 0.2:1 to about 0.5:1, about 0.2:1 to about 0.6:1, about 0.2:1 to about 0.7:1, about 0.2:1 to about 0.8:1, about 0.2:1 to about 0.9:1, about 0.25:1 to about 0.3:1, about 0.25:1 to about 0.35:1, about 0.25:1 to about 0.4:1, about 0.25:1 to about 0.5:1, about 0.25:1 to about 0.6:1, about 0.25:1 to about 0.7:1, about 0.25:1 to about 0.8:1, about 0.25:1 to about 0.9:1, about 0.3:1 to about 0.35:1, about 0.3:1 to about 0.4:1, about 0.3:1 to about 0.5:1, about 0.3:1 to about 0.6:1, about 0.3:1 to about 0.7:1, about 0.3:1 to about 0.8:1, about 0.3:1 to about 0.9:1, about 0.35:1 to about 0.4:1, about 0.35:1 to about 0.5:1, about 0.35:1 to about 0.6:1, about 0.35:1 to about 0.7:1, about 0.35:1 to about 0.8:1, about 0.35:1 to about 0.9:1, about 0.4:1 to about 0.5:1, about 0.4:1 to about 0.6:1, about 0.4:1 to about 0.7:1, about 0.4:1 to about 0.8:1, about 0.4:1 to about 0.9:1, about 0.5:1 to about 0.6:1, about 0.5:1 to about 0.7:1, about 0.5:1 to about 0.8:1, about 0.5:1 to about 0.9:1, about 0.6:1 to about 0.7:1, about 0.6:1 to about 0.8:1, about 0.6:1 to about 0.9:1, about 0.7:1 to about 0.8:1, about 0.7:1 to about 0.9:1, or about 0.8:1 to about 0.9:1. Optionally, in this or any other embodiment, a ratio between the constriction gap width and the maximum inner width is about 0.2:1, about 0.25:1, about 0.3:1, about 0.35:1, about 0.4:1, about 0.5:1, about 0.6:1, about 0.7:1, about 0.8:1, or about 0.9:1. Optionally, in this or any other embodiment, a ratio between the constriction gap width and the maximum inner width is at least about 0.2:1, about 0.25:1, about 0.3:1, about 0.35:1, about 0.4:1, about 0.5:1, about 0.6:1, about 0.7:1, about 0.8:1, or about 0.9:1. Optionally, in this or any other embodiment, a ratio between the constriction gap width and the maximum inner width is at most about 0.2:1, about 0.25:1, about 0.3:1, about 0.35:1, about 0.4:1, about 0.5:1, about 0.6:1, about 0.7:1, about 0.8:1, or about 0.9:1.

Optionally, in this or any other embodiment, a ratio between the constriction height and the maximum inner width is about 0.7:1 to about 0.99:1. Optionally, in this or any other embodiment, a ratio between the constriction height and the maximum inner width is at least about 0.7:1. Optionally, in this or any other embodiment, a ratio between the constriction height and the maximum inner width is at most about 0.99:1. Optionally, in this or any other embodiment, a ratio between the constriction height and the maximum inner width is about 0.7:1 to about 0.725:1, about 0.7:1 to about 0.75:1, about 0.7:1 to about 0.775:1, about 0.7:1 to about 0.8:1, about 0.7:1 to about 0.825:1, about 0.7:1 to about 0.85:1, about 0.7:1 to about 0.875:1, about 0.7:1 to about 0.9:1, about 0.7:1 to about 0.925:1, about 0.7:1 to about 0.95:1, about 0.7:1 to about 0.99:1, about 0.725:1 to about 0.75:1, about 0.725:1 to about 0.775:1, about 0.725:1 to about 0.8:1, about 0.725:1 to about 0.825:1, about 0.725:1 to about 0.85:1, about 0.725:1 to about 0.875:1, about 0.725:1 to about 0.9:1, about 0.725:1 to about 0.925:1, about 0.725:1 to about 0.95:1, about 0.725:1 to about 0.99:1, about 0.75:1 to about 0.775:1, about 0.75:1 to about 0.8:1, about 0.75:1 to about 0.825:1, about 0.75:1 to about 0.85:1, about 0.75:1 to about 0.875:1, about 0.75:1 to about 0.9:1, about 0.75:1 to about 0.925:1, about 0.75:1 to about 0.95:1, about 0.75:1 to about 0.99:1, about 0.775:1 to about 0.8:1, about 0.775:1 to about 0.825:1, about 0.775:1 to about 0.85:1, about 0.775:1 to about 0.875:1, about 0.775:1 to about 0.9:1, about 0.775:1 to about 0.925:1, about 0.775:1 to about 0.95:1, about 0.775:1 to about 0.99:1, about 0.8:1 to about 0.825:1, about 0.8:1 to about 0.85:1, about 0.8:1 to about 0.875:1, about 0.8:1 to about 0.9:1, about 0.8:1 to about 0.925:1, about 0.8:1 to about 0.95:1, about 0.8:1 to about 0.99:1, about 0.825:1 to about 0.85:1, about 0.825:1 to about 0.875:1, about 0.825:1 to about 0.9:1, about 0.825:1 to about 0.925:1, about 0.825:1 to about 0.95:1, about 0.825:1 to about 0.99:1, about 0.85:1 to about 0.875:1, about 0.85:1 to about 0.9:1, about 0.85:1 to about 0.925:1, about 0.85:1 to about 0.95:1, about 0.85:1 to about 0.99:1, about 0.875:1 to about 0.9:1, about 0.875:1 to about 0.925:1, about 0.875:1 to about 0.95:1, about 0.875:1 to about 0.99:1, about 0.9:1 to about 0.925:1, about 0.9:1 to about 0.95:1, about 0.9:1 to about 0.99:1, about 0.925:1 to about 0.95:1, about 0.925:1 to about 0.99:1, or about 0.95:1 to about 0.99:1. Optionally, in this or any other embodiment, a ratio between the constriction height and the maximum inner width is about 0.7:1, about 0.725:1, about 0.75:1, about 0.775:1, about 0.8:1, about 0.825:1, about 0.85:1, about 0.875:1, about 0.9:1, about 0.925:1, about 0.95:1, or about 0.99:1. Optionally, in this or any other embodiment, a ratio between the constriction height and the maximum inner width is at least about 0.7:1, about 0.725:1, about 0.75:1, about 0.775:1, about 0.8:1, about 0.825:1, about 0.85:1, about 0.875:1, about 0.9:1, about 0.925:1, about 0.95:1, or about 0.99:1. Optionally, in this or any other embodiment, a ratio between the constriction height and the maximum inner width is at most about 0.7:1, about 0.725:1, about 0.75:1, about 0.775:1, about 0.8:1, about 0.825:1, about 0.85:1, about 0.875:1, about 0.9:1, about 0.925:1, about 0.95:1, or about 0.99:1.

Optionally, in this or any other embodiment, a ratio between the inferior height and the maximum inner width is about 0.15:1 to about 0.6:1. Optionally, in this or any other embodiment, a ratio between the inferior height and the maximum inner width is at least about 0.15:1. Optionally, in this or any other embodiment, a ratio between the inferior height and the maximum inner width is at most about 0.6:1. Optionally, in this or any other embodiment, a ratio between the inferior height and the maximum inner width is about 0.15:1 to about 0.2:1, about 0.15:1 to about 0.25:1, about 0.15:1 to about 0.3:1, about 0.15:1 to about 0.35:1, about 0.15:1 to about 0.4:1, about 0.15:1 to about 0.45:1, about 0.15:1 to about 0.5:1, about 0.15:1 to about 0.55:1, about 0.15:1 to about 0.6:1, about 0.2:1 to about 0.25:1, about 0.2:1 to about 0.3:1, about 0.2:1 to about 0.35:1, about 0.2:1 to about 0.4:1, about 0.2:1 to about 0.45:1, about 0.2:1 to about 0.5:1, about 0.2:1 to about 0.55:1, about 0.2:1 to about 0.6:1, about 0.25:1 to about 0.3:1, about 0.25:1 to about 0.35:1, about 0.25:1 to about 0.4:1, about 0.25:1 to about 0.45:1, about 0.25:1 to about 0.5:1, about 0.25:1 to about 0.55:1, about 0.25:1 to about 0.6:1, about 0.3:1 to about 0.35:1, about 0.3:1 to about 0.4:1, about 0.3:1 to about 0.45:1, about 0.3:1 to about 0.5:1, about 0.3:1 to about 0.55:1, about 0.3:1 to about 0.6:1, about 0.35:1 to about 0.4:1, about 0.35:1 to about 0.45:1, about 0.35:1 to about 0.5:1, about 0.35:1 to about 0.55:1, about 0.35:1 to about 0.6:1, about 0.4:1 to about 0.45:1, about 0.4:1 to about 0.5:1, about 0.4:1 to about 0.55:1, about 0.4:1 to about 0.6:1, about 0.45:1 to about 0.5:1, about 0.45:1 to about 0.55:1, about 0.45:1 to about 0.6:1, about 0.5:1 to about 0.55:1, about 0.5:1 to about 0.6:1, or about 0.55:1 to about 0.6:1. Optionally, in this or any other embodiment, a ratio between the inferior height and the maximum inner width is about 0.15:1, about 0.2:1, about 0.25:1, about 0.3:1, about 0.35:1, about 0.4:1, about 0.45:1, about 0.5:1, about 0.55:1, or about 0.6:1. Optionally, in this or any other embodiment, a ratio between the inferior height and the maximum inner width is at least about 0.15:1, about 0.2:1, about 0.25:1, about 0.3:1, about 0.35:1, about 0.4:1, about 0.45:1, about 0.5:1, about 0.55:1, or about 0.6:1. Optionally, in this or any other embodiment, a ratio between the inferior height and the maximum inner width is at most 0.15:1, about 0.2:1, about 0.25:1, about 0.3:1, about 0.35:1, about 0.4:1, about 0.45:1, about 0.5:1, about 0.55:1, or about 0.6:1.

Optionally, in this or any other embodiment, the arched rod has a thickness, wherein the thickness is measured as a maximum normal cross-sectional width of at least a portion of at least one of the first arm, the second arm, and the bridge. Optionally, in this or any other embodiment, the device of the penile constriction system has a thickness of about 0.125 inches to about 0.8 inches. Optionally, in this or any other embodiment, the device of the penile constriction system has a thickness of at least about 0.125 inches. Optionally, in this or any other embodiment, the device of the penile constriction system has a thickness of at most about 0.8 inches. Optionally, in this or any other embodiment, the device of the penile constriction system has a thickness of about 0.125 inches to about 0.15 inches, about 0.125 inches to about 0.2 inches, about 0.125 inches to about 0.25 inches, about 0.125 inches to about 0.3 inches, about 0.125 inches to about 0.35 inches, about 0.125 inches to about 0.4 inches, about 0.125 inches to about 0.45 inches, about 0.125 inches to about 0.5 inches, about 0.125 inches to about 0.6 inches, about 0.125 inches to about 0.7 inches, about 0.125 inches to about 0.8 inches, about 0.15 inches to about 0.2 inches, about 0.15 inches to about 0.25 inches, about 0.15 inches to about 0.3 inches, about 0.15 inches to about 0.35 inches, about 0.15 inches to about 0.4 inches, about 0.15 inches to about 0.45 inches, about 0.15 inches to about 0.5 inches, about 0.15 inches to about 0.6 inches, about 0.15 inches to about 0.7 inches, about 0.15 inches to about 0.8 inches, about 0.2 inches to about 0.25 inches, about 0.2 inches to about 0.3 inches, about 0.2 inches to about 0.35 inches, about 0.2 inches to about 0.4 inches, about 0.2 inches to about 0.45 inches, about 0.2 inches to about 0.5 inches, about 0.2 inches to about 0.6 inches, about 0.2 inches to about 0.7 inches, about 0.2 inches to about 0.8 inches, about 0.25 inches to about 0.3 inches, about 0.25 inches to about 0.35 inches, about 0.25 inches to about 0.4 inches, about 0.25 inches to about 0.45 inches, about 0.25 inches to about 0.5 inches, about 0.25 inches to about 0.6 inches, about 0.25 inches to about 0.7 inches, about 0.25 inches to about 0.8 inches, about 0.3 inches to about 0.35 inches, about 0.3 inches to about 0.4 inches, about 0.3 inches to about 0.45 inches, about 0.3 inches to about 0.5 inches, about 0.3 inches to about 0.6 inches, about 0.3 inches to about 0.7 inches, about 0.3 inches to about 0.8 inches, about 0.35 inches to about 0.4 inches, about 0.35 inches to about 0.45 inches, about 0.35 inches to about 0.5 inches, about 0.35 inches to about 0.6 inches, about 0.35 inches to about 0.7 inches, about 0.35 inches to about 0.8 inches, about 0.4 inches to about 0.45 inches, about 0.4 inches to about 0.5 inches, about 0.4 inches to about 0.6 inches, about 0.4 inches to about 0.7 inches, about 0.4 inches to about 0.8 inches, about 0.45 inches to about 0.5 inches, about 0.45 inches to about 0.6 inches, about 0.45 inches to about 0.7 inches, about 0.45 inches to about 0.8 inches, about 0.5 inches to about 0.6 inches, about 0.5 inches to about 0.7 inches, about 0.5 inches to about 0.8 inches, about 0.6 inches to about 0.7 inches, about 0.6 inches to about 0.8 inches, or about 0.7 inches to about 0.8 inches. Optionally, in this or any other embodiment, the device of the penile constriction system has a thickness of about 0.125 inches, about 0.15 inches, about 0.2 inches, about 0.25 inches, about 0.3 inches, about 0.35 inches, about 0.4 inches, about 0.45 inches, about 0.5 inches, about 0.6 inches, about 0.7 inches, or about 0.8 inches. Optionally, in this or any other embodiment, the device of the penile constriction system has a thickness of at least about 0.125 inches, about 0.15 inches, about 0.2 inches, about 0.25 inches, about 0.3 inches, about 0.35 inches, about 0.4 inches, about 0.45 inches, about 0.5 inches, about 0.6 inches, about 0.7 inches, or about 0.8 inches. Optionally, in this or any other embodiment, the device of the penile constriction system has a thickness of at most about 0.125 inches, about 0.15 inches, about 0.2 inches, about 0.25 inches, about 0.3 inches, about 0.35 inches, about 0.4 inches, about 0.45 inches, about 0.5 inches, about 0.6 inches, about 0.7 inches, or about 0.8 inches.

Optionally, in this or any other embodiment, the first terminus diverges from the constriction region to form a first elbow, and wherein the second terminus diverges from the constriction region to form a second elbow. Optionally, in this or any other embodiment, the first elbow and the second elbow are configured to removably affix to a band.

Optionally, in this or any other embodiment, the compression region comprises: a first dorsal vein protrusion comprising: a first dorsal apex; and a first dorsal height measured as a first minimum normal distance between the first dorsal apex and a first lateral edge of the first dorsal vein protrusion where the first dorsal vein protrusion rises from the inferior side of the bridge; a second dorsal vein protrusion comprising: a second dorsal apex; and a second dorsal height measured as a second minimum normal distance between the second dorsal apex and a second lateral edge of the second dorsal vein protrusion where the second dorsal vein protrusion rises from the inferior side of the bridge; and a dorsal vein valley between the first dorsal vein apex and the second dorsal vein apex.

Optionally, in this or any other embodiment, the first dorsal vein protrusion, the dorsal vein valley, and the second dorsal vein protrusion are arranged sequentially within the compression region in a direction along the bridge from the first arm to the second arm.

Optionally, in this or any other embodiment, the device of the penile constriction system comprises a dorsal vein valley distance between the first dorsal apex and the second dorsal apex. Optionally, in this or any other embodiment, the dorsal vein valley distance is about 0.15 inches to about 0.75 inches. Optionally, in this or any other embodiment, the dorsal vein valley distance is at least about 0.15 inches. Optionally, in this or any other embodiment, the dorsal vein valley distance is at most about 0.75 inches. Optionally, in this or any other embodiment, the dorsal vein valley distance is about 0.15 inches to about 0.2 inches, about 0.15 inches to about 0.25 inches, about 0.15 inches to about 0.3 inches, about 0.15 inches to about 0.35 inches, about 0.15 inches to about 0.4 inches, about 0.15 inches to about 0.45 inches, about 0.15 inches to about 0.5 inches, about 0.15 inches to about 0.55 inches, about 0.15 inches to about 0.6 inches, about 0.15 inches to about 0.65 inches, about 0.15 inches to about 0.75 inches, about 0.2 inches to about 0.25 inches, about 0.2 inches to about 0.3 inches, about 0.2 inches to about 0.35 inches, about 0.2 inches to about 0.4 inches, about 0.2 inches to about 0.45 inches, about 0.2 inches to about 0.5 inches, about 0.2 inches to about 0.55 inches, about 0.2 inches to about 0.6 inches, about 0.2 inches to about 0.65 inches, about 0.2 inches to about 0.75 inches, about 0.25 inches to about 0.3 inches, about 0.25 inches to about 0.35 inches, about 0.25 inches to about 0.4 inches, about 0.25 inches to about 0.45 inches, about 0.25 inches to about 0.5 inches, about 0.25 inches to about 0.55 inches, about 0.25 inches to about 0.6 inches, about 0.25 inches to about 0.65 inches, about 0.25 inches to about 0.75 inches, about 0.3 inches to about 0.35 inches, about 0.3 inches to about 0.4 inches, about 0.3 inches to about 0.45 inches, about 0.3 inches to about 0.5 inches, about 0.3 inches to about 0.55 inches, about 0.3 inches to about 0.6 inches, about 0.3 inches to about 0.65 inches, about 0.3 inches to about 0.75 inches, about 0.35 inches to about 0.4 inches, about 0.35 inches to about 0.45 inches, about 0.35 inches to about 0.5 inches, about 0.35 inches to about 0.55 inches, about 0.35 inches to about 0.6 inches, about 0.35 inches to about 0.65 inches, about 0.35 inches to about 0.75 inches, about 0.4 inches to about 0.45 inches, about 0.4 inches to about 0.5 inches, about 0.4 inches to about 0.55 inches, about 0.4 inches to about 0.6 inches, about 0.4 inches to about 0.65 inches, about 0.4 inches to about 0.75 inches, about 0.45 inches to about 0.5 inches, about 0.45 inches to about 0.55 inches, about 0.45 inches to about 0.6 inches, about 0.45 inches to about 0.65 inches, about 0.45 inches to about 0.75 inches, about 0.5 inches to about 0.55 inches, about 0.5 inches to about 0.6 inches, about 0.5 inches to about 0.65 inches, about 0.5 inches to about 0.75 inches, about 0.55 inches to about 0.6 inches, about 0.55 inches to about 0.65 inches, about 0.55 inches to about 0.75 inches, about 0.6 inches to about 0.65 inches, about 0.6 inches to about 0.75 inches, or about 0.65 inches to about 0.75 inches. Optionally, in this or any other embodiment, the dorsal vein valley distance is about 0.15 inches, about 0.2 inches, about 0.25 inches, about 0.3 inches, about 0.35 inches, about 0.4 inches, about 0.45 inches, about 0.5 inches, about 0.55 inches, about 0.6 inches, about 0.65 inches, or about 0.75 inches. Optionally, in this or any other embodiment, the dorsal vein valley distance is at least about 0.15 inches, about 0.2 inches, about 0.25 inches, about 0.3 inches, about 0.35 inches, about 0.4 inches, about 0.45 inches, about 0.5 inches, about 0.55 inches, about 0.6 inches, about 0.65 inches, or about 0.75 inches. Optionally, in this or any other embodiment, the dorsal vein valley distance is at most about 0.15 inches, about 0.2 inches, about 0.25 inches, about 0.3 inches, about 0.35 inches, about 0.4 inches, about 0.45 inches, about 0.5 inches, about 0.55 inches, about 0.6 inches, about 0.65 inches, or about 0.75 inches.

Optionally, in this or any other embodiment, the device of the penile constriction system comprises a compression region width between the first lateral edge and the second lateral edge. Optionally, in this or any other embodiment, the compression region width is about 0.2 inches to about 0.8 inches. Optionally, in this or any other embodiment, the compression region width is at least about 0.2 inches. Optionally, in this or any other embodiment, the compression region width is at most about 0.8 inches. Optionally, in this or any other embodiment, the compression region width is about 0.2 inches to about 0.25 inches, about 0.2 inches to about 0.3 inches, about 0.2 inches to about 0.35 inches, about 0.2 inches to about 0.4 inches, about 0.2 inches to about 0.45 inches, about 0.2 inches to about 0.5 inches, about 0.2 inches to about 0.55 inches, about 0.2 inches to about 0.6 inches, about 0.2 inches to about 0.7 inches, about 0.2 inches to about 0.8 inches, about 0.25 inches to about 0.3 inches, about 0.25 inches to about 0.35 inches, about 0.25 inches to about 0.4 inches, about 0.25 inches to about 0.45 inches, about 0.25 inches to about 0.5 inches, about 0.25 inches to about 0.55 inches, about 0.25 inches to about 0.6 inches, about 0.25 inches to about 0.7 inches, about 0.25 inches to about 0.8 inches, about 0.3 inches to about 0.35 inches, about 0.3 inches to about 0.4 inches, about 0.3 inches to about 0.45 inches, about 0.3 inches to about 0.5 inches, about 0.3 inches to about 0.55 inches, about 0.3 inches to about 0.6 inches, about 0.3 inches to about 0.7 inches, about 0.3 inches to about 0.8 inches, about 0.35 inches to about 0.4 inches, about 0.35 inches to about 0.45 inches, about 0.35 inches to about 0.5 inches, about 0.35 inches to about 0.55 inches, about 0.35 inches to about 0.6 inches, about 0.35 inches to about 0.7 inches, about 0.35 inches to about 0.8 inches, about 0.4 inches to about 0.45 inches, about 0.4 inches to about 0.5 inches, about 0.4 inches to about 0.55 inches, about 0.4 inches to about 0.6 inches, about 0.4 inches to about 0.7 inches, about 0.4 inches to about 0.8 inches, about 0.45 inches to about 0.5 inches, about 0.45 inches to about 0.55 inches, about 0.45 inches to about 0.6 inches, about 0.45 inches to about 0.7 inches, about 0.45 inches to about 0.8 inches, about 0.5 inches to about 0.55 inches, about 0.5 inches to about 0.6 inches, about 0.5 inches to about 0.7 inches, about 0.5 inches to about 0.8 inches, about 0.55 inches to about 0.6 inches, about 0.55 inches to about 0.7 inches, about 0.55 inches to about 0.8 inches, about 0.6 inches to about 0.7 inches, about 0.6 inches to about 0.8 inches, or about 0.7 inches to about 0.8 inches. Optionally, in this or any other embodiment, the compression region width is about 0.2 inches, about 0.25 inches, about 0.3 inches, about 0.35 inches, about 0.4 inches, about 0.45 inches, about 0.5 inches, about 0.55 inches, about 0.6 inches, about 0.7 inches, or about 0.8 inches. Optionally, in this or any other embodiment, the compression region width is at least about 0.2 inches, about 0.25 inches, about 0.3 inches, about 0.35 inches, about 0.4 inches, about 0.45 inches, about 0.5 inches, about 0.55 inches, about 0.6 inches, about 0.7 inches, or about 0.8 inches. Optionally, in this or any other embodiment, the compression region width is at most about 0.2 inches, about 0.25 inches, about 0.3 inches, about 0.35 inches, about 0.4 inches, about 0.45 inches, about 0.5 inches, about 0.55 inches, about 0.6 inches, about 0.7 inches, or about 0.8 inches.

Optionally, in this or any other embodiment, the compression region within the dorsal vein valley at a center of the dorsal vein valley is superior to or has a same height relative to the first lateral edge as the first minimum normal distance or relative to the second lateral edge as the second minimum normal distance, or both. Optionally, in this or any other embodiment, the compression region at the center of the dorsal vein valley is inferior to the first lateral edge, the second lateral edge, or both.

Optionally, in this or any other embodiment, the device of the penile constriction system further comprises a plurality of friction protrusions on a superior side of the bridge. Optionally, in this or any other embodiment, the plurality of friction protrusions comprises about 2 protrusions to about 60 protrusions. Optionally, in this or any other embodiment, the plurality of friction protrusions comprises at least about 2 protrusions. Optionally, in this or any other embodiment, the plurality of friction protrusions comprises at most about 60 protrusions. Optionally, in this or any other embodiment, the plurality of friction protrusions comprises about 2 protrusions to about 4 protrusions, about 2 protrusions to about 6 protrusions, about 2 protrusions to about 8 protrusions, about 2 protrusions to about 10 protrusions, about 2 protrusions to about 15 protrusions, about 2 protrusions to about 20 protrusions, about 2 protrusions to about 25 protrusions, about 2 protrusions to about 30 protrusions, about 2 protrusions to about 40 protrusions, about 2 protrusions to about 50 protrusions, about 2 protrusions to about 60 protrusions, about 4 protrusions to about 6 protrusions, about 4 protrusions to about 8 protrusions, about 4 protrusions to about 10 protrusions, about 4 protrusions to about 15 protrusions, about 4 protrusions to about 20 protrusions, about 4 protrusions to about 25 protrusions, about 4 protrusions to about 30 protrusions, about 4 protrusions to about 40 protrusions, about 4 protrusions to about 50 protrusions, about 4 protrusions to about 60 protrusions, about 6 protrusions to about 8 protrusions, about 6 protrusions to about 10 protrusions, about 6 protrusions to about 15 protrusions, about 6 protrusions to about 20 protrusions, about 6 protrusions to about 25 protrusions, about 6 protrusions to about 30 protrusions, about 6 protrusions to about 40 protrusions, about 6 protrusions to about 50 protrusions, about 6 protrusions to about 60 protrusions, about 8 protrusions to about 10 protrusions, about 8 protrusions to about 15 protrusions, about 8 protrusions to about 20 protrusions, about 8 protrusions to about 25 protrusions, about 8 protrusions to about 30 protrusions, about 8 protrusions to about 40 protrusions, about 8 protrusions to about 50 protrusions, about 8 protrusions to about 60 protrusions, about 10 protrusions to about 15 protrusions, about 10 protrusions to about 20 protrusions, about 10 protrusions to about 25 protrusions, about 10 protrusions to about 30 protrusions, about 10 protrusions to about 40 protrusions, about 10 protrusions to about 50 protrusions, about 10 protrusions to about 60 protrusions, about 15 protrusions to about 20 protrusions, about 15 protrusions to about 25 protrusions, about 15 protrusions to about 30 protrusions, about 15 protrusions to about 40 protrusions, about 15 protrusions to about 50 protrusions, about 15 protrusions to about 60 protrusions, about 20 protrusions to about 25 protrusions, about 20 protrusions to about 30 protrusions, about 20 protrusions to about 40 protrusions, about 20 protrusions to about 50 protrusions, about 20 protrusions to about 60 protrusions, about 25 protrusions to about 30 protrusions, about 25 protrusions to about 40 protrusions, about 25 protrusions to about 50 protrusions, about 25 protrusions to about 60 protrusions, about 30 protrusions to about 40 protrusions, about 30 protrusions to about 50 protrusions, about 30 protrusions to about 60 protrusions, about 40 protrusions to about 50 protrusions, about 40 protrusions to about 60 protrusions, or about 50 protrusions to about 60 protrusions. Optionally, in this or any other embodiment, the plurality of friction protrusions comprises about 2 protrusions, about 4 protrusions, about 6 protrusions, about 8 protrusions, about 10 protrusions, about 15 protrusions, about 20 protrusions, about 25 protrusions, about 30 protrusions, about 40 protrusions, about 50 protrusions, or about 60 protrusions. Optionally, in this or any other embodiment, the plurality of friction protrusions comprises at most about 2 protrusions, about 4 protrusions, about 6 protrusions, about 8 protrusions, about 10 protrusions, about 15 protrusions, about 20 protrusions, about 25 protrusions, about 30 protrusions, about 40 protrusions, about 50 protrusions, or about 60 protrusions. Optionally, in this or any other embodiment, the plurality of friction protrusions comprises at least about 2 protrusions, about 4 protrusions, about 6 protrusions, about 8 protrusions, about 10 protrusions, about 15 protrusions, about 20 protrusions, about 25 protrusions, about 30 protrusions, about 40 protrusions, about 50 protrusions, or about 60 protrusions.

Optionally, in this or any other embodiment, the friction protrusions have a height of about 0.01 inches to about 0.06 inches. Optionally, in this or any other embodiment, the friction protrusions have a height of about 0.01 inches to about 0.02 inches, about 0.01 inches to about 0.03 inches, about 0.01 inches to about 0.04 inches, about 0.01 inches to about 0.05 inches, about 0.01 inches to about 0.06 inches, about 0.02 inches to about 0.03 inches, about 0.02 inches to about 0.04 inches, about 0.02 inches to about 0.05 inches, about 0.02 inches to about 0.06 inches, about 0.03 inches to about 0.04 inches, about 0.03 inches to about 0.05 inches, about 0.03 inches to about 0.06 inches, about 0.04 inches to about 0.05 inches, about 0.04 inches to about 0.06 inches, or about 0.05 inches to about 0.06 inches. Optionally, in this or any other embodiment, the friction protrusions have a height of about 0.01 inches, about 0.02 inches, about 0.03 inches, about 0.04 inches, about 0.05 inches, or about 0.06 inches. Optionally, in this or any other embodiment, the friction protrusions have a height of at least about 0.01 inches, about 0.02 inches, about 0.03 inches, about 0.04 inches, or about 0.05 inches. Optionally, in this or any other embodiment, the friction protrusions have a height of at most about 0.02 inches, about 0.03 inches, about 0.04 inches, about 0.05 inches, or about 0.06 inches.

Optionally, in this or any other embodiment, the friction protrusions have a width of about 0.01 inches to about 0.06 inches. Optionally, in this or any other embodiment, the friction protrusions have a width of about 0.01 inches to about 0.02 inches, about 0.01 inches to about 0.03 inches, about 0.01 inches to about 0.04 inches, about 0.01 inches to about 0.05 inches, about 0.01 inches to about 0.06 inches, about 0.02 inches to about 0.03 inches, about 0.02 inches to about 0.04 inches, about 0.02 inches to about 0.05 inches, about 0.02 inches to about 0.06 inches, about 0.03 inches to about 0.04 inches, about 0.03 inches to about 0.05 inches, about 0.03 inches to about 0.06 inches, about 0.04 inches to about 0.05 inches, about 0.04 inches to about 0.06 inches, or about 0.05 inches to about 0.06 inches. Optionally, in this or any other embodiment, the friction protrusions have a width of about 0.01 inches, about 0.02 inches, about 0.03 inches, about 0.04 inches, about 0.05 inches, or about 0.06 inches. Optionally, in this or any other embodiment, the friction protrusions have a width of at least about 0.01 inches, about 0.02 inches, about 0.03 inches, about 0.04 inches, or about 0.05 inches. Optionally, in this or any other embodiment, the friction protrusions have a width of at most about 0.02 inches, about 0.03 inches, about 0.04 inches, about 0.05 inches, or about 0.06 inches.

Optionally, in this or any other embodiment, the arched rod comprises a cover substantially surrounding a frame, wherein a frame modulus of elasticity of the frame is higher than a cover modulus of elasticity of the cover.

These and other embodiments are described in further detail in the following description related to the appended drawing figures.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1111 shows a side cross-sectioned view of the manufacturing marks of penile constriction device of FIG. 11A;

FIG. 12J shows a perspective view of the frame of a non-limiting example of the frame of FIG. 12A;

FIG. 12K shows a front view of the frame of a non-limiting example of the frame of FIG. 12A;

FIG. 12L shows a front view of the frame of a non-limiting example of the frame of FIG. 12A;

FIG. 25 shows a first exemplary exercise guide; per an embodiment herein;

FIG. 26 shows a second exemplary exercise guide; per an embodiment herein;

FIG. 27 shows a third exemplary exercise guide; per an embodiment herein;

FIG. 28 shows a fourth exemplary exercise guide; per an embodiment herein;

FIG. 29 shows a fifth exemplary exercise guide; per an embodiment herein;

FIG. 30 shows a sixth exemplary exercise guide; per an embodiment herein;

FIG. 32 shows a second page of an exemplary instruction booklet; per an embodiment herein;

FIG. 33 shows a third page of an exemplary instruction booklet; per an embodiment herein;

FIG. 34 shows a fourth page of an exemplary instruction booklet; per an embodiment herein;

FIG. 35 shows a fifth page of an exemplary instruction booklet; per an embodiment herein;

FIG. 36 shows a sixth page of an exemplary instruction booklet; per an embodiment herein;

FIG. 38 shows an eighth page of an exemplary instruction booklet; per an embodiment herein;

FIG. 39 shows a ninth page of an exemplary instruction booklet; per an embodiment herein;

FIG. 40 shows a tenth page of an exemplary instruction booklet; per an embodiment herein;

FIG. 41 shows an eleventh page of an exemplary instruction booklet; per an embodiment herein;

FIG. 42 shows a twelfth page of an exemplary instruction booklet; per an embodiment herein;

FIG. 43 shows a thirteenth page of an exemplary instruction booklet; per an embodiment herein;

FIG. 44 shows a fourteenth page of an exemplary instruction booklet; per an embodiment herein;

FIG. 45 shows a fifteenth page of an exemplary instruction booklet; per an embodiment herein;

FIG. 46 shows a sixteenth page of an exemplary instruction booklet; per an embodiment herein.

DETAILED DESCRIPTION OF THE INVENTION

Specific embodiments of the disclosed system, method, and device will now be described with reference to the drawings. Nothing in this detailed description is intended to imply that any particular component, feature, or step is essential to the invention.

Penile Constriction Devices

Figure 1:
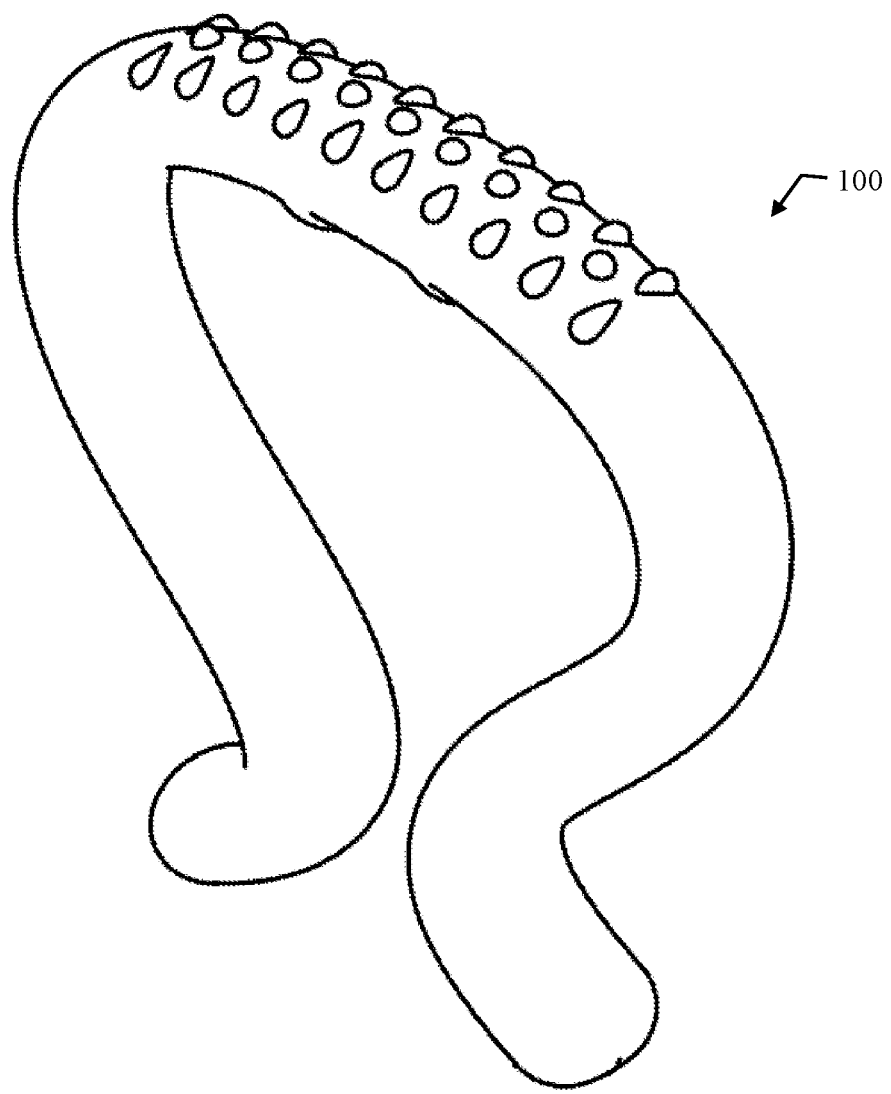
FIG. 1 shows a perspective view of a non-limiting example of a first penile constriction device, per an embodiment herein.

Provided herein, per FIGS. 1-12, are exemplary embodiments of a penile constriction device. FIG. 1 shows a perspective view of a non-limiting example of a first penile constriction device 100.

Figure 2A:
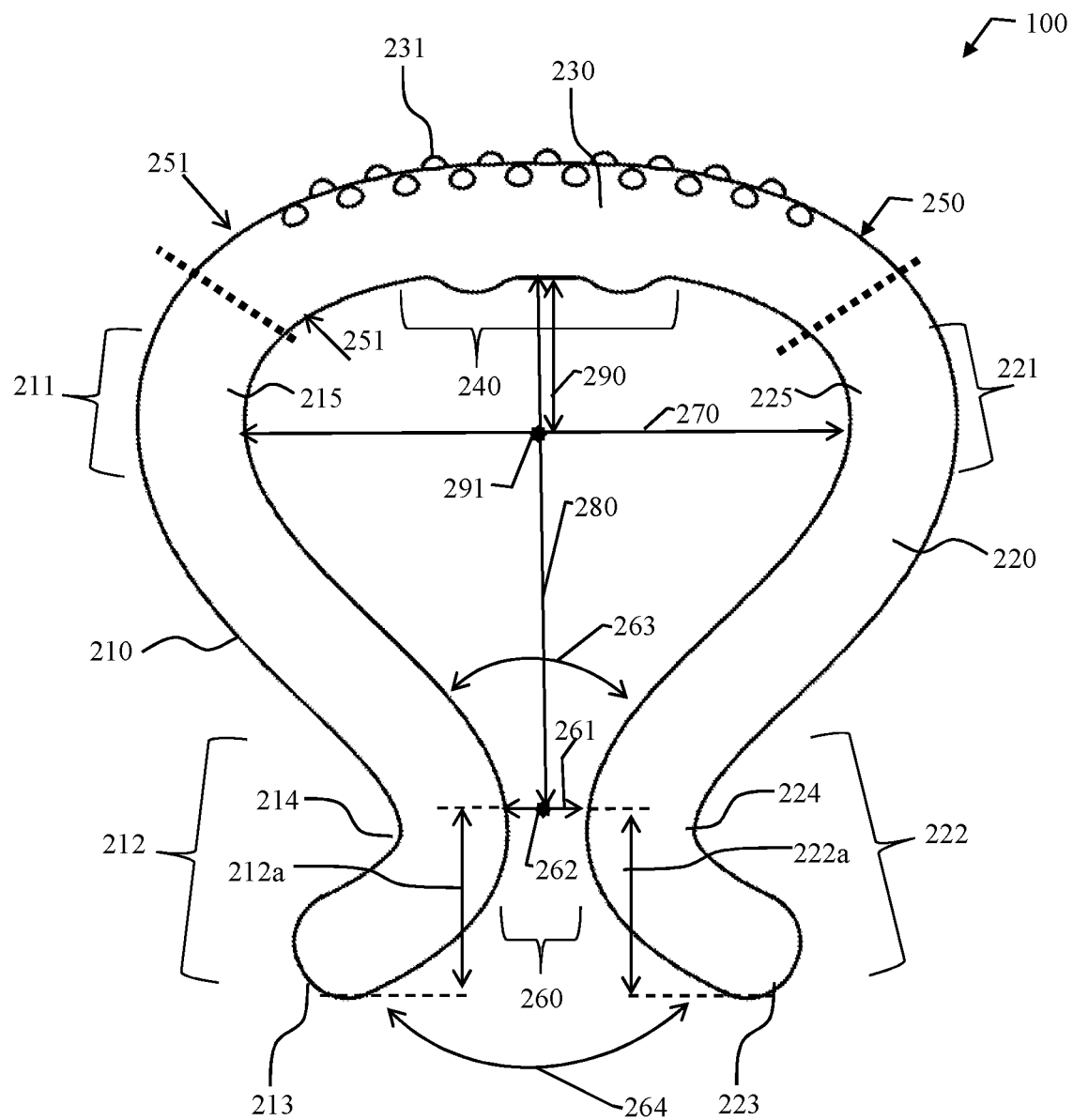
FIG. 2A shows a front view of a non-limiting example of the penile constriction device of FIG. 1.

FIG. 2A shows a front view of a non-limiting example of the penile constriction device of FIG. 1. The device 100 comprises an arched rod 250 comprising a first arm 210, a second arm 210, and a bridge 230. The first arm 210 comprises at least one of a first coupling end 211 and a first converging end 212. The first converging end 212 comprises a first terminus 213. Further, the second arm 220 comprises at least one of a second coupling end 221 and a second converging end 222. The second converging 222 end has a second terminus 223. Optionally, in this and other embodiments, the second terminus 223 is disconnected from the first terminus 213. In other embodiments, the second terminus may be connected with the first terminus. In the present embodiment, the first converging end 212 and the second converging end 222 converge to form a constriction region 260. The bridge 230 is generally disposed between the first arm 210 and the second arm 220. Additionally, the bridge 230 connects the first coupling end 211 to the second coupling end 221. Optionally, in this and other embodiments, the bridge 230 comprises a compression region 240. The compression region 240 rises inferiorly from an inferior side of the bridge 230. Optionally, in some embodiments, the device does not comprise the compression region. The bridge 230 further comprises a plurality of friction protrusions 231 on a superior side of the bridge 230. Optionally, in other embodiments, the device does not comprise a plurality of friction protrusions FIG. 2A portrays the arched rod 250, which optionally may comprise a curvilinear rod. Optionally, in this or any other embodiment, at least one of the first arm 210 and the second arm 220 is S-shaped. Alternatively, in this or any other embodiment, at least one of the first arm 210 and the second arm 220 is optionally C-shaped, J-shaped, L-shaped, U-shaped, or V-shaped. Optionally, in this or any other embodiment, the arched rod 250 has the shape of the Greek capital letter omega ($\Omega$). Optionally, in this or any other embodiment, the arched rod 250 is U-shaped. In some embodiments, the first terminus 213 extends beyond the second terminus 223. In some embodiments, the second terminus 223 extends beyond the first terminus 213. In some embodiments, the first terminus 213 and the second terminus 223 have the same shape. In some embodiments, the first terminus 213 and the second terminus 223 have the different shapes. As shown in FIG. 2A, the first terminus 213 and the second terminus 223 can be rounded. Alternatively, in some embodiments, at least one of the first terminus 213 and the second terminus 223 are tapered, pointed, twisted, pinched, flat, or have any other geometrical shape. In some embodiments, the arms and terminus connect so the penile constriction device is an overall oval shape.

The first arm 210 and the second arm 220 extend from opposing ends of the bridge 230. Optionally, in this or any other embodiment, at least one of the first arm 210 and the second arm 220 extends radially and transversely from the bridge 230. Optionally, in this or any other embodiment, at least one of the first arm 210 and the second arm 220 extend downward relative to the superior side of the bridge 230. Optionally, in this or any other embodiment, at least one of the first arm 210 and the second arm 220 extend radially and transversely downward relative to the superior side of the bridge 230. Optionally, in this or any other embodiment, at least one of the first arm 210 below the first coupling end 211 and the second arm 220 extends radially and mesially below the second coupling end 221. Optionally, in this or any other embodiment, at least one of the first arm 210 below the first coupling end 211 and the second arm 220 extends radially and medially below the second coupling end 221. Optionally, in this or any other embodiment, at least one of the first arm 210 below the first coupling end 211 and the second arm 220 extends downward towards the constriction region 260 below the second coupling end 221. Optionally, in this or any other embodiment, at least one of the first arm 210 below the first coupling end 211 and the second arm 220 below the second coupling end 221 extend radially, mesially, and downward towards the constriction region 260. Optionally, in this or any other embodiment, at least one of the first arm 210 below the first coupling end 211 and the second arm 220 below the second coupling end 221 extend radially, medially and downward towards the constriction region 260.

Optionally, in this or any other embodiment, the first arm 210 and the second arm 220 extend symmetrically from opposing ends of the bridge 230. Optionally, in this or any other embodiment, at least one of the first arm 210 and the second arm 220 are symmetric about a center plane of the bridge 230. Optionally, in this or any other embodiment, the arched rod 250 is symmetric about one or more planes. Optionally, in this or any other embodiment, the arched rod 250 is symmetric about two planes. Optionally, in this or any other embodiment, the arched rod 250 is symmetric about two perpendicular planes. Optionally, in this or any other embodiment, the arched rod 250 comprises a curvilinear rod. Optionally, in this or any other embodiment, the first arm 210 and the second arm 220 are asymmetric about the bridge 230. Optionally, in this or any other embodiment, at least one of the first arm 210 and the second arm 220 are asymmetric about a center plane of the bridge 230. Optionally, in this or any other embodiment, the arched rod 250 is asymmetric about one or more planes.

Optionally, in this or any other embodiment, at least one of the first arm and the second arm 220 extends radially and transversely below the constriction region 260. Optionally, in this or any other embodiment, at least one of the first arm and the second arm 220 extends downward towards the first terminus 213 and the second terminus 223, respectively, below the constriction region 260. Optionally, in this or any other embodiment, at least one of the first arm and the second arm 220 extends radially, transversely, and downward towards the first terminus 213 and the second terminus 223, respectively, below the constriction region 260.

Optionally, in this and other embodiments, the penile constriction device may portray a mesial divergence of at least one of the first arm 210 and the second arm 220 from the bridge 230. A first mesial divergence 215 may optionally form within the first coupling end 211 of the first arm 210 and a second mesial divergence 225 may optionally form within the second coupling end 221 of the second arm 220, respectively. The transverse divergence of at least one of the first arm 210 and the second arm 220 from the constriction region 260 may forms a first elbow 214 within the first converging end 212 of the first arm 210 and a second elbow 224 within the second converging end 222 of the second arm 220, respectively.

Per FIG. 2A, the first coupling end 211, the second coupling end 221, the first converging end 212, the second converging end 222, the first terminus 213, the second terminus 223, the first mesial bend 215, the second mesial bend 225, the first elbow 214, and the second elbow 224 is inferior to the superior side of the bridge 230. Optionally, in this or any other embodiment, at least one of the first coupling end 211, the second coupling end 221, the first converging end 212, the second converging end 222, the first terminus 213, the second terminus 223, the first mesial bend 215, the second mesial bend 225, the first elbow 214, and the second elbow 224 may be inferior to the inferior side of the bridge 230. Optionally, in this or any other embodiment, at least one of the first coupling end 211, the second coupling end 221, the first converging end 212, the second converging end 222, the first terminus 213, the second terminus 223, the first mesial bend 215, the second mesial bend 225, the first elbow 214, and the second elbow 224 is inferior to the superior side of the bridge 230. Optionally, in this or any other embodiment, at least a portion of the first coupling end 211 is superior to at least a portion of the second coupling end 221. Optionally, in this or any other embodiment, at least a portion of the first coupling end 211 is inferior to at least a portion of the second coupling end 221. Optionally, in this or any other embodiment, the first coupling end 211 is neither inferior, nor superior to the second coupling end 221. Optionally, in this or any other embodiment, at least a portion of the first converging end 212 is superior to at least a portion of the second converging end 222. Optionally, in this or any other embodiment, at least a portion of the first converging end 212 is inferior to at least a portion of the second converging end 222. Optionally, in this or any other embodiment, the first converging end 212 is neither superior nor inferior to the second converging end 222. Optionally, in this or any other embodiment, the first terminus 213 is superior to the second terminus 223. Optionally, in this or any other embodiment, the first terminus 213 is inferior to the second terminus 223. Optionally, in this or any other embodiment, the first terminus 213 is neither inferior nor superior to the second terminus 223. Optionally, in this or any other embodiment, at least a portion of the first mesial bend 215 is superior to at least a portion of the second mesial bend 225. Optionally, in this or any other embodiment, at least a portion of the first mesial bend 215 is inferior to at least a portion of the second mesial bend 225. Optionally, in this or any other embodiment, the entirety of the first mesial bend 215 is neither inferior nor superior to the entirety of the second mesial bend 225. Optionally, in this or any other embodiment, at least a portion of the first elbow 214 is superior to at least a portion of the second elbow 224. Optionally, in this or any other embodiment, at least a portion of the first elbow 214 is inferior to at least a portion of the second elbow 224. Optionally, in this or any other embodiment, the entirety of the first elbow 214 is neither inferior nor superior to the entirety of the second elbow 224.

Optionally, in this or any other embodiment, a demarcation between the first arm 210 and the bridge 230 may comprise the termination of the first mesial bend 215. Optionally, in this or any other embodiment, a demarcation between the first arm 210 and the bridge 230 comprises the location of the friction protrusion 231 closest to the first arm 210. Optionally, in this or any other embodiment, a demarcation between the second arm 220 and the bridge 230 comprises the termination of the second mesial bend 225. Optionally, in this or any other embodiment, a demarcation between the second arm 220 and the bridge 230 comprises the location of the friction protrusion 231 closest to the second arm 220.

As seen in FIG. 2A, at least a portion of the first arm 210 may be tangent to a portion of the bridge 230. Optionally, in this or any other embodiment, at least a portion of the first coupling end 211 is tangent to a portion of the bridge 230. Optionally, in this or any other embodiment, at least a portion of the first arm 210 is tangent to a portion of the inferior side of bridge 230. Optionally, in this or any other embodiment, at least a portion of the first coupling end 211 is tangent to a portion of the inferior side of bridge 230. Optionally, in this or any other embodiment, at least a portion of the first arm 210 is tangent to a portion of the superior side of bridge 230. Optionally, in this or any other embodiment, at least a portion of the first coupling end 211 is tangent to a portion of the superior side of bridge 230. Optionally, in this or any other embodiment, at least a portion of the second arm 220 is tangent to a portion of the bridge 230. Optionally, in this or any other embodiment, at least a portion of the second coupling end 221 is tangent to a portion of the bridge 230. Optionally, in this or any other embodiment, at least a portion of the second arm 220 is tangent to a portion of the inferior side of bridge 230. Optionally, in this or any other embodiment, at least a portion of the second coupling end 221 is tangent to a portion of the inferior side of bridge 230. Optionally, in this or any other embodiment, at least a portion of the second arm 220 is tangent to a portion of the superior side of bridge 230. Optionally, in this or any other embodiment, at least a portion of the second coupling end 221 is tangent to a portion of the superior side of bridge 230.

The first terminus 213 and the second terminus 223, per FIG. 2A, comprise a rounded shape. Optionally, in this or any other embodiment, at least one of the first terminus 213 and the second terminus 223 comprise a pointed shape, a tapered shape, a twisted shape, a blunt shape, a polygonal shape, a bulge shape, or any combination thereof. Per FIG. 2, the first terminus 213 and the second terminus 223 may be equivalent. Optionally, in any other embodiment, the first terminus 213 and the second terminus 223 are not equivalent.

The penile constriction device 100 in FIG. 2A has a constriction gap width 261 wherein the constriction gap width 261 is measured as a minimum distance between the first converging end 212 and the second converging end 222 within the constriction region 260. Optionally, in this or any other embodiment, the constriction gap width 261 is measured as a minimum distance between a mesial vertex of the surface of the first elbow 214 and a mesial vertex of the surface of the second elbow 224. Optionally, in this or any other embodiment, the constriction gap width 261 is measured as a minimum distance between the first arm 210 and the second arm 220. Optionally, in this or any other embodiment, the constriction gap distance 261 is measured as a minimum normal distance between the first elbow 214 and the second elbow 214 within the constriction region 260. Optionally, in this or any other embodiment, the constriction gap width 261 is normal to at least one of a mesial vertex of the surface of the first converging end 212 a mesial vertex of the surface of the second converging end 212, the first arm 210, and the second arm 220.

The penile constriction device 100 in FIG. 2A has a constriction gap distance 261 of greater than 0 inches. Optionally, in this or any other embodiment, the constriction gap distance 261 is negligible or equal to zero, wherein the first arm 210 and the second arm 220 are in temporary and divisible contact. Optionally, in other embodiments, the penile constriction device may have no constriction gap distance (or no constriction region) because the first elbow and the second elbow are permanently physically connected. Optionally, in other embodiments, the penile constriction device may have no constriction gap distance (or no constriction region) because the first arm and the second are permanently physically connected. Optionally, in this or any other embodiment, a recess is formed between the first arm 210, the second arm 220, the bridge 230, and the constriction region 260. Optionally, in this or any other embodiment, the recess is configured to fit around a penis. Optionally, in this or any other embodiment, the constriction region 260 is superior to at least one of the first terminus 213 and the second terminus 223. Optionally, in this or any other embodiment, the constriction region 260 is inferior to at least one of the first terminus 213 and the second terminus 223.

The penile constriction device 100 in FIG. 2A has a constriction height 280, wherein the constriction height 280 may be measured as a normal distance between a constriction point 262 and the constriction region 240. Optionally, in this or any other embodiment, the constriction height 280 is measured as a normal distance between the constriction point 262 and the inferior side of the bridge 230. Optionally, in this or any other embodiment, the constriction height 280 is measured as a normal distance between the constriction point 262 and the inferior side of the bridge 230. Optionally, in this or any other embodiment, the constriction height 280 is measured as a normal distance between the first elbow 214 and the inferior side of the bridge 230. Optionally, in this or any other embodiment, the constriction height 280 is measured as a normal distance between the second elbow 224 and the inferior side of the bridge 230. Optionally, in this or any other embodiment, the constriction height 280 is measured as a normal distance between the most mesial point of the first converging end 212 and the inferior side of the bridge 230. Optionally, in this or any other embodiment, the constriction height 280 is measured as a normal distance between the most mesial point of the second converging end 222 and the inferior side of the bridge 230. Optionally, in this or any other embodiment, the constriction height 280 is measured as a normal distance between the first elbow 214 and the compression region 240. Optionally, in this or any other embodiment, the constriction height 280 is measured as a normal distance between the second elbow 224 and the compression region 240. Optionally, in this or any other embodiment, the constriction height 280 is measured as a normal distance between the most mesial point of the first converging end 212 and the compression region 240. Optionally, in this or any other embodiment, the constriction height 280 is measured as a normal distance between the most mesial point of the second converging end 222 and the compression region 240. Optionally, in this or any other embodiment, the constriction height 280 is measured as a normal distance between the first elbow 214 and the most inferior point of the compression region 240. Optionally, in this or any other embodiment, the constriction height 280 is measured as a normal distance between the second elbow 224 and the most inferior point of the compression region 240. Optionally, in this or any other embodiment, the constriction height 280 is measured as a normal distance between the most mesial point of the first converging end 212 and the most inferior point of the compression region 240. Optionally, in this or any other embodiment, the constriction height 280 is measured as a normal distance between the most mesial point of the second converging end 222 and the most inferior point of the compression region 240. Optionally, in this or any other embodiment, the constriction height 280 is measured as a normal distance between the first elbow 214 and the most superior point of the compression region 240. Optionally, in this or any other embodiment, the constriction height 280 is measured as a normal distance between the second elbow 224 and the most superior point of the compression region 240. Optionally, in this or any other embodiment, the constriction height 280 is measured as a normal distance between the most mesial point of the first converging end 212 and the most superior point of the compression region 240. Optionally, in this or any other embodiment, the constriction height 280 is measured as a normal distance between the most mesial point of the second converging end 222 and the most superior point of the compression region 240. Per FIG. 2, the constriction height 280 is perpendicular to at least one of the constriction gap width 261 and the inferior side of the bridge 230. Alternatively, the constriction height 280 is oblique to at least one of the constriction gap width 261 and the inferior side of the bridge 230.

The penile constriction device 100 in FIG. 2A has a constriction point 262, wherein the constriction point 262 may be defined as the midpoint of the constriction gap width 261. Optionally, in this or any other embodiment, the constriction point 262 is defined as a minimally equidistant point from the first converging end 212 and the second converging end 222. Optionally, in this or any other embodiment, the constriction point 262 is defined as a minimally equidistant point from the first arm 210 and the second arm 220. Optionally, in this or any other embodiment, the constriction point 262 is defined as a minimally equidistant point from the first elbow 214 and the second elbow 224.

The penile constriction device 100 in FIG. 2A, has a maximum inner width 270, wherein the maximum inner width 270 may be measured as a maximum normal distance between a mesial vertex of the surface of the first arm 210 and a mesial vertex of the surface of the second arm 220. Optionally, in this or any other embodiment, the maximum inner width 270 is measured as a maximum normal distance between a mesial vertex of the surface of the first converging end 212 and a mesial vertex of the surface of the second converging end 222. Optionally, in this or any other embodiment, the maximum inner width 270 is measured as major axis of an ellipse formed by the first coupling end 211, the bridge 230, and the second coupling end 221. Optionally, in this or any other embodiment, the maximum inner width 270 and the constriction gap width 261 are parallel. Optionally, in this or any other embodiment, the maximum inner width 270 and the constriction gap width 261 are oblique. Optionally, in this or any other embodiment, the maximum inner width 270 and the constriction gap width 261 are coplanar. Optionally, in this or any other embodiment, the maximum inner width 270 and the constriction gap width 261 are non-coplanar. Optionally, in this or any other embodiment, the maximum inner width 270 is superior to the constriction gap 260.

The penile constriction device 100 in FIG. 2A has a center point 291 defined as the midpoint of a maximum normal distance between a mesial vertex of the surface of the first arm 210 and a mesial vertex of the surface of the second arm 220. Optionally, in this or any other embodiment, the center point 291 is defined as the midpoint of the maximum inner width 270. Optionally, in this or any other embodiment, the center point 291 is defined as a point minimally equidistant from a mesial vertex of the surface of the first arm 210 and a mesial vertex of the surface of the second arm 220. Optionally, in this or any other embodiment, the center point 291 is defined as point minimally equidistant from the first converging end 211 and the second converging end 221. Optionally, in this or any other embodiment, the center point 291 is defined as the center of an ellipse formed by the first coupling end 211, the bridge 230, and the second coupling end 221.

The device 100, per FIG. 2A, has an inferior height 290, wherein the maximum inferior height 290 may be measured as a normal distance between the center point 291 and the compression region 240. Optionally, in this or any other embodiment, the inferior height 290 is measured as a normal distance between the center point 291 and the inferior side of the bridge 230. Optionally, in this or any other embodiment, the inferior height 290 is parallel to the constriction height 280. Optionally, in this or any other embodiment, the inferior height 290 and the constriction height 280 are collinear. Optionally, in this or any other embodiment, the inferior height 290 is perpendicular to at least one of the constriction gap width 261 and the maximum inner width 270. Optionally, in this or any other embodiment, the inferior height 290 is coplanar with at least one of the constriction gap width 261, the maximum inner width 270, the constriction height 280, and the constriction point 262.

The device 100, per FIG. 2A, has a thickness 251, wherein the thickness 251 may be measured as a maximum normal cross-sectional width of at least a portion of the first arched rod 250. Optionally, in this or any other embodiment, the thickness 251 of the arched rod 250 is measured as a maximum outer distance between two opposing points of its normal cross-section. Optionally, in this or any other embodiment, the thickness 251 is measured as a maximum normal cross-sectional width of at least a portion of at least one of the first arm 210 and the second arm 220. Optionally, in this or any other embodiment, the thickness 251 of the first arm 210, the second arm 220, and the bridge 230, is measured as a maximum outer distance between two opposing points on the surfaces of their respective normal cross-sections. Optionally, in this or any other embodiment, the thickness 251 of at least two of the first arm 210, the second arm 220, and the bridge 230 are the same. Optionally, in this or any other embodiment, the thickness 251 of at least two of the first arm 210, the second arm 220, and the bridge 230 are unequal. Optionally, in this or any other embodiment, at least one of the first arm 210, the second arm 220, and the bridge 230 have a uniform thickness 251. Optionally, in this or any other embodiment, at least one of the first arm 210, the second arm 220, and the bridge 230 have a non-uniform thickness 251, wherein the thickness 251 varies along its span.

The device 100, per FIG. 2A, has a first termination distance 212a and a second termination distance 222a, wherein the first termination distance 212a may be measured as the maximum normal distance between the constriction gap width 261 and the first terminus 213, and wherein the second termination distance 222a may be measured as the maximum normal distance between the constriction gap width 261 and the second terminus 223. Optionally, in this or any other embodiment, the first termination distance 212a is measured as the maximum normal distance between the first elbow 214 and the first terminus 213. Optionally, in this or any other embodiment, the first termination distance 212a is measured as the maximum normal distance between the second elbow 224 and the second terminus 223. Optionally, in this or any other embodiment, at least one of the first termination distance 212a and the second termination distance 222a is about 0.2 inches to about 0.8 inches. Optionally, in this or any other embodiment, at least one of the first termination distance 212a and the second termination distance 222a is at least about 0.2 inches. Optionally, in this or any other embodiment, at least one of the first termination distance 212a and the second termination distance 222a is at most about 0.8 inches. Optionally, in this or any other embodiment, at least one of the first termination distance 212a and the second termination distance 222a is a constant and does not scale with the maximum inner width 270, the constriction height 280, the inferior height 290, or the constriction gap width 261.

As seen in FIG. 2A, the first arm 210 and the second arm 220 may be generally parallel at a point superior to the constriction region 260. Optionally, in this or any other embodiment, the first arm 210 and the second arm 220 are not parallel at a point superior to the constriction region 260. Optionally, in this or any other embodiment, the first arm 210 and the second arm 220 are separated at a point superior to the constriction region 260 by a constriction angle 263. Optionally, in this or any other embodiment, the constriction angle 263 is measured as a normal interior angle between the first arm 210 and the second arm 220 at a point superior to the constriction region 260.

As further seen in FIG. 2A, the first arm 210 and the second arm 220 may be generally parallel at a point inferior to the constriction region 260. Optionally, in this or any other embodiment, the first arm 210 and the second arm 220 are not parallel at a point inferior to the constriction region 260. Optionally, in this or any other embodiment, the first arm 210 and the second arm 220 are separated at a point inferior to the constriction region 260 by a termination angle 264. Optionally, in this or any other embodiment, the termination angle 264 is measured as a normal interior angle between the first arm 210 and the second arm 220 at a point inferior to the constriction region 260.

Optionally, in this or any other embodiment, the first arm 210 and the second arm 220 have a first arm length and a second arm length, respectively. Optionally, in this or any other embodiment, the first arm 210 has a first length measured a maximal span between the first coupling end 211 and the first terminus 213. Optionally, in this or any other embodiment, the second arm 220 has a second arm length measured as a maximal span between the second coupling end 221 and the second terminus 223. Optionally, in this or any other embodiment, the bridge 230 has a bridge length measured as a maximal span of the bridge 230 between the first arm 210 and the second arm 220. Optionally, in this or any other embodiment, the bridge 230 has a bridge length measured as a maximal span of the bridge 230 between the first coupling end 211 and the second coupling end 221. Optionally, in this or any other embodiment, the first arm length is equal to the second arm length. Optionally, in this or any other embodiment, the first arm length is greater or less than the second arm length. Optionally, in this or any other embodiment, at least one of the first arm length and the second arm length is greater or less than the bridge length. Optionally, in this or any other embodiment, at least one of the first arm length and the second arm length is equal to the bridge length.

Optionally, in this or any other embodiment, the first mesial divergence 215, the second mesial divergence 225, the first elbow 214, and the second elbow 224 have a first mesial radius, a second mesial radius, a first elbow radius, and a second elbow radius, respectively. Optionally, in this or any other embodiment, the first mesial radius is equal to or greater than at least one of the second mesial radius, the first elbow radius, and the second elbow radius. Optionally, in this or any other embodiment, the second mesial radius is equal to or greater than at least one of the first mesial radius, the first elbow radius, and the second elbow radius. Optionally, in this or any other embodiment, the first elbow radius is equal to or greater than at least one of the first mesial radius, the second mesial radius, and the second elbow radius. Optionally, in this or any other embodiment, the second elbow radius is equal to or greater than at least one of the first mesial radius, the second mesial radius, and the first elbow radius.

Figure 2B:
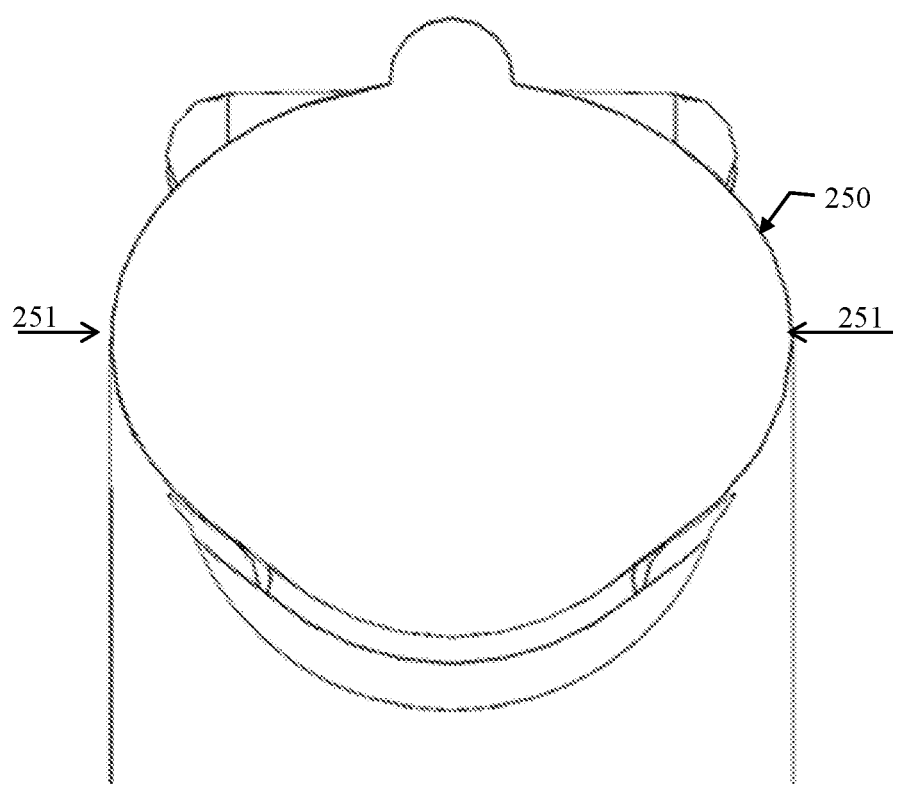
FIG. 2B shows a side cross-sectional view of a non-limiting example of the penile constriction device of FIG. 1.

FIG. 2B shows a side cross-sectional view of a non-limiting example of the penile constriction device of FIG. 1. Optionally, in this or any other embodiment, at least one of the first arm 210, the second arm 220, and the bridge 230 has a uniform normal cross sectional shape. Optionally, in this or any other embodiment, at least one of the first arm 210, the second arm 220, and the bridge 230 have a uniform normal cross sectional shape. Optionally, in this or any other embodiment, at least one of the first arm 210, the second arm 220, and the bridge 230 have a non-uniform normal cross sectional shape. Optionally, in this or any other embodiment, at least two of the first arm 210, the second arm 220, and the bridge 230 have the same normal cross sectional shape. Optionally, in this or any other embodiment, at least two of the first arm 210, the second arm 220, and the bridge 230 have dissimilar normal cross sectional shapes. Per FIG. 2B, the bridge 230 may have a normal cross section comprising an ellipse. Optionally, in this or any other embodiment, at least one of the first arm 210, the second arm 220, and the bridge 230 have a normal cross section comprising a circle, an oval, an ellipse, a polygon, an irregular shape, a hollow shape, or any combination thereof. Optionally, in this or any other embodiment, at least one of the first arm 210, the second arm 220, and the bridge 230 have a normal cross section comprising a c-shape, an x-shape, a T-shape, or an H-shape.

Figure 2C:
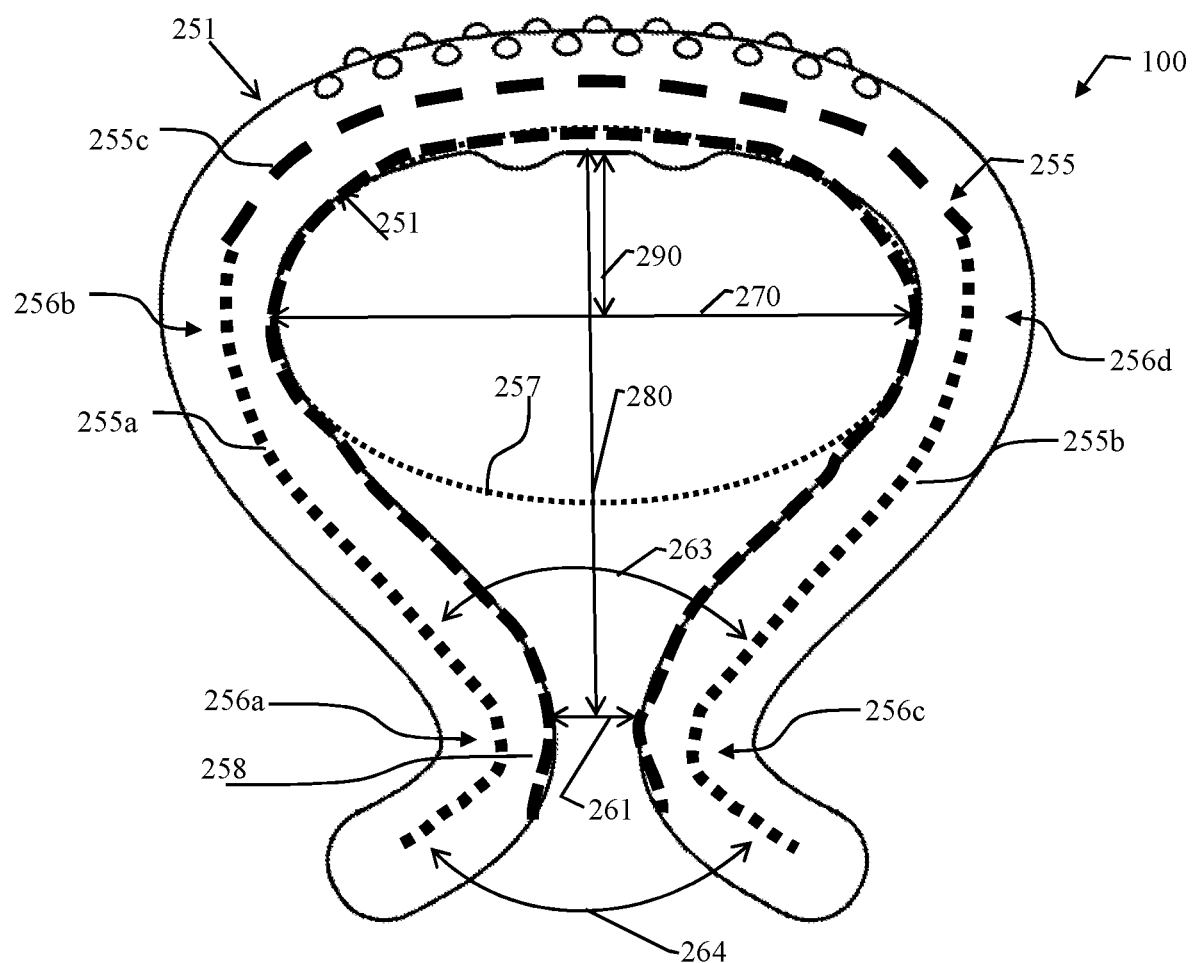
FIG. 2C shows an alternative front view of a non-limiting example of the penile constriction device of FIG. 1.

FIG. 2C shows an alternative front view of a non-limiting example of the penile constriction device of FIG. 1. Optionally, in this or any other embodiment, the arched rod 250 comprises an arched axis 255 comprising a curve defined by the centroids of the normal cross sections of the arched rod 250 along its span. Optionally, in this or any other embodiment, the first arm 210, the second arm 220, and the bridge 230 comprise a first arched axis 255a, a second arched axis 255b, and a third arched axis 255c, respectively. Optionally, in this or any other embodiment, the first arched axis 255a and the second arched axis 255b are coincident, tangent, or both. Optionally, in this or any other embodiment, the second arched axis 255b and the third arched axis 255c are coincident, tangent, or both. Optionally, in this or any other embodiment, at least one of the first arched axis 255a, the second arched axis 255b, and the third arched axis 255c comprises a planar curve which is completely coincident with a single plane. Optionally, in this or any other embodiment, at least two of the first arched axis 255a, the second arched axis 255b, and the third arched axis 255c are coplanar.

Per FIG. 2C, the first arched axis 255a may comprise at least one of a first transverse bend 256a and a first mesial bend 256b. Optionally, in this or any other embodiment, the third arched axis 255c comprises the first mesial bend 256b. Optionally, in this or any other embodiment, the first transverse bend 256a comprises the first elbow 214. Optionally, in this or any other embodiment, the first mesial bend 256b comprises the first mesial divergence 215. Optionally, in this or any other embodiment, the first mesial bend 256c is superior to the first transverse bend 256a. Optionally, in this or any other embodiment, the second arched axis 255b comprises at least one of a second transverse bend 256c and a second mesial bend 256d. Optionally, in this or any other embodiment, the third arched axis 255c comprises the second mesial bend 256d. Optionally, in this or any other embodiment, the second transverse bend 256c comprises the second elbow 224. Optionally, in this or any other embodiment, the second mesial bend 256d comprises the second mesial divergence 225. Optionally, in this or any other embodiment, the second mesial bend 256c is superior to the second transverse bend 256d. Optionally, in this or any other embodiment, a demarcation between the first arched axis 255a and the bridge 255c comprises the termination of the first mesial bend 256b. Optionally, in this or any other embodiment, a demarcation between the first arched axis 255a and the bridge 255c comprises the location of the friction protrusion 231 closest to the first arched axis 255a. Optionally, in this or any other embodiment, a demarcation between the second arched axis 255b and the bridge 255c comprises the termination of the second mesial bend 256d. Optionally, in this or any other embodiment, a demarcation between the second arched axis 255b and the bridge 255c comprises the location of the friction protrusion 331 closest to the second arched axis 255b. Optionally, in this or any other embodiment, the radius of the first transverse bend 256a is equal to or greater than the radius of the first mesial bend 256b. Optionally, in this or any other embodiment, the radius of the first transverse bend 256a is less than the radius of the first mesial bend 256b. Optionally, in this or any other embodiment, the radius of the second transverse bend 256c is equal to or greater than the radius of the second mesial bend 256d. Optionally, in this or any other embodiment, the radius of the second transverse bend 256c is less than the radius of the second mesial bend 256d. Optionally, in this or any other embodiment, the radius of the first transverse bend 256a is equal to or greater than the radius of the second transverse bend 256c. Optionally, in this or any other embodiment, the radius of the first transverse bend 256a is less than the radius of the second transverse bend 256c. Optionally, in this or any other embodiment, the radius of the first mesial bend 256b is equal to or greater than the radius of the second mesial bend 256d. Optionally, in this or any other embodiment, the radius of the first mesial bend 256b is less than the radius of the second mesial bend 256d.

Per FIG. 2C, at least a portion of the first arched axis 255a, the second arched axis 255b, and the third arched axis 255c may form a portion of an ellipse 257. Optionally, in this or any other embodiment, the ellipse 257 has a major axis and a minor axis, wherein the major axis greater than the minor axis. Optionally, in this or any other embodiment, the major axis is oriented from the first arched axis 255a to the second arched axis 255b, along the third arched axis 255c.

As seen in FIG. 2C, the arched rod 250 may comprise a mesial vertex arched axis 258. Optionally, in this or any other embodiment, the mesial vertex arched axis 258 is defined as a single continuous line that is coincident to the surface of the arched rod 250 and closest to the center point 291. Optionally, in this or any other embodiment, the mesial vertex arched axis 258 is substantially planar. Optionally, in this or any other embodiment, the mesial vertex arched axis 258 and the arched axis 255 are substantially coplanar. Optionally, in this or any other embodiment, the mesial vertex arched axis 258 and at least one of the first arched axis 255a, the second arched axis 255b, and the third arched axis 255c are substantially coplanar.

Per FIG. 2C, the constriction gap width 261 of the arched rod 250 may be measured as a minimum separation of the mesial vertex arched axis 255 within the constriction region 260. Optionally, in this or any other embodiment, the first arm length, the second arm length, and the bridge a length are measured as an arc length of the first arched axis 255a, the second arched axis 255b, and the third arched axis 255c, respectively. Optionally, in this or any other embodiment, the inferior height 290 is measured as a half the minor axis of the ellipse formed by the first coupling end 211, the bridge 230, and the second coupling end 221. Optionally, in this or any other embodiment, the constriction height 280 is measured as a maximum normal distance between the constriction point 262 and the mesial arched axis 255. Optionally, in this or any other embodiment, the constriction height 280, is perpendicular to the mesial vertex arched axis 258. Optionally, in this or any other embodiment, the maximum inner width 270, is measured as a maximum normal separation distance of the mesial vertex arched axis 270. Optionally, in this or any other embodiment, the inferior height 290 is measured, as a normal distance between the center point 291 and the mesial vertex arched axis 258. Optionally, in this or any other embodiment, the minor axis is twice the inferior height 290. Optionally, in this or any other embodiment, a center point of the ellipse 257 is the center point 291.

Per FIG. 2C, the constriction angle 263 of the arched rod 250 may be measured as a normal interior angle between the first arched axis 255a and the second arched axis 255b at a point inferior to the constriction region 260. Optionally, in this or any other embodiment, the first arched axis 255a and the second arched axis 255b are parallel at a point inferior to the constriction region 260. Optionally, in this or any other embodiment, the first arched axis 255a and the second arched axis 255b are not parallel a point inferior to the constriction region 260.

Per FIG. 2C, the termination angle 264 may be measured as a normal interior angle between the first arched axis 255a and the second arched axis 255b at a point inferior to the constriction region 260. Optionally, in this or any other embodiment, the first arched axis 255a and the second arched axis 255b are parallel at a point inferior to the constriction region 260. Optionally, in this or any other embodiment, the first arched axis 255a and the second arched axis 255b are not parallel a point inferior to the constriction region 260.

Per FIG. 2C, the thickness 251 may be measured, as twice the normal distance between the mesial vertex arched axis 255 and at least one of the first arched axis 255a, the second arched axis 255b, and the third arched axis 255c. Optionally, in this or any other embodiment, the thickness 251 of the first arm 210, the second arm 220, and the bridge 230 are measured as a maximum outer distance that is normal to the first arched axis 255a, the second arched axis 255b, and the third arched axis 255c, respectively. Optionally, in this or any other embodiment, the normal cross section is defined as being normal to at least one of the first arched axis 255a, the second arched axis 255b, and the third arched axis 255c. Optionally, in this or any other embodiment, the normal cross section of at least one of the first arm 210, the second arm 220, and the bridge 230 helically twists along the first arched axis 210, the second arched axis 220, and the third arched axis 230, respectively. Optionally, in this or any other embodiment, the arched rod has a two-dimensional cavity area measured as a two-dimensional area confined by the constriction gap width, and the mesial vertex arched axis 258.

As seen in FIGS. 1 and 2A-C, at least one of the first elbow 214 and the second elbow 224, the first mesial bend 215, the second mesial bend 225, the first converging end 212, the second converging end 222, the first terminus 213, and the second terminus 223 may be configured to enable a user to grasp and apply a force to the device 100. Optionally, in this or any other embodiment, at least one of the first elbow 214, the second elbow 224, the first mesial bend 215, the second mesial bend 225 the first terminus 213, and the second terminus 223 enable a user to grasp and apply a force between the first arm 210 and the second arm 220. Optionally, in this or any other embodiment, at least one of the first elbow 214, the second elbow 224, the first mesial bend 215, the second mesial bend 225 the first terminus 213, and the second terminus 223 enable a user to grasp and apply a force to the device 100 to increase the constriction gap 261. Optionally, in this or any other embodiment, at least one of the first elbow 214, the second elbow 224, the first mesial bend 215, the second mesial bend 225, the first terminus 213, and the second terminus 223 enable a user to grasp and apply a force to the device 100 to increase the constriction gap 261 and install the device by passing the penis through the constriction gap 260.

Optionally, in this or any other embodiment, the device 100 is ductile (flexible and/or elastic), wherein an applied force modifies the shape of the arched rod 250, and wherein the arched rod 250 returns to its original shape upon cessation of the applied force. Optionally, in this or any other embodiment, at least one of the first arm 210, the second arm 220, and the bridge 230 is ductile. Optionally, in this or any other embodiment, the device 100 is pliable, wherein an applied force modifies the shape of the arched rod 250, and wherein the shape of the arched rod 250 does not return to its original shape upon cessation of the applied force. Optionally, in this or any other embodiment, at least one of the first arm 210, the second arm 220, and the bridge 230 is pliable. Optionally, in this or any other embodiment, the arched rod 250 is ductile and pliable. Optionally, in this or any other embodiment, at least one of the first arm 210, the second arm 220, and the bridge 230 is ductile and pliable. Optionally, in this or any other embodiment, at least one of the first arm 210, the second arm 220, and the bridge 230 is ductile and not pliable. Optionally, in this or any other embodiment, at least one of the first arm 210, the second arm 220, and the bridge 230 is pliable and not ductile. Optionally, in this or any other embodiment, at least one of the first arm 210, the second arm 220, is more ductile than the bridge 230. Optionally, in this or any other embodiment, at least one of the first arm 210, the second arm 220, is more pliable than the bridge 230. Optionally, in this or any other embodiment, at least one of the first arm 210, the second arm 220, is less ductile than the bridge 230. Optionally, in this or any other embodiment, at least one of the first arm 210, the second arm 220, is less pliable than the bridge 230. Optionally, in this or any other embodiment, the first arm 210 is more pliable than the second arm 220. Optionally, in this or any other embodiment, the first arm 210 is more ductile than the second arm 220. Optionally, in this or any other embodiment, the first arm 210 is less pliable than the second arm 220. Optionally, in this or any other embodiment, the first arm 210 is less ductile than the second arm 220.

Optionally, in this or any other embodiment, the arched rod 250 is ductile, wherein the constriction gap 261 returns to its original size upon cessation of the applied force. Optionally, in this or any other embodiment, the ductility of the arched rod 250 enables a user to apply the device 100 to the penis by applying a tensile force between the first converging end 212 and/or the first terminus 213 and the second converging end 222 and/or the second terminus 223 to increase the constriction gap 261, inserting the device 100 onto the penile area, and releasing the tensile force. Optionally, in this or any other embodiment, once the tensile force is released, the constriction gap 261 of the arched rod 250 is greater than the constriction gap 261 of an unstressed and/or unapplied device 100. Optionally, in this or any other embodiment, once the tensile force is released, the ductile arched rod 250 maintains a compressive force against the penile area.

Optionally, in this or any other embodiment, a tensile force applied between the first converging end 212 and/or the first terminus 213 and the second converging end 222 and/or the second terminus 223, increases the constriction gap 260. Optionally, in this or any other embodiment, a compressive force applied between the first converging end 212 and the second converging end 222 decreases the constriction gap 261.

Figure 3A:
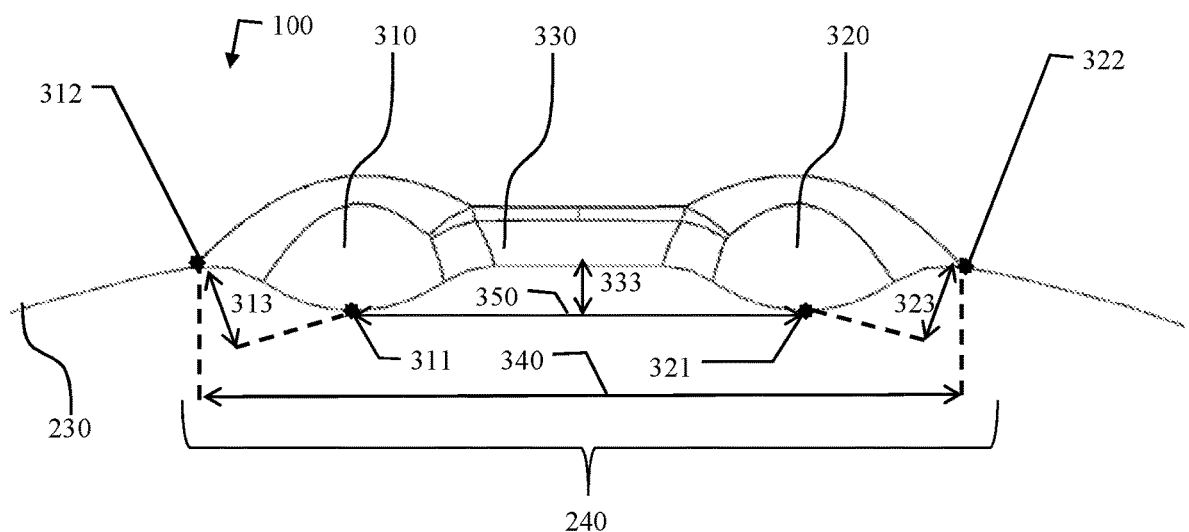
FIG. 3A shows a detailed front view of the compression region of a non-limiting example of the penile constriction device of FIG. 1.
Figure 3B:
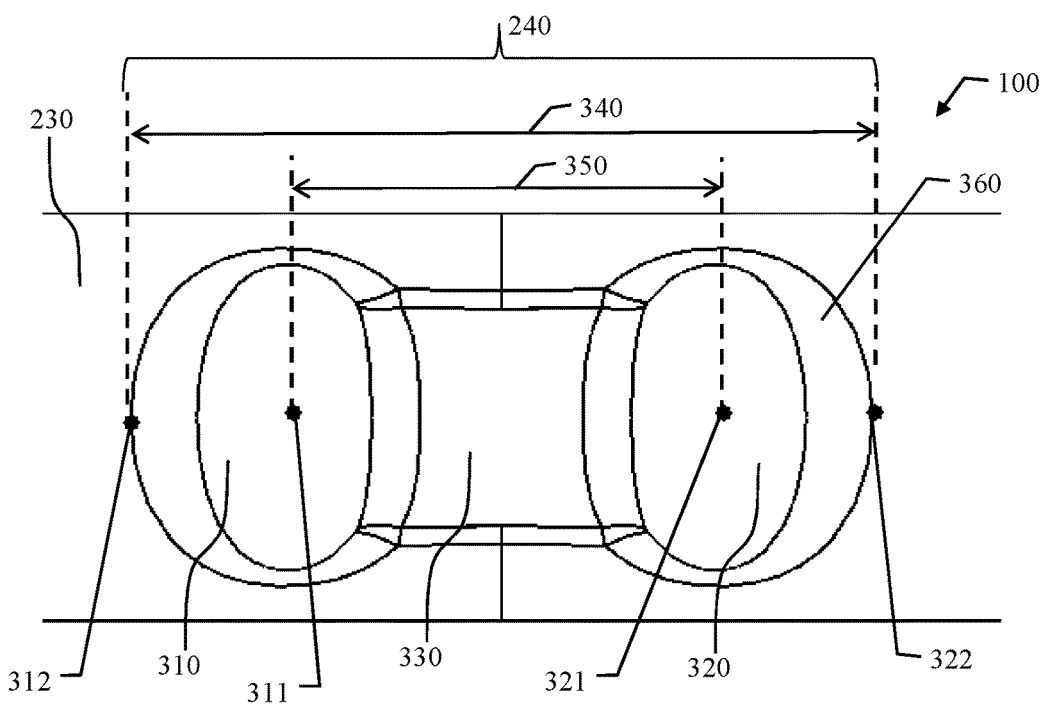
FIG. 3B shows a detailed bottom view of the compression region of a non-limiting example of the penile constriction device of FIG. 1.

FIG. 3A shows a detailed front view of the compression region 240 of a non-limiting example of the penile constriction device 100 of FIG. 1. FIG. 3B shows a detailed bottom view of the compression region 240 of the penile constriction device 100 of FIG. 1. Provided herein is a penile constriction device 100 comprising an arched rod 250 comprising a bridge 230 having a compression region 240 rising inferiorly from an inferior side of the bridge 230.

Per FIGS. 3A-B, the compression region 240 may comprise a first dorsal vein protrusion 310 and a second dorsal vein protrusion 320 rising from the inferior side of the bridge 230. Further, the first dorsal vein protrusion 310 may comprise at least one of a first dorsal apex 311 and a first lateral edge 312. The first lateral edge 312, per FIG. 3A, may be disposed at the most transverse point along the intersection between the first dorsal vein protrusion 310 and the inferior side of the bridge 230. Alternatively, in this or any other embodiment, the first lateral edge 312 may be disposed at the most transverse point of the compression region 240 that is closest a first arm. The first dorsal apex 311, per FIG. 3A, may be disposed at the most inferior point on the first dorsal vein protrusion 310. Alternatively, in this or any other embodiment, the first dorsal apex 311 may be disposed at an inflection point of the first dorsal vein protrusion 310. Optionally, in this or any other embodiment, the second dorsal vein protrusion 320 comprises at least one of a second dorsal apex 321 and a second lateral edge 322. Optionally, per FIG. 3A, the second lateral edge 322 may be disposed at the most transverse point along the intersection between the second dorsal vein protrusion 320 and the inferior side of the bridge 230. Alternatively, in this or any other embodiment, the second lateral edge 322 may be disposed at the most transverse point of the compression region 240 that is closest a second arm. The second dorsal apex 321, per FIG. 3A, may be disposed at the most inferior point on the second dorsal vein protrusion 320. Alternatively, in this or any other embodiment, the second dorsal apex 321 may be disposed at an inflection point of the second dorsal vein protrusion 320. Optionally, in this or any other embodiment, the compression region 240 is integral with the inferior side of the bridge 230. Optionally, in this or any other embodiment, the compression region 240 is separate and distinct from the inferior side of the bridge 230. Optionally, in this or any other embodiment, the compression region 240 within the dorsal vein valley 330 at a center of the dorsal vein valley 330 is superior to, or has a same height relative to, the first lateral edge 312 as the first minimum normal distance or relative to the second lateral edge 322 as the second minimum normal distance, or both. Optionally, in this or any other embodiment, the compression region 240 at a center of the dorsal vein valley 330 is superior to the first lateral edge 312, the second lateral edge 322, or both. Optionally, in this or any other embodiment, the compression region 240 at a center of the dorsal vein valley 330 is inferior to the first lateral edge 312, the second lateral edge 322, or both. Optionally, in this or any other embodiment, a boundary between the first dorsal vein protrusion 310 and the dorsal vein valley 330 comprises a plane coincident with the first dorsal apex 311, and perpendicular to the dorsal vein valley distance. Optionally, in this or any other embodiment, a boundary between the second dorsal vein protrusion 220 and the dorsal vein valley 330 comprises a plane coincident with the second dorsal apex 321, and normal to the dorsal vein valley distance 350. Optionally, in this or any other embodiment, the first dorsal vein protrusion 310, the dorsal vein valley 330, and the second dorsal vein protrusion 320 are arranged sequentially within the compression region 240 in a direction along the bridge 230 from the first arm 210 to the second arm 220.

Per FIG. 3A, at least a portion of a perimeter of the compression region 240, where the compression region 240 meets inferior side of the bridge 230, optionally comprises a fillet 360. Optionally, in this or any other embodiment, the portion of a perimeter of the compression region 240 where the compression region 240 meets the inferior side of the bridge 230 comprises at least one of the intersection between the first dorsal protrusion 310 and the inferior side of the bridge 230, the intersection between the second dorsal protrusion 320 and the inferior side of the bridge 230, and the intersection between the dorsal vein valley 330 and the inferior side of the bridge 230. Optionally, in this or any other embodiment, at least one of the first dorsal protrusion 310, the second dorsal protrusion 320, and the dorsal vein valley 330 comprise a first portion, a second portion, and a fillet 360 between the first portion and the second portion. Optionally, in this or any other embodiment, the fillet 360 comprises a concave fillet, a miter fillet, or a convex fillet. Optionally, in this or any other embodiment, the fillet 360 comprises a constant fillet. Optionally, in this or any other embodiment, the fillet 360 comprises a variable fillet. Optionally, in this or any other embodiment, the fillet 360 improves the manufacturability of the device 100. Optionally, in this or any other embodiment, the fillet 360 increases the rigidity of at least one of the first dorsal vein protrusion 210, the second dorsal vein protrusion 220, and the dorsal vein valley 230. Optionally, in this or any other embodiment, the fillet 360 prevents pinching between the compression region 240 and the inferior side of the bridge 230.

As seen in FIGS. 3A-B, at least one of the first dorsal vein protrusion 210 and the second dorsal vein protrusion 220 may comprise a cross sectional shape comprising an ellipse. Optionally, in this or any other embodiment, at least one of the first dorsal vein protrusion 210 and the second dorsal vein protrusion 220 comprise a cross sectional shape comprising a circle, an oval, a polygon, or any combination thereof. Optionally, in this or any other embodiment, the first dorsal vein protrusion 210 and the second dorsal vein protrusion 220 have equivalent cross sectional shapes. Optionally, in this or any other embodiment, the first dorsal vein protrusion 210 and the second dorsal vein protrusion 220 have cross sectional shapes with a mirrored symmetry. Optionally, in this or any other embodiment, the first dorsal vein protrusion 210 and the second dorsal vein protrusion 220 have mirrored symmetry. Optionally, in this or any other embodiment, the first dorsal vein protrusion 210 and the second dorsal vein protrusion 220 have inequivalent cross sectional shapes. Optionally, in this or any other embodiment, the first dorsal vein protrusion 210 and the second dorsal vein protrusion 220 have equivalent cross sectional shapes. Optionally, in this or any other embodiment, the dorsal vein valley 230 is generally concave in one or more directions. Optionally, in this or any other embodiment, the dorsal vein valley 230 is generally convex in one or more directions.

Per FIGS. 3A-B, the compression region 240 comprises a compression region width 340 measured as a distance between the first lateral edge 312 and the second lateral edge 322. Optionally, in this or any other embodiment, the compression region width 340 is measured as a maximum width of the compression region 240 in a dimension from the first arm 210 to the second arm 220 along the inferior surface of the bridge 230. Optionally, in this or any other embodiment, the compression region width 340 is measured as a maximum normal width of the compression region 240 in a dimension from the first arm 210 to the second arm 220 along the inferior surface of the bridge 230.

Per FIGS. 3A-B, the dorsal vein valley 330 has a dorsal vein valley distance 350 measured as a distance between the first dorsal apex 311 and the second dorsal apex 321. Optionally, in this or any other embodiment, the dorsal vein valley distance 350 is measured as a maximum transverse span of the dorsal vein valley 330. Optionally, in this or any other embodiment, the dorsal vein valley distance 350 is measured as a maximum transverse and normal span of the dorsal vein valley 330

As seen in FIG. 3A, the first dorsal protrusion 310 has a first dorsal height 313 measured as a first minimum normal distance between the first dorsal apex 311 and the first lateral edge 312. Further, the second dorsal protrusion 320 may comprise a second dorsal height 323 measured as a second minimum normal distance between the second dorsal apex 321 and the second lateral edge 322. Optionally, in this or any other embodiment, the first dorsal height 313 is measured as a minimum normal distance between the first dorsal apex 311 and a perimeter of the compression region 240. Optionally, in this or any other embodiment, the second dorsal height 323 is measured as a minimum normal distance between the second dorsal apex 321 and a perimeter of the compression region 240. Optionally, in this or any other embodiment, the first dorsal height 313 is measured as a maximum normal distance between the first dorsal apex 311 and a perimeter of the compression region 240. Optionally, in this or any other embodiment, the second dorsal height 323 is measured as a maximum normal distance between the second dorsal apex 321 and a perimeter of the compression region 240. Optionally, in this or any other embodiment, the first dorsal height 313 is measured as an average normal distance between the first dorsal apex 311 and a perimeter of the compression region 240. Optionally, in this or any other embodiment, the second dorsal height 323 is measured as an average normal distance between the second dorsal apex 321 and a perimeter of the compression region 240. Optionally, in this or any other embodiment, the first dorsal height 313 is greater than the second dorsal height 323. Optionally, in this or any other embodiment, the first dorsal height 313 is less than the second dorsal height 323. Optionally, in this or any other embodiment, the first dorsal height 313 and the second dorsal height 323 are approximately equal.

The dorsal vein valley 330, per FIG. 3A, comprises a dorsal vein valley depth 333 measured as a normal distance between the first dorsal apex 311 and the center of the dorsal vein valley 330. Optionally, in this or any other embodiment, the dorsal vein valley depth 333 is measured as a normal distance between the second dorsal apex 321 and the center of the dorsal vein valley 330. Optionally, in this or any other embodiment, the dorsal vein valley depth 333 is measured as a minimal normal distance between the second dorsal apex 321 and the center of the dorsal vein valley 330. Optionally, in this or any other embodiment, the dorsal vein valley depth 333 is measured as a traverse dimension of the dorsal vein valley 330 normal to the dorsal vein valley distance 350. Optionally, in this or any other embodiment, the dorsal vein valley 330 comprises two or more dorsal vein valley depths 333. Optionally, in this or any other embodiment, the dorsal vein valley depth 333 of the dorsal vein valley 330 at its intersection with the first dorsal vein protrusion 210 is equal to the dorsal vein valley depth 333 of the dorsal vein valley 330 at its intersection with the center of the dorsal vein valley 330. Optionally, in this or any other embodiment, the dorsal vein valley depth 333 of the dorsal vein valley 330 at its intersection with the first dorsal vein protrusion 210 is smaller or larger than the dorsal vein valley depth 333 of the dorsal vein valley 330 at its intersection with the center of the dorsal vein valley 330. Optionally, in this or any other embodiment, the dorsal vein valley depth 333 of the dorsal vein valley 330 at its intersection with the second dorsal vein protrusion 220 is equal to the dorsal vein valley depth 333 of the dorsal vein valley 330 at its intersection with the center of the dorsal vein valley 330. Optionally, in this or any other embodiment, the dorsal vein valley depth 333 of the dorsal vein valley 330 at its intersection with the second dorsal vein protrusion 220 is smaller or larger than the dorsal vein valley depth 333 of the dorsal vein valley 330 at its intersection with the center of the dorsal vein valley 330. Optionally, in this or any other embodiment, the dorsal vein valley depth 333 of the dorsal vein valley 330 at its intersection with the first dorsal vein protrusion 210 is equal to the dorsal vein valley depth 333 of the dorsal vein valley 330 at its intersection with the second dorsal vein protrusion 220. Optionally, in this or any other embodiment, the dorsal vein depth of the dorsal vein valley 330 at its intersection with the first dorsal vein protrusion 210 is smaller or larger than the dorsal vein valley depth 333 of the dorsal vein valley 330 at its intersection with the second dorsal vein protrusion 220.

Optionally, in this or any other embodiment, at least one of the first dorsal height 313, the second dorsal height 323, the dorsal vein valley distance 350, the compression region width 340, and the dorsal vein valley depth are scaled with respect to at least one of the maximum inner width 270, the constriction gap 261, inferior height 290, and the constriction height 280.

Optionally, in this or any other embodiment, at least one of the first dorsal height and the second dorsal height is about 0.02 inches to about 0.08 inches. Optionally, in this or any other embodiment, at least one of the first dorsal height and the second dorsal height is at least about 0.02 inches. Optionally, in this or any other embodiment, at least one of the first dorsal height and the second dorsal height is at most about 0.08 inches. Optionally, in this or any other embodiment, a dorsal vein valley distance is about 0.15 inches to about 0.7 inches. Optionally, in this or any other embodiment, a dorsal vein valley distance is at least about 0.15 inches. Optionally, in this or any other embodiment, a dorsal vein valley distance is at most about 0.7 inches. Optionally, in this or any other embodiment, a dorsal vein valley depth is about 0.02 inches to about 0.08 inches. Optionally, in this or any other embodiment, a dorsal vein valley depth is at least about 0.02 inches. Optionally, in this or any other embodiment, a dorsal vein valley depth is at most about 0.08 inches. Optionally, in this or any other embodiment, a ratio between the dorsal vein valley distance and at least one of the first dorsal height and the second dorsal height is about 4:1 to about 16:1. Optionally, in this or any other embodiment, a ratio between the dorsal vein valley distance and at least one of the first dorsal height and the second dorsal height is at least about 4:1. Optionally, in this or any other embodiment, a ratio between the dorsal vein valley distance and at least one of the first dorsal height and the second dorsal height is at most about 16:1. Optionally, in this or any other embodiment, the compression region width is about 0.2 inches to about 0.8 inches. Optionally, in this or any other embodiment, the compression region width is at least about 0.2 inches. Optionally, in this or any other embodiment, the compression region width is at most about 0.8 inches. Optionally, in this or any other embodiment, a ratio between the compression region width and a dorsal vein valley distance is about 1.1:1 to about 2:1. Optionally, in this or any other embodiment, a ratio between the compression region width and a dorsal vein valley distance is at least about 1.1:1. Optionally, in this or any other embodiment, a ratio between the compression region width and a dorsal vein valley distance is at most about 2:1. Optionally, in this or any other embodiment, a dorsal vein depth is about 0.15 inches to about 0.65 inches. Optionally, in this or any other embodiment, a dorsal vein depth is at least about 0.15 inches. Optionally, in this or any other embodiment, a dorsal vein depth is at most about 0.65 inches. Optionally, in this or any other embodiment, a ratio between the compression region width and the maximum inner width is about 0.2:1 to about 0.7:1. Optionally, in this or any other embodiment, a ratio between the compression region width and the maximum inner width is at least about 0.2:1. Optionally, in this or any other embodiment, a ratio between the compression region width and the maximum inner width is at most about 0.7:1. Optionally, in this or any other embodiment, a dorsal vein valley distance is about 0.15 inches to about 0.75 inches. Optionally, in this or any other embodiment, a dorsal vein valley distance is at least about 0.15 inches. Optionally, in this or any other embodiment, the dorsal vein valley distance is at most about 0.75 inches. Optionally, in this or any other embodiment, the compression region width is about 0.2 inches to about 0.8 inches. Optionally, in this or any other embodiment, the compression region width is at least about 0.2 inches. Optionally, in this or any other embodiment, the compression region width is at most about 0.8 inches.

Per FIGS. 3A-B, the compression region 240 may comprise the first dorsal vein protrusion 310 and the second dorsal vein protrusion 320. Optionally, in this or any other embodiment, compression region 240 may further comprise 1, 2, 3, 4, 5, or more dorsal vein protrusions. Optionally, in this or any other embodiment, the three or more dorsal vein protrusions are arranged sequentially within the compression region 240 in a direction along the bridge 230 from the first arm 210 to the second arm 220. Optionally, in this or any other embodiment, the three or more dorsal vein protrusions are arranged in a linear pattern, a circular pattern, a checkerboard pattern, a random pattern, or any combination thereof. Optionally, in this or any other embodiment, at least two of the three or more dorsal vein protrusions have the same cross sectional shape. Optionally, in this or any other embodiment, at least two of the three or more dorsal vein protrusions have different cross sectional shapes. Optionally, in this or any other embodiment, the dorsal height of each of the three or more dorsal vein protrusions are equal. Optionally, in this or any other embodiment, the dorsal vein height of each of the three or more dorsal vein protrusions are unequal.

Optionally, in this or any other embodiment, the compression region 240 comprises three or more dorsal vein protrusions, wherein each dorsal vein protrusion is separated from one or more other dorsal vein protrusions by a dorsal vein valley 330, wherein the compression region 240 comprises two or more dorsal vein valleys Optionally, in this or any other embodiment, at least two of the two or more dorsal vein valleys have the same cross sectional shape. Optionally, in this or any other embodiment, at least two of the three or more dorsal vein protrusions have different cross sectional shapes. Optionally, in this or any other embodiment, the dorsal vein valley distance 350 of each of the two or more dorsal vein valleys are equal. Optionally, in this or any other embodiment, the dorsal vein valley distance 350 of each of the two or more dorsal vein valleys are unequal. Optionally, in this or any other embodiment, the dorsal vein valley depths 333 of each of the two or more dorsal vein valleys are equal. Optionally, in this or any other embodiment, the dorsal vein valley depths 333 of each of the two or more dorsal vein valleys are unequal.

Optionally, in this or any other embodiment, at least one three or more dorsal protrusions has a dorsal height of about 0.02 inches to about 0.08 inches. Optionally, in this or any other embodiment, at least one three or more dorsal protrusions has a dorsal height of least about 0.02 inches. Optionally, in this or any other embodiment, at least one three or more dorsal protrusions has a dorsal height of at most about 0.08 inches. Optionally, in this or any other embodiment, a dorsal vein valley distance of at least one of the dorsal vein valleys is about 0.15 inches to about 0.7 inches. Optionally, in this or any other embodiment, the dorsal vein valley distance of at least one of the dorsal vein valleys is at least about 0.15 inches. Optionally, in this or any other embodiment, the dorsal vein valley distance of at least one of the dorsal vein valleys is at most about 0.7 inches. Optionally, in this or any other embodiment, a dorsal vein valley depth of at least one of the dorsal vein valleys is about 0.02 inches to about 0.08 inches. Optionally, in this or any other embodiment, the dorsal vein valley depth of at least one of the dorsal vein valleys is at least about 0.02 inches. Optionally, in this or any other embodiment, the dorsal vein valley depth of at least one of the dorsal vein valleys is at most about 0.08 inches.

Figure 4:
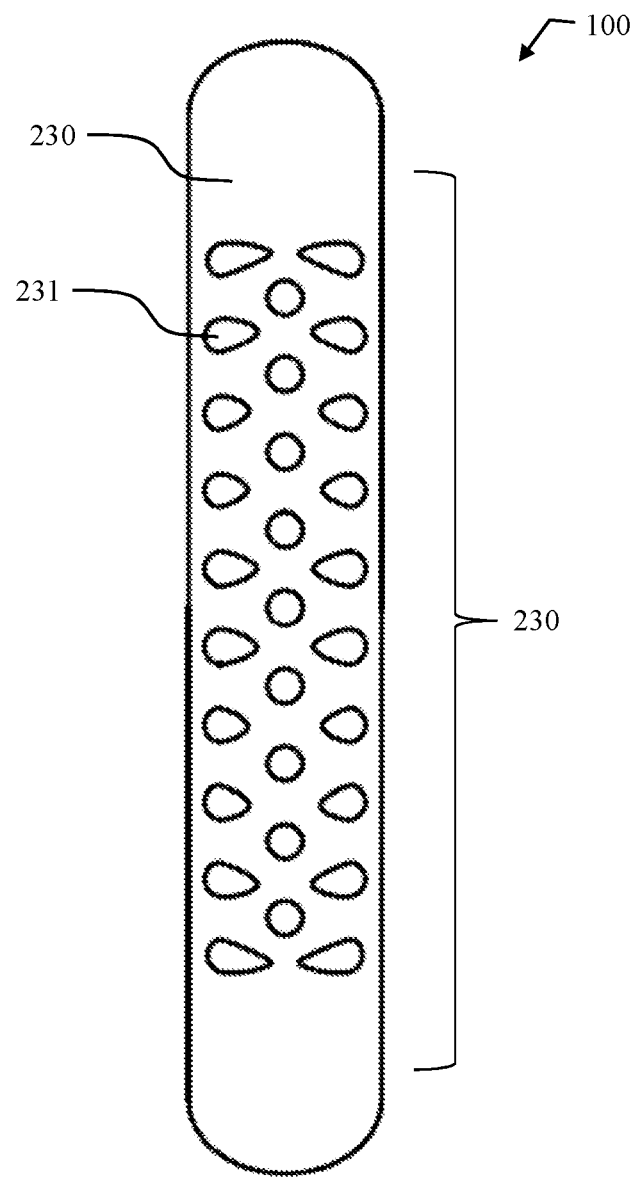
FIG. 4 shows a top view of the friction protrusions of a non-limiting example of the penile constriction device of FIG. 1.

FIG. 4 shows a top view of the friction protrusions of the penile constriction device 100 of FIG. 1. Optionally, in this or any other embodiment, the penile constriction device 100 comprises a plurality of friction protrusions 231 on a superior side of the bridge 230.

In one exemplary embodiment, per FIG. 4, the bridge 230 comprises 29 friction protrusions 231 in a staggered rectilinear array comprising 3 columns and 19 rows, wherein each column is arranged in a direction from the first arm 210 to the second arm 220. Optionally, in this or any other embodiment, the plurality of friction protrusions is arranged in a circular array, a polygonal array, a curvilinear array, or any combination thereof. Optionally, in this or any other embodiment, the friction protrusions 251 comprise a cross sectional shape comprising a circle, a half circle, an oval, an ellipse, a teardrop, a polygon, an irregular shape, a hollow shape, or any combination thereof. Optionally, in this or any other embodiment, at least two of the friction protrusions 251 comprise the same cross sectional shape. Optionally, in this or any other embodiment, at least two of the friction protrusions 251 comprise different cross sectional shapes. In this exemplary embodiment, at least one of the shape and the size of the friction protrusions 231 are configured to be easily producible by a molding process or an over-molding process. Optionally, in this or any other embodiment, the plurality of friction protrusions 231 comprises about 2 protrusions to about 60 protrusions. Alternatively, in this or any other embodiment, the plurality of friction protrusions 231 comprises at least about 2 protrusions. Alternatively, in this or any other embodiment, the plurality of friction protrusions 231 comprises at most about 60 protrusions.

Figure 5:
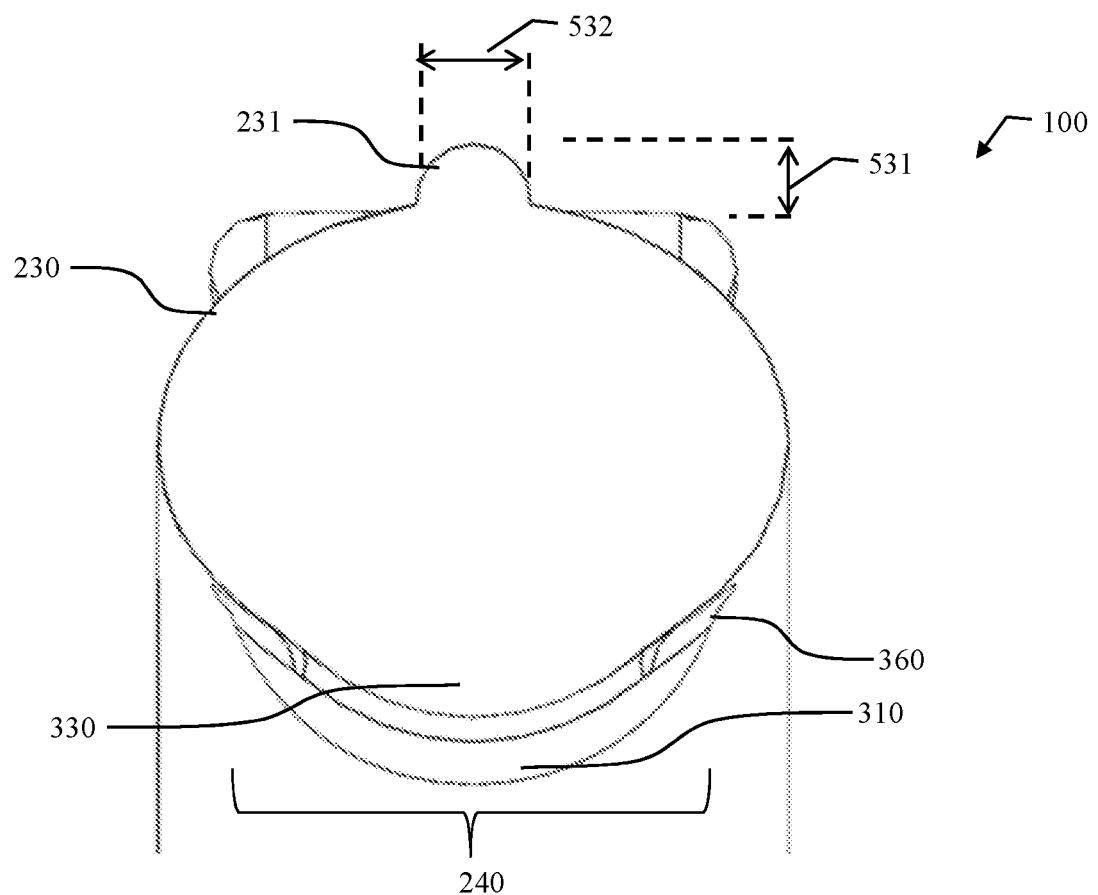
FIG. 5 shows a side cross-sectioned view of the friction protrusions and compression region of the penile constriction device of FIG. 1.

FIG. 5 shows a side cross-sectioned view of the friction protrusions and compression region of the penile constriction device 100 of FIG. 1. Per FIG. 5 the friction protrusion height 531 is measured as a maximal normal distance between an apex of the friction protrusion 251 and the superior side of the bridge 230. Optionally, in this or any other embodiment, the friction protrusion height 531 is measured as a maximum normal distance between the apex of the friction protrusion 251 and its intersection with the superior side of the bridge 230. Optionally, in this or any other embodiment, the friction protrusion height 531 is measured as a minimum normal distance between the apex of the friction protrusion 251 and its intersection with the superior side of the bridge 230. Optionally, in this or any other embodiment, at least two of the friction protrusions 251 have the same friction protrusion height 531. Optionally, in this or any other embodiment, at least two of the friction protrusions 251 have different friction protrusion heights 531. Optionally, in this or any other embodiment, the friction protrusion height 531 is about 0.01 inches to about 0.06 inches. Optionally, in this or any other embodiment, the friction protrusion height 531 is at least about 0.01 inches. Optionally, in this or any other embodiment, the friction protrusion height 531 is at most about 0.06 inches.

Per FIG. 5 the friction protrusion width 532 is measured as a maximal normal distance between a first intersection between the friction protrusion 251 and the superior side of the bridge 230, and a second opposing intersection between the friction protrusion 251 and the superior side of the bridge 230. Optionally, in this or any other embodiment, the friction protrusion width 532 is measured as a minimal normal distance between a first intersection between the friction protrusion 251 and the superior side of the bridge 230, and a second opposing intersection between the friction protrusion 251 and the superior side of the bridge 230. Optionally, in this or any other embodiment, at least two of the friction protrusions 251 have the same friction protrusion width 532. Optionally, in this or any other embodiment, at least two of the friction protrusions 251 have different friction protrusion widths 532. Optionally, in this or any other embodiment, the friction protrusion width 532 is about 0.01 inches to about 0.06 inches. Optionally, in this or any other embodiment, the friction protrusion width 532 is at least about 0.01 inches. Optionally, in this or any other embodiment, the friction protrusion width 532 is at most about 0.06 inches.

Optionally, in this or any other embodiment, the plurality of friction protrusion 231 is configured to interact with the female genitalia during intercourse. Optionally, in this or any other embodiment, the plurality of friction protrusion 231 is configured to stimulate the female genitalia during intercourse. Optionally, in this or any other embodiment, the plurality of friction protrusion 231 is configured to interact with the clitoris during intercourse. Optionally, in this or any other embodiment, at least one of the array of the plurality of friction protrusions 231, the cross sectional shape of the plurality of friction protrusions 231, and the friction protrusion height 531 are configured for increased stimulation of the female genitalia during intercourse. Optionally, in this or any other embodiment, at least one of the array of the plurality of friction protrusions 231, the cross sectional shape of the plurality of friction protrusions 231, and the friction protrusion height 531 are configured to prevent damage to the female genitalia during intercourse.

Figure 19:
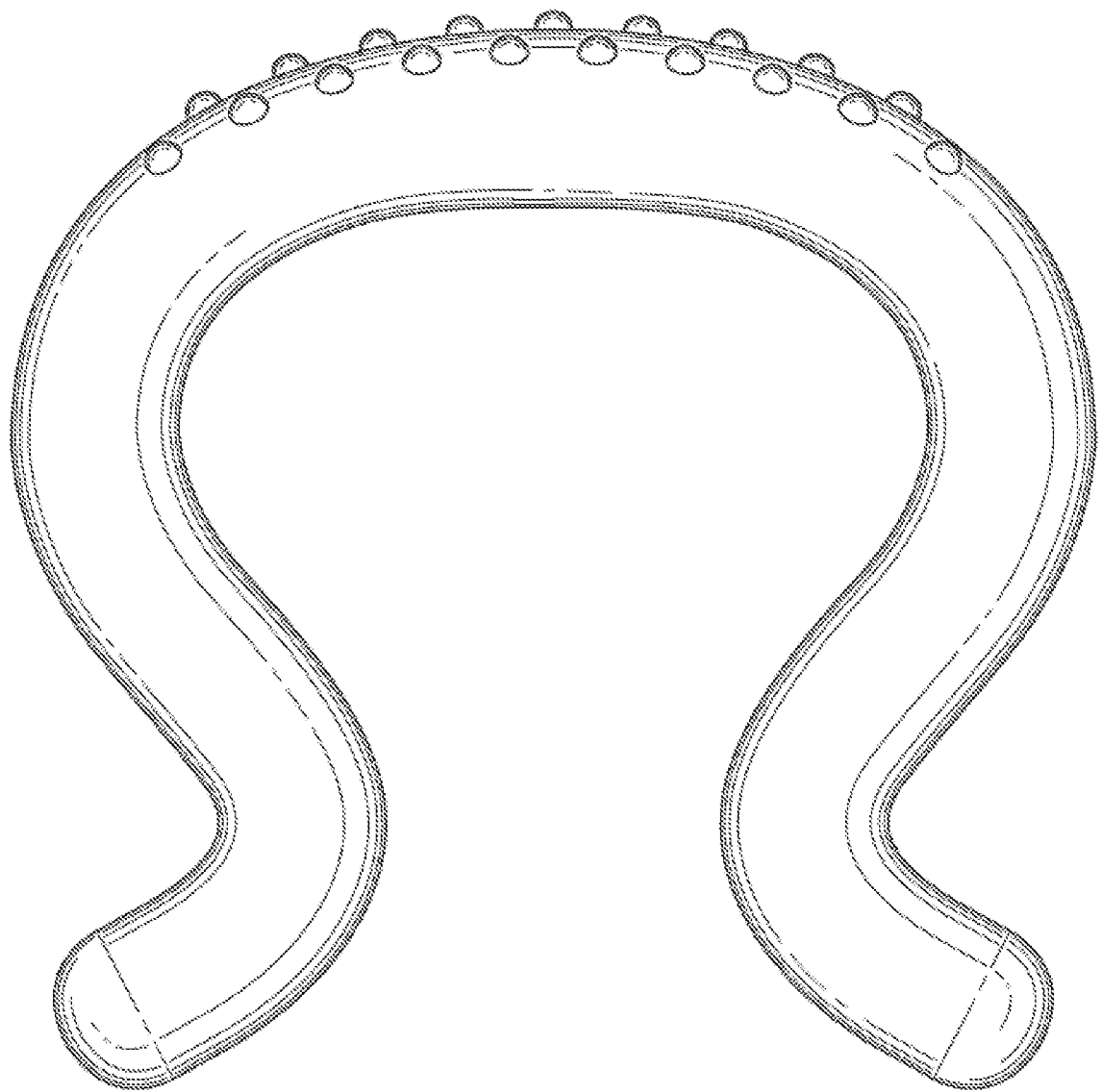
FIG. 19 shows a front view of a non-limiting example of a penile constriction device having friction protrusions but no first dorsal vein protrusion or second dorsal vein protrusion; per an embodiment herein.
Figure 20:
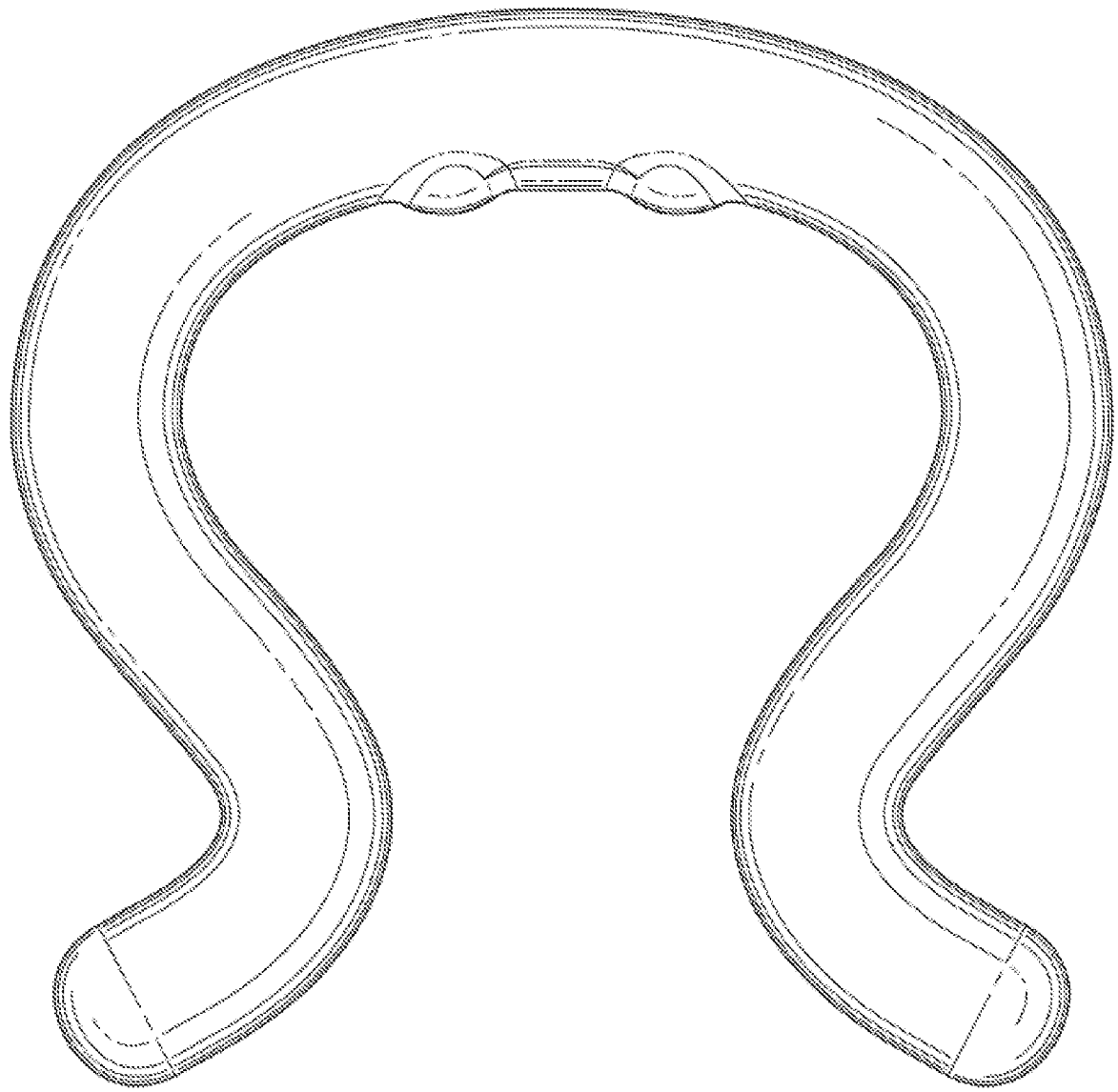
FIG. 20 shows a front view of a non-limiting example of a penile constriction device having the first dorsal vein protrusion and second dorsal vein protrusion, but no friction protrusions; per an embodiment herein.
Figure 21:
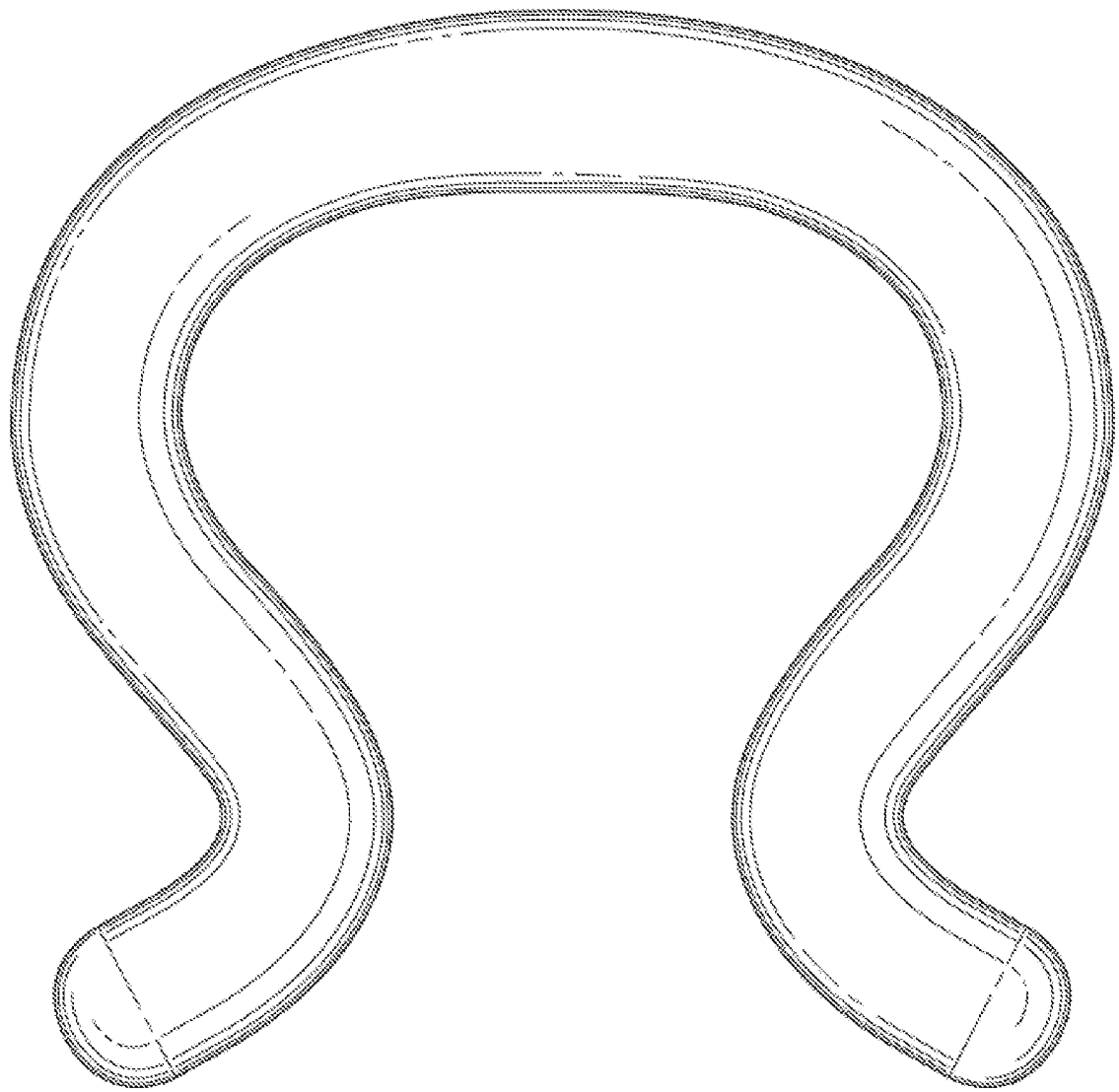
FIG. 21 shows a front view of a non-limiting example of a penile constriction device having no first dorsal vein protrusion, second dorsal vein protrusion, or friction protrusions; per an embodiment herein.

Optionally, in this or any other embodiment the penile constriction device does not comprise the first dorsal vein protrusion or the second dorsal vein protrusion. As shown in one embodiment, per FIG. 19, the penile constriction device comprises the friction protrusions and does not comprise the first dorsal vein protrusion or the second dorsal vein protrusion. Optionally, in this or any other embodiment, the penile constriction device does not comprise the friction protrusions. As shown in one embodiment, per FIG. 20, the penile constriction device comprises the first dorsal vein protrusion and the second dorsal vein protrusion and does not comprise the friction protrusions. Optionally, in this or any other embodiment, the penile constriction device does not comprise the friction protrusions, the first dorsal vein protrusion, or the second dorsal vein protrusion. As shown in one embodiment, per FIG. 21, the penile constriction device does not comprise the friction protrusion, the first dorsal vein protrusion, or the second dorsal vein protrusion.

Figure 6:
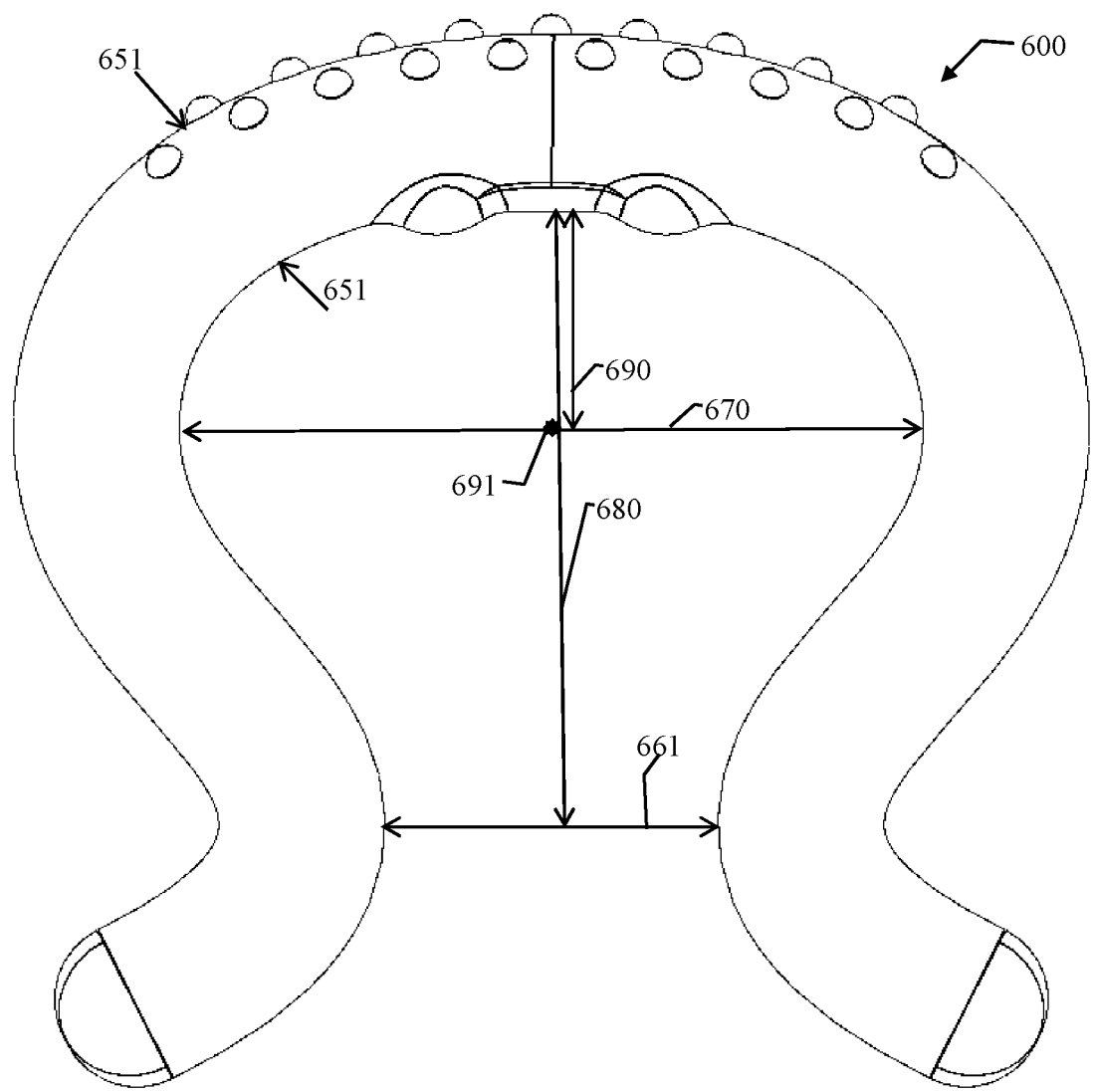
FIG. 6 shows a front view of a non-limiting example of a second penile constriction device, per an embodiment here.
Figure 7:
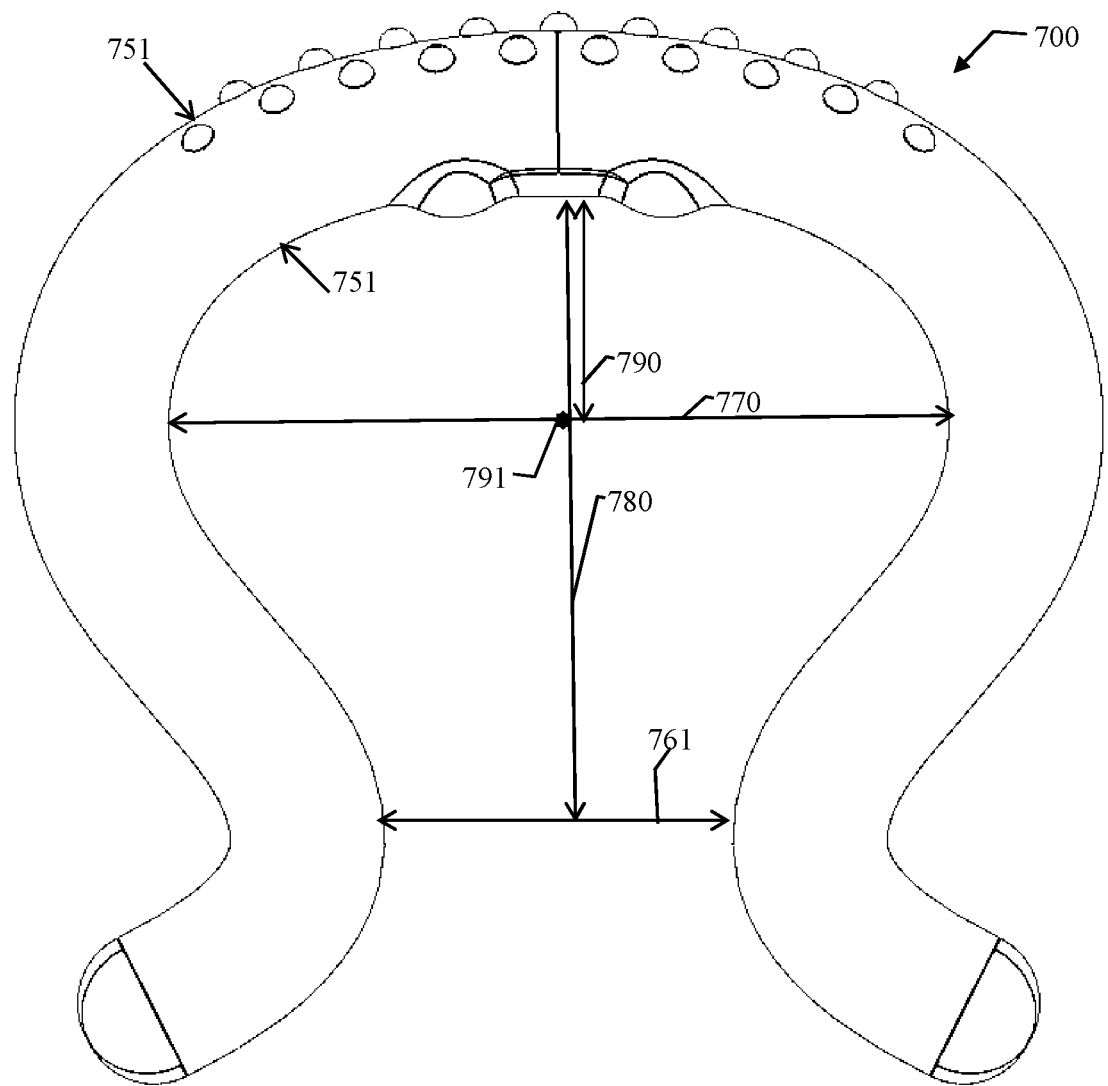
FIG. 7 shows a front view of a non-limiting example of a third penile constriction device, per an embodiment herein.
Figure 8:
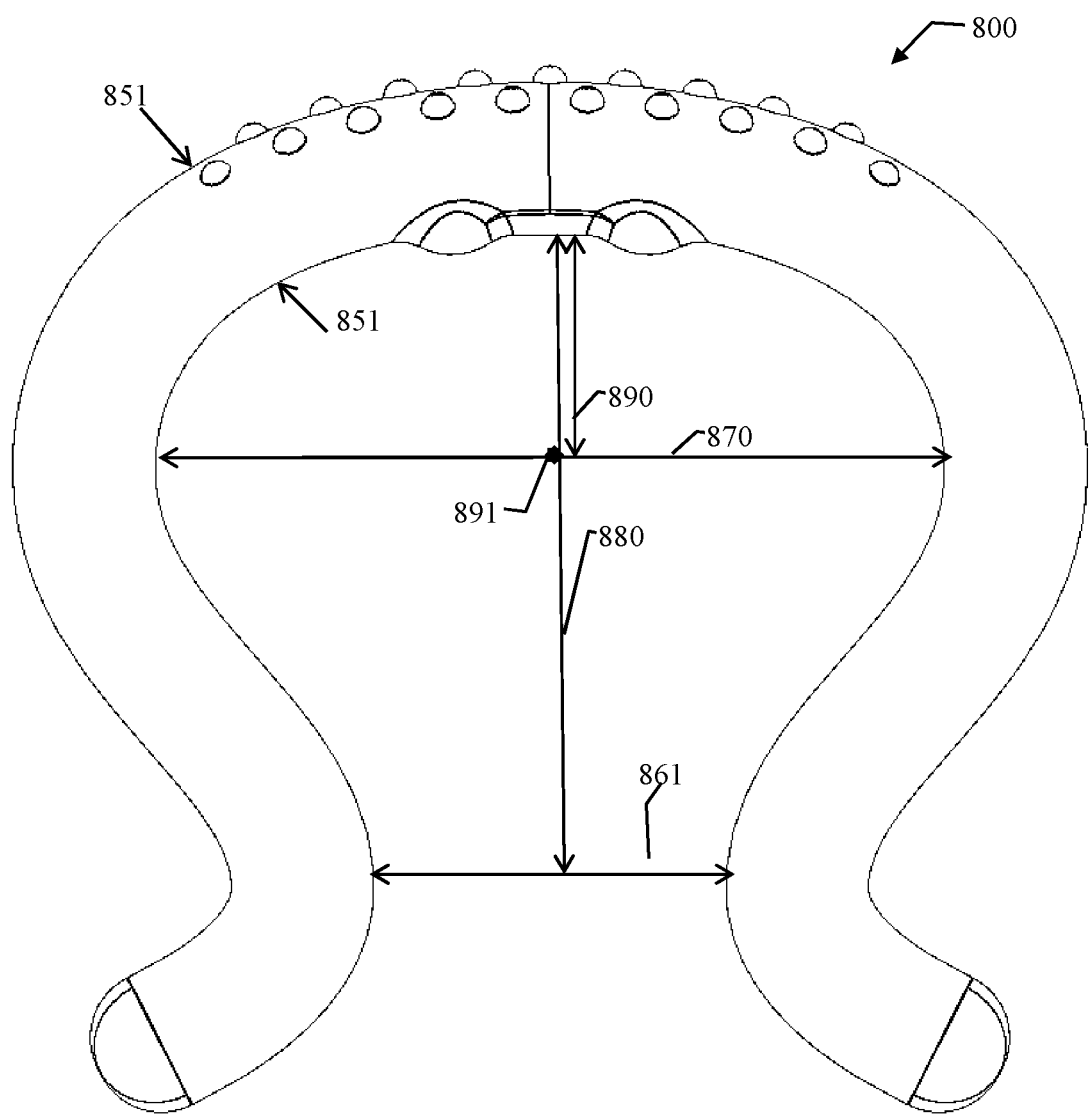
FIG. 8 shows a front view of a non-limiting example of a fourth penile constriction device, per an embodiment herein.
Figure 9:
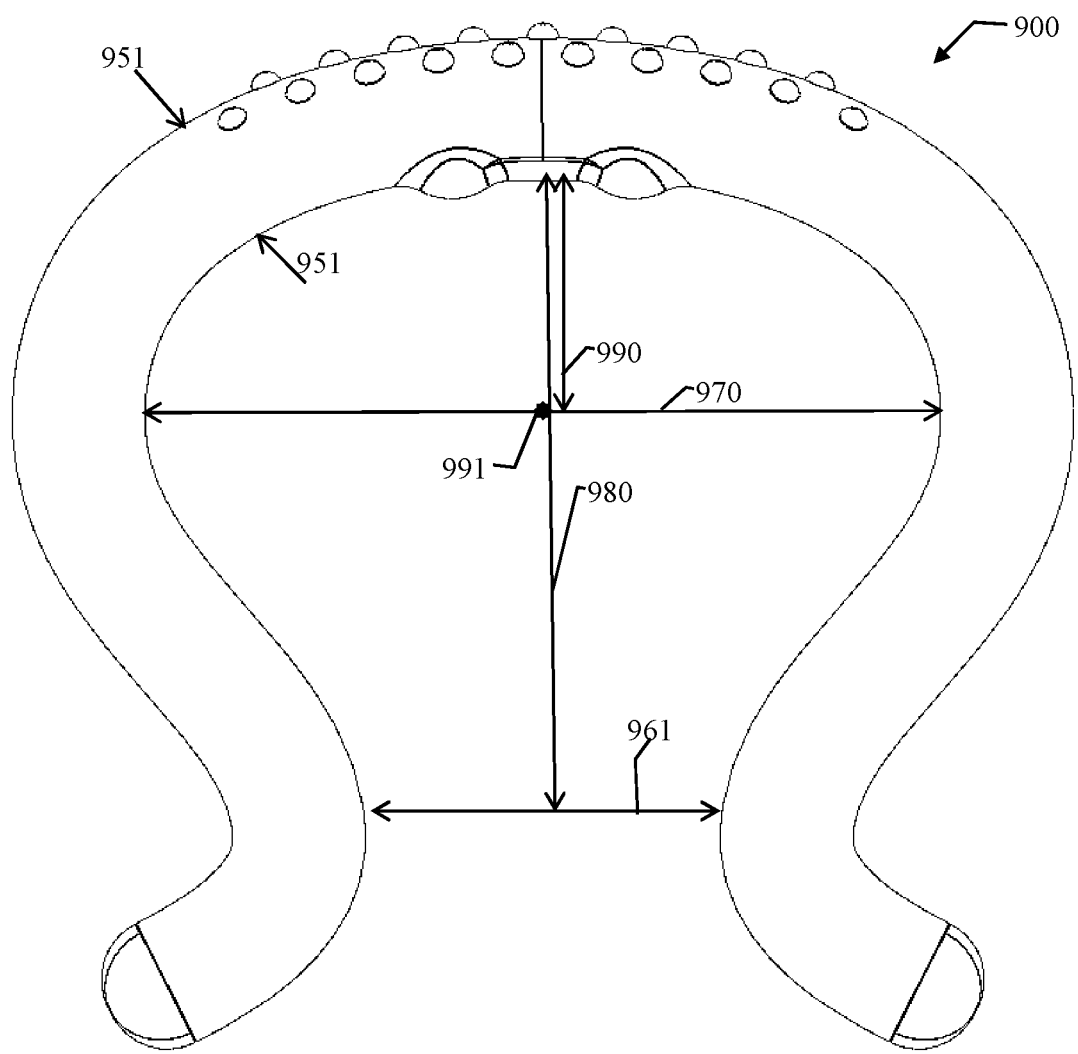
FIG. 9 shows a front view of a non-limiting example of a fifth penile constriction device, per an embodiment herein.

FIG. 6 shows a front view of a non-limiting second example of a penile constriction device 600. FIG. 7 shows a front view of a non-limiting example of a third penile constriction device 700. FIG. 8 shows a front view of a non-limiting example of a fourth penile constriction device 800. FIG. 9 shows a front view of a non-limiting example of a fifth penile constriction device 900.

Figure 10A:
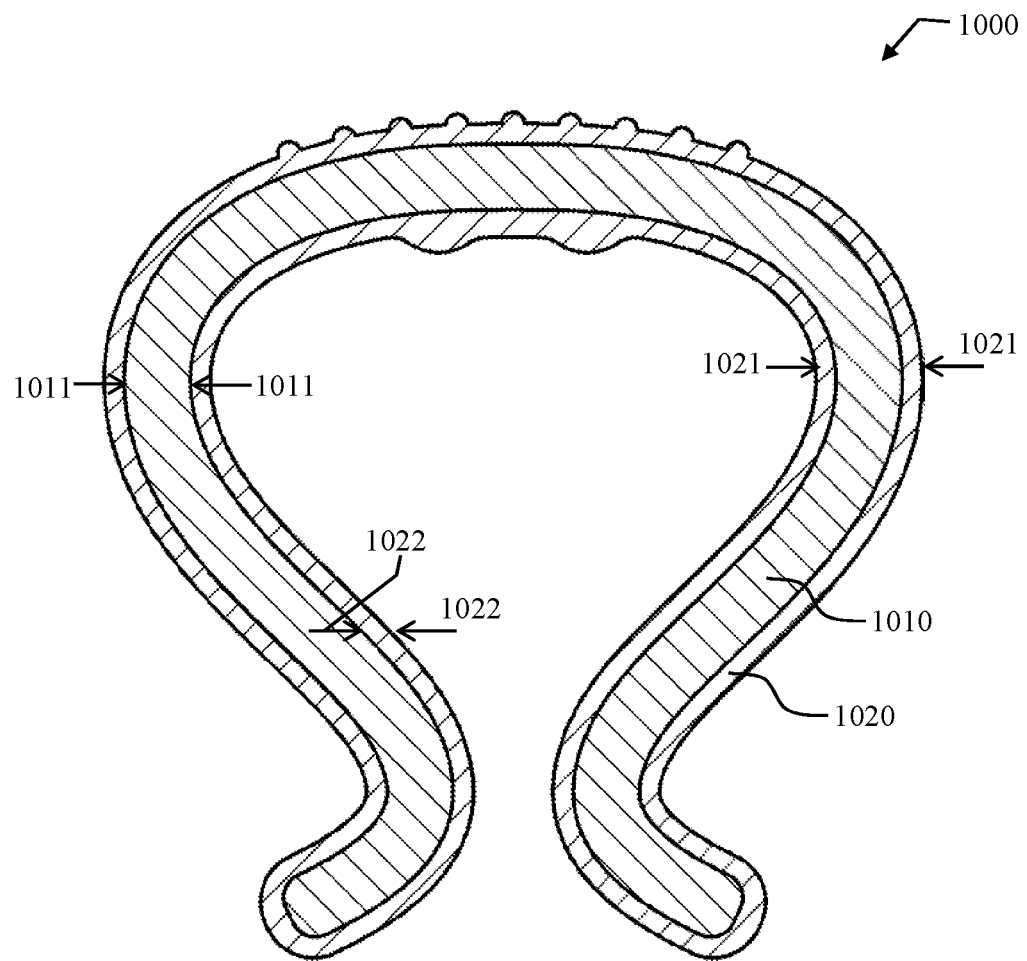
FIG. 10A shows a front cross-sectioned view of a non-limiting example of a penile constriction device comprising a frame and a cover, per an embodiment herein.
Figure 10B:
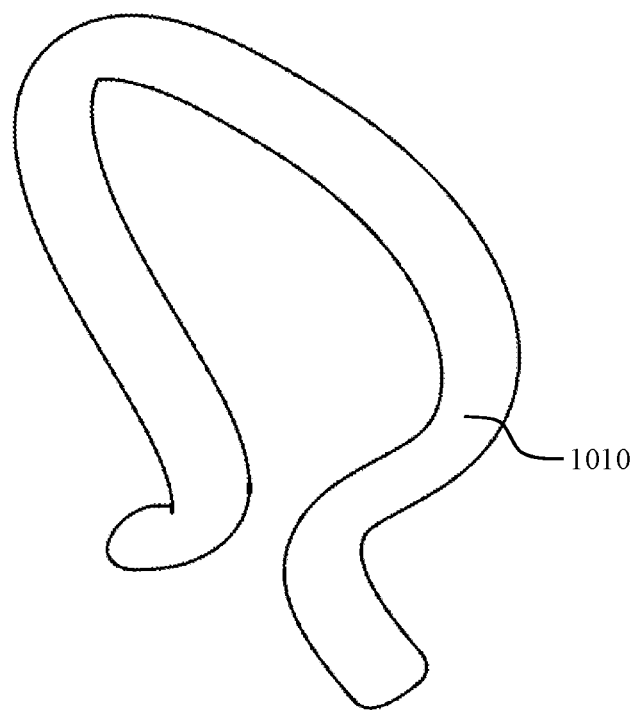
FIG. 10B shows a perspective view of a non-limiting example of the frame of FIG. 10A.
Figure 10C:
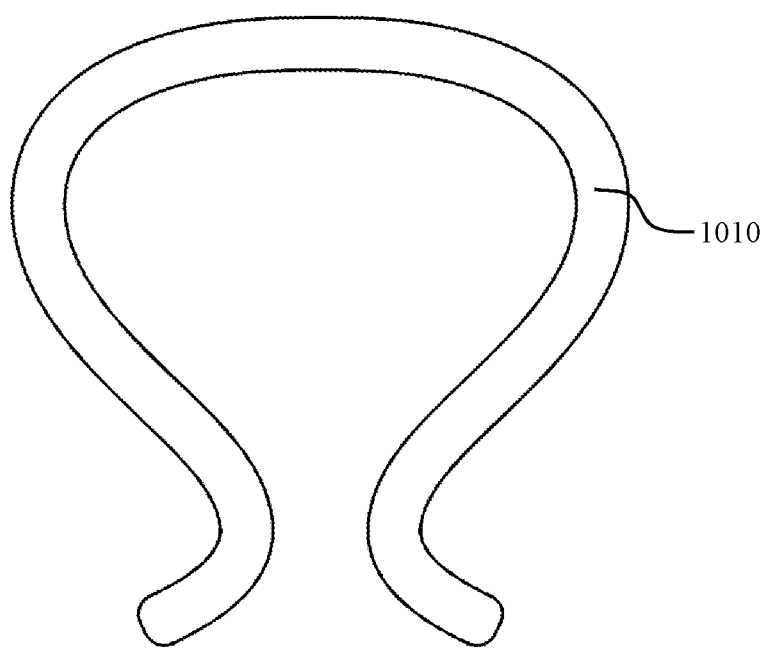
FIG. 10C shows a front view of a non-limiting example of the frame of FIG. 10A.

FIG. 10 shows a front cross-sectioned view of a non-limiting example of a penile constriction device comprising a frame and a cover. Optionally, in this or any other embodiment, the penile constriction device 1000 comprises an arched rod comprising a cover 1020 substantially surrounding a frame 1010.

Optionally, in this or any other embodiment, the frame 1010 comprises a frame portion of the first arm, a frame portion of the second arm, and a frame portion of the bridge. Optionally, in this or any other embodiment, the frame portion of the first arm is rigidly attached the frame portion of the bridge. Optionally, in this or any other embodiment, the frame portion of the second arm is rigidly attached to the frame portion of the bridge. Optionally, in this or any other embodiment, the frame portion of the first arm is flexibly attached to the frame portion of the bridge. Optionally, in this or any other embodiment, the frame portion of the second arm is flexibly attached to the frame portion of the bridge. Optionally, in this or any other embodiment, the frame portion of the first arm is removably attached the frame portion of the bridge. Optionally, in this or any other embodiment, the frame portion of the second arm is removably attached the frame portion of the bridge. Optionally, in this or any other embodiment, the frame portion of the first arm is not rigidly attached to the frame portion of the bridge. Optionally, in this or any other embodiment, the frame portion of the second arm is not attached the frame portion of the bridge.

Optionally, in this or any other embodiment, the cover 1020 comprises a cover portion of the first arm, a cover portion of the second arm, and a cover portion of the bridge. Optionally, in this or any other embodiment, the cover portion of the first arm is rigidly attached the cover portion of the bridge. Optionally, in this or any other embodiment, the cover portion of the second arm is rigidly attached to the cover portion of the bridge. Optionally, in this or any other embodiment, the cover portion of the first arm is flexibly attached to the cover portion of the bridge. Optionally, in this or any other embodiment, the cover portion of the second arm is flexibly attached to the cover portion of the bridge. Optionally, in this or any other embodiment, the cover portion of the first arm is removably attached the cover portion of the bridge. Optionally, in this or any other embodiment, the cover portion of the second arm is removably attached the cover portion of the bridge. Optionally, in this or any other embodiment, the cover portion of the first arm is not rigidly attached to the cover portion of the bridge. Optionally, in this or any other embodiment, the cover portion of the second arm is not attached the cover portion of the bridge.

Optionally, in this or any other embodiment, the frame 1010 comprises the compression region, wherein the cover 1020 surrounds the compression region. Optionally, in this or any other embodiment, the frame 1010 does not comprise the compression region, wherein the cover 1020 comprises the compression region. Optionally, in this or any other embodiment, both the frame 1010 and the cover 1020 comprise the compression region. Optionally, in this or any other embodiment, the frame 1010 comprises the plurality of friction protrusions, wherein the cover 1020 surrounds the plurality of friction protrusions. Optionally, in this or any other embodiment, the frame 1010 does not comprise the plurality of friction protrusions, wherein the cover 1020 comprises the plurality of friction protrusions. Optionally, in this or any other embodiment, both the frame 1010 and the cover 1020 comprise the plurality of friction protrusions. Optionally, in this or any other embodiment, the penile constriction device 1000 comprises an arched rod comprising a cover 1020 without a frame 1010. Optionally, in this or any other embodiment, the penile constriction device 1000 comprises an arched rod comprising a frame 1010 without a cover 1020.

As seen in FIG. 10, the frame 1010 is completely surrounded by the cover 1020. Optionally, in this or any other embodiment, the cover 1020 completely surrounds a portion of the frame 1010. Optionally, in this or any other embodiment, the cover 1020 does not surround at least a portion of the first terminus. Optionally, in this or any other embodiment, the cover 1020 does not surround at least a portion of the second terminus. Optionally, in this or any other embodiment, the cover 1020 is tubular in shape. Optionally, in this or any other embodiment, the cover 1020 does not comprise one or more of an appendage and a band. Optionally, in this or any other embodiment, the cover 1020 does not have a ribbed core. Optionally, in this or any other embodiment, the cover 1020 surrounds the frame 1010 of at least one of the first terminus and the second terminus. Optionally, in this or any other embodiment, the cover 1020 does not surround the frame 1010 of at least one of the first terminus and the second terminus.

Per FIG. 10, the frame 1010 may comprise a frame thickness 1011 measured as a maximum outer distance of a cross-section of the frame 1010. Optionally, in this or any other embodiment, the frame thickness 1011 is measured as a normal outer distance of a cross-section of the frame 1010. Optionally, in this or any other embodiment, the frame thickness 1011 comprises a uniform inner thickness 1021. Optionally, in this or any other embodiment, the frame thickness 1011 comprises a non-uniform inner thickness 1021. Optionally, in this or any other embodiment, the frame thickness 1011 of the first arm 210 is greater than or equal to the frame thickness 1011 of the second arm 220. Optionally, in this or any other embodiment, the frame thickness 1011 of the first arm 210 is less than to the frame thickness 1011 of the second arm 220. Optionally, in this or any other embodiment, the frame thickness 1011 of the first arm 210 is greater than or equal to the frame thickness 1011 of the bridge 230. Optionally, in this or any other embodiment, the frame thickness 1011 of the first arm 210 is less than to the frame thickness 1011 of the bridge 230.

Per FIG. 10, the cover 1020 may comprise a cover thickness 1021 measured as a maximum normal outer distance of the cross-section of the cover 1020. Optionally, in this or any other embodiment, the cover thickness 1021 is measured as a maximum or a minimum outer distance of the cross-section of the cover 1020. Optionally, in this or any other embodiment, the cover thickness 1021 comprises a uniform cover thickness 1021. Optionally, in this or any other embodiment, the cover thickness 1021 comprises a non-uniform cover thickness 1021.

Optionally, in this or any other embodiment, at least two of the cover portion of the first arm, the cover portion of the second arm, and the cover portion of the bridge have the same cover thickness 1021. Optionally, in this or any other embodiment, at least two of the cover portion of the first arm, the cover portion of the second arm, and the cover portion of the bridge have the different cover thickness 1021. Optionally, in this or any other embodiment, the cover thickness 1021 of at least a portion of the cover 1020 corresponds to the frame thickness 1011 of the frame 1010. Optionally, in this or any other embodiment, the frame 1010 comprises the compression region, wherein the frame thickness 1011 of a portion of the frame 1010 within the compression region is greater than the frame thickness 1011 of a portion of the frame 1010 outside the compression region. Optionally, in this or any other embodiment, the frame 1010 does not comprise the compression region, wherein the cover 1020 comprises the compression region, and wherein the cover thickness 1021 of a portion of the cover 1020 within the compression region is greater than the cover thickness 1021 of a portion of the cover 1020 outside the compression region. Optionally, in this or any other embodiment, both the frame 1010 and the cover 1020 comprise the compression region, wherein the frame thickness 1011 of a portion of the frame 1010 within the compression region is greater than the frame thickness 1011 of a portion of the frame 1010 outside the compression region, and wherein the cover thickness 1021 of a portion of the cover 1020 within the compression region is greater than the cover thickness 1021 of a portion of the cover 1020 outside the compression region.

Per FIG. 10, the cover 1020 may comprise a cover depth 1022 measured as a normal distance between the boundary of the frame 1010 and the cover 1020, and the outer face of the cover 1020. Optionally, in this or any other embodiment, the cover depth 1022 is measured as a minimum or maximum distance between the boundary of the frame 1010 and the cover 1020, and a point on outer face of the cover 1020. Optionally, in this or any other embodiment, the cover depth 1022 comprises a single cover depth 1022. Optionally, in this or any other embodiment, the cover depth 1022 comprises a plurality of cover depths 1022.

Optionally, in this or any other embodiment, a ratio between the frame thickness 1011 and the cover thickness 1021 is about 1:1 to about 5:1. Optionally, in this or any other embodiment, a ratio between the frame thickness 1011 and the cover depth 1022 is about 1:1 to about 10:1.

Optionally, in this or any other embodiment, the cover 1020 and the frame 1010 comprise the same material. Optionally, in this or any other embodiment, the cover 1020 and the frame 1010 comprise different materials. Optionally, in this or any other embodiment, at least one of the cover 1020 and the frame 1010 is pliable. Optionally, in this or any other embodiment, at least one of the cover 1020 and the frame 1010 is ductile. Optionally, in this or any other embodiment, at least one of the cover 1020 and the frame 1010 is pliable and ductile. Optionally, in this or any other embodiment, at least one of the cover 1020 and the frame 1010 is pliable and not ductile. Optionally, in this or any other embodiment, at least one of the cover 1020 and the frame 1010 is ductile and not pliable. Optionally, in this or any other embodiment, the cover 1020 is formed of a material that is safe for prolonged human contact, and which does not irritate or cut the skin the penile area.

Optionally, in this or any other embodiment, a frame modulus of elasticity of the frame 1010 of the first arm is higher than a frame modulus of elasticity of the frame 1010 of the second arm. Optionally, in this or any other embodiment, the frame modulus of elasticity of the frame 1010 of the first arm is less than or equal to the frame modulus of elasticity of the frame 1010 of the second arm. Optionally, in this or any other embodiment, a frame modulus of elasticity of the frame 1010 of the first arm is higher than a frame modulus of elasticity of the frame 1010 of the bridge. Optionally, in this or any other embodiment, the frame modulus of elasticity of the frame 1010 of the first arm is less than or equal to the frame modulus of elasticity of the frame 1010 of the bridge.

Optionally, in this or any other embodiment, at least one of the cover 1020 and the frame 1010 comprise plastic, silicone, glass, wood, metal, carbon fiber, fiberglass, or any combination thereof. Optionally, in this or any other embodiment, at least one of the cover 1020 and the frame 1010 comprise polyamide, polycarbonate, polyester, polyethylene, polyethylene terephthalate, polypropylene, polystyrene, polyurethanes, polyvinyl chloride, polyvinylidene chloride acrylonitrile butadiene styrene acrylonitrile butadiene styrene, polyethylene/acrylonitrile butadiene styrene, polyepoxide, polymethyl methacrylate, polytetrafluoroethylene, phenolics melamine formaldehyde urea-formaldehyde, polyetheretherketone, maleimide/bismaleimide, polyetherimide, polyimide, polylactic acid, furan silicone, polysulfone, or any combination thereof.

Optionally, in this or any other embodiment, the frame thickness is about 0.005 inches to about 0.55 inches. Optionally, in this or any other embodiment, the frame thickness is at least about 0.005 inches. Optionally, in this or any other embodiment, the frame thickness is at most about 0.55 inches. Optionally, in this or any other embodiment, the cover thickness is about 0.08 inches to about 0.6 inches. Optionally, in this or any other embodiment, the cover thickness is at least about 0.08 inches. Optionally, in this or any other embodiment, the cover thickness is at most about 0.6 inches. Optionally, in this or any other embodiment, the cover depth is about 0.005 inches to about 0.55 inches. Optionally, in this or any other embodiment, the cover depth is at least about 0.005 inches. Optionally, in this or any other embodiment, the cover depth is at most about 0.55 inches.

Figure 11A:
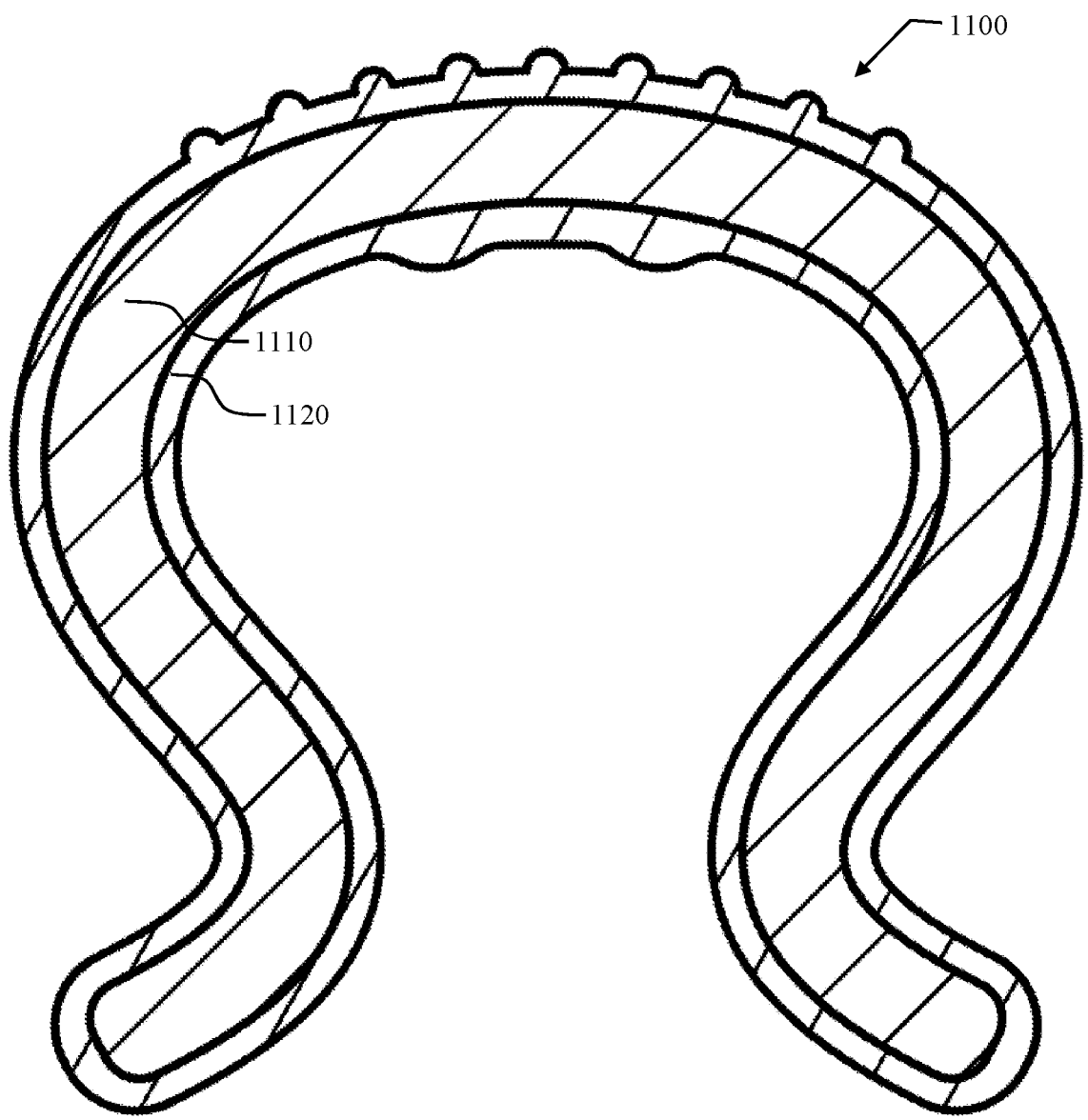
FIG. 11A shows a front cross-sectioned view of an alternative non-limiting example of a penile constriction device comprising a frame and a cover, per an embodiment herein.
Figure 11B:
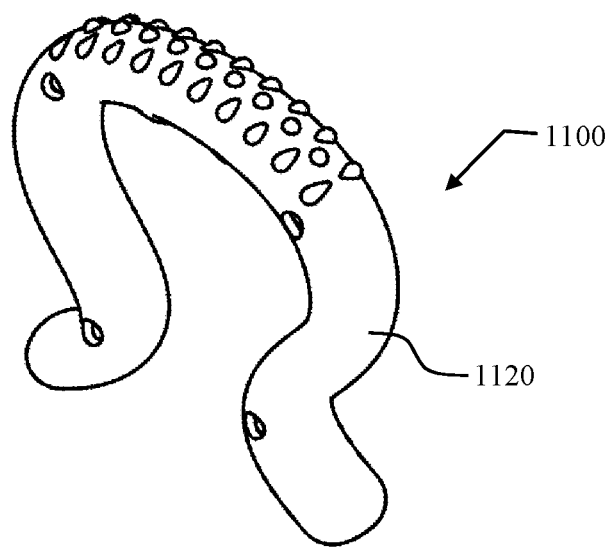
FIG. 11B shows a perspective view of the manufacturing marks of penile constriction device of FIG. 11A.
Figures 11C, 11D:
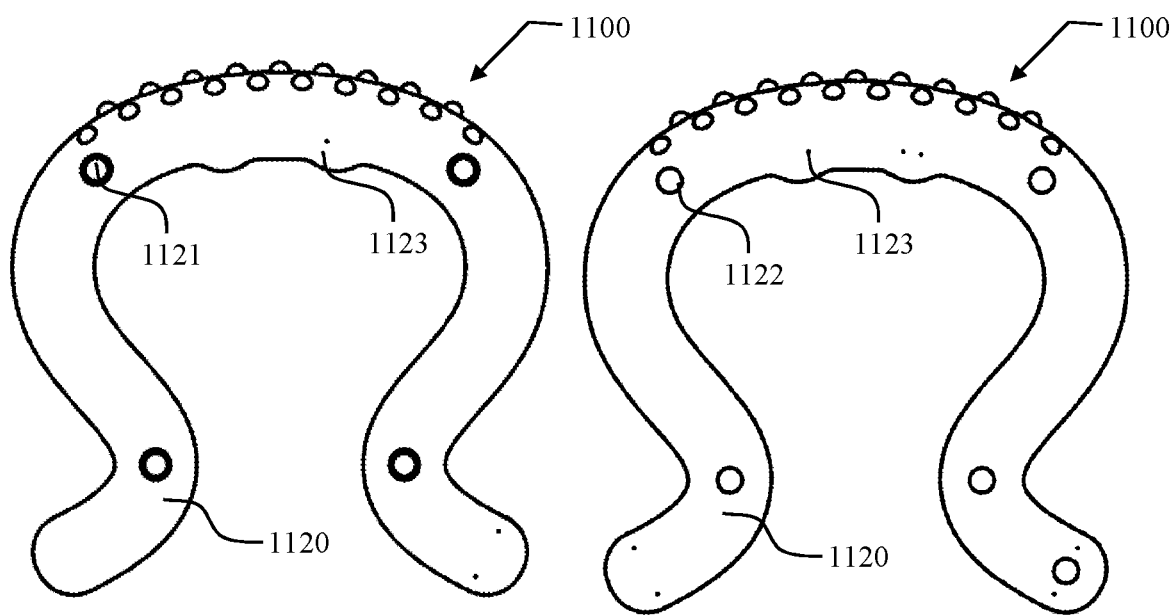
FIG. 11C shows a front view of the manufacturing marks of penile constriction device of FIG. 11A.
FIG. 11D shows a back view of the manufacturing marks of penile constriction device of FIG. 11A.
Figures 11E, 11F:
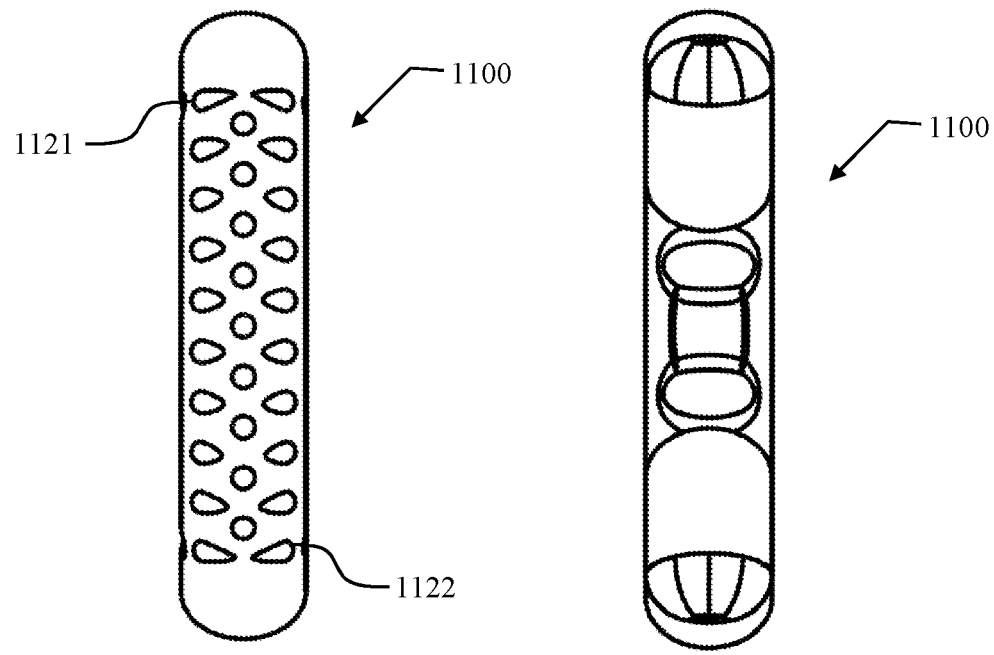
FIG. 11E shows a top view of the manufacturing marks of penile constriction device of FIG. 11A.
FIG. 11F shows a bottom view of the manufacturing marks of penile constriction device of FIG. 11A.
Figures 11G, 11H:
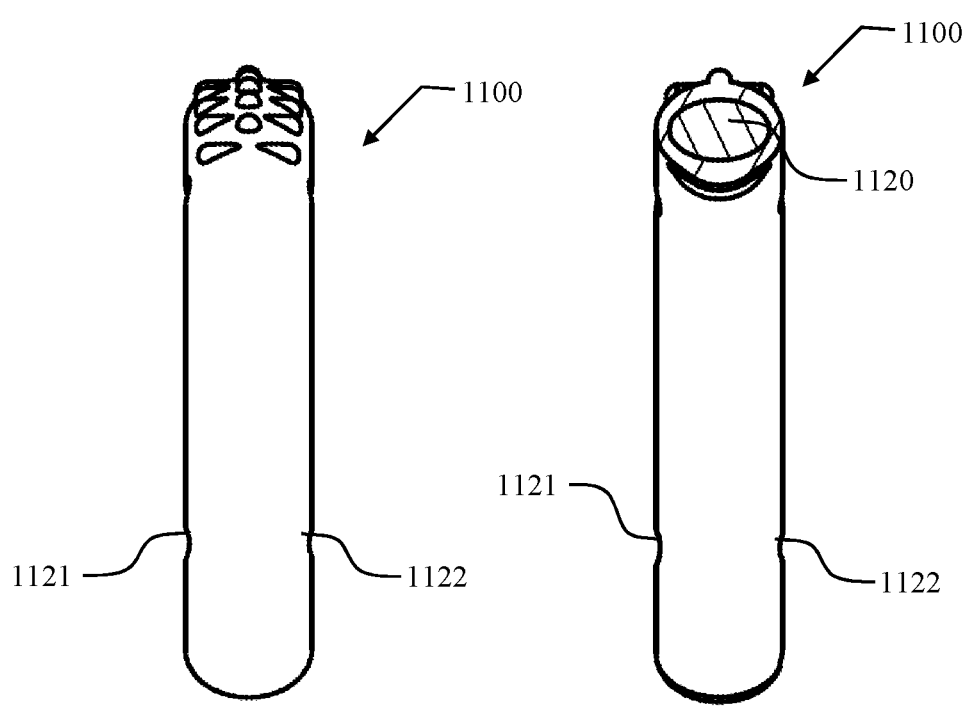
FIG. 11G shows a side view of the manufacturing marks of penile constriction device of FIG. 11A.

FIG. 11A shows a front cross-sectioned view of an alternative non-limiting example of a penile constriction device 1100 comprising a frame 1110 and a cover 1120. FIGS. 11B-H show the manufacturing marks of penile constriction device 1100 of FIG. 11A. As seen in FIGS. 11A-H, at least a portion of the cover 1120 surrounds the frame 1110. Per FIGS. 11A-H, the cover 1120 of the penile constriction device 1100 comprises a first cover manufacturing mark 1121, a second cover manufacturing mark 1123, and a third cover manufacturing mark 1123.

Figure 11J:
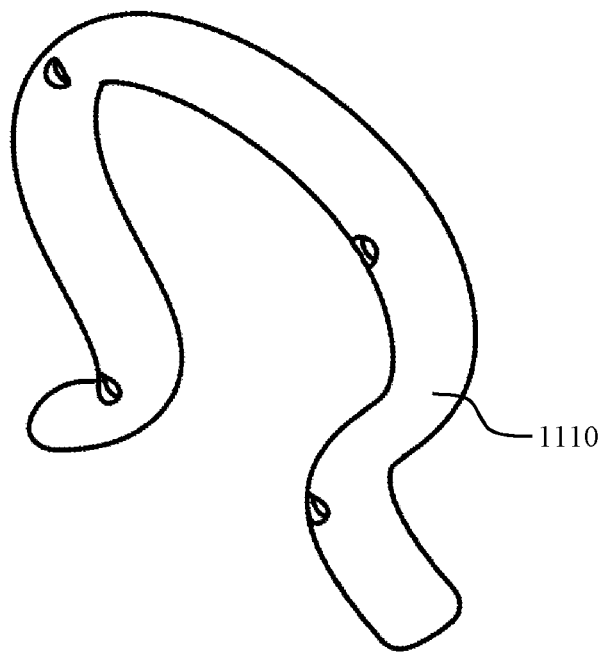
FIG. 11J shows a perspective view of the frame of a non-limiting example of the frame of FIG. 11A.
Figure 11K:
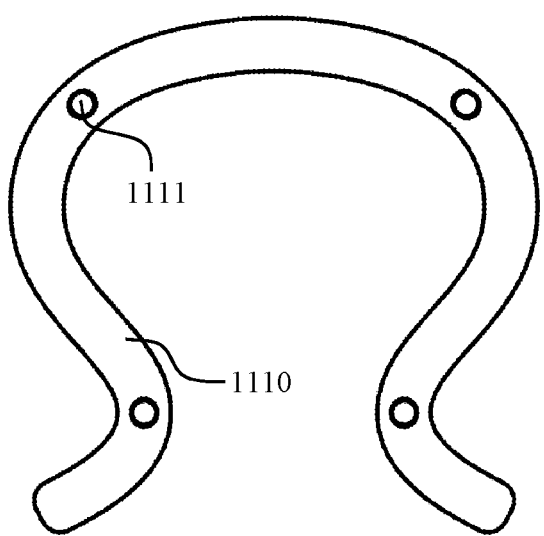
FIG. 11K shows a front view of the frame of a non-limiting example of the frame of FIG. 11A.
Figure 11L:
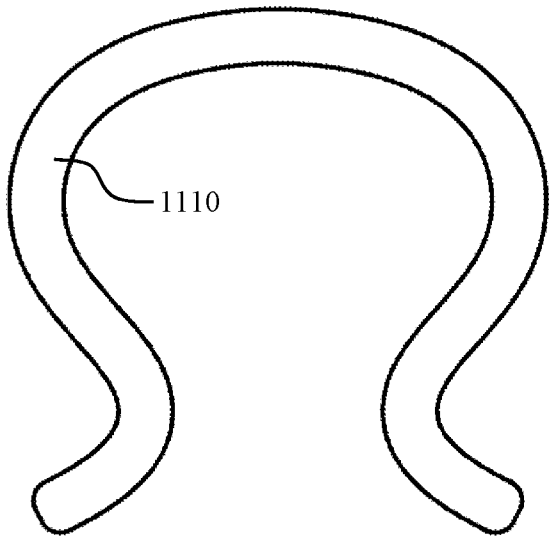
FIG. 11L shows a front view of the frame of a non-limiting example of the frame of FIG. 11A.

FIGS. 11J-L show a non-limiting example of the frame 1220 of FIG. 11A. Per FIGS. 11J-L, the frame 1110 of the penile constriction device 1100 comprises a first frame manufacturing mark 1111. Optionally, in this or any other embodiment, at least one of the first cover manufacturing mark 1121, the second cover manufacturing mark 1123, and the third cover manufacturing mark 1123 are configured to allow the cover 1210 to be over-molded around the frame 1110. Optionally, in this or any other embodiment, at least one of the first cover manufacturing mark 1211, the second cover manufacturing mark 1123, and the third cover manufacturing mark 1123 comprise a witness mark.

As seen in FIGS. 11J-L the penile constriction device 1100 comprises the four first manufacturing marks 1121, five second manufacturing marks 1123, and ten third manufacturing marks 1123.

Alternatively, the number of first cover manufacturing marks 1121 is optionally about 1 to about 10. Alternatively, the number of second cover manufacturing marks 1122 is optionally about 1 to about 10. Alternatively, the number of third cover manufacturing marks 1123 is optionally about 1 to about 20.

Figure 12A:
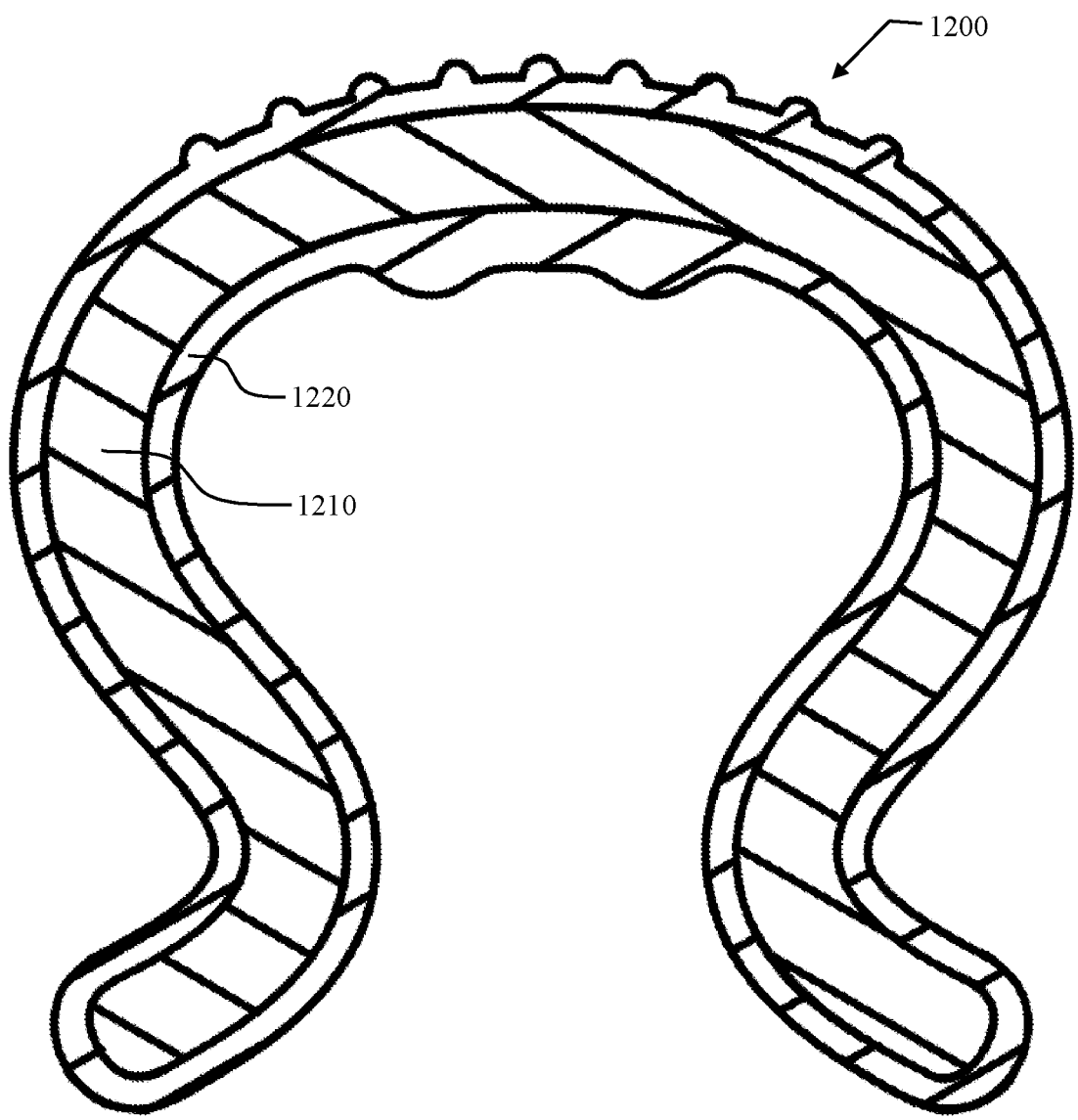
FIG. 12A shows a front cross-sectioned view of another alternative non-limiting example of a penile constriction device comprising a frame and a cover, per an embodiment herein.
Figure 12B:
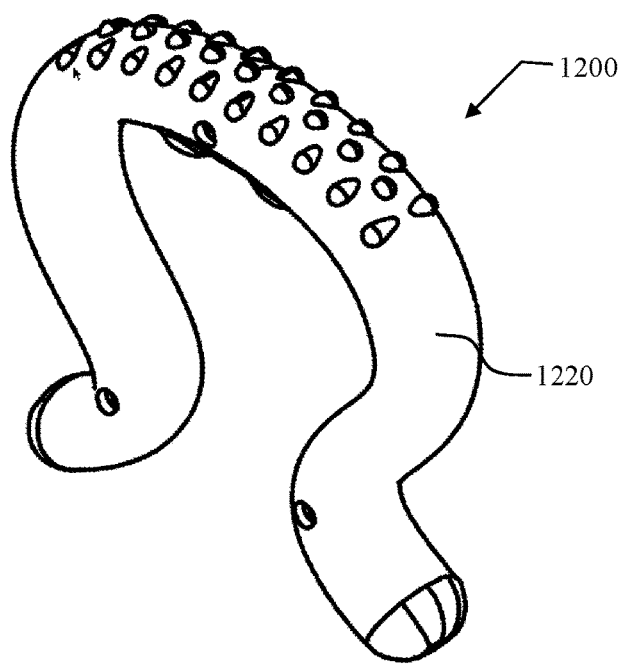
FIG. 12B shows a perspective view of the manufacturing marks of penile constriction device of FIG. 12A.
Figure 12C:
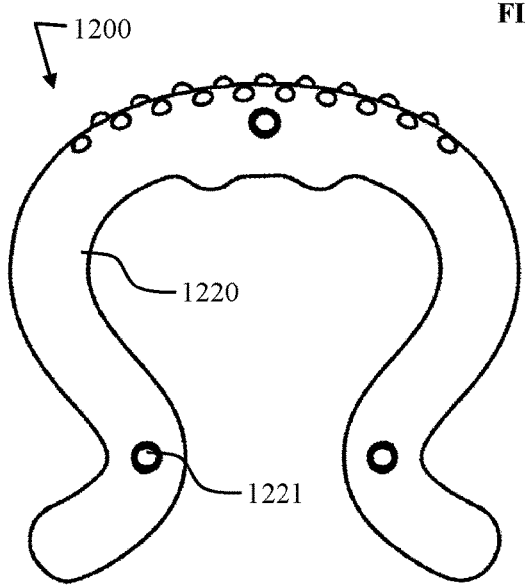
FIG. 12C shows a front view of the manufacturing marks of penile constriction device of FIG. 12A.
Figure 12D:
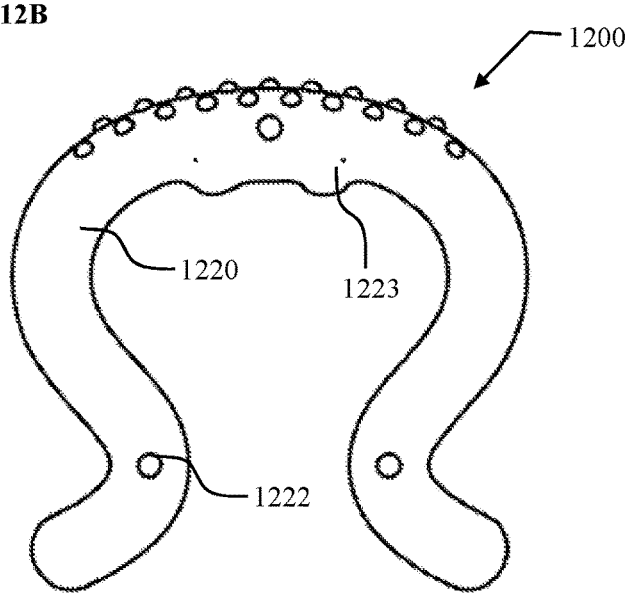
FIG. 12D shows a back view of the manufacturing marks of penile constriction device of FIG. 12A.
Figures 12E, 12F:
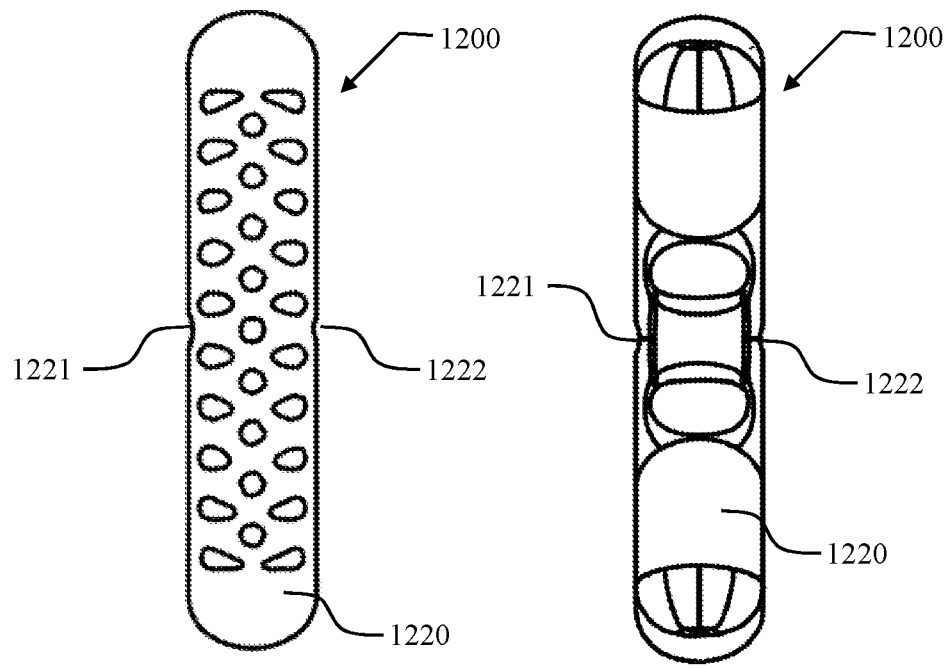
FIG. 12E shows a top view of the manufacturing marks of penile constriction device of FIG. 12A.
FIG. 12F shows a bottom view of the manufacturing marks of penile constriction device of FIG. 12A.
Figures 12G, 12H:
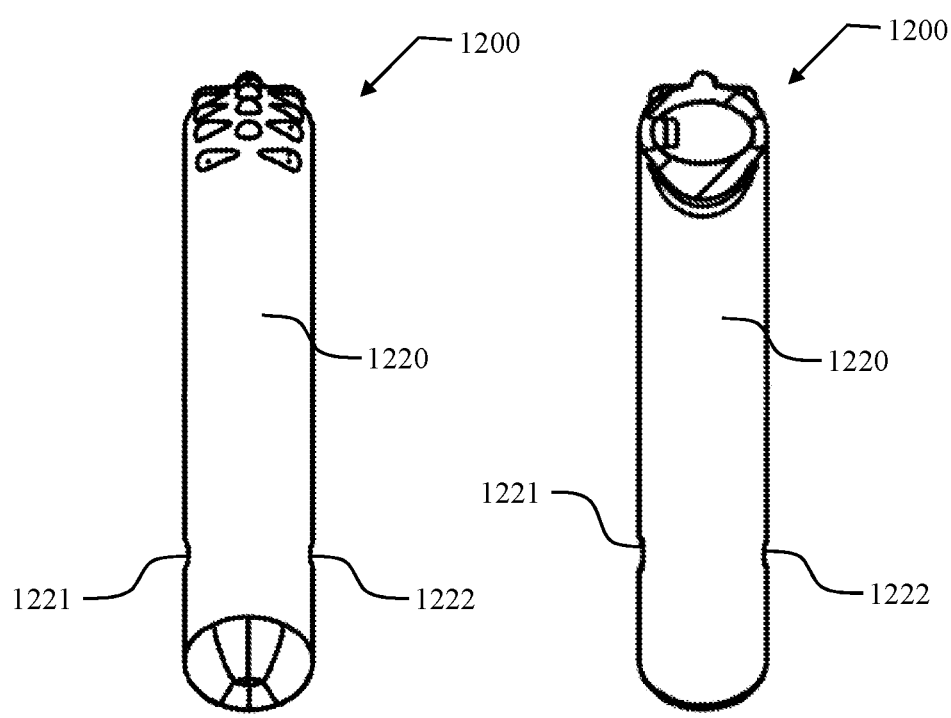
FIG. 12G shows a side view of the manufacturing marks of penile constriction device of FIG. 12A.
FIG. 12H shows a side cross-sectioned view of the manufacturing marks of penile constriction device of FIG. 12A.

FIG. 12A shows a front cross-sectioned view of another alternative non-limiting example of a penile constriction device comprising a frame and a cover FIGS. 12B-H show the manufacturing marks of penile constriction device of FIG. 12A. FIGS. 12J-L show a non-limiting example of the frame of FIG. 12A.

Figure 13:
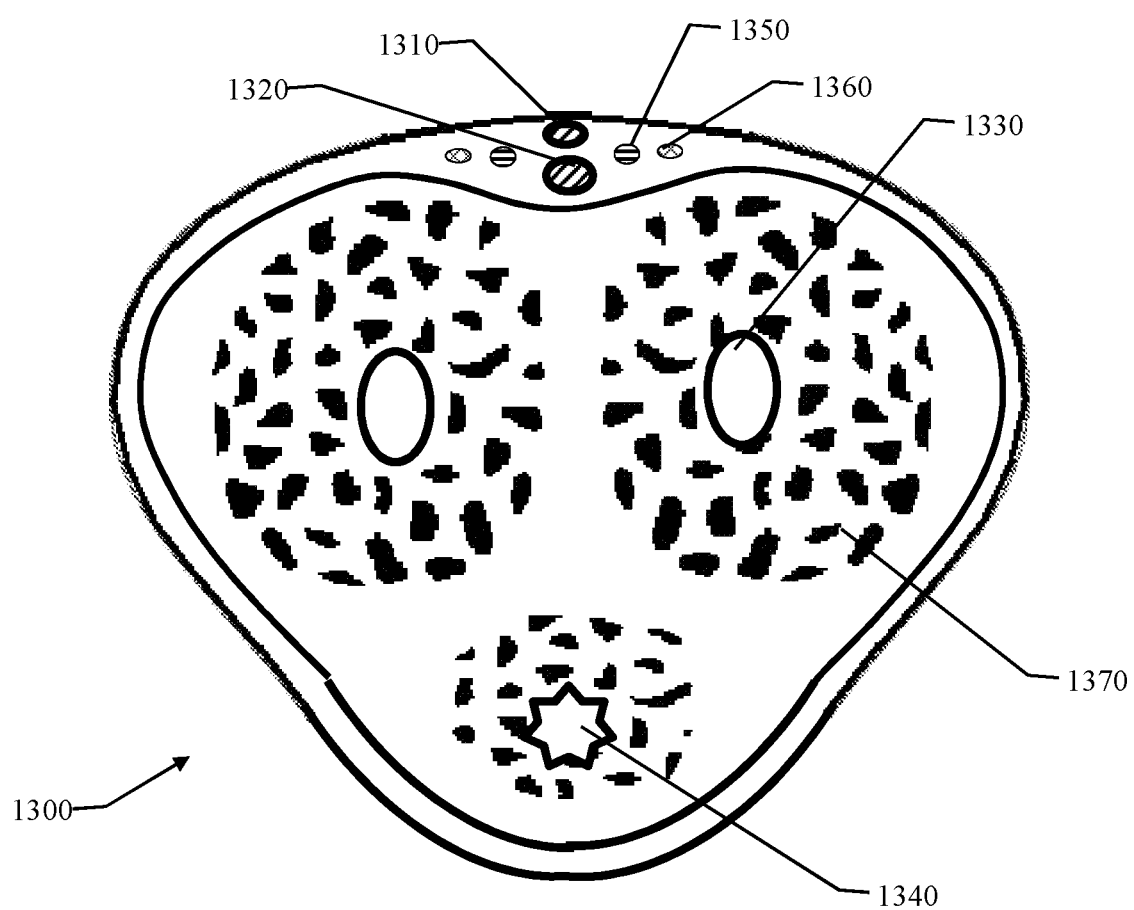
FIG. 13 shows a front cross-sectioned view of the veins and arteries in a human penis.

FIG. 13 shows a front cross-sectioned view of the veins and arteries in a human penis. Per FIG. 13 the human penis 1300 comprises a superficial dorsal vein 1310, a deep dorsal vein 1320, deep arteries 1330, a urethra 1340, dorsal arteries 1350, and dorsal nerves 1360. The average human penis 1300 has a general cross section shape comprising an ellipse toward the top portion and a smaller ellipse cross section shape toward the bottom portion. Erection is enabled in men through increased blood flow into the penis 1300 through the deep arteries 1330, and decreased blood flow out from the penis 1300 through the superficial dorsal vein 1310 and the deep dorsal vein 1320.

Figure 14:
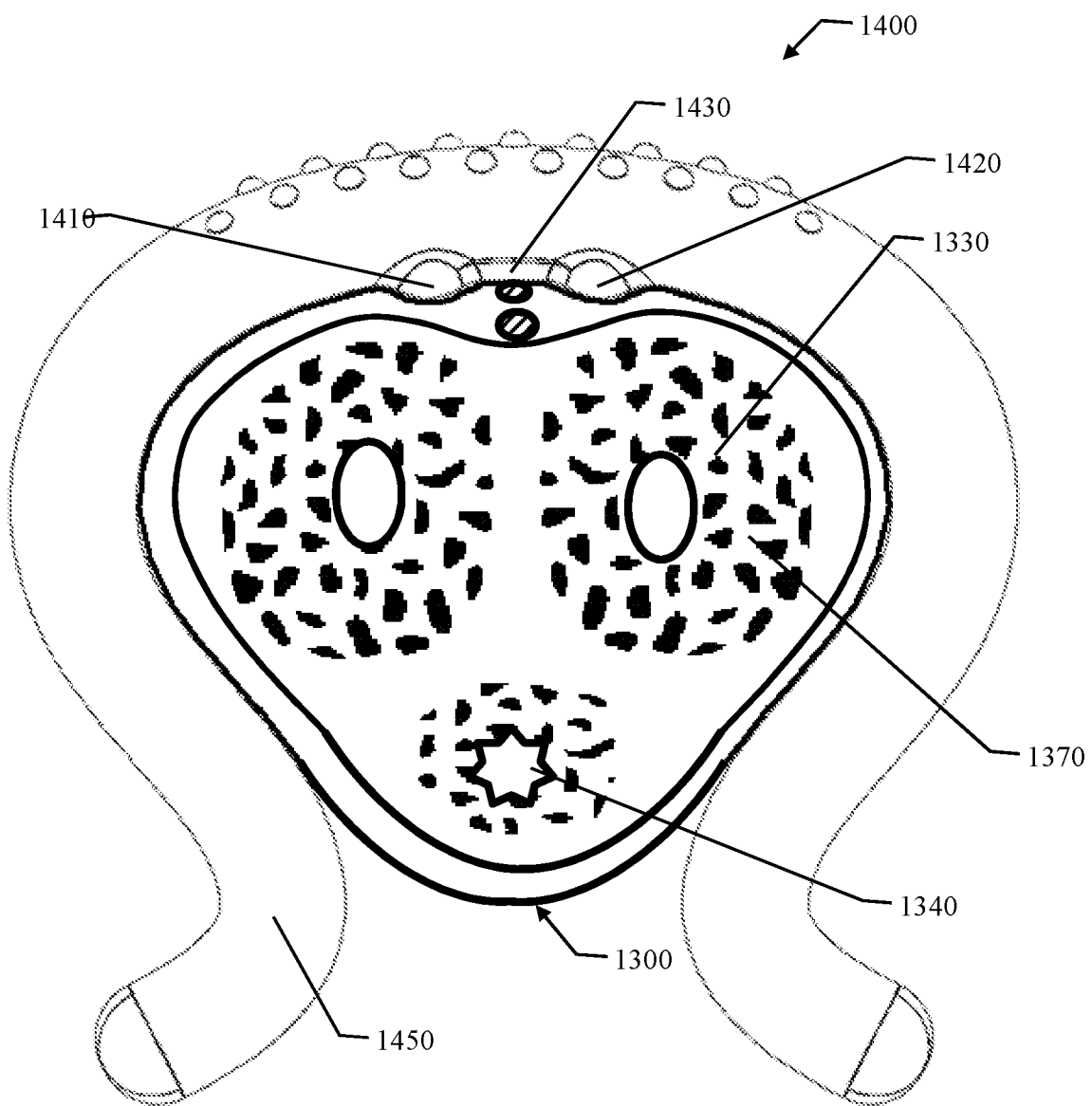
FIG. 14 shows a front cross-sectioned view of a non-limiting example of a penile constriction device on a human penis, per an embodiment herein.

FIG. 14 shows a front cross-sectioned view of a non-limiting example of a penile constriction device on a human penis. Optionally, in this or any other embodiment, at least one of the shape and elasticity of device 1400 is configured to prevent outwards blood flow from the penis 1300 to the body. Optionally, in this or any other embodiment, at least one of the shape and elasticity of device 1400 is configured to enable and/or not hinder blood flow from the body to the penis 1300.

Optionally, in this or any other embodiment, at least one of the shape and elasticity of the device 1400 is configured to provide at least one of the non-uniform pressure and the selective non-uniform pressure is to at least one of a flaccid penis, a slightly flaccid penis, a slightly rigid penis, and an erect penis. Optionally, in this or any other embodiment, the at least one of the non-uniform pressure and the selective non-uniform pressure is to at least one of a flaccid penis, a slightly flaccid penis, a slightly rigid penis, and an erect penis 1300 enables the device to facilitate erection initiation. Optionally, in this or any other embodiment, at least one of the non-uniform pressure and the selective non-uniform pressure is to at least one of a flaccid penis, a slightly flaccid penis, a slightly rigid penis, and an erect penis 1300 enables to device 1400 to aid in erection stamina. Optionally, in this or any other embodiment, the at least one of the non-uniform pressure and the selective non-uniform pressure is to at least one of a flaccid penis, a slightly flaccid penis, a slightly rigid penis, and an erect penis 1300 enables to device 1400 to facilitate erection initiation and erection stamina.

Optionally, in this or any other embodiment, at least one of the shape and elasticity of the device 1400 is configured to provide at least one of the non-uniform pressure and the selective non-uniform pressure to compress at least one of the girth and the cross section area of a flaccid penis, a slightly flaccid penis, a slightly rigid penis, and an erect penis.

Optionally, in this or any other embodiment, at least one of the shape and elasticity of an arched rod 1450 is configured to a compress the penis 1300 against at least one of the first dorsal vein protrusion 1410, the second dorsal vein protrusion 1420, and the dorsal valley 1430. Optionally, in this or any other embodiment, a compressive force applied to the penis 1300 by at least one of the first dorsal vein protrusion 1410, the second dorsal vein protrusion 1420, and the dorsal valley 1430, constricts blood flowing out of the penis 1300 through at least the superficial dorsal vein 1310 and the deep dorsal vein 1320. Optionally, in this or any other embodiment, a compressive force applied to the penis 1300 by at least one of the first dorsal vein protrusion 1410, the second dorsal vein protrusion 1420, and the dorsal valley 1430, does not constrict at least one of the dorsal arteries 1350 and the urethra 1340. Optionally, in this or any other embodiment, the device 1400 applies pressure to the veins of the penis to reduce blood flow out of the penis. This allows for the pressure to build up in the corpus cavernosa 1370 to achieve and/or maintain an erection. Optionally, in this or any other embodiment, the device 1400 has no negative effect on the dorsal nerve 1360.

Optionally, in this or any other embodiment, the constriction gap width of the device 1400 is configured such that an erect or flaccid penis having an erect diameter and a flaccid diameter, respectively, can pass through the constriction gap. Optionally, in this or any other embodiment, the constriction gap width is configured such that an erect or flaccid penis, having an erect diameter and a flaccid diameter, respectively, can pass through the constriction gap when an opposing force is applied between the first converging end and the second converging end. Optionally, in this or any other embodiment, the device 1400 applies pressure to the veins of the penis to reduce blood outflow from the penis. Such outflow allows for the pressure to build up in the corpus cavernosa 1370 to achieve and or maintain an erection. Optionally, in this or any other embodiment, the device 1400 has no negative effect on the dorsal nerve.

Optionally, in this or any other embodiment, the constriction gap width is configured to impart minimal compressive force on the urethra, when worn on an erect penis. Optionally, in this or any other embodiment, the constriction height of the device 1400 is configured to impart minimal compressive force on the urethra 1340, when worn on an erect penis. Optionally, in this or any other embodiment, the constriction height is configured to impart maximal compressive force on the deep arteries 1330, on an erect or a flaccid penis having an erect diameter and a flaccid diameter, respectively. Optionally, in this or any other embodiment, the maximum inner width of the device 1400, is configured to impart minimal or negligible compressive force on the deep arteries 1330, the urethra 1340, and the dorsal nerves 1360 of an erect or a flaccid penis having an erect diameter and a flaccid diameter, respectively. Optionally, in this or any other embodiment, the inferior height is configured to impart a significant compressive force on at least one of the superficial dorsal vein 1310 and the deep dorsal vein 1320. Optionally, in this or any other embodiment, the thickness of the device 1400 is configured to provide at least one of a sufficient elasticity, rigidity, and pliability to enable the device 1400 to provide a specific pressure against an erect or a flaccid penis having an erect diameter and a flaccid diameter, respectively.

Optionally, in this or any other embodiment, at least one of the first dorsal vein protrusion 1410, the second dorsal vein protrusion 1420, and the dorsal valley 1430 are configured to apply no force, or a minimal force to at least one of the dorsal arteries 1350 and the urethra 1340. Optionally, in this or any other embodiment, at least one of the shape and elasticity of the device 100 is configured to apply a non-uniform pressure to the penis 1300. Optionally, in this or any other embodiment, at least one of the shape and elasticity of the device 100 is configured to apply a selective non-uniform pressure to the penis 1300. Optionally, in this or any other embodiment, at least one of the non-uniform pressure and the selective non-uniform pressure is configured to allow at least one of blood and seminal fluids to flow into the penis 1300. Optionally, in this or any other embodiment, at least one of the non-uniform pressure and the selective non-uniform pressure is configured to allow a user to perform Kegel exercises to increase blood flow into the penis 1300. Optionally, in this or any other embodiment, at least one of the non-uniform pressure and the selective non-uniform pressure is configured to maintain the health of at least one of cells, arteries, and veins within the penis 1300. Optionally, in this or any other embodiment, at least one of the shape and elasticity of the device 100 is configured to apply a greater or equal pressure to the penis 1300 at the compression region than by at least one of the first arm and the second arm. Optionally, in this or any other embodiment, at least one of the shape and elasticity of the device 100 is configured to apply less pressure to the penis 1300 at the compression region than by at least one of the first arm and the second arm.

Optionally, in this or any other embodiment, at least one of the dorsal vein valley distance, the compression region width, the first dorsal height, the second dorsal height, the maximum inner width, the constriction distance, and the constriction gap are configured to constrict blood flowing out of the penis 1300 through at least the superficial dorsal vein 1310 and the deep dorsal vein 1320. Optionally, in this or any other embodiment, at least one of the dorsal vein valley distance, the compression region width, the first dorsal height, the second dorsal height, and the constriction gap are configured to apply no force, or a minimal force to at least one of the dorsal arteries 1350 and the urethra 1340. Optionally, in this or any other embodiment, at least one of the dorsal vein valley distance, the compression region width, the first dorsal height, the second dorsal height, the maximum inner width, the constriction distance, and the constriction gap are configured to constricts blood flowing out of the penis 1300 through at least the superficial dorsal vein 1310 and the deep dorsal vein 1320 and to apply no force, or a minimal force to at least one of the dorsal arteries 1350 and the urethra 1340.

Optionally, in this or any other embodiment, the elasticity of at least one of the first arm, the second arm, and the bridge enables the device 1400 to provide continuous pressure on both a flaccid and erect penis 1300. Optionally, in this or any other embodiment, the pliability of at least one of the first arm, the second arm, and the bridge enables the device 1400 to provide continuous pressure on flaccid penis 1300 as it becomes erect.

Optionally, in this or any other embodiment, at least one of the shape and elasticity of the device 100 is configured to provide at least one of the non-uniform pressure and the selective non-uniform pressure that compresses at least one of the girth of the penis 1300 and the cross section area of the penis 1300 by at least about 10%. Optionally, in this or any other embodiment, at least one of the shape and elasticity of the device 100 is configured to provide at least one of the non-uniform pressure and the selective non-uniform pressure that compresses at least one of the girth of the penis 1300 and the cross section area of the penis 1300 by at most about 60%. Optionally, in this or any other embodiment, at least one of the shape and elasticity of the device 100 is configured to provide at least one of the non-uniform pressure and the selective non-uniform pressure that compresses at least one of the girth of the penis 1300 and the cross section area of the penis 1300 by about 10% to about 60%. Optionally, in this or any other embodiment, at least one of the shape and elasticity of the device 100 is configured to provide at least one of the non-uniform pressure and the selective non-uniform pressure that compresses at least one of the girth of the penis 1300 and the cross section area of the penis 1300 by about 15% to about 45%. Optionally, in this or any other embodiment, at least one of the shape and elasticity of the device 100 is configured to provide at least one of the non-uniform pressure and the selective non-uniform pressure that compresses at least one of the girth of the penis 1300 and the cross section area of the penis 1300 by about 37%.

Optionally, in this or any other embodiment, the negligible or minimal force applied by the device 100 on the dorsal arteries 1350 allows blood and oxygen to flow into the penis 1300 1300, with or without the aid of Kegel exercises, which prevents damage to the cells of the penis 1300 1300 and to ensure their ability to achieve an erection. Optionally, in this or any other embodiment, the negligible or minimal force applied by the device 100 on the urethra 1340 enables the release of pre-seminal fluid that act as a lubricant during sexual intercourse. Optionally, in this or any other embodiment, the negligible or minimal force applied by the device 100 on the urethra 1340 prevents injaculation or retrograde ejaculation, wherein a blockage within the seminal vesicle causes semen to flow backwards into the bladder. Such injaculation causes infertility, by damaging the perineum, nerves, and blood vessels within the male reproductive system. Optionally, in this or any other embodiment, at least one of the first elbow 214 and the second elbow 224 are configured to prevent abrasion or lacerations of the penis 1300.

Optionally, in this or any other embodiment, at least one of the shape and elasticity of the device 100 is configured to avoid inhibiting male pleasure during intercourse. Optionally, in this or any other embodiment, at least one of the first dorsal vein protrusion, the second dorsal vein protrusion, and the dorsal valley are configured to prevent rotation of the device 100 about the penis 1300.

Penile Constriction Systems

Figure 15A:
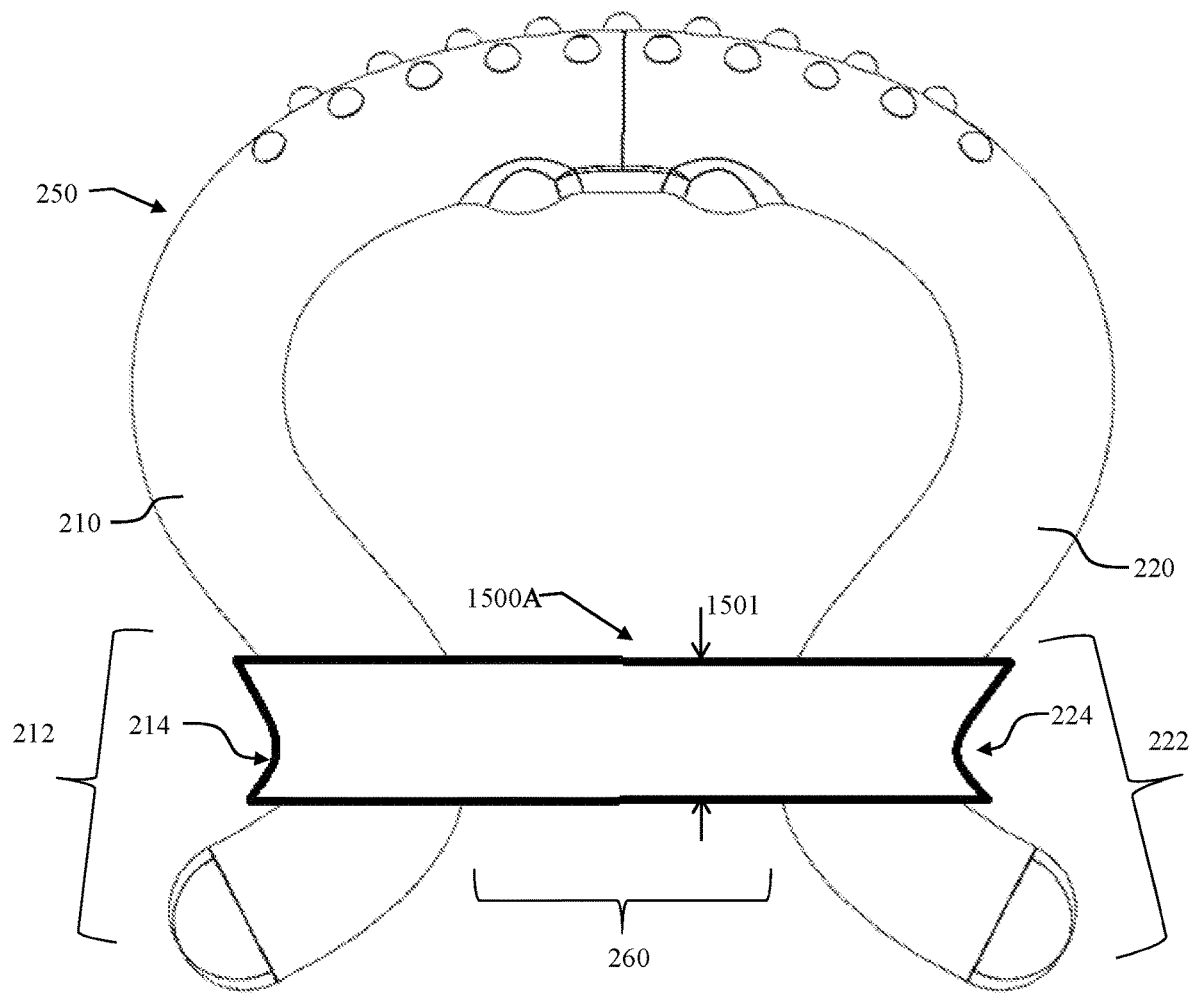
FIG. 15A shows a front view of a non-limiting example of a penile constriction system comprising an exemplary penile constriction device and a band, per an embodiment herein.
Figure 15B:
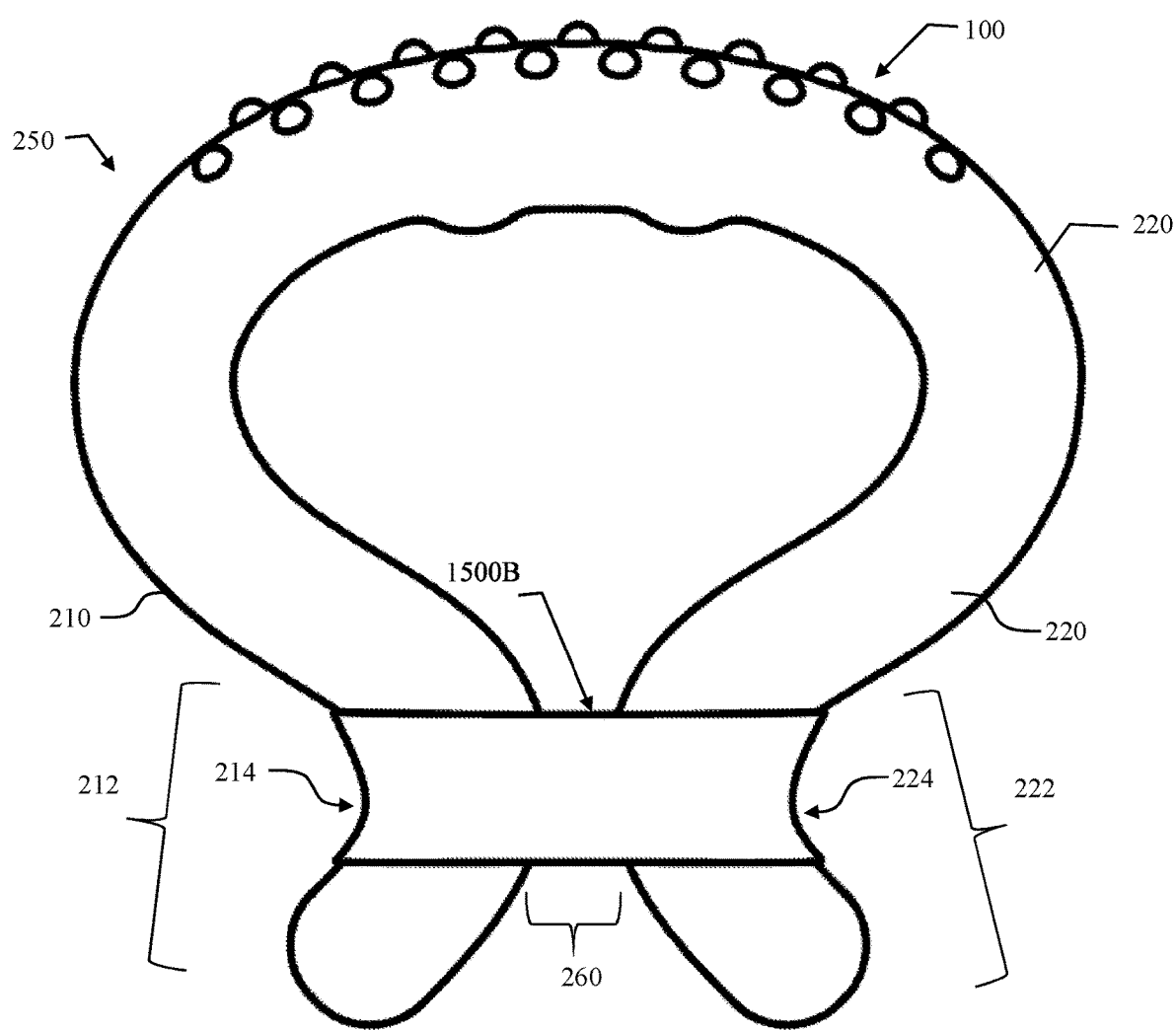
FIG. 15B shows a front view of a non-limiting example of a penile constriction system comprising an exemplary penile constriction device and a high tension band, per an embodiment herein.

FIG. 15A shows a front view of a non-limiting example of a penile constriction system comprising an exemplary penile constriction device and a band. FIG. 15B shows a front view of a non-limiting example of a penile constriction system comprising an exemplary penile constriction device and a high tension band. Provided herein, per FIGS. 15A-B, is a system comprises a penile constriction device 100 and a band 1500. Optionally, in this or any other embodiment, the band 1500 is configured to attach to the first converging end 212 and the second converging end 212 of the device 100. Optionally, in this or any other embodiment, the band 1500 is configured to attach to the first elbow 214 and at least one of the second elbow 224, the second converging end 222, and the second terminus 223 of the device 100. Optionally, in this or any other embodiment, the band 1500 is configured to attach to the first converging end 212 and at least one of the second elbow 224, the second converging end 222, and the second terminus 223 of the device 100. Optionally, in this or any other embodiment, the band 1500 is configured to attach to the first terminus 213 and at least one of the second elbow 224, the second converging end 222, and the second terminus 223 of the device 100.

Penile Constriction Bands

Optionally, in this or any other embodiment, at least one of the first arm 210, the second arm 220, the first converging end 212, the second converging end 222, first elbow 214, and the second elbow 224 of the arched rod device 100 is configured to couple to a band 1500. Optionally, in this or any other embodiment, the arched rod 250 does not comprise the band 1500. Optionally, in this or any other embodiment, the penile constriction device 100 does not comprise the band 1500.

Optionally, in this or any other embodiment, the band 1500 is configured to removably attach, temporarily attach, or both to the device 100. Optionally, in this or any other embodiment, the band 1500 is rigidly attached to the device 100. Optionally, in this or any other embodiment, the band is separate and distinct from the device. Optionally, in this or any other embodiment, the band is not rigidly attached to the device. Optionally, in this or any other embodiment, the band is removably attached to the first converging end, the second converging end, or the bridge of the device 100.

Optionally, in this or any other embodiment, the band 1500 is configured to impart a compressive force between the first converging 212 and the second converging 212 of the device 100. Optionally, in this or any other embodiment, the band 1500 is configured to impart a compressive force between the first elbow 214 and the second elbow 224 of the device 100. Optionally, in this or any other embodiment, the band 1500 is configured to impart a compressive force between the first converging 212 and the second elbow 224 of the device 100. Optionally, in this or any other embodiment, the band 1500 is configured to impart a compressive force between the second converging 212 and the first elbow 214 of the device 100.

Optionally, in this or any other embodiment, per FIG. 15A, the band 1500 comprises a low tension band 1500A. Alternatively, in this or any other embodiment, per FIG. 15B, the band 1500 comprises a high tension band 1500B, wherein the high tension band 1600 is configured to impart a greater force between the first arm 210 and the second arm 220 than the low tension band 1500.

Optionally, in this or any other embodiment, the band 1500 is configured to provide increased penile compressive force. Optionally, in this or any other embodiment, the penile compressive force compresses the cross section area of the penis by at least about 10%. Optionally, in this or any other embodiment, the penile compressive force compresses the cross section area of the penis by at most about 60%. Optionally, in this or any other embodiment, the penile compressive force compresses the cross section area of the penis by about 10% to about 60%. Optionally, in this or any other embodiment, the penile compressive force compresses the cross section area of the penis by about 37%. Optionally, in this or any other embodiment, the increased penile compressive force prevents the device 100 from rotating or translating from its originally worn position during intercourse.

Optionally, in this or any other embodiment, per FIG. 15A, the shape and elasticity of at least one of the band 1500 and the device 100 are configured such that, the shape of the device is relatively undeformed when the band 1500 is affixed to the device 100. Optionally, in this or any other embodiment, the shape and elasticity of at least one of the band 1500 and the device 100 are configured such that the band 1500 only slightly increases the penile compressive force (e.g. by less than about 10%), whereby the band 1500 is configured to increase device 100 stability about the penis by acting as a friction surface.

Optionally, in this or any other embodiment, per FIG. 15B, the shape and elasticity of at least one of the band 1500 and the device 100 are configured such that, the shape of the device is significantly deformed when the band 1500 is affixed to the device 100. Optionally, in this or any other embodiment, the shape and elasticity of at least one of the band 1500 and the device 100 are configured such that the band 1500 substantially increases the penile compressive force (e.g. by more than about 10%), whereby the band 1500 is configured to decrease at least one of the constriction gap, the constriction height, the maximum inner width, and the inferior height of the device 100. Optionally, in this or any other embodiment, the shape and elasticity of at least one of the band 1500 and the device 100 are configured such that, the shape of the device is significantly deformed when the band 1500 is affixed to the device 100, to allow the device 100 to be employed on a penis with a smaller girth or circumference.

Optionally, in this or any other embodiment, per FIG. 15A, the band 1500 comprises a band width 1501. Optionally, in this or any other embodiment, the band width 1501 is about 0.1 inches to about 1.5 inches. Optionally, in this or any other embodiment, the band width 1501 is at least about 0.1 inches. Optionally, in this or any other embodiment, the band width 1501 is at most about 1.5 inches. Optionally, in this or any other embodiment, the band 1500 has a spring constant of about 0.1 pounds/inches to about 1 pound/inch. Optionally, in this or any other embodiment, the band 1500 has a spring constant of at least about 0.1 pounds/inches. Optionally, in this or any other embodiment, the band 1500 has a spring constant of at most about 1 pound/inch.

Optionally, in this or any other embodiment, the band 1500 is elastic. Optionally, in this or any other embodiment, the band 1500 is inelastic. Optionally, in this or any other embodiment, the band 1500 is rigid. Optionally, in this or any other embodiment, the band 1500 comprises a spring, a loop, a cam, a hook or any combination thereof. Optionally, in this or any other embodiment, the bands herein are soft to the touch and/or non-abrasive. Optionally, in this or any other embodiment, the bands herein are non-allergenic. Optionally, in this or any other embodiment, the bands herein are formed from a material that is washable. Optionally, in this or any other embodiment, the bands herein have a sufficient tensile strength to prevent breaking or tearing when installing the band between the first elbow and the second elbow of the device 100. Optionally, in this or any other embodiment, the bands herein have a sufficient modulus of elasticity such that the band can be stretched by hand over first converging end and the second converging end and onto the first elbow and the second elbow of the device 100. Optionally, in this or any other embodiment, the bands herein have a sufficient durometer to prevent breaking or tearing during over-extension and frequent reuse. Optionally, in this or any other embodiment, a surface of the bands herein have a texture that prevents the bands from sliding off the device 100.

Optionally, in this or any other embodiment, the bands herein are formed from a thermoplastic elastomer. Optionally, in this or any other embodiment, the band comprises rubber, plastic, metal, wood, silicone, Kevlar, string, fabric, or any combination thereof. Optionally, in this or any other embodiment, the band comprises plastic, glass, wood, metal, carbon fiber, fiberglass, or any combination thereof. Optionally, in this or any other embodiment, the band comprises polyamide, polycarbonate, polyester, polyethylene, polyethylene terephthalate, polypropylene, polystyrene, polyurethanes, polyvinyl chloride, polyvinylidene chloride acrylonitrile butadiene styrene acrylonitrile butadiene styrene, polyethylene/acrylonitrile butadiene styrene, polyepoxide, polymethyl methacrylate, polytetrafluoroethylene, phenolics melamine formaldehyde urea-formaldehyde, polyetheretherketone, maleimide/bismaleimide, polyetherimide, polyimide, polylactic acid, furan silicone, polysulfone, or any combination thereof. Optionally, in this or any other embodiment, the bands herein are not formed from PVC, latex, phthalates, or any combination thereof.

Figure 47:
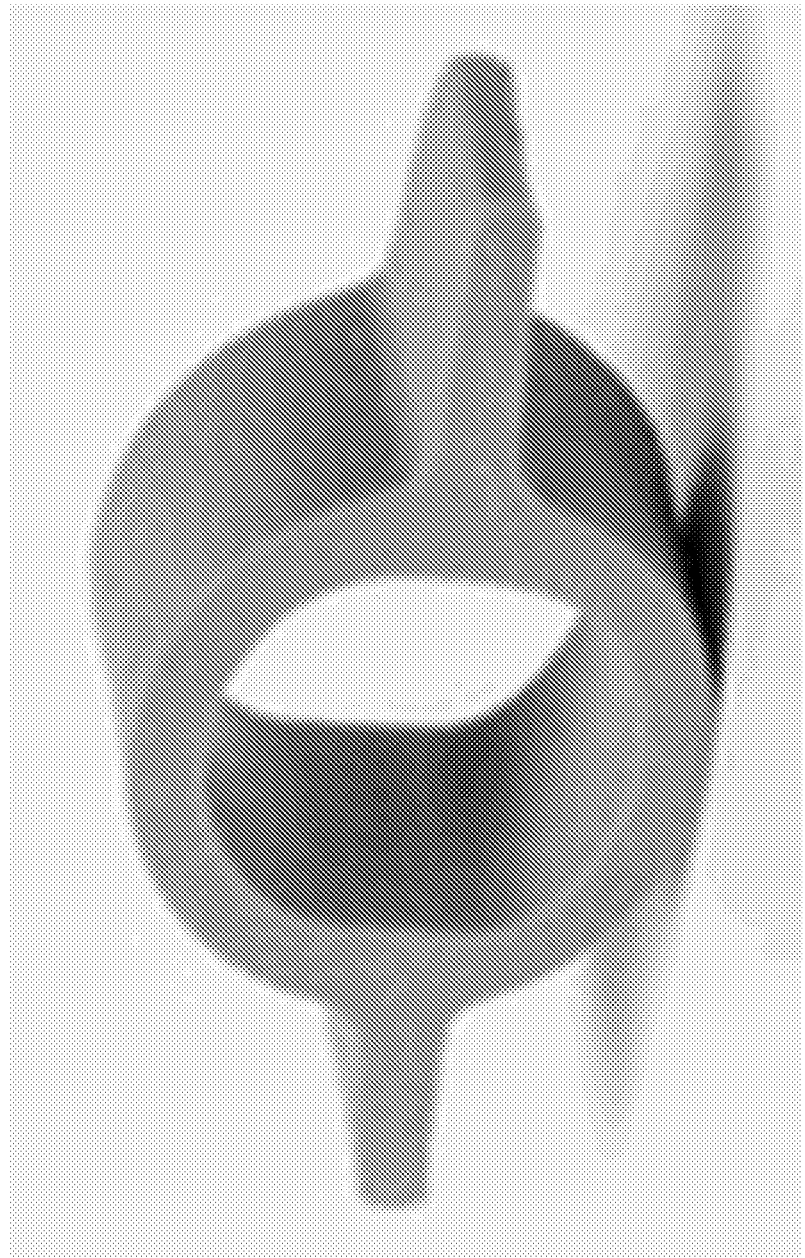
FIG. 47 shows a perspective image of a non-limiting example of a first size of a primary band of the penile constriction device herein, per an embodiment herein.
Figure 48:
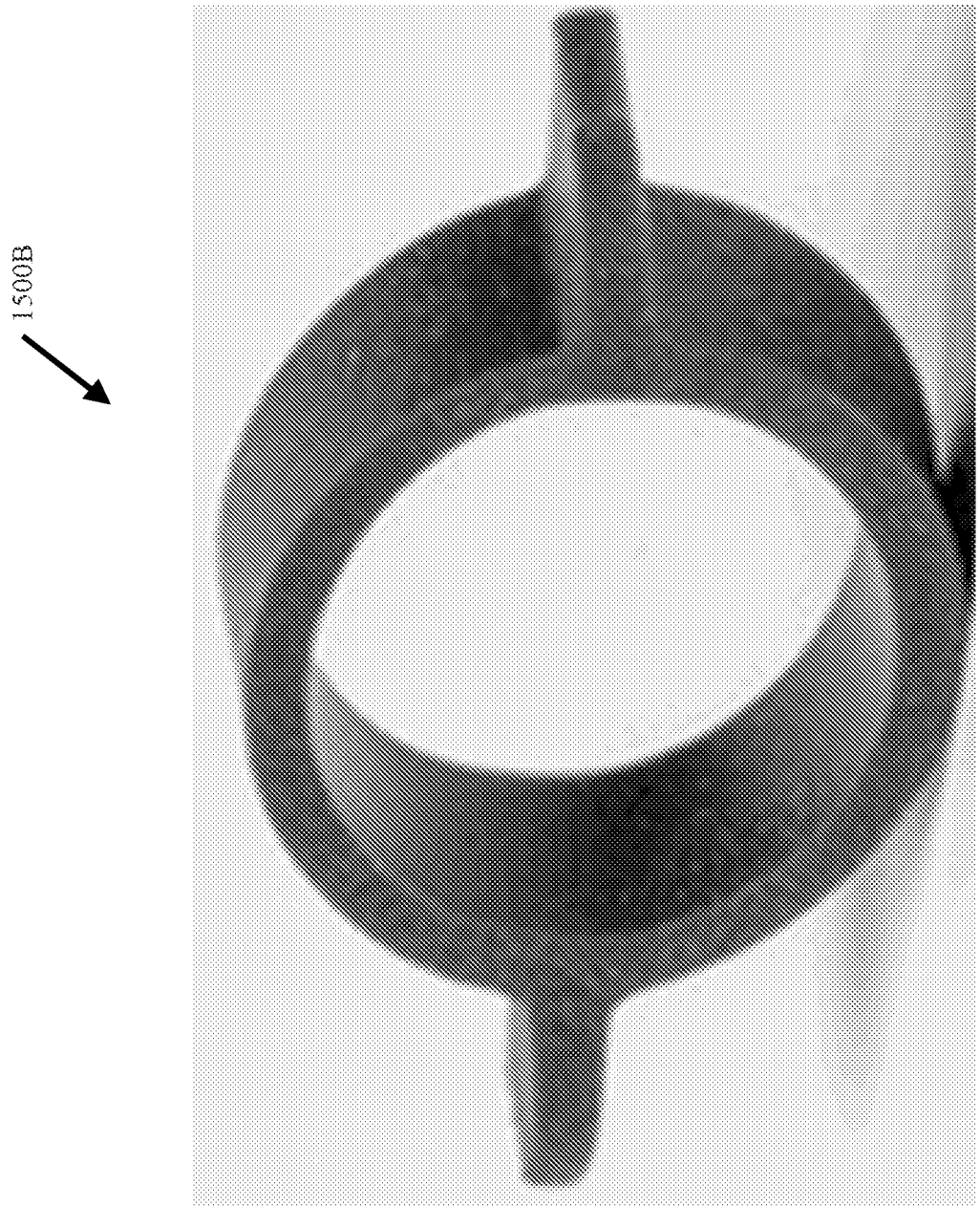
FIG. 48 shows a perspective view image of a non-limiting example of a third size of a primary band of the penile constriction device herein, per an embodiment herein.
Figure 49:
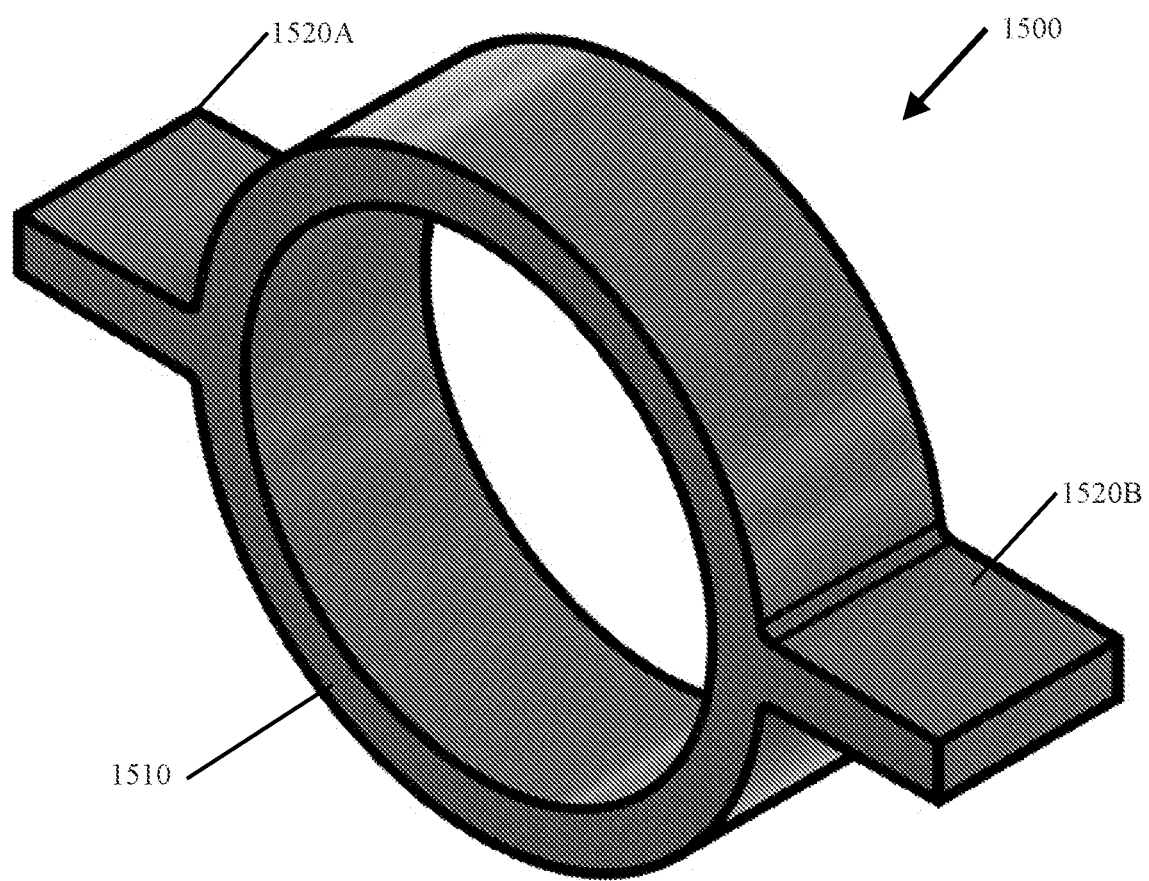
FIG. 49 shows a perspective view illustration of a non-limiting example of a primary band of the penile constriction device herein, per an embodiment herein.

FIGS. 47-52 show non-limiting exemplary images of a primary band 1500 penile constriction device herein. FIG. 47 shows a non-limiting exemplary image of a low tension primary band 1500A. FIG. 48 shows a non-limiting exemplary image of a high tension primary band 1500B. Per FIG. 49 the primary band 1500 comprises a hoop 1510, a first tab 1520A, and a second tab 1520B. Per FIG. 51, the secondary band 1600 an elongated hoop 1510, the first tab 1520A, and the second tab 1520B. As shown, the first tab 1520A, and the second tab 1520B have equal tab lengths from their distal edges to their intersection with the hoop 1610. Alternatively, in this or any other embodiment, the tab length of the first tab 1520A is greater than the tab length of the second tab 1520B. Alternatively, in this or any other embodiment, the tab length of the first tab 1520A is less than the tab length of the second tab 1520B.

Figure 50A:
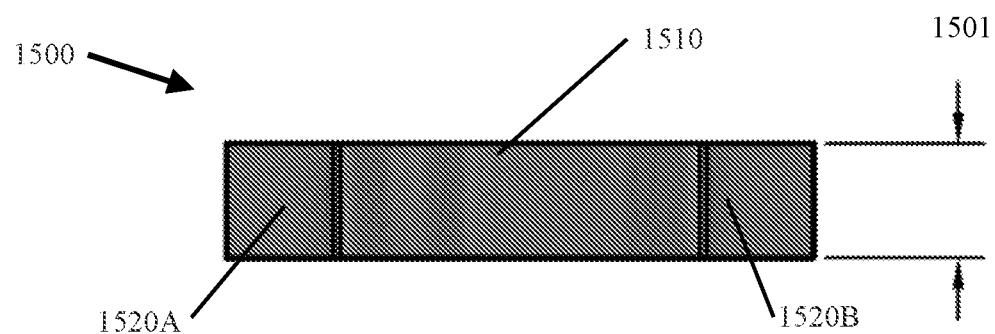
FIG. 50A shows a top view illustration of a non-limiting example of a primary band of the penile constriction device herein, per an embodiment herein.
Figure 50B:
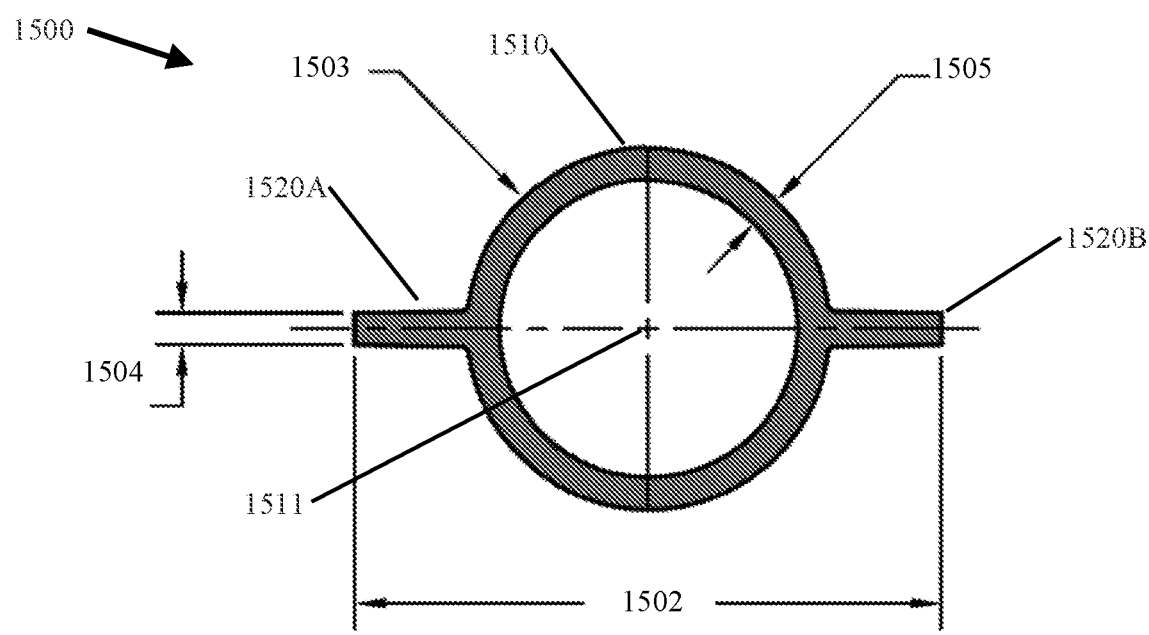
FIG. 50B shows a front view illustration of a non-limiting example of a primary band of the penile constriction device herein, per an embodiment herein.

As shown per FIG. 50B, the tabs 1520A 1520B extend perpendicularly from a center axis 1511 of the hoop 1510 from opposite sides of the hoop 1510. Alternatively, in this or any other embodiment, the primary band 1500 comprises 3, 4, 5, 6 or more tabs. Alternatively, in this or any other embodiment, the tabs 1520A 1520B extend parallel to a center axis 1511 of the hoop 1510 from opposite sides of the hoop 1510. The tabs 1520A 1520B provide a grip for a user to place the primary band 1500 on the device. Optionally, in this or any other embodiment, an upper surface, a lower surface, or both of one or more of the first tab 1520A and the second tab 1520B has a raised or embossed texture for increased grip.

As shown, the primary band 1500 has a depth 1501 measured from a front surface to a back surface of the primary band 1500. Optionally, in this or any other embodiment, the depth 1501 is measured as a minimum depth, a maximum depth, or an average depth. As shown, the hoop 1510 and the tabs 1520A 1520B have equal depths 1501. Optionally, in this or any other embodiment, a depth 1501 of the hoop 1510 is greater than a depth 1501 of the tabs 1520A 1520B. Optionally, in this or any other embodiment, a depth 1501 of the hoop 1510 is less than a depth 1501 of the tabs 1520A 1520B.

Further per FIG. 50B, the primary band 1500 has a width 1502 measured from a distal surface of the first tab 1520A to a distal surface of the second tab 1520B. Alternatively, in this or any other embodiment, the width 1502 is measured as a maximum, an average, or a minimum distance from a distal surface of the first tab 1520A to the distal surface of the second tab 1520B. Alternatively, in this or any other embodiment, the width 1502 is measured as a maximum, an average, or a minimum width of the primary band 1500. Optionally, in this or any other embodiment, the width 1502 is measured when the primary band 1500 is at rest and not applied to the device.

As shown, the hoop 1510 of the primary band 1500 has an outer diameter 1503. Optionally, in this or any other embodiment, the outer diameter 1503 is measured as a maximum, an average, or a minimum outer diameter of the hoop 1510. Optionally, in this or any other embodiment, the outer diameter 1503 is measured as a maximum, an average, or a minimum outer diameter of a portion of the hoop 1510 not connected to the tabs 1520A 1520B. Optionally, in this or any other embodiment, the outer diameter 1503 is measured when the primary band 1500 is at rest and not applied to the device.

Also as shown, the tabs 1520A 1520B have a tab thickness 1504 measured as a distance between opposing faces of each of the tabs 1520A 1520B. Optionally, in this or any other embodiment, the tab thickness 1504 is measured as a maximum, an average, or a minimum thickness of the tabs 1520A 1520B. Optionally, in this or any other embodiment, the first tab 1520A and the second tab 1520B have the same the tab thickness 1504. Optionally, in this or any other embodiment, the first tab 1520A has a greater tab thickness 1504 than the second tab 1520B. Optionally, in this or any other embodiment, the first tab 1520A has a smaller tab thickness 1504 than the second tab 1520B. Optionally, in this or any other embodiment, the tab thickness 1504 is uniform from a distal edge to a proximal edge of the tabs 1520A 1520B. Optionally, in this or any other embodiment, the tab thickness 1504 is measured when the primary band 1500 is at rest and not applied to the device.

Further, per FIG. 50B the hoop 1510 has a hoop thickness 1505 measured as a normal distance between an outer surface and an inner surface of the hoop 1510. Optionally, in this or any other embodiment, the hoop thickness 1505 is measured as a maximum, an average, or a minimum distance. Optionally, in this or any other embodiment, the hoop thickness 1505 is equal across the circumference of the hoop 1510. Optionally, in this or any other embodiment, the hoop thickness 1505 varies across the circumference of the hoop 1510. Optionally, in this or any other embodiment, the hoop thickness 1505 is measured when the primary band 1500 is at rest and not applied to the device.

Figure 51:
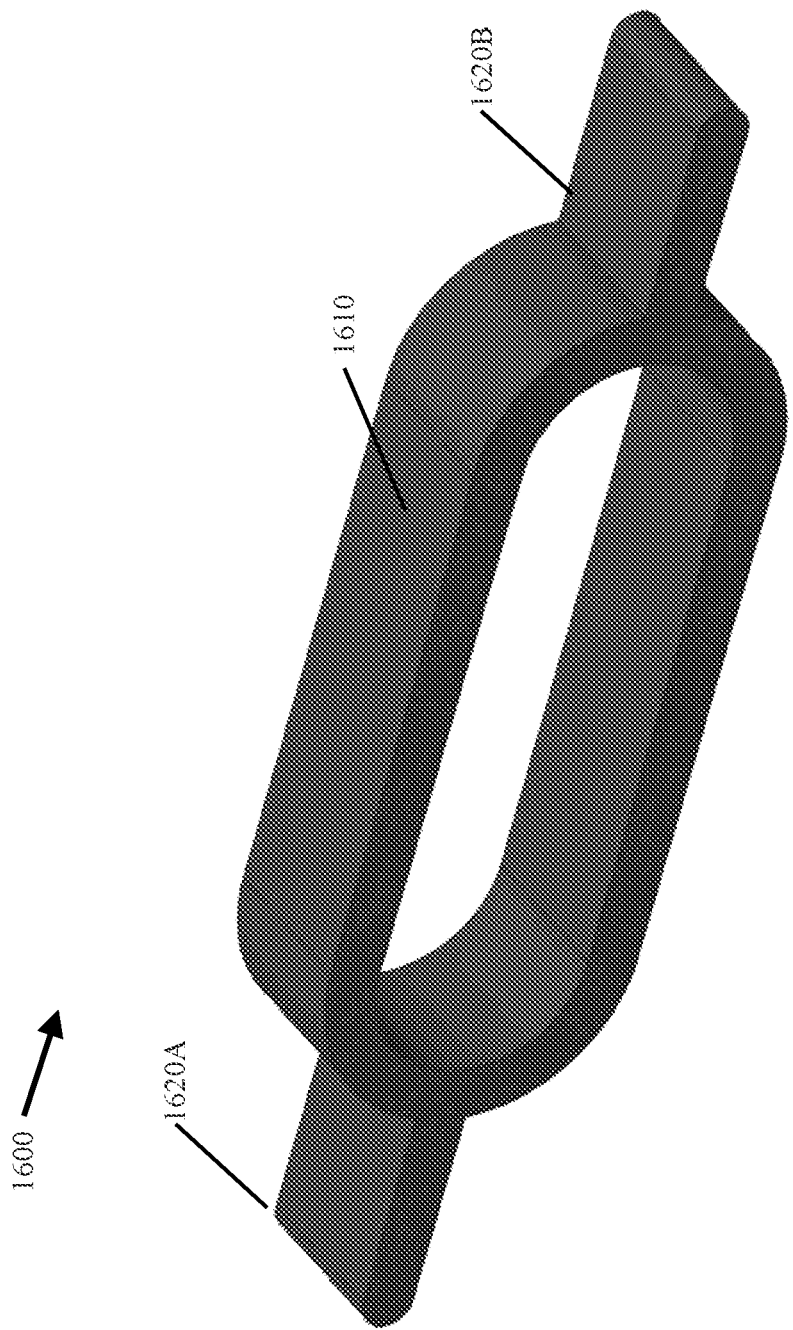
FIG. 51 shows a perspective view illustration of a non-limiting example of a secondary band of the penile constriction device herein, per an embodiment herein.
Figure 52:
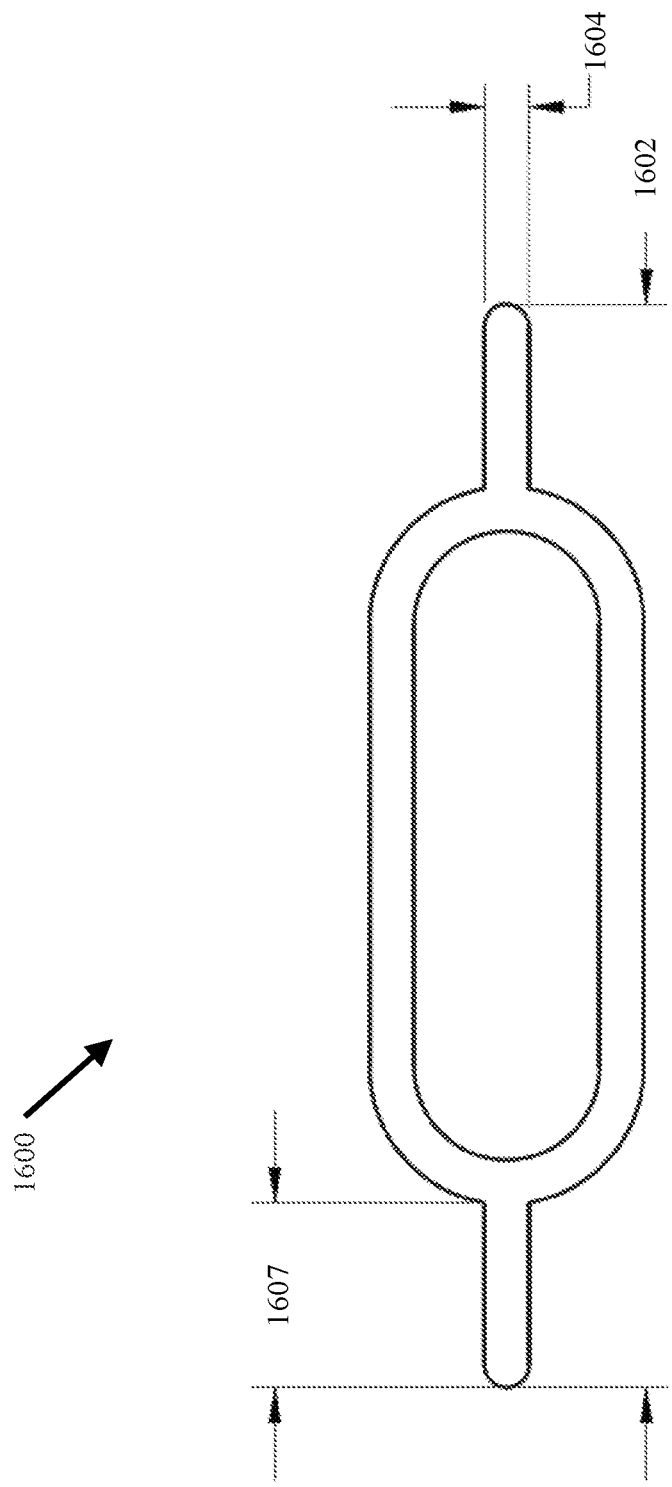
FIG. 52 shows a front view illustration of a non-limiting example of a secondary band of the penile constriction device herein, per an embodiment herein.

FIGS. 51 and 52 show exemplary illustrations of a secondary band 1600. As shown, the secondary band 1600 comprises an elongated hoop 1610, a first secondary tab 1620A, a second secondary tab 1620B. Further as shown, the first secondary tab 1620A and the second secondary tab 1620B extend outwards from opposite sides of the elongated hoop 1610. Per FIG. 52, the secondary band 1600 has an elongated width 1602. Optionally, in this or any other embodiment, the elongated width 1602 is measured from a distal surface of the first secondary tab 1620A to a distal surface of the second secondary tab 1620B. Alternatively, in this or any other embodiment, the width 1602 is measured as a maximum, an average, or a minimum distance from a distal surface of the first secondary tab 1620A to the distal surface of the second secondary tab 1620B. Alternatively, in this or any other embodiment, the elongated width 1602 is measured as a maximum, an average, or a minimum width of the secondary band 1600. Optionally, in this or any other embodiment, the width 1602 is measured when the secondary band 1600 is at rest and not applied to the device. Further as shown, the secondary tabs 1620A 1620B have a tab thickness 1604 measured as a distance between opposing faces of each of the secondary tabs 1620A 1620B. Optionally, in this or any other embodiment, the tab thickness 1604 is measured as a maximum, an average, or a minimum thickness of the secondary tabs 1620A 1620B. Optionally, in this or any other embodiment, the first secondary tab 1620A and the second secondary tab 1620B have the same the tab thickness 1604. Optionally, in this or any other embodiment, the first secondary tab 1620A has a greater tab thickness 1604 than the second secondary tab 1620B. Optionally, in this or any other embodiment, the first secondary tab 1620A has a smaller tab thickness 1604 than the second secondary tab 1620B. Optionally, in this or any other embodiment, the tab thickness 1604 is uniform from a distal edge to a proximal edge of the secondary tabs 1620A 1620B. Optionally, in this or any other embodiment, the tab thickness 1604 is measured when the secondary band 1600 is at rest and not applied to the device. Also as shown, the first secondary tab 1620A, and the second secondary tab 1620B have equal tab lengths 1607 from their distal edges to their intersection with the hoop 1610. Alternatively, in this or any other embodiment, the tab length 1607 of the first secondary tab 1620A is greater than the tab length 1607 of the second secondary tab 1620B. Alternatively, in this or any other embodiment, the tab length 1607 of the first secondary tab 1620A is less than the tab length 1607 of the second secondary tab 1620B. Optionally, in this or any other embodiment, the elongated width 1602 is about 1 inch to about 2 inches. Optionally, in this or any other embodiment, the tab thickness 1604 is about 0.04 inches to about 0.08 inches. Optionally, in this or any other embodiment, the tab length 1607 is about 0.2 inches to about 0.3 inches.

Optionally, in this or any other embodiment, the primary band 1500 comprises a high tension primary band 1500A. Optionally, in this or any other embodiment, the primary band 1500 comprises a low tension primary band 1500B.

Optionally, in this or any other embodiment, the high tension primary band 1500A has one or more of a depth 1501 of about 0.1 inches to about 0.4 inches, a width 1502 of about 0.7 inches to about 1.0 inches, an outer diameter 1503 of about 0.2 inches to about 0.6 inches, a tab thickness 1504 of about 0.05 inches to about 0.1 inches, and a hoop thickness 1505 of about 0.05 inches to about 0.1 inches. Optionally, in this or any other embodiment, the high tension primary band 1500A has one or more of a depth 1501 of at least about 0.1 inches, a width 1502 of at least about 0.7 inches, an outer diameter 1503 of at least about 0.2 inches, a tab thickness 1504 of at least about 0.05 inches, and a hoop thickness 1505 of at least about 0.05 inches. Optionally, in this or any other embodiment, the high tension primary band 1500A has a depth 1501 of at most about 0.4 inches, a width 1502 of at most about 1.0 inches, an outer diameter 1503 of at most about 0.6 inches, a tab thickness 1504 of at most about 0.1 inches, and a hoop thickness 1505 of at most about 0.1 inches.

Optionally, in this or any other embodiment, the low tension primary band 1500B has a depth 1501 of about 0.1 inches to about 0.4 inches, a width 1502 of about 0.8 inches to about 1.4 inches, an outer diameter 1503 of about 0.4 inches to about 1.5 inches, a tab thickness 1504 of about 0.05 inches to about 0.1 inches, and a hoop thickness 1505 of about 0.05 inches to about 0.1 inches. Optionally, in this or any other embodiment, the low tension primary band 1500B has a depth 1501 of at least about 0.1 inches, a width 1502 of at least about 0.8 inches, an outer diameter 1503 of at least about 0.4 inches, a tab thickness 1504 of at least about 0.05 inches, and a hoop thickness 1505 of at least about 0.05 inches. Optionally, in this or any other embodiment, the low tension primary band 1500B has a depth 1501 of at most about 0.4 inches, a width 1502 of at most about 1.4 inches, an outer diameter 1503 of at most about 1.5 inches, a tab thickness 1504 of at most about 0.05 inches to about 0.1 inches, and a hoop thickness 1505 of at most about 0.1 inches.

Methods for Using the Penile Constriction Devices Herein

Figure 16A:
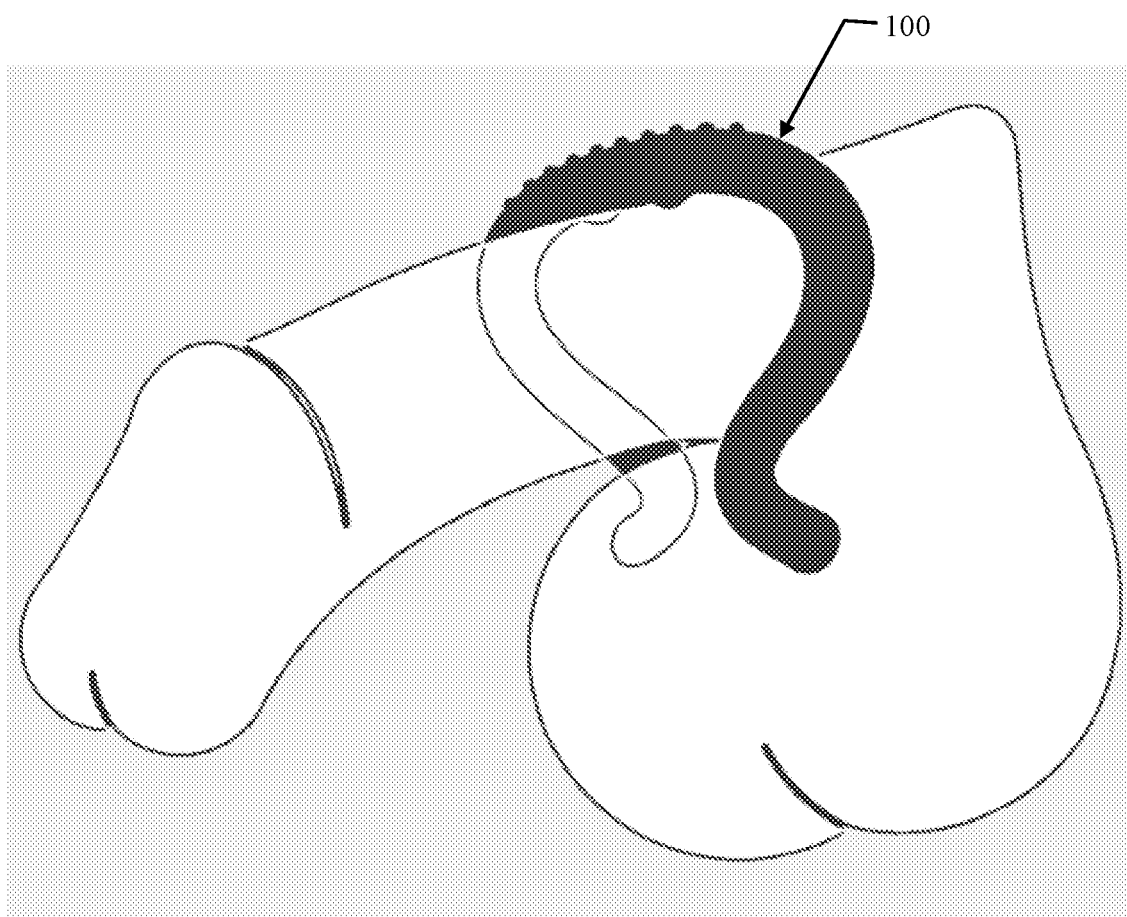
FIG. 16A shows a perspective view of a non-limiting example of a penile constriction device on a flaccid human penis, per an embodiment herein.
Figure 16B:
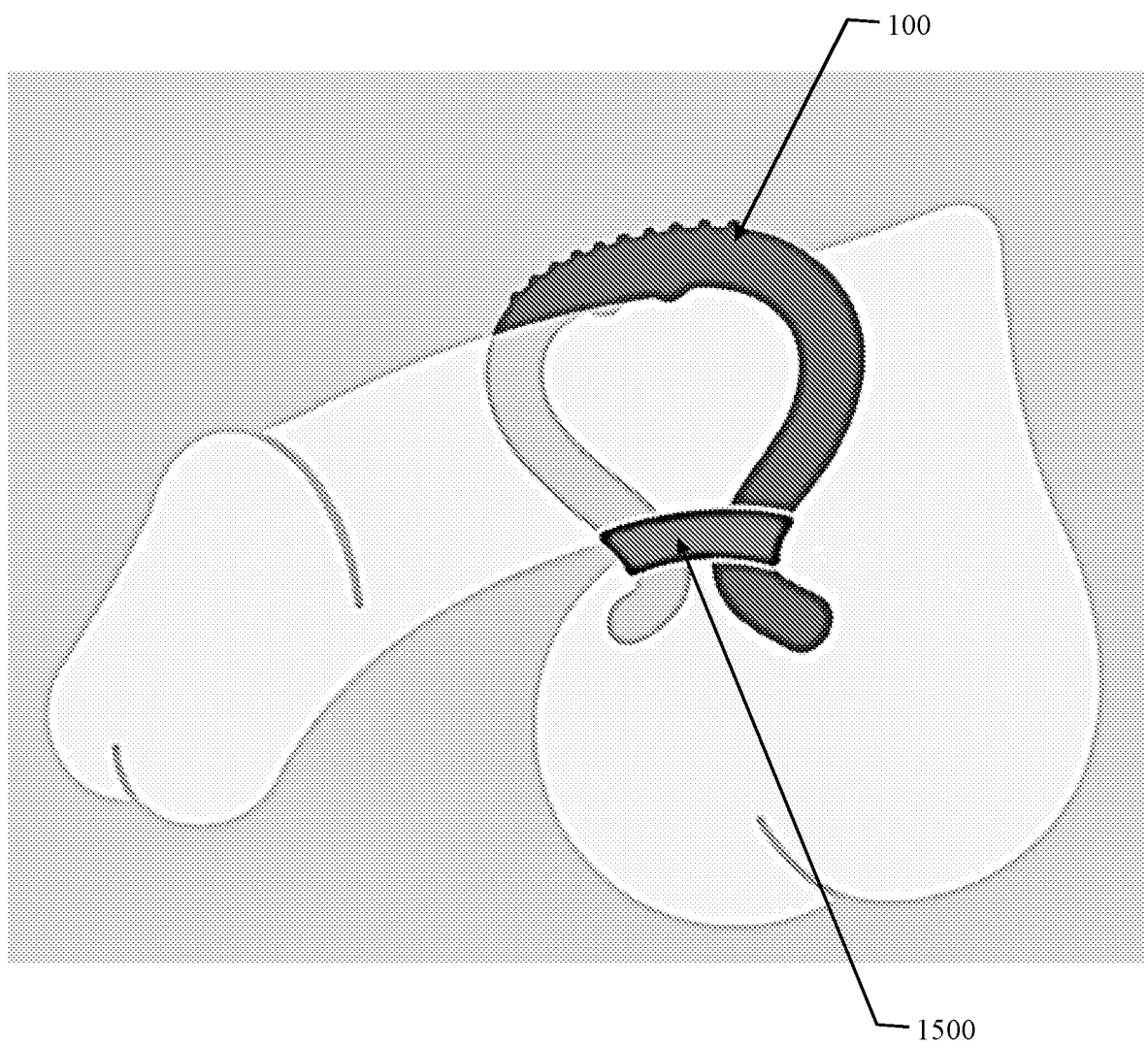
FIG. 16B shows a perspective view of a non-limiting example of a penile constriction device and a band on a flaccid human penis, per an embodiment herein.
Figure 16C:
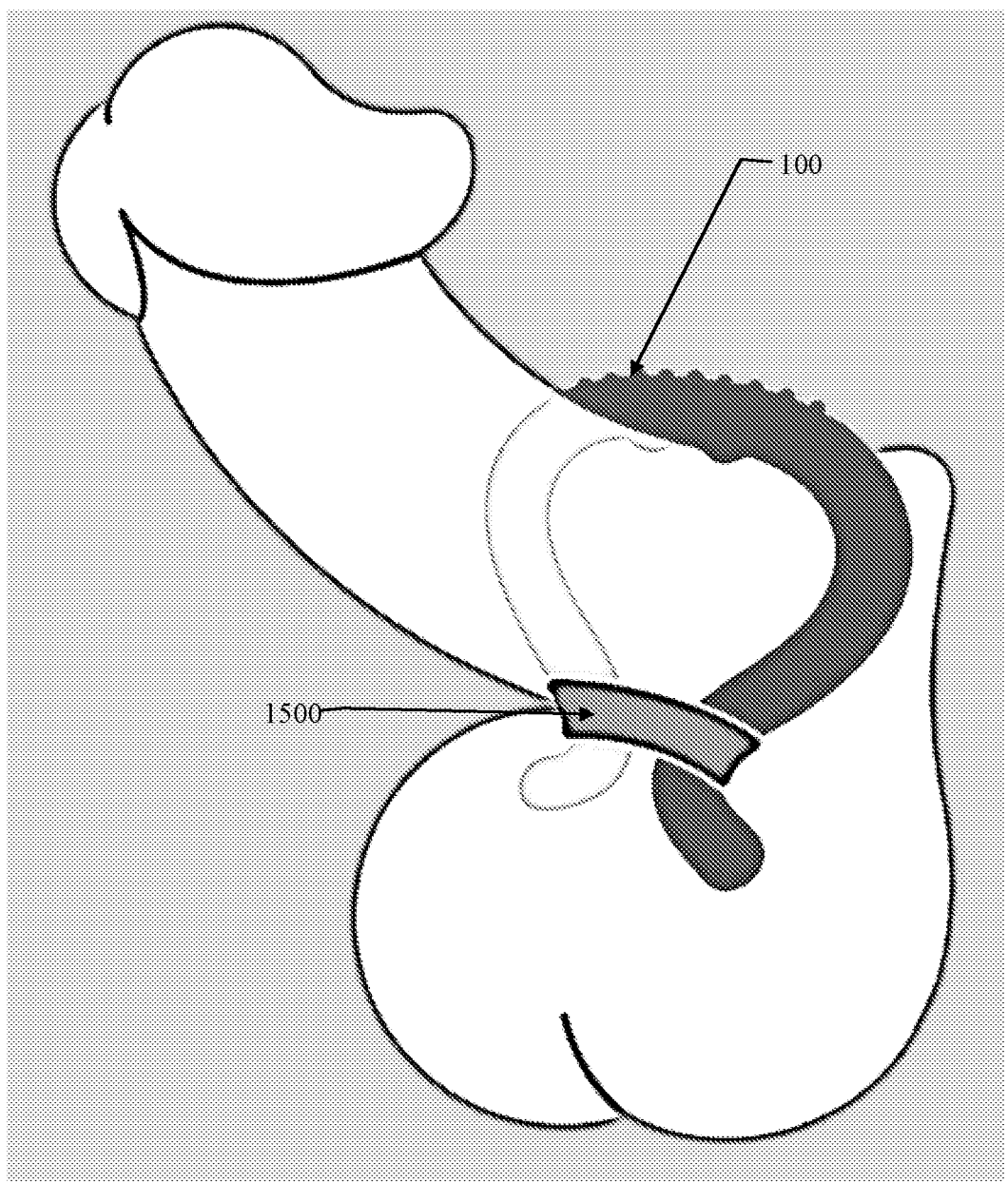
FIG. 16C shows a perspective view of a non-limiting example of a penile constriction device and a band on an erect human penis, per an embodiment herein.

Further provided herein, per FIGS. 16A-C, are methods for using a penile constriction device for alleviating erectile dysfunction (ED). FIG. 16A shows a perspective view a non-limiting example of a penile constriction device on a flaccid human penis. FIG. 16B shows a perspective view a non-limiting example of a penile constriction device and a band on a flaccid human penis. FIG. 16C shows a perspective view a non-limiting example of a penile constriction device and a band on an erect human penis. Optionally, in this or any other embodiment, the penile constriction device comprises an arched rod. Optionally, in this or any other embodiment, the arched rod comprises a first arm, a second arm, and a bridge. Optionally, in this or any other embodiment, the first arm comprises at least one of a first coupling end and a first converging end having a first terminus. Optionally, in this or any other embodiment, the second arm comprises at least one of a second coupling end and a second converging end having a second terminus. Optionally, in this or any other embodiment, the second terminus is disconnected from the first terminus. Optionally, in this or any other embodiment, the first converging end and the second converging end converge to form a constriction region. Optionally, in this or any other embodiment, the bridge connects the first coupling end to the second coupling end. Optionally, in this or any other embodiment, the bridge comprises a plurality of friction protrusions on a superior side of the bridge. Optionally, in this or any other embodiment, the bridge comprises a compression region rising inferiorly from an inferior side of the bridge.

Optionally, in this or any other embodiment, the method comprises applying a force between the first terminus and the second terminus of the device 100 to increase a constriction gap between the first converging end and the second converging end, and passing the penis through the constriction gap. Optionally, in this or any other embodiment, the method comprises applying a force between the first coupling end and the second coupling end to increase the constriction gap.

Optionally, in this or any other embodiment, per FIG. 16A, the method further comprises passing the penis through the constriction gap of the device 100. Optionally, in this or any other embodiment, the method further comprises moving the device 100 to the proximal base of the penis. Optionally, in this or any other embodiment, the method further comprises aligning the device such that at least one of the friction protrusions and the compression region are oriented on the penis opposite the testis.

Optionally, in this or any other embodiment, per FIGS. 16B-C, the method further comprises installing a band 1500 on the device 100. Optionally, in this or any other embodiment, installing a band 1500 on the device comprises installing the band 1500 between the first elbow and the second elbow of the device 100. Optionally, in this or any other embodiment, installing a band 1500 on the device comprises installing the band 1500 over the first terminus and over the second terminus of the device 100. Optionally, in this or any other embodiment, installing a band 1500 on the device comprises installing the band 1500 within the constriction region of the device 100.

Methods for Selecting a Penile Constriction Device

Additionally, provided herein, is a method for selecting a penile constriction device.

TABLE 1

| General Penis Size | | Girth | | Circular Diameter | | Cross-Sectional Area | |
|---|---|---|---|---|---|---|---|
| | | Flaccid | Erect | Flaccid | Erect | Flaccid | Erect |
| A | Min | 2.990 | 3.750 | 0.952 | 1.194 | 0.712 | 1.119 |
| | Max | 3.373 | 4.230 | 1.074 | 1.346 | 0.905 | 1.424 |
| B | Min | 3.373 | 4.230 | 1.074 | 1.346 | 0.905 | 1.424 |
| | Max | 3.692 | 4.630 | 1.175 | 1.474 | 1.085 | 1.706 |
| C | Min | 3.692 | 4.630 | 1.175 | 1.474 | 1.085 | 1.706 |
| | Max | 4.003 | 5.020 | 1.274 | 1.598 | 1.275 | 2.005 |

TABLE 1-continued

| General | Girth | | Circular Diameter | | Cross-Sectional Area | |
|---|---|---|---|---|---|---|
| Penis Size | Flaccid | Erect | Flaccid | Erect | Flaccid | Erect |
| D  Min | 4.003 | 5.020 | 1.274 | 1.598 | 1.275 | 2.005 |
|    Max | 4.633 | 5.810 | 1.475 | 1.849 | 1.708 | 2.686 |

To ensure proper fit for a wide range of human anatomies, devices herein can be configured with an array of dimensions and shapes. Table 1, above, shows that penile anatomical dimensions can be categorized into four groups to allow for easy selection of the proper sized device by a user. As the devices provided herein are flexible and configured to impart a pressure force against a portion of the erect or flaccid penis, the recommended size and shape for a particular user correlates to the size of their particular anatomy, as well as the severity of their erectile dysfunction conditions.

Optionally, in this or any other embodiment, the method comprises at least one of a user and a medical practitioner measuring at least one of a circular diameter and a girth of a user's erect or flaccid penis, and selecting a penile constriction device associated with at least one of the circular diameter and the girth of a user's penis according to the information provided in Table 1. Optionally, in this or any other embodiment, the method comprises the user estimating or measuring the size of their erect or flaccid penis as belonging to two or more general sizes, and selecting a penile constriction device associated with the general size. Optionally, in this or any other embodiment, the method further comprises the user trying the selected penile constriction device to confirm a proper fit and comfortability. Optionally, in this or any other embodiment, the method further comprises the user trying the selected penile constriction device and the band to confirm a proper fit and comfortability. Optionally, in this or any other embodiment, trying the selected penile construction device to confirm a proper fit and comfortability comprises confirming that the penile construction device does not freely rotate about at least one of the user's flaccid penis, and the user's erect penis. Optionally, in this or any other embodiment, trying the selected penile constriction device to confirm a proper fit and comfortability comprises performing vaginal intercourse, anal intercourse, oral sex, or masturbation with the device installed.

Methods for Selecting a Penile Constriction Band

Additionally, provided herein, is a method for selecting a band for a penile constriction device. Optionally, in this or any other embodiment, the method comprises selecting a low tension band or a high tension band. Optionally, in this or any other embodiment, the method comprises trying on the device with the low tension band and replacing the low tension band with the high tension band if the device significantly shifts during intercourse with the low tension band is employed. Optionally, in this or any other embodiment, the method comprises trying on the device with the high tension band and replacing the high tension band with the low tension band if the device is uncomfortable with the high tension band employed. Optionally, in this or any other embodiment, the method further comprises selecting a size of the low tension band or the high tension band based on the device size.

Methods for Using the Penile Constriction Band Herein

Further provided herein, are methods for using the bands herein. In one embodiment, the method comprises a user pinching the first tab between two of their fingers of a first hand, pinching the second tab between two of their fingers of a second hand, and inserting the first converging end and the second converging end of the device herein into the hoop of the band, such that the band rests between the first elbow and the second elbow of the device. In one embodiment, the method comprises a user pinching the first tab between two of their fingers of a first hand, pinching the second tab between two of their fingers of a second hand, inserting the first converging end of the device herein into the hoop of the band, and inserting the second converging end of the device herein into the hoop of the band, such that the band rests between the first elbow and the second elbow of the device. Optionally, in this or any other embodiment, the two fingers comprise a thumb and a pointer finger. Optionally, in this or any other embodiment, the band is installed onto the device while the user wears the device. Optionally, in this or any other embodiment, the band is installed onto the device while the user is not wearing the device.

Kits Comprising a Penile Constriction Device

Finally, provided herein is a kit comprising a penile constriction device and instructions for using the device to alleviate erectile dysfunction (ED). Optionally, in this or any other embodiment, the penile constriction device comprises an arched rod comprising: a first arm comprising a first coupling end and a first converging end having a first terminus; a second arm comprising a second coupling end, and a second converging end having a second terminus disconnected from the first terminus, wherein the first converging end and the second converging end converge to form a constriction region; and a bridge connecting the first coupling end to the second coupling end, the bridge comprising a plurality of friction protrusions on a superior side of the bridge, and a compression region rising inferiorly from an inferior side of the bridge.

Optionally, in this or any other embodiment, the kit further comprises at least one of: a box, a low tension band, a high tension band, printed Instructions for Use, and "Date Night" content series. Optionally, in this or any other embodiment, the band is configured to attach to the first coupling end and the second coupling end to provide increased penile compressive force. Optionally, in this or any other embodiment, the box comprises a label. Optionally, in this or any other embodiment, the container comprises a plurality of segments. Optionally, in this or any other embodiment, the measuring tool comprises at least one of a ruler, a tape, a jig, and a caliper. Optionally, in this or any other embodiment, the cleaning element comprises an alcohol pad, a wet pad, alcohol, or any combination thereof.

In one example a 1-Pack kit is assembled by:
1) Placing 1 device into three separate inner boxes
2) Placing 3 high tension bands and 3 low tension bands in a plastic polyfold bag, and place the bag into an inner box, and repeat two more times, so that there are 3 boxes with 6 bands each
3) Placing 2 inner boxes along with 1 Filler Box into the Main Box, creating a snug square of inner boxes inside the bottom layer of the Main Box
4) Placing 2 inner boxes with the devices into the Main Box, creating another snug square of inner boxes on top of the bottom tow inner boxes and 1 filler Box
5) Placing 2 inner boxes with bands into the Main Box, creating another snug square of inner boxes on top of the bottom tow inner boxes and 1 filler Box
6) Placing a printed instruction booklet on top of inner boxes
7) Closing a flap and slide Outer Sleeve over main box 8) Placing a UPC sticker on the text that states "PLACE UPC HERE"
9) Placing a UDI sticker on the text that states "PLACE UDI HERE"
10) Putting a shrink-wrap around entire closed box container and sleeve In one example a 2-Pack kit is assembled by:
1) Placing 2 devices into three separate inner boxes
2) Placing 3 high tension bands and 3 low tension bands in a plastic polyfold bag, and place the bag into an inner box, and repeat two more times, so that there are 3 boxes with 6 bands each
3) Placing 2 inner boxes along with 1 Filler Box into the Main Box, creating a snug square of inner boxes inside the bottom layer of the Main Box
4) Placing 2 inner boxes with the devices into the Main Box, creating another snug square of inner boxes on top of the bottom tow inner boxes and 1 filler Box
5) Placing 2 inner boxes with bands into the Main Box, creating another snug square of inner boxes on top of the bottom tow inner boxes and 1 filler Box
6) Placing a printed instruction booklet on top of inner boxes
7) Closing a flap and slide Outer Sleeve over main box
8) Placing a UPC sticker on the text that states "PLACE UPC HERE"
9) Placing a UDI sticker on the text that states "PLACE UDI HERE"
10) Putting a shrink-wrap around entire closed box container and sleeve In one example a 3-Pack kit is assembled by:
1) Placing 3 devices into three separate inner boxes
2) Placing 3 high tension bands and 3 low tension bands in a plastic polyfold bag, and place the bag into an inner box, and repeat two more times, so that there are 3 boxes with 6 bands each
3) Placing 2 inner boxes along with 1 Filler Box into the Main Box, creating a snug square of inner boxes inside the bottom layer of the Main Box
4) Placing 2 inner boxes with the devices into the Main Box, creating another snug square of inner boxes on top of the bottom tow inner boxes and 1 filler Box
5) Placing 2 inner boxes with bands into the Main Box, creating another snug square of inner boxes on top of the bottom tow inner boxes and 1 filler Box
6) Placing a printed instruction booklet on top of inner boxes
7) Closing a flap and slide Outer Sleeve over main box
8) Placing a UPC sticker on the text that states "PLACE UPC HERE"
9) Placing a UDI sticker on the text that states "PLACE UDI HERE"
10) Putting a shrink-wrap around entire closed box container and sleeve In one example a 4-Pack kit is assembled by:
1) Placing 4 devices into four separate inner boxes
2) Placing 3 high tension bands and 3 low tension bands in a plastic polyfold bag, and place the bag into an inner box, repeat three more times, so that there are 4 boxes with 6 bands each
3) Placing 4 inner boxes with the devices into the Main Box, creating a snug square of boxes along the bottom layer of the Main Box
4) Placing 4 inner boxes with bands on top of the 4 devices, creating another snug square of inner boxes on top of the bottom four inner boxes
5) Placing a printed instruction booklet on top of inner boxes
6) Closing flap and slide Outer Sleeve over main box
7) Placing an UPC sticker on the text that states "PLACE UPC HERE"
8) Placing an UDI sticker on the text that states "PLACE UDI HERE"
9) Putting a shrink-wrap around entire closed box container and sleeve In some embodiments, the instruction booklet, per FIGS. 31-46 contains the following instructions:

About your ED Device
Intended Use
This device is intended to maintain penile rigidity in men with erectile dysfunction (ED). The device is intended to be placed around the base of the penis for the duration of sexual intercourse, to restrict venous blood flow leaving the penis, to maintain sufficient penile rigidity for sexual intercourse. This product is intended for use by men ages 18+.

Manual Safety Release
Constriction from the device can be manually released by removing the tension band from the legs of the device, then widening the legs of the device, and removing the device from the penis with two hands.

Pliable Materials
Your device was designed to minimize the risk of injury to yourself and your partner when used as intended, by using soft, medical grade materials including polycarbonate coated in medical-grade proprietary thermoplastic elastomer (TPE). Your device was designed to be body-safe and is free of Polyvinyl Chloride (PVC), latex, and phthalates.

Shape & Surface Design
Your device features a smooth, oval-shaped design that conforms to the natural shape of the penis. There are special protrusions (dorsal apexes) on your device designed to provide pressure on the dorsal vein for assisting with achieving and maintaining erections. Your device also features small protrusions (enhancement ridges) designed to provide added stimulation for female partners.

Instructions for Use
Important: Read these instructions before using your device
Please refer to Giddy's Size Calculator (GetMeGiddy.com/Size-Calculator), to determine the appropriate sizing for your device. Please note that improper use of the Size Calculator can result in the improper sizing of your device, which can increase the risk of damage, injury, or lessened effect of the device. Please contact support at customercare@getmegiddy.com for assistance. 1. Place the device at the base of the shaft of your penis, in front of the testicles, with the opening facing down. The device is reversible; your penis can be inserted into either side.
2. Once your device is around the base of your penis, apply one of the variable-strength tension bands.
3. The device can be applied safely whether your penis is flaccid (soft) or erect (hard). When an erection can be achieved but not maintained, the device can be used alone, or when creating an erection is not possible, it can be used in conjunction with vacuum pumps How to Clean the Device
Follow all instructions for cleaning, storing, and transporting the device and Tension Bands between uses. Rinse the device and any used Tension Bands with warm water. Then lather them with a non-abrasive, anti-bacterial soap. Avoid using bleach, chlorine, or any chemicals that could irritate the skin. Always take into account any allergies you or your partner may have while using and cleaning your device and Tension Bands. Once lathered with soap and thoroughly washed with a washcloth or clean hands, rinse your device and Tension Bands again. Dry them using a paper towel, a towel, or air-dry. It is recommended to replace your device every 4 months depending on your frequency of use.

Warnings

Consult a physician if any complications occur for you or your partner.

Discontinue use of the device if complications continue for you or your partner.

When using lubricants with the device, use water-based, oil-based, or silicone-based lubricants only.

Do not fall asleep while wearing the device, since prolonged use may cause permanent injury to the penis.

Allow at least 60 minutes between uses, as more frequent use may increase the risk of injury to the penis.

It is not recommended to use the same device with multiple partners if one partner is diagnosed with a sexually transmitted infection or other contagious medical conditions.

This device does not prevent pregnancy.

This device does not protect against sexually transmitted infections.

Do not use the device under the influence of alcohol or drugs, since such use may impair your judgment and increase the risk of injury to the penis.

Misuse of the device may cause bruising, painful injury, or permanent damage to the penis.

Delayed Diagnosis of Other Conditions

If you have symptoms of erectile dysfunction (the inability to achieve an erection that is sufficient for sexual intercourse), consult your physician prior to using this device to avoid a potentially harmful delay in diagnosing any of the most common causes of this condition, such as diabetes, multiple sclerosis, cirrhosis of the liver, chronic renal failure, or alcoholism.

Use with Impaired Pain Perception

Do not use this device if you have decreased sensation of pain in the area of the penis, to avoid accidental injury as a result of lack of sensation.

Use with Decreased Hand Strength

Do not use the device if you have decreased hand strength because this may make removal of the device difficult. An alternative method for applying the device for users with reduced hand strength is to wrap the Tension Band around the legs of the device before placing it on your penis. Using two hands, pull apart the legs of the device, holding them apart slightly to create a wider opening, while sliding the device onto your penis. To avoid damaging the device, use caution not to pull apart the legs too far.

For a second alternative method, cover the device in lubricant, and slide it onto your penis until it reaches the base. Feel free to use any water-based, oil-based, or silicone-based lubricants. If you experience any pain or bruising, stop and consult your physician before continuing use.

Precautions

Use of the device may aggravate already existing medical conditions such as Peyronie's disease (the formation of hardened tissue in the penis that causes pain, curvature, and distortion, usually during erection); priapism (persistent, usually painful erection of the penis as a consequence of disease and not related to sexual arousal); and urethral strictures (urethral stricture is an area of hardened tissue, which narrows the urethra sometimes making it difficult to urinate).

Limit use of the device to no longer than 30 minutes per use.

Prolonged use of the device (i.e., without removal) may cause permanent injury to the penis.

Device use may bruise or rupture the blood vessels within the penis or scrotum, resulting in petechiae (a small purplish spot on a body surface, such as the skin or a mucous membrane, caused by a minute hemorrhage), hemorrhage (flow of blood from ruptured blood vessels), or the formation of a hematoma (localized swelling filled with blood resulting from a break in a blood vessel).

Use the least constrictive device size that maintains an erection, since excessive constriction could injure the penis. See previous information regarding the Size Calculator.

Alternative Treatment Methods

Alternative treatment methods for erectile dysfunction include counseling, drug therapy, hormonal therapy, vascular surgery, and implanted prosthetic devices. Contact your physician for more information regarding these alternative treatments. In some embodiments, the kit may further include further instructions to treat erectile dysfunction through, per FIGS. 25-30, diet, stress relief, exercise, nutrition, Kegel exercises, and tracking.

Optionally, in this or any other embodiment, the number of penile constriction devices is 1 to 500. Optionally, in this or any other embodiment, the penile constriction devices comprises two or more different sizes, models or and/or shapes of penile constriction devices. Optionally, in this or any other embodiment, the two or more different sizes, models or and/or shapes of penile constriction devices are color coded. Optionally, in this or any other embodiment, the two or more different sizes, models or and/or shapes of penile constriction devices are labeled. Optionally, in this or any other embodiment, the two or more different sizes, models or and/or shapes of penile constriction devices enable a user to select a device that functions best, is most comfortable, and most optimally corresponds with the size, shape, and biology of their penis.

Optionally, in this or any other embodiment, the number of bands is 1 to 500. Optionally, in this or any other embodiment, the bands comprises two or more different sizes, models or and/or shapes of bands. Optionally, in this or any other embodiment, the two or more different sizes, models or and/or shapes of bands are color coded. Optionally, in this or any other embodiment, two or more different sizes, models or and/or shapes of bands are labeled. Optionally, in this or any other embodiment, two or more different sizes, models or and/or shapes of bands enable a user to customize the compressive force imparted by the device onto the penis that is most optimal for with the size, shape, and biology of their penis.

Current Penile Construction Devices

Figure 17:
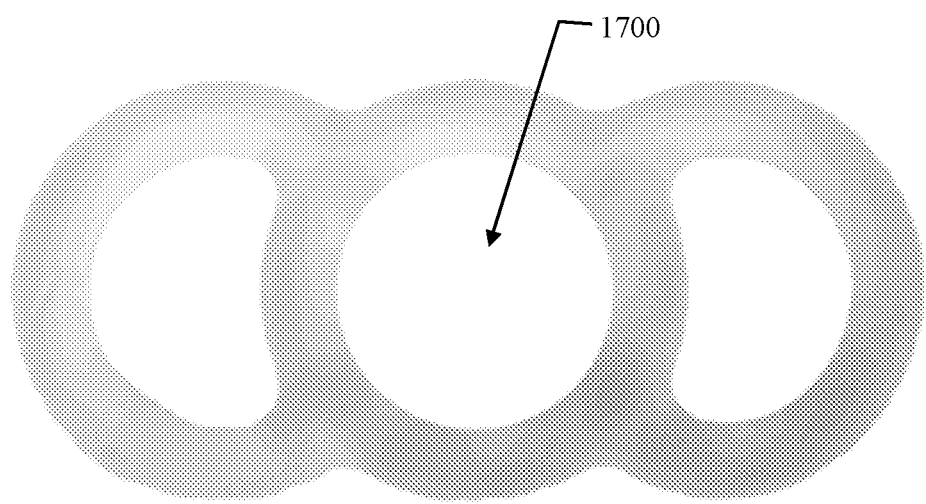
FIG. 17 shows a front view of a penile constriction device in the prior art.
Figure 18:
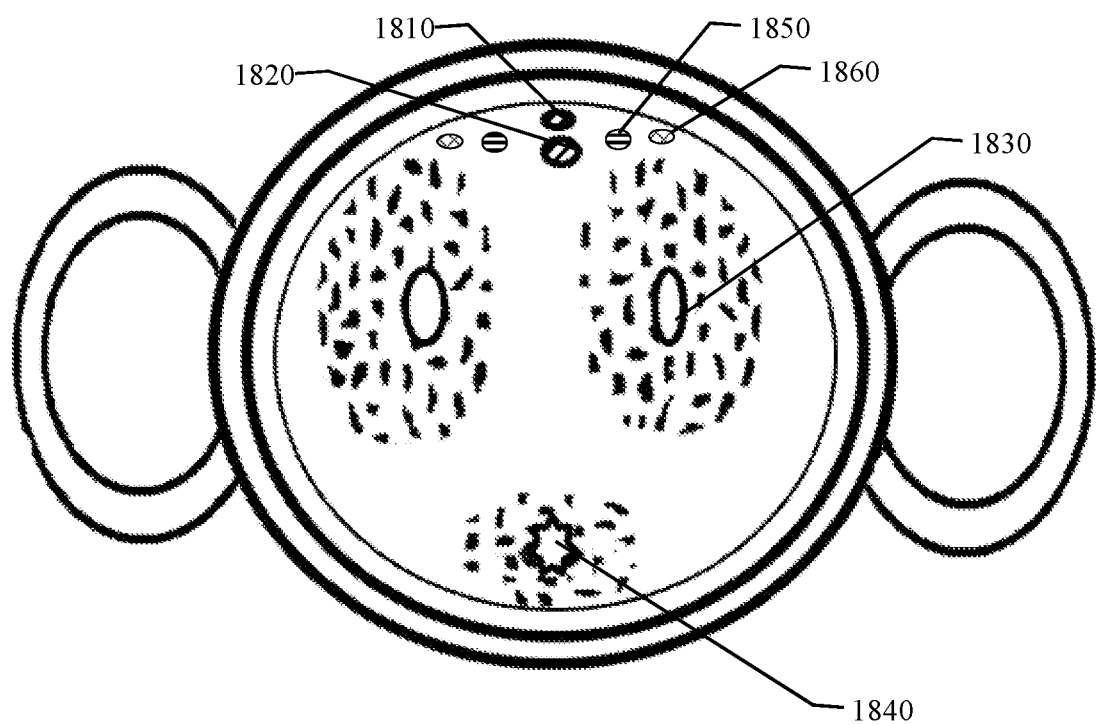
FIG. 18 shows a front cross-sectioned view of the prior art penile constriction device in FIG. 17 on a human penis.

FIG. 17 shows a front view of a penile constriction device in the prior art. FIG. 18 shows a front cross-sectioned view of the prior art penile constriction device in FIG. 17 on a human penis. To highlight, by contrast, the prior art Encore Tension Device, per FIGS. 17 and 18, is configured to apply both a uniform pressure and a non-selective pressure on the entire circumference of the penis, because its penile cavity 1700 is circular, continuous, elastic, and non-rigid. Further, the prior art Encore Tension Band is not configured to apply a non-uniform pressure or a selective non-uniform pressure on the circumference of the penis, because its penile cavity 2000 is circular, continuous, elastic, and non-rigid. As such, in contrast to the devices and systems of the current disclosure, the Encore Tension Band per FIG. 18 is configured to apply a significant compressive force to the deep arteries 1830, the dorsal arteries 1850, the urethra 1870, and the dorsal nerves 1860, which prevents blood from flowing into the penis, prevents the use of Kegel exercises to maintain an erection, and causes injaculation and damages the dorsal nerves 1860.

Further, because the prior art Encore Tension Band has a circular penile cavity 2000, and as the cross sectional shape of the human penis is elliptical, the majority of the uniform pressure applied by the Encore Tension Band is directed towards the deep arteries 1830, which bring blood into the penis to maintain an erection.

Additionally, because the prior art Encore Tension Band is fully elastic and configured to provide a uniform penile pressure, it is only effective when worn on an erect penis, and is ineffective when worn on a flaccid penis, a slightly flaccid penis, or a slightly rigid penis. As such, the prior art Encore Tension Band is incapable of facilitating erection initiation.

Figure 22:
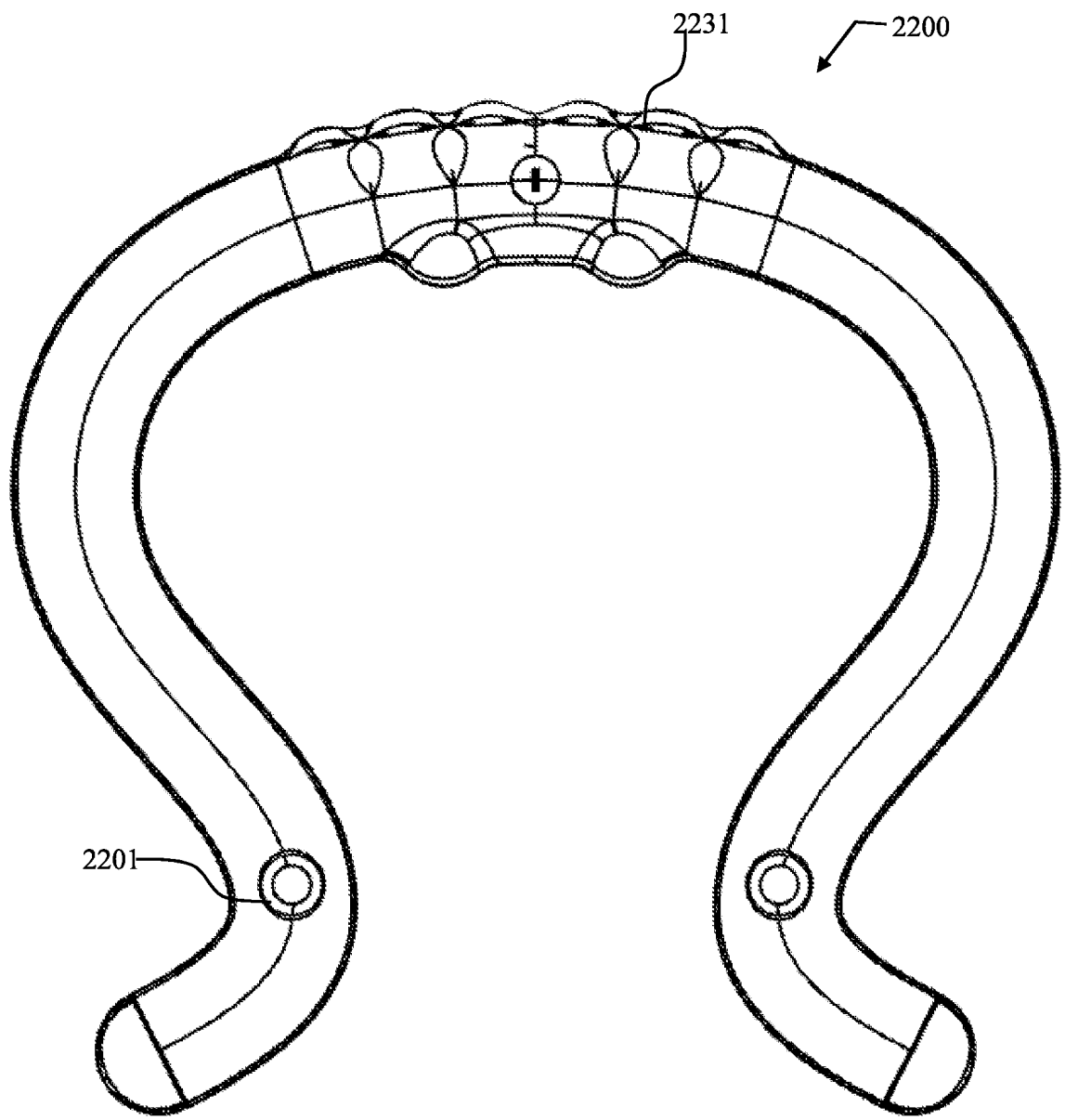
FIG. 22 shows a front view of a non-limiting example of a penile constriction device having a manufacturing mark; per an embodiment herein.
Figure 23:
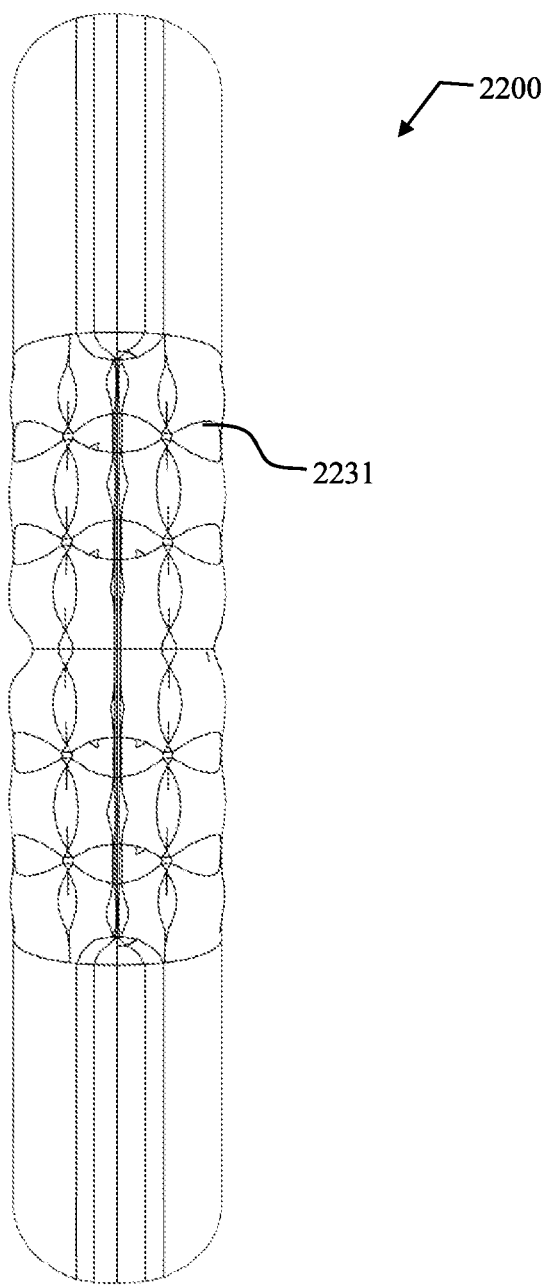
FIG. 23 shows a top view image of the penile constriction device of FIG. 22; per an embodiment herein.
Figure 24:
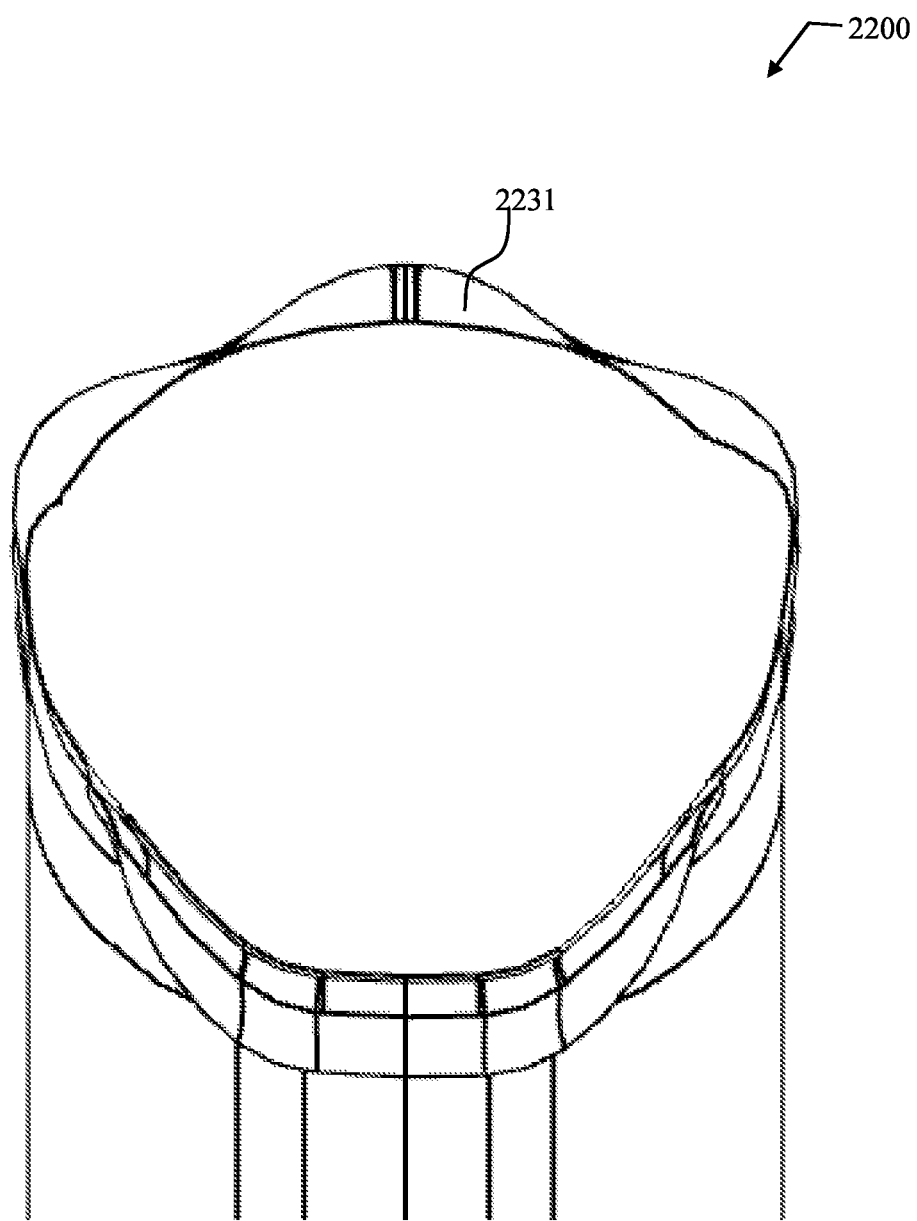
FIG. 24 shows a right side cross-sectioned view image of the penile constriction device of FIG. 22; per an embodiment herein.
Figure 31:
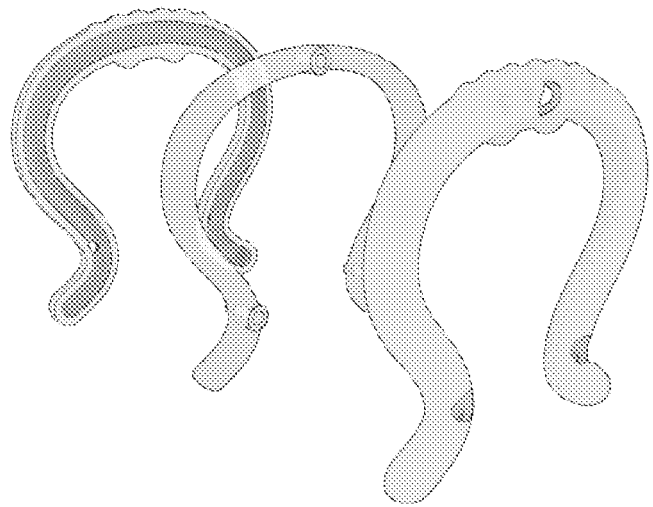
FIG. 31 shows a first page of an exemplary instruction booklet; per an embodiment herein.
Figure 37:
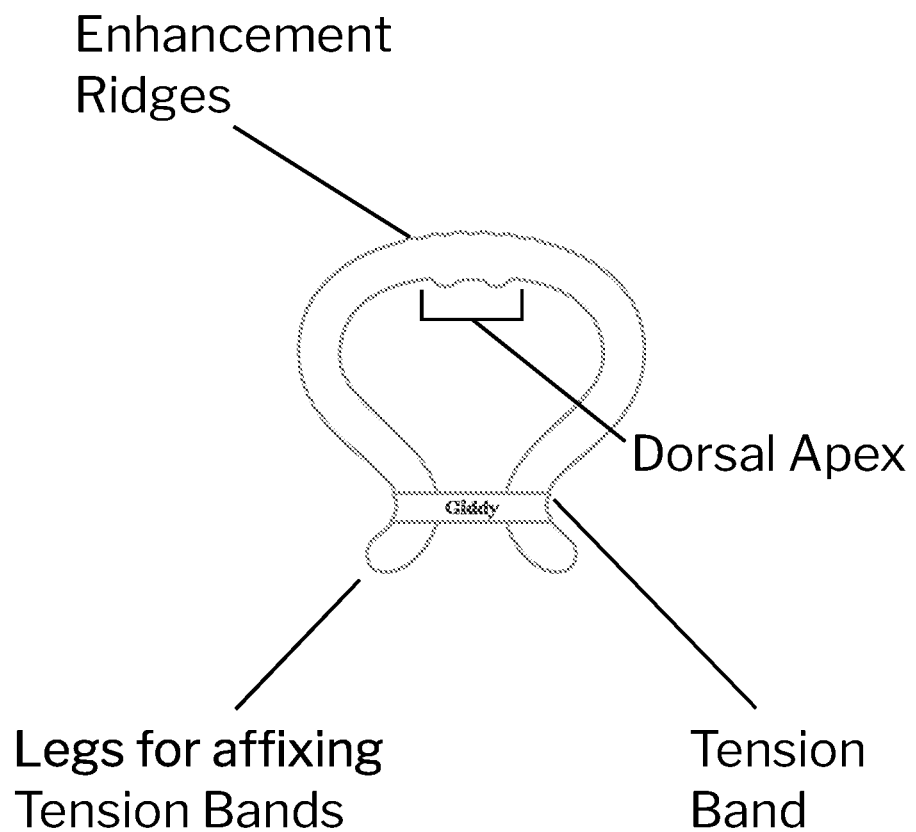
FIG. 37 shows a seventh page of an exemplary instruction booklet; per an embodiment herein.

FIGS. 22-24 shows a non-limiting example of a penile constriction device 2200 having a manufacturing mark 2201. In some embodiments, a size, orientation, location, depth, or any combination thereof of the manufacturing mark 2201 enables the production of the penile constriction device 2200 that provides sufficient force between its arms.

Terms and Definitions

Unless otherwise defined, all technical terms used herein have the same meaning as commonly understood by one of ordinary skill in the art to which this disclosure belongs.

As used herein, the singular forms "a," "an," and "the" include plural references unless the context clearly dictates otherwise. Any reference to "or" herein is intended to encompass "and/or" unless otherwise stated.

As used herein, the term "about" refers to an amount that is at the stated amount or near the stated amount by 25%, 20%, 15%, 10%, 5%, 2%, or 1%, including increments therein. When the amount is a percentage, the term "about" means a range around the given amount, e.g. about 10% refers to 10%+/−1% (i.e. 9%-11%), or 10%+/−2% (i.e. 8%-12%), etc. depending on the embodiment and amount.

As used herein, the term "mesial" refers to a longitudinal direction or relation towards the center.

As used herein, the term "transverse" refers to a longitudinal direction or relation away from the center.

As used herein, the term "apex" refers to a point of inflection in one or more directions.

As used herein, the term "normal" refers to perpendicularity in one or more directions.

As used herein, the term "curvilinear" refers to a shape comprising one or more curves.

As used herein, the term "girth" refers to a circumference of a portion of a male human penis.

As used herein, the term "circular diameter" refers to an outer width, e.g. a transverse width, of a portion of a male human penis.

EXAMPLES

The following illustrative examples are representative of embodiments of the applications, systems, and methods described herein and are not meant to be limiting in any way. Optionally, in other embodiments, each of the following examples can additionally include any of the aforementioned embodiments and elements.

Example 1: First Penile Constriction Device

Provided herein, per FIG. 6, is a first penile constriction device 600 comprising an arched rod having a constriction gap width 661, a constriction height 680, a maximum inner width 670, an inferior height 690, and a thickness 651, as shown in Table 2 below. For the first penile constriction device 600, the constriction gap width 661 is measured as a minimum distance between the first converging end and the second converging end within the constriction region. For the first penile constriction device 600, the constriction height 680 is measured as a normal distance between a constriction point 662 and the inferior side of the bridge, wherein the constriction point 662 is defined as the midpoint of the constriction gap width 661. For the first penile constriction device 600, the maximum inner width 670 is measured as a maximum normal distance between a mesial vertex of the surface of the first arm and a mesial vertex of the surface of the second arm. For the first penile constriction device 600, the inferior height 690 is measured as a normal distance between the center point 662 and the inferior side of the bridge. For the first penile constriction device 600, the thickness 651 is measured as a maximum normal cross-sectional width of at least a portion of at least one of the first arm, the second arm, and the bridge.

TABLE 2

| Dimension | Min | Max |
| --- | --- | --- |
| Constriction Gap Width | 0.526 | 0.594 |
| Constriction Height | 0.975 | 1.099 |
| Maximum Inner Width | 1.170 | 1.319 |
| Inferior Height | 0.390 | 0.440 |
| Thickness | 0.2 | 0.7 |

A cross-sectional area of a penis may be defined as the cross sectional area within the circumference of a flaccid or erect penis. Alternatively, the cross-sectional area is defined as the area of a circle having a diameter equal to the girth of a flaccid or erect penis. Alternatively, the cross-sectional area is defined as the area of a circle having a diameter equal to the circular diameter of a flaccid or erect penis. Exemplary cross sectional areas are shown in Tables 10 and 11. A cross-sectional constriction percentage is defined as a percentage by which the cross-sectional area of the flaccid or erect penis at the intersection of the device 600 and the flaccid or erect penis is reduced when the device 600 is worn on the flaccid or erect penis. Alternatively, the cross-sectional constriction percentage is defined as a percentage by which the cross-sectional area of the flaccid or erect penis at a point on the flaccid or erect penis is reduced when the device 600 is worn on the flaccid or erect penis. In some embodiments, the flaccid and erect cross-sectional constriction percentages represent a uniform cross-sectional constriction of the flaccid penis and the erect penis, respectively. In some embodiments, the flaccid and erect cross-sectional constriction percentages represent a non-uniform cross-sectional constriction of the flaccid penis and the erect penis, respectively. The cross-sectional constriction percentage imparted by the first penile constriction device 600 on a penis of general size A, per Table 1, is shown in Table 3 below.

TABLE 3

|  | Flaccid | Erect |
|---|---|---|
| Min | 20.00% | 10.36% |
| Max | 37.13% | 29.55% |

In some cases, the minimum and maximum cross sectional constriction percentages per Table 3, represent the minimum and maximum cross sectional constrictions recommended for use of the first penile constriction device 600 on a flaccid penis or an erect penis, respectively. In some cases, the minimum and maximum cross sectional constriction percentages per Table 3, and the dimensions of the first penile constriction device 600 (Size S), per Table 3, indicate the recommended penis size dimensions, per Table 10 or 11 below. In some embodiments, the first penile constriction device 600 does not comprise the friction protrusions. In some embodiments, the first penile constriction device 600 does not comprise the first dorsal vein protrusion or the second dorsal vein protrusion. In some embodiments, the first penile constriction device 600 does not comprise the friction protrusions, the first dorsal vein protrusion, or second dorsal vein protrusion.

Example 2: Second Penile Constriction Device

Provided herein, per FIG. 7, is a second penile constriction device 700 comprising an arched rod having a constriction gap width 761, a constriction height 780, a maximum inner width 770, an inferior height 790, and a thickness 751, as shown in Table 4 below. For the second penile constriction device 700, the constriction gap width 761 is measured as a minimum distance between the first converging end and the second converging end within the constriction region. For the second penile constriction device 700, the constriction height 780 is measured as a normal distance between a constriction point 762 and the inferior side of the bridge, wherein the constriction point 762 is defined as the midpoint of the constriction gap width 761. For the second penile constriction device 700, the maximum inner width 770 is measured as a maximum normal distance between a mesial vertex of the surface of the first arm and a mesial vertex of the surface of the second arm. For the second penile constriction device 700, the inferior height 790 is measured as a normal distance between the center point 762 and the inferior side of the bridge. For the second penile constriction device 700, the thickness 751 is measured as a maximum normal cross-sectional width of at least a portion of at least one of the first arm, the second arm, and the bridge.

TABLE 4

| Dimension | Min | Max |
|---|---|---|
| Constriction Gap Width | 0.594 | 0.650 |
| Constriction Height | 1.099 | 1.203 |
| Maximum Inner Width | 1.319 | 1.444 |
| Inferior Height | 0.440 | 0.481 |
| Thickness | 0.2 | 0.7 |

A cross-sectional area of a penis may be defined as the cross sectional area within the circumference of a flaccid or erect penis. Alternatively, the cross-sectional area is defined as the area of a circle having a diameter equal to the girth of a flaccid or erect penis. Alternatively, the cross-sectional area is defined as the area of a circle having a diameter equal to the circular diameter of a flaccid or erect penis. Exemplary cross sectional areas are shown in Tables 10 and 11. A cross-sectional constriction percentage is defined as a percentage by which the cross-sectional area of the flaccid or erect penis at the intersection of the device 600 and the flaccid or erect penis is reduced when the device 600 is worn on the flaccid or erect penis. Alternatively, the cross-sectional constriction percentage is defined as a percentage by which the cross-sectional area of the flaccid or erect penis at a point on the flaccid or erect penis is reduced when the device 600 is worn on the flaccid or erect penis. In some embodiments, the flaccid and erect cross-sectional constriction percentages represent a uniform cross-sectional constriction of the flaccid penis and the erect penis, respectively. In some embodiments, the flaccid and erect cross-sectional constriction percentages represent a non-uniform cross-sectional constriction of the flaccid penis and the erect penis, respectively. The cross-sectional constriction percentage imparted by the second penile constriction device 700 on a penis of general size B, per Table 1, is shown in Table 5 below.

TABLE 5

|  | Flaccid | Erect |
|---|---|---|
| Min | 20.00% | 10.36% |
| Max | 33.22% | 25.18% |

In some cases, the minimum and maximum cross sectional constriction percentages per Table 5, represent the minimum and maximum cross sectional constrictions recommended for use of the second penile constriction device 700 on a flaccid penis or an erect penis, respectively. In some cases, the minimum and maximum cross sectional constriction percentages per Table 5, and the dimensions of the second penile constriction device 700 (Size M), per Table 5, indicate the recommended penis size dimensions, per Table 10 or 11 below. In some embodiments, the first penile constriction device 600 does not comprise the friction protrusions. In some embodiments, the first penile constriction device 600 does not comprise the first dorsal vein protrusion or the second dorsal vein protrusion. In some embodiments, the first penile constriction device 600 does not comprise the friction protrusions, the first dorsal vein protrusion, or second dorsal vein protrusion.

Example 3: Third Penile Constriction Device

Provided herein, per FIG. 8, is a third penile constriction device 800 comprising an arched rod having a constriction gap width 861, a constriction height 880, a maximum inner width 870, an inferior height 890, and a thickness 851, as shown in Table 6 below. For the third penile constriction device 800, the constriction gap width 861 is measured as a minimum distance between the first converging end and the second converging end within the constriction region. For the third penile constriction device 800, the constriction height 880 is measured as a normal distance between a constriction point 862 and the inferior side of the bridge, wherein the constriction point 862 is defined as the midpoint of the constriction gap width 861. For the third penile constriction device 800, the maximum inner width 870 is measured as a maximum normal distance between a mesial vertex of the surface of the first arm and a mesial vertex of the surface of the second arm. For the third penile constriction device 800, the inferior height 890 is measured as a normal distance between the center point 862 and the inferior side of the bridge. For the third penile constriction device 800, the thickness 851 is measured as a maximum normal cross-sectional width of at least a portion of at least one of the first arm, the second arm, and the bridge.

TABLE 6

| Dimension | Min | Max |
| --- | --- | --- |
| Constriction Gap Width | 0.650 | 0.705 |
| Constriction Height | 1.203 | 1.305 |
| Maximum Inner Width | 1.444 | 1.566 |
| Inferior Height | 0.481 | 0.522 |
| Thickness | 0.2 | 0.7 |

A cross-sectional area of a penis may be defined as the cross sectional area within the circumference of a flaccid or erect penis. Alternatively, the cross-sectional area is defined as the area of a circle having a diameter equal to the girth of a flaccid or erect penis. Alternatively, the cross-sectional area is defined as the area of a circle having a diameter equal to the circular diameter of a flaccid or erect penis. Exemplary cross sectional areas are shown in Tables 10 and 11. A cross-sectional constriction percentage is defined as a percentage by which the cross-sectional area of the flaccid or erect penis at the intersection of the device 600 and the flaccid or erect penis is reduced when the device 600 is worn on the flaccid or erect penis. Alternatively, the cross-sectional constriction percentage is defined as a percentage by which the cross-sectional area of the flaccid or erect penis at a point on the flaccid or erect penis is reduced when the device 600 is worn on the flaccid or erect penis. In some embodiments, the flaccid and erect cross-sectional constriction percentages represent a uniform cross-sectional constriction of the flaccid penis and the erect penis, respectively. In some embodiments, the flaccid and erect cross-sectional constriction percentages represent a non-uniform cross-sectional constriction of the flaccid penis and the erect penis, respectively. The cross-sectional constriction percentage imparted by the third penile constriction device 800 on a penis of general size C, per Table 1, is shown in Table 7 below.

TABLE 7

|  | Flaccid | Erect |
| --- | --- | --- |
| Min | 20.00% | 10.36% |
| Max | 31.95% | 23.75% |

In some cases, the minimum and maximum cross sectional constriction percentages per Table 7, represent the minimum and maximum cross sectional constrictions recommended for use of the third penile constriction device 800 on a flaccid penis or an erect penis, respectively. In some cases, the minimum and maximum cross sectional constriction percentages per Table 7, and the dimensions of the third penile constriction device 800 (Size L), per Table 7, indicate the recommended penis size dimensions, per Table 10 or 12 below. In some embodiments, the third penile constriction device 800 does not comprise the friction protrusions. In some embodiments, the third penile constriction device 800 does not comprise the first dorsal vein protrusion or the second dorsal vein protrusion. In some embodiments, the third penile constriction device 800 does not comprise the friction protrusions, the first dorsal vein protrusion, or second dorsal vein protrusion.

Example 4: Fourth Penile Constriction Device

Provided herein, per FIG. 9, is a fourth penile constriction device 900 comprising an arched rod having a constriction gap width 961, a constriction height 980, a maximum inner width 970, an inferior height 990, and a thickness 951, as shown in Table 8 below. For the fourth penile constriction device 900, the constriction gap width 961 is measured as a minimum distance between the first converging end and the second converging end within the constriction region. For the fourth penile constriction device 900, the constriction height 980 is measured as a normal distance between a constriction point 962 and the inferior side of the bridge, wherein the constriction point 962 is defined as the midpoint of the constriction gap width 961. For the fourth penile constriction device 900, the maximum inner width 970 is measured as a maximum normal distance between a mesial vertex of the surface of the first arm and a mesial vertex of the surface of the second arm. For the fourth penile constriction device 900, the inferior height 990 is measured as a normal distance between the center point 962 and the inferior side of the bridge. For the fourth penile constriction device 900, the thickness 951 is measured as a maximum normal cross-sectional width of at least a portion of at least one of the first arm, the second arm, and the bridge.

TABLE 8

| Dimension | Min |
| --- | --- |
| Constriction Gap Width | 0.705 |
| Constriction Height | 1.305 |
| Maximum Inner Width | 1.566 |
| Inferior Height | 0.522 |
| Thickness | 0.2 |

A cross-sectional area of a penis may be defined as the cross sectional area within the circumference of a flaccid or erect penis. Alternatively, the cross-sectional area is defined as the area of a circle having a diameter equal to the girth of a flaccid or erect penis. Alternatively, the cross-sectional area is defined as the area of a circle having a diameter equal to the circular diameter of a flaccid or erect penis. Exemplary cross sectional areas are shown in Tables 10 and 11. A cross-sectional constriction percentage is defined as a percentage by which the cross-sectional area of the flaccid or erect penis at the intersection of the device 600 and the flaccid or erect penis is reduced when the device 600 is worn on the flaccid or erect penis. Alternatively, the cross-sectional constriction percentage is defined as a percentage by which the cross-sectional area of the flaccid or erect penis at a point on the flaccid or erect penis is reduced when the device 600 is worn on the flaccid or erect penis. In some embodiments, the flaccid and erect cross-sectional constriction percentages represent a uniform cross-sectional constriction of the flaccid penis and the erect penis, respectively. In some embodiments, the flaccid and erect cross-sectional constriction percentages represent a non-uniform cross-sectional constriction of the flaccid penis and the erect penis, respectively. The cross-sectional constriction percentage imparted by the fourth penile constriction device 900 on a penis of general size D, per Table 1, is shown in Table 9 below.

TABLE 9

|  | Flaccid | Erect |
|---|---|---|
| Min | 20.00% | 10.36% |
| Max | 40.27% | 30.08% |

In some cases, the minimum and maximum cross sectional constriction percentages per Table 9, represent the minimum and maximum cross sectional constrictions recommended for use of the fourth penile constriction device 900 on a flaccid penis or an erect penis, respectively. In some cases, the minimum and maximum cross sectional constriction percentages per Table 9, and the dimensions of the fourth penile constriction device 900 (Size XL), per Table 8, indicate the recommended penis size dimensions, per Table 10 or 11 below. In some embodiments, the fourth penile constriction device 900 does not comprise the friction protrusions. In some embodiments, the fourth penile constriction device 900 does not comprise the first dorsal vein protrusion or the second dorsal vein protrusion. In some embodiments, the fourth penile constriction device 900 does not comprise the friction protrusions, the first dorsal vein protrusion, or second dorsal vein protrusion.

Although the exemplary, first, second, third, and fourth penile constriction devices 600 700 800 900 may be formed to different sizes, each exemplary device can include any of the elements in one or more of the embodiments herein.

Example 5: Chart for Constriction Device Sizing

As described in the examples above, the exemplary second, third, fourth, and fifth penile constriction devices 600, 700, 800, 900, respectively, alternatively denoted das sizes S, M, L, and XL, respectively may be generally prescribed to alleviate erectile dysfunction in males with a general penis size of A, B, C, and D, respectively. However, if a greater cross-sectional constriction percentage than those listed in Tables 3, 5, 7, and 9 is required to alleviate a severe ED condition, the S, M, L, and XL, devices may be prescribed per Table 10 below.

TABLE 10

| General Penis Size | | Girth (cm) | | Circular Diameter (cm) | | ED Device ED Condition | |
|---|---|---|---|---|---|---|---|
| | | Flaccid | Erect | Flaccid | Erect | Mild | Severe |
| A | Min | 2.990 | 3.750 | 0.952 | 1.194 | S | S |
| | Max | 3.373 | 4.230 | 1.074 | 1.346 | | |
| B | Min | 3.373 | 4.230 | 1.074 | 1.346 | M | S |
| | Max | 3.692 | 4.630 | 1.175 | 1.474 | | |
| C | Min | 3.692 | 4.630 | 1.175 | 1.474 | L | M |
| | Max | 4.003 | 5.020 | 1.274 | 1.598 | | |
| D | Min | 4.003 | 5.020 | 1.274 | 1.598 | XL | L |
| | Max | 4.633 | 5.810 | 1.475 | 1.849 | | |

Further, Table 10 can be employed as a template for a user to select the correct exemplary constriction device based on their general penis size and the severity of their ED condition.

Example 6: First Example of Selecting an ED Device

Sam does not have ED, but wants to purchase an ED device to enhance his erection. However, Sam does not know which size ED device is appropriate for his situation. Sam reads the sizing recommendations per Table 10 above and sees that the table provides a range of penis sizes for different categories that correspond to different sizes. Measuring the girth of his erect penis, Sam learns that his erect penis falls within the range of a Min. and Max. for a general penis size "C". Sam visits his local store and purchases a Size L device. When he goes home, he finds out that the Size L device is a perfect fit. Because of the table, Sam does not have to guess which device is appropriate for his situation.

Example 7: Second Example of Selecting an ED Device

Joe has been experiencing mild signs of erectile dysfunction and decides to buy an ED device. Joe measures the girth of his flaccid and erect penis as 3.5 inches and 4.5 inches, respectively, using a tape measure. Joe references the sizing recommendations chart, per Table 10 above, to determine that his general penis size is size "B" and that, as his ED symptoms are mild, he should purchase a Size M ED device. Joe purchases the Size M ED device, which comes with a tension band separately so the Size M ED device and tension bands are two separate pieces. Joe fits the Size M ED device along with the tension band, which alleviates his mild ED symptoms.

As Joe ages his mild ED symptoms exacerbate and become severe. Joe references the user manual to determine that, as his symptoms have worsened, the use of a Size S ED device is now recommended. Joe purchases the Size 1 ED devices, which comes with a tension band separately. Joe opts to fit the Size S ED device without the tension band and finds that the Size 1 ED device alleviates his severe ED symptoms.

Example 8: Third Example of Selecting an ED Device

Tom has been experiencing severe signs of erectile dysfunction and decides to buy an ED device. Tom measures the circular diameter of his flaccid and erect penis as 1.2 inches and 1.5 inches, respectively, using a ruler. Tom references the sizing recommendations chart, per Table 10 above, to determine that his general penis size is size "C" and that, as his ED symptoms are severe, he should purchase a Size M ED device. Tom purchases the Size M ED device, which comes with a tension band attached so the Size M ED device and tension band is one piece. The Size M ED device fits Tom well and alleviates his severe ED symptoms.

Example 9: Band Dimensions

Optionally, in this or any other embodiment, the dimensions of the primary band, per FIG. 50B, vary based on a tension level provided the primary band 1500. Optionally, in this or any other embodiment, the primary band 1500 comprises a high tension primary band 1500A. Optionally, in this or any other embodiment, the primary band 1500 comprises a low tension primary band 1500B. The dimensions (in inches) of the depth 1501, the width 1502, the outer diameter 1503, the tab thickness 1504, and the hoop thickness 1505 for the high tension band 1500A (having sizes 1 and 2) and for the low tension band 1500B (having sizes 1-4) are shown in table 11 below.

TABLE 11

| Tension | Size | For Device Size | 1501 | 1502 | 1503 | 1504 | 1505 |
|---|---|---|---|---|---|---|---|
| High | 1 | S/M | 0.2-0.3 | 0.8-0.9 | 0.3-0.4 | 0.06-0.07 | 0.06-0.07 |
| | 2 | L/XL | 0.2-0.3 | 0.85-0.95 | 0.4-0.5 | 0.06-0.07 | 0.06-0.07 |
| Low | 1 | S | 0.2-0.3 | 1.0-1.2 | 0.5-0.7 | 0.06-0.07 | 0.06-0.07 |
| | 2 | M | 0.2-0.3 | 1.0-1.2 | 0.6-0.8 | 0.06-0.07 | 0.06-0.07 |
| | 3 | L | 0.2-0.3 | 1.0-1.2 | 0.6-0.8 | 0.06-0.07 | 0.06-0.07 |
| | 4 | XL | 0.2-0.3 | 1.0-1.3 | 0.6-0.8 | 0.06-0.07 | 0.06-0.07 |

Optionally, in this or any other embodiment, as the dimensions of the high tension band 1500A are smaller than the dimensions of the low tension band 1500B, the high tension band 1500A imparts a greater force when applied on the devices herein. Optionally, in this or any other embodiment, the high tension band 1500A high tension band 1500A high tension band 1500A and the low tension band 1500B are formed of the same material. Optionally, in this or any other embodiment, the high tension band 1500A and the low tension band 1500B are formed of different materials. Optionally, in this or any other embodiment, the high tension band 1500A are formed of a material having a higher modulus of elasticity than the material of the low tension band 1500B.

Example 10: Choosing a Low Tension Band

After measuring his flaccid and erect penis, Paul determines that his general penis size is size "D" and that, as his ED symptoms are mild, he should purchase a Size XL ED device. However, during intercourse, the size XL ED device rotates and translates from its initial position on his penis such that the efficacy of the XL ED device is diminished. Paul then pinches each tab of a high tension band that arrived with his XL ED device, and applies tension on the band while inserting the elbows of his XL ED band into the hoop of the band. Wearing his XL ED device with the high tension band placed thereon Paul finds that the device maintains its position and orientation during intercourse, but is uncomfortably tight. As such, Paul pinches the tabs of the high tension band and applies tension to the high tension band to remove the high tension band from his XL ED device. Paul then replaces the high tension band with a low tension band in the same way he attached the high tension band to his XL ED device. Now during intercourse, his XL ED device is comfortable and maintains its position and efficacy.

Example 11: Choosing a High Tension Band

After measuring his flaccid and erect penis, Gary determines that his general penis size is size "D" and that, as his ED symptoms are severe, he should purchase a Size L ED device. However, during intercourse, his size L ED device rotates and translates from its initial position on his penis such that the efficacy of his size L ED device is diminished. Gary then pinches each tab of a low tension band that arrived with his size L ED device, and applies tension on the band while inserting the elbows of his size LED band into the hoop of the band. Wearing his size L ED device with the low tension band placed thereon Gary experiences an improved efficacy but notices that his size L ED device rotates and translates slightly from its initial position on his penis. As such, Gary pinches the tabs of the low tension band and applies tension to the low tension band to remove the low tension band from his size L ED device. Gary then replaces the low tension band with a high tension band in the same way he attached the low tension band to his size L ED device. Now during intercourse, his size L ED device is maintaining its position and provides its full efficacy.

The invention claimed is:

1. A penile constriction device comprising an arched rod comprising:
   a first arm comprising
      a first coupling end, and
      a first converging end having a first terminus;
   a second arm comprising
      a second coupling end, and
      a second converging end having a second terminus disconnected from the first terminus, wherein the first converging end and the second converging end converge to form a constriction region; and
   a bridge connecting the first coupling end to the second coupling end, the bridge comprising
      a compression region rising inferiorly from an inferior side of the bridge, wherein the compression comprises:
         a first dorsal vein protrusion comprising:
            a first dorsal apex; and
            a first dorsal height measured as a first minimum normal distance between the first dorsal apex and a first lateral edge of the first dorsal vein protrusion where the first dorsal vein protrusion rises from the inferior side of the bridge;
         a second dorsal vein protrusion comprising:
            a second dorsal apex, and
            a second dorsal height measured as a second minimum normal distance between the second dorsal apex and a second lateral edge of the second dorsal vein protrusion where the second dorsal vein protrusion rises from the inferior side of the bridge; and
         a dorsal vein valley between the first dorsal vein apex and the second dorsal vein apex,
      wherein the compression region at a center of the dorsal vein valley is inferior to the first lateral edge, the second lateral edge, or both.

2. The device of claim 1, having a constriction gap width of about 0 inches to about 1.25 inches, wherein the constriction gap width is measured as a minimum distance between a surface of the first converging end and a surface of the second converging end within the constriction region.

3. The device of claim 2, having a constriction height of about 0.5 inches to about 2.5 inches, wherein the constriction height is measured as a normal distance between a constriction point and the inferior side of the bridge, and wherein the constriction point is defined as a midpoint of the constriction gap width.

4. The device of claim 3, having a maximum inner width of about 0.5 inches to about 3 inches, wherein the maximum inner width is defined as a maximum normal distance between a mesial side of the first arm and a mesial side of the second arm, and wherein the maximum inner width is superior to the constriction gap.

5. The device of claim 4, having an inferior height of about 0.2 inches to about 1 inch, wherein the inferior height is defined as a normal distance between a center point, and the inferior side of the bridge, wherein the center point comprises a midpoint of the maximum inner width.

6. The device of claim 5, wherein a ratio between the inferior height and the maximum inner width is about 0.15:1 to about 0.6:1.

7. The device of claim 4, wherein a ratio between the constriction height and the maximum inner width is about 0.7:1 to about 0.99:1.

8. The device of claim 4, wherein a ratio between the constriction gap width and the maximum inner width is about 0.2:1 to about 0.9:1.

9. The device of claim 1, having a thickness of about 0.125 inches to about 0.8 inches, wherein the thickness is measured as a maximum normal cross-sectional width of at least a portion of at least one of the first arm and the second arm.

10. The device of claim 1, wherein the first terminus diverges from the constriction region to form a first elbow, and wherein the second terminus diverges from the constriction region to form a second elbow.

11. The device of claim 10, wherein at least one of the first arm and the second arm are configured to removably affix to a band.

12. The device of claim 1, wherein the arched rod comprises a cover substantially surrounding a frame, wherein a frame modulus of elasticity of the frame is higher than a cover modulus of elasticity of the cover.

13. The device of claim 1, wherein the first dorsal vein protrusion, the dorsal vein valley, and the second dorsal vein protrusion are arranged sequentially within the compression region in a direction along the bridge from the first arm to the second arm.

14. The device of claim 1, comprising a dorsal vein valley distance between the first dorsal apex and the second dorsal apex of about 0.15 inches to about 0.75 inches.

15. The device of claim 1, comprising a compression region width between the first lateral edge and the second lateral edge of about 0.2 inches to about 0.8 inches.

16. The device of claim 1, wherein the compression region within the dorsal vein valley at a center of the dorsal vein valley is superior to or has a same height relative to the first lateral edge as the first minimum normal distance or relative to the second lateral edge as the second minimum normal distance, or both.

17. The device of claim 1, further comprising a plurality of friction protrusions on a superior side of the bridge.

\* \* \* \* \*